US008314098B2

(12) United States Patent
Yamamoto et al.

(10) Patent No.: US 8,314,098 B2
(45) Date of Patent: Nov. 20, 2012

(54) PYRAZOLO-PYRIMIDINE COMPOUNDS

(75) Inventors: Takashi Yamamoto, Kawasaki (JP);
Ayatoshi Andou, Kawasaki (JP);
Nobuhiko Hayakawa, Kawasaki (JP);
Masatsugu Noguchi, Kawasaki (JP);
Kanna Kuribayashi, Kawasaki (JP);
Agung Eviryanti, Kawasaki (JP);
Ryohei Yokoyama, Kawasaki (JP);
Shunsuke Fukuda, Kawasaki (JP);
Toshihiko Sugiura, Kawasaki (JP);
Shunsuke Kageyama, Kawasaki (JP);
Yoichiro Shima, Kawasaki (JP); Misato
Noguchi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/169,958

(22) Filed: Jun. 27, 2011

(65) Prior Publication Data

US 2011/0294781 A1    Dec. 1, 2011

Related U.S. Application Data

(63) Continuation of application No. PCT/JP2009/071786, filed on Dec. 28, 2009.

(30) Foreign Application Priority Data

Dec. 26, 2008  (JP) .................................. 2008-334965
Sep. 30, 2009  (JP) .................................. 2009-228755

(51) Int. Cl.
  A61K 31/535      (2006.01)
(52) U.S. Cl. ............. 514/233.2; 514/210.21; 514/259.3;
  514/232.5; 514/252.16; 514/230.5; 544/8;
  544/281; 544/117; 544/105
(58) Field of Classification Search .............. 514/210.21,
  514/259.3, 233.2, 232.5, 252.16, 230.5; 544/8,
  544/281, 117, 105
See application file for complete search history.

(56) References Cited

U.S. PATENT DOCUMENTS

| 7,557,110 B2 | 7/2009 | Kataoka et al. |
| 2003/0114446 A1 | 6/2003 | Sun et al. |
| 2003/0139403 A1 | 7/2003 | Ono et al. |
| 2004/0024206 A1 | 2/2004 | Sun et al. |
| 2004/0048873 A1 | 3/2004 | Ono et al. |
| 2004/0053937 A1 | 3/2004 | Sun et al. |
| 2004/0198725 A1 | 10/2004 | Sun et al. |
| 2005/0136065 A1 | 6/2005 | Valiante, Jr. |
| 2005/0250770 A1 | 11/2005 | Ono et al. |
| 2005/0250774 A1 | 11/2005 | Ono et al. |
| 2005/0250787 A1 | 11/2005 | Sun et al. |
| 2005/0282809 A1 | 12/2005 | Ono et al. |
| 2006/0025409 A1 | 2/2006 | Ono et al. |
| 2006/0030560 A1 | 2/2006 | Sun et al. |
| 2006/0063739 A1 | 3/2006 | Sun et al. |
| 2006/0122156 A1 | 6/2006 | Sun et al. |
| 2006/0189632 A1 | 8/2006 | Kataoka et al. |
| 2006/0205743 A1 | 9/2006 | Kataoka et al. |
| 2006/0223996 A1 | 10/2006 | Sun et al. |
| 2006/0281711 A1 | 12/2006 | Demko et al. |
| 2007/0027151 A1 | 2/2007 | Sun et al. |
| 2007/0027156 A1 | 2/2007 | Nakai et al. |
| 2007/0060595 A1 | 3/2007 | Yoshizawa et al. |
| 2007/0078136 A1 | 4/2007 | Vaccaro et al. |
| 2008/0045536 A1 | 2/2008 | Vaccaro et al. |
| 2008/0167300 A1 | 7/2008 | Ono et al. |
| 2009/0253694 A1 | 10/2009 | Ono et al. |
| 2010/0173413 A1 | 7/2010 | Ono et al. |
| 2010/0204212 A1 | 8/2010 | Vaccaro et al. |
| 2010/0256132 A1 | 10/2010 | Sun et al. |

FOREIGN PATENT DOCUMENTS

| JP | 2006-519226 | 8/2006 |
| JP | 2006-523219 | 10/2006 |
| WO | WO 03/047516 | 6/2003 |
| WO | WO 2004/035740 | 4/2004 |
| WO | WO 2004/087153 | 10/2004 |
| WO | WO 2004/110454 | 12/2004 |
| WO | WO 2005/026126 | 3/2005 |
| WO | WO 2005/035516 | 4/2005 |
| WO | WO2005/046603 | 5/2005 |
| WO | WO 2005/046604 | 5/2005 |
| WO | WO 2005/046698 | 5/2005 |
| WO | WO 2006/007532 | 1/2006 |
| WO | WO 2006/053109 | 5/2006 |
| WO | WO 2006/053227 | 5/2006 |
| WO | WO 2006/124662 | 11/2006 |
| WO | WO 2007/038314 | 4/2007 |

OTHER PUBLICATIONS

Written Opinion mailed Mar. 23, 2010. (w/English Translation).
International Search Report mailed on Mar. 23, 2010.
H. Reimlinger, et al., "Weitere Reaktionen mit 5-Oxo-pyrazolo-pyrimidinen", Chemische Berichte, 1971, vol. 104, pp. 2237-2240.
H. Reimlinger, et al., "Reaktionen des 3(5)-Amino-pyrazols mit α, β-ungesattigten Estern. Darstellung und Charakterisierung isomerer Oxo-dihydro-pyrazolo-pyrimidine", Chemische Berichte, 1970, vol. 103, pp. 3252-3265.

Primary Examiner — Brandon Fetterolf
Assistant Examiner — Jean Cornet
(74) Attorney, Agent, or Firm — Oblon, Spivak, McClelland, Maier & Neustadt, L.L.P.

(57) ABSTRACT

The present invention has searched for a variety of compounds which show IL-12/IL-23 production-inhibitory activities and herein provides a pharmaceutical composition and an agent for preventing or treating IL-12/IL-23 excess production-related diseases, which comprise the compound.

23 Claims, 1 Drawing Sheet

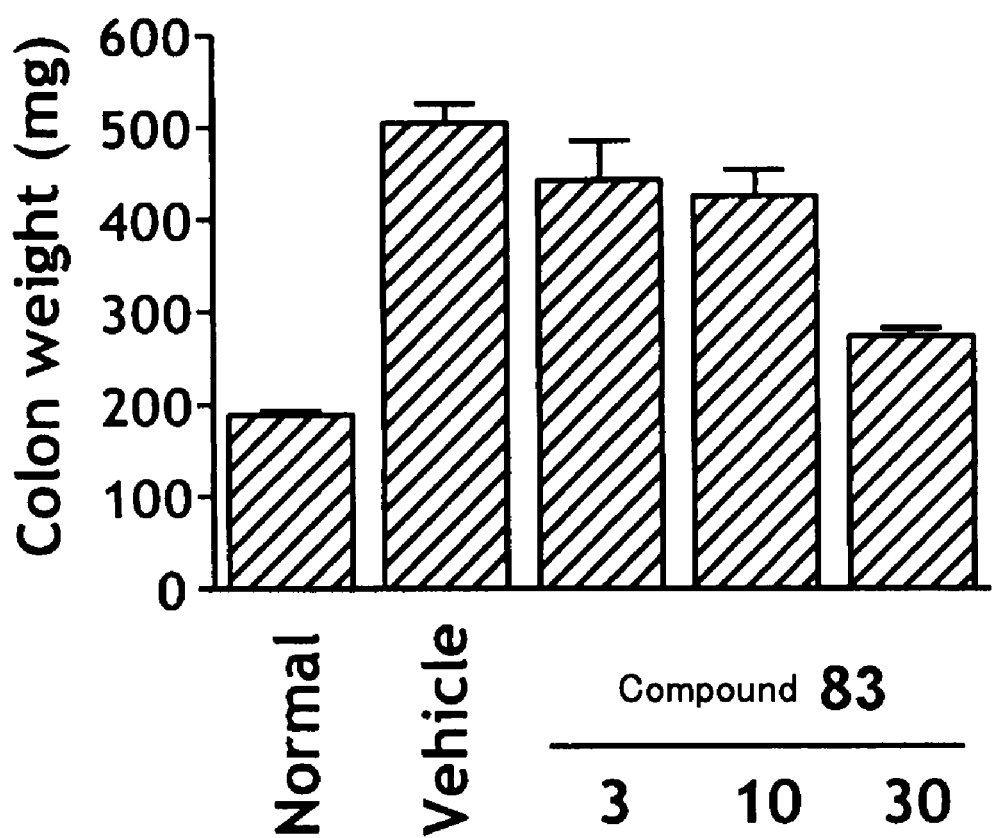

PYRAZOLO-PYRIMIDINE COMPOUNDS

TECHNICAL FIELD

The present invention relates to a novel pyrazolo-pyrimidine compound or a pharmaceutically acceptable salt thereof, which shows IL-12/IL-23 production-inhibitory activity as well as a pharmaceutical composition or a prophylactic or therapeutic agent for IL-12/IL-23 hyperproduction-related diseases, which comprises the compound or a pharmaceutically acceptable salt thereof, as an effective component.

In this respect, the term "inhibition of IL-12/IL-23 production" herein used means the inhibition of the production of IL-12, the inhibition of the production of IL-23 or the inhibition of the production of IL-12 and IL-23. Similarly, the term "IL-12/IL-23 hyperproduction" used herein means the hyperproduction of IL-12, the hyperproduction of IL-23 or the hyperproduction of IL-12 and IL-23.

BACKGROUND ART

Interleukin-12 (IL-12) is a hetero-dimeric inflammatory cytokine (also called IL-12p70) comprising two subunits named p35 and p40 respectively and plays an important role in the immune response through a mediatory action between the innate resistance and the antigen-specific adaptive immunity. In addition, IL-12 is produced by the phagocyte and the antigen-presenting cells, in particular, macrophages and the dendritic cells through the stimulative actions of, for instance, bacteria, bacterial products such as lipopolysaccharides (LPS) and intracellular parasites. A well-known biological function of IL-12 is to express interferon-γ (IFN-γ) through T cells and NK cells and to induce the differentiation thereof into a Th1 T lymphocyte type one. On the other hand, interleukin-23 (IL-23) is, like IL-12, a hetero-dimeric inflammatory cytokine comprising two subunits named p19 and p40 respectively and it is involved in the type I immunological protection and induces the secretion of IFN-γ through T cells.

As has been discussed above, IL-12 and IL-23 possess p40 common thereto and play an important role in the immunological inflammatory reactions, while it has been suggested that the production of IL-12 is enhanced by IFN-γ in the chronic diseases accompanied by the continuous production of IFN-γ. Accordingly, it has been recognized that the quite strong feedback loop appearing subsequent to the infectious stimulation or inflammatory stimulation which would induce the production of IL-12 may accelerate the further production of IL-12 by the action of the IL-12 inducible and IL-23 inducible IFN-γ and thus results in the excess production (hyperproduction) of inflammation-accelerative cytokines.

It have been known that the excess production of IL-12/IL-23 takes part in a variety of diseases and, more specifically, it would be involved in various diseases, examples of which include, but are not limited to, multiple sclerosis, systemic sclerosis, sepsis, myasthenia gravis, autoimmune neurosis, Guillain-Barre syndrome, autoimmune uveitis, autoimmune hemolytic anemia, pernicious anemia, autoimmune thrombocytopenia, temporal arteritis, anti-phospholipid syndrome, vasculitis, Wegener granulomatosis, Behcet disease, psoriasis, psoriatic arthritis, herpetic dermatitis, pemphigus vulgaris, leukoma, Crohn's disease, ulcerative colitis, interstitial pulmonary fibrosis, myelofibrosis, hepatic fibrosis, myocarditis, autoimmune thyroiditis (such as Grebs' disease and Hashimoto's disease), primary biliary cirrhosis, autoimmune hepatitis, immune-mediated diabetes mellitus, autoimmune ovaritis and orchitis, autoimmune adrenalitis, articular rheumatism, juvenile articular rheumatism, systemic lupus erythematosus, scleroderma, multiple myositis, dermatomyositis, spondyloarthropathy, rigid spondylitis, Sjogren's syndrome, and graft-versus-host disease.

On the other hand, TNF-α is, like IL-12/IL-23, one of the inflammatory cytokines which play a central role in, for instance, the pathema-formation of articular rheumatism. In fact, there have been used, even in the clinical practice in Japan, a biological preparation which acts on TNF-α as a target and there have been adapted, for instance, etanercept which is a fused protein comprising sTNFR and immunoglobulin G and infliximab and adalimumab which are anti-TNF-α monoclonal antibodies. However, TNF-α is considered to be a cytokine which is quite important in the immune response and positioned upstream of the immune response signal and all of the aforementioned drugs in fact suffer from various side effects and accordingly, there would be apprehension that the use thereof may accompanied with much risks of causing infectious diseases and of producing cancers.

For this reason, the compounds each capable of inhibiting the production of IL-12/IL-23 show a high selectivity for IL-12/IL-23-excess production-related diseases, are free of any harmful side effect and can serve as clinically quite useful agents for preventing and treating a variety of inflammatory diseases inclusive of the aforementioned respective diseases.

Patent Documents 1 to 9 each disclose a compound possessing the IL-12 excess production-inhibitory action, but the compounds disclosed therein each have a skeleton different from the pyrazolo[1,5-a]pyrimidine skeleton according to the present invention.

Patent Documents 10 and 11 each disclose a condensed heterocyclic compound having a MAPKAP kinase-2 (MK2)-inhibitory action, but these documents never state that these compounds possess any IL-12/IL-23 production-inhibitory action like that of the compound according to the present invention. Patent Document 12 discloses condensed heterocyclic compounds each showing a cJun N-terminal kinase (JNK)-inhibitory action, but this document never states that these compounds show any IL-12/IL-23 production-inhibitory action like that of the compound according to the present invention. Patent Document 13 discloses a bicyclic heterocyclic compound useful for the immunological enhancement, but this document never states that these compounds show any IL-12/IL-23 production-inhibitory action like that of the compound according to the present invention. Cited Reference 14 discloses bicyclic heterocyclic compounds each possessing an agonist activity against adenosine receptor A2, but this document never states that these compounds show any IL-12/IL-23 production-inhibitory action like that of the compound according to the present invention. Cited Reference 15 discloses bicyclic heterocyclic compounds each possessing an antagonistic action against corticotrophin-release factor, but this document never states that these compounds show any IL-12/IL-23 production-inhibitory action like that of the compound according to the present invention.

Accordingly, there has been desired for the development of a clinically quite useful agent for preventing or treating a variety of inflammatory diseases including those specified above, shows an IL-12/IL-23 production-inhibitory action, has a high selectivity for IL-12/IL-23-excess production-related diseases, and are free of any harmful side effect.

PRIOR TECHNICAL LITERATURE

Patent Documents
 Patent Document 1: WO2003/047516A2, Official Gazette
 Patent Document 2: WO2005/046698A1, Official Gazette
 Patent Document 3: WO2004/035740A2, Official Gazette Patent Document 4: WO2005/046603A2, Official Gazette
Patent Document 5: WO2005/046604A2, Official Gazette
Patent Document 6: WO2006/007532A2, Official Gazette
Patent Document 7: WO2006/053109A1, Official Gazette
Patent Document 8: WO2006/053227A2, Official Gazette
Patent Document 9: WO2006/124662A1, Official Gazette
Patent Document 10: US2008/0045536A1, Official Gazette
Patent Document 11: WO2007/038314A2, Official Gazette
Patent Document 12: WO2005/035516A1, Official Gazette
Patent Document 13: WO2004/087153A2, Official Gazette
Patent Document 14: WO2004/110454A1, Official Gazette
Patent Document 15: WO2005/026126A1, Official Gazette

SUMMARY OF THE INVENTION

Problems that the Invention is to Solve

It is an object of the present invention to search for and provide a variety of variation compounds which show IL-12/IL-23 production-inhibitory activity and more particularly to provide a pharmaceutical composition and an agent for preventing or treating IL-12/IL-23 excess production-related diseases, which comprise the compound.
Means for the Solution of the Problems The inventors of this invention have searched for any compound possessing IL-12/IL-23 production-inhibitory activity and as a result, they have surprisingly found that a certain number of novel pyrazolo-pyrimidine compounds or pharmaceutically acceptable salts thereof show an excellent IL-12/IL-23 production-inhibitory activity and have thus completed the present invention.

The pyrazolo-pyrimidine compounds or pharmaceutically acceptable salts thereof may be used as useful pharmaceutical compositions or serve as effective agents for the prevention or treatment of IL-12/IL-23 excess production-related diseases.

More specifically, the present invention herein provides a pyrazolo-pyrimidine compound represented by the following general formula (I) or (IA), or a pharmaceutically acceptable salt thereof:

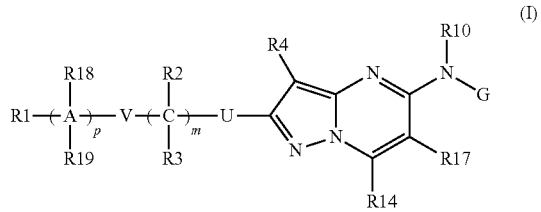

(I)

wherein
m=0, 1, 2, 3, 4 or 5;
p=0 or 1;
U and V independently represent a single bond, O, S, S(O), $S(O_2)$, $NR^a$, C(O), C(O)O, $C(O)NR^b$, OC(O), $NR^aC(O)$, $NR^aC(O)NR^b$, $OC(O)NR^a$, $NR^aC(O)O$, $S(O)NR^a$, $S(O_2)NR^a$, $NR^aS(O)$, $NR^aS(O_2)$, $CR^{20}=CR^{21}$, $C\equiv C$, or $C=NR^b$;

A is an aryl group, a heterocyclic group or an aliphatic ring group;
$R^1$, $R^{18}$ and $R^{19}$ may be the same or different and independently represent a hydrogen atom, a halogeno group, a hydroxyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, a sulfonamido group which may have a substituent(s), a sulfinamido group which may have a substituent(s), an aliphatic ring group which may have a substituent(s), an alkenyl group which may have a substituent(s), an alkynyl group which may have a substituent(s), a benzyloxy group which may have a substituent(s), an aryloxy group which may have a substituent(s), an aryl-vinyl group which may have a substituent(s), a hetero-aryloxy group which may have a substituent(s), an arylamino group which may have a substituent(s), a hetero-arylamino group which may have a substituent(s), an aryl-ethynyl group which may have a substituent(s), an aryl group which may have a substituent(s) or a heterocyclic group which may have a substituent(s);
$R^2$ and $R^3$ may be the same or different and independently represent a hydrogen atom, a halogeno group, a hydroxyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, a sulfonamido group which may have a substituent(s), a sulfinamido group which may have a substituent(s), an aliphatic ring group which may have a substituent(s), an alkenyl group which may have a substituent(s), an alkynyl group which may have a substituent(s), a benzyloxy group which may have a substituent(s), an aryloxy group which may have a substituent(s), an aryl-vinyl group which may have a substituent(s), a hetero-aryloxy group which may have a substituent(s), an arylamino group which may have a substituent(s), a hetero-arylamino group which may have a substituent(s), an aryl-ethynyl group which may have a substituent(s), an aryl group which may have a substituent(s) or a heterocyclic group which may have a substituent(s);
$R^{20}$ and $R^{21}$ may be the same or different and independently represent a hydrogen atom, a halogeno group, an alkyl group which may have a substituent(s), an alkoxy group which may have a substituent(s), an alkylthio group which may have a substituent(s), an alkylsulfonyl group which may have a substituent(s), an acyl group which may have a substituent(s), an acyloxy group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, a sulfonamido group which may have a substituent(s), a sulfinamido group which may have a substituent(s), an aliphatic ring group which may have a substituent(s), an alkenyl group which may have a substituent(s), an alkynyl group which may have a substituent(s), a benzyloxy group which may have a substituent(s), an aryloxy group which may have a substituent(s), an aryl-vinyl group which may have a substituent(s), a heteroaryloxy group which may have a substituent(s), an arylamino group which may have a substituent(s), a hetero-arylamino group which may have a substituent(s), an aryl-ethynyl group which may have a substituent(s), an aryl group which may have a substituent(s) or a heterocyclic group which may have a substituent(s);

$R^4$ is a group selected from the group consisting of a hydrogen atom, a halogeno group, a hydroxyl group, a nitro group, a cyano group, an acyloxy group, a carboxyl group, a sulfonic acid group, a sulfonamido group which may have a substituent(s), a sulfinamido group which may have a substituent(s), an amino group which may have a substituent(s), an alkyl group which may have a substituent(s), an alkoxy group which may have a substituent(s), a mono- or di-alkylamino group which may have a substituent(s), or an aryl group which may have a substituent(s), or a heterocyclic group which may have a substituent(s);

$R^{10}$ is a group selected from the group consisting of a hydrogen atom, an alkyl group which may have a substituent(s), an acyl group which may have a substituent(s), an alkylsulfonyl group which may have a substituent(s), an alkoxycarbonyl group which may have a substituent(s), a carbamoyl group which may have a substituent(s), or an aryl group which may have a substituent(s), an aliphatic ring group which may have a substituent(s), or a heterocyclic group which may have a substituent(s);

$R^{14}$ is a group selected from the group consisting of a group: $NR^cR^d$, an aliphatic ring group which may have a substituent(s), or a heterocyclic group which may have a substituent(s);

$R^{17}$ is a hydrogen atom;

G is a member selected from the group consisting of those represented by the following general formulas:

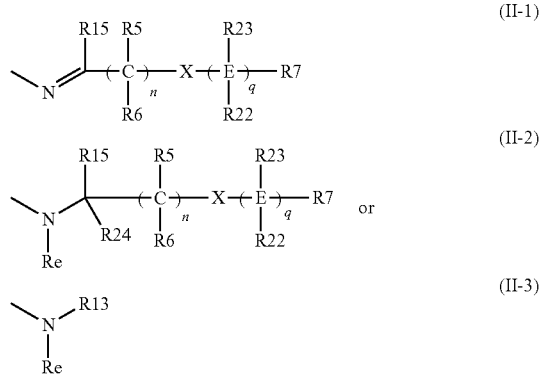

n=0, 1, 2, 3, 4 or 5;
q=0 or 1;
$R^{15}$ and $R^{24}$ may be the same or different and independently represent a hydrogen atom, an alkyl group which may have a substituent(s), an aliphatic ring group which may have a substituent(s), an aryl group which may have a substituent(s), or a heterocyclic group which may have a substituent(s);

$R^5$ and $R^6$ may be the same or different and independently represent a hydrogen atom, a halogeno group, a hydroxyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, a sulfonamido group which may have a substituent(s), a sulfinamido group which may have a substituent(s), an aliphatic ring group which may have a substituent(s), an alkenyl group which may have a substituent(s), an alkynyl group which may have a substituent(s), a benzyloxy group which may have a substituent(s), an aryloxy group which may have a substituent(s), an aryl-vinyl group which may have a substituent(s), a heteroaryloxy group which may have a substituent(s), an arylamino group which may have a substituent(s), a hetero-arylamino group which may have a substituent(s), an aryl-ethynyl group which may have a substituent(s), an aryl group which may have a substituent(s), or a heterocyclic group which may have a substituent(s);

X represents a single bond, O, S, S(O), $S(O_2)$, $NR^a$, C(O), C(O)O, $C(O)NR^a$, OC(O), $NR^aC(O)$, $NR^aC(O)NR^b$, $OC(O)NR^a$, $NR^aC(O)O$, $S(O)NR^a$, $S(O_2)NR^a$, $NR^aS(O)$, $NR^aS(O_2)$, $CR^{20}=CR^{21}$, C≡C, or $C=NR^b$;

E represents an aryl group, a heterocyclic group or an aliphatic ring group;

$R^7$, $R^{22}$ and $R^{23}$ may be the same or different and independently represent a hydrogen atom, a halogeno group, a hydroxyl group, an alkyl group which may have a substituent(s), a mercapto group, a boronyl group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, a sulfonamido group which may have a substituent(s), a sulfinamido group which may have a substituent(s), an aliphatic ring group which may have a substituent(s), an alkenyl group which may have a substituent(s), an alkynyl group which may have a substituent(s), a benzyloxy group which may have a substituent(s), an aryloxy group which may have a substituent(s), an aryl-vinyl group which may have a substituent(s), a heteroaryloxy group which may have a substituent(s), an arylamino group which may have a substituent(s), a hetero-arylamino group which may have a substituent(s), an aryl-ethynyl group which may have a substituent(s), an aryl group which may have a substituent(s), or a heterocyclic group which may have a substituent(s);

$R^a$ and $R^b$ may be the same or different and independently represent a hydrogen atom, an alkyl group which may have a substituent(s), an alkoxy group which may have a substituent(s), an acyl group which may have a substituent(s), an alkylsulfonyl group which may have a substituent(s), an alkoxycarbonyl group which may have a substituent(s), carbamoyl group which may have a substituent(s), an aliphatic ring group which may have a substituent(s), an aryl group which may have a substituent(s), or a heterocyclic group which may have a substituent(s);

$R^{13}$ represents a hydrogen atom, an aryl group which may have a substituent(s), a heterocyclic group which may have a substituent(s) or an aliphatic ring group which may have a substituent(s);

$R^c$ and $R^d$ may be the same or different and independently represent an alkyl group which may have a substituent(s), an alkoxy group which may have a substituent(s), an acyl group which may have a substituent(s), an alkylsulfonyl group which may have a substituent(s), an alkoxycarbonyl group which may have a substituent(s), a carbamoyl group which may have a substituent(s), an aliphatic ring group which may have a substituent(s), an aryl group which may have a substituent(s) or a heterocyclic group which may have a substituent(s);

R$^e$ represents a hydrogen atom, an alkyl group which may have a substituent(s), an alkoxy group which may have a substituent(s), an acyl group which may have a substituent(s), an alkylsulfonyl group which may have a substituent(s), an alkoxycarbonyl group which may have a substituent(s), a carbamoyl group which may have a substituent(s), an aliphatic ring group which may have a substituent(s), an aryl group which may have a substituent(s) or a heterocyclic group which may have a substituent(s);

provided that each of the foregoing substituents may be one selected from the group consisting of halogeno groups, hydroxyl group, lower alkyl groups, mercapto groups, alkoxy groups, alkylthio groups, alkylsulfonyl groups, acyl groups, acyloxy groups, amino groups, alkylamino groups, carboxyl groups, alkoxycarbonyl groups, carbamoyl groups, nitro groups, cyano groups, trifluoromethyl group, aryl groups, and heterocyclic groups; and

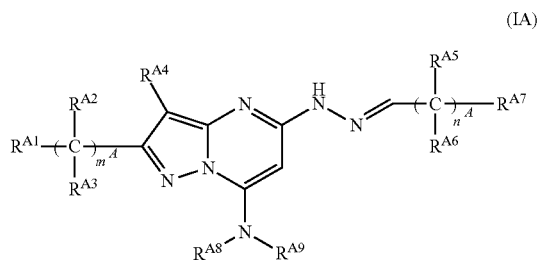

(IA)

wherein
m$^A$=0, 1, or 2;
n$^A$=0, 1, or 2;
R$^{A1}$ and R$^{A4}$ each are one independently selected from the group consisting of a hydrogen atom, halogeno groups, a hydroxyl group, a nitro group, a sulfonic acid group, amino groups, alkyl groups each of which may have a substituent(s), alkoxy groups each of which may have a substituent(s), mono- or di-alkylamino groups each of which may have a substituent(s), carbamoyl groups each of which may have a substituent(s), or aryl groups each of which may have a substituent(s), heteroaryl groups each of which may have a substituent(s), or heterocyclic groups each of which may have a substituent(s);

each of the substituents R$^{A2}$, R$^{A3}$, R$^{A5}$ and R$^{A6}$ is one independently selected from the group consisting of a hydrogen atom, halogeno groups, a hydroxyl group, a nitro group, a sulfonic acid group, amino groups, alkyl groups each of which may have a substituent(s), alkoxy groups each of which may have a substituent(s), or mono- or di-alkylamino groups each of which may have a substituent(s);

R$^{A7}$ is a member selected from the group consisting of aryl groups each of which may have a substituent(s), or heteroaryl groups each of which may have a substituent(s); and Each of the substituents R$^{A8}$ and R$^{A9}$ independently represents an alkyl group which may have a substituent(s), or the group: NR$^{A8}$R$^{A9}$ may represent a cyclic amino group which may have a substituent(s).

In addition, the present invention likewise provides a pharmaceutical composition or an agent for preventing or treating the IL-12/IL-23-excess production-related diseases, which comprises the pyrazolo-pyrimidine compound represented by the foregoing general formula (I) or (IA) or a pharmaceutically acceptable salt thereof.

Effects of the Invention

The compound of the present invention can selectively inhibit the production of IL-12/IL-23, while it never significantly inhibits the TNF-α production from activated macrophage and accordingly, the compound of the present invention shows a high selectivity as an agent for preventing or treating the IL-12/IL-23-excess production-related diseases and the compound is not accompanied by a risk of causing any side effect such as those observed for the compound possessing the TNF-α production-inhibitory action. Moreover, the IL-12/IL-23 production-inhibitory activity of the preferred compounds of the present invention is not considerably reduced even in the presence of the human serum albumin (HAS) and a 1-acidic glycoprotein (α1-AGP), which are proteins present in the human plasma and therefore, the compound would show quite excellent effect even when it is administered to human beings in the clinical practice. In addition, the preferred compounds of the present invention never show any conspicuous reduction in their IL-12/IL-23 production-inhibitory activity even in the whole blood and it can show quite excellent effect even when it is administered to human beings in the clinical practice. Accordingly, the present invention can thus provide an extremely excellent efficacy even when administering the compound to human beings in the clinical practice.

BRIEF DESCRIPTION OF THE DRAWING

FIG. 1 is a graph showing the results obtained when inspecting Compound 83 for the inflammation-inhibitory action in a mouse enteritis model.

MODE FOR CARRYING OUT THE INVENTION

The present invention will hereunder be described in more detail.

In the present invention, the term "aryl group" means a carbon-based monocyclic or bicyclic aromatic substituent having 5 to 12 carbon atoms and specific examples thereof include a phenyl group, an indenyl group, a naphthyl group, and a fluorenyl group, with a phenyl group being preferred.

The term "halogeno group" herein used includes, for instance, a fluorine atom, a chlorine atom, a bromine atom or an iodine atom.

The term "alkyl group" herein used means a linear or branched or cyclic alkyl group having 1 to 18 carbon atoms, and specific examples thereof include a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an isopropyl group, an isobutyl group, a sec-butyl group, a tert-butyl group, an isopentyl group, a tert-pentyl group, a neopentyl group, a 2-pentyl group, a 3-pentyl group, a 3-hexyl group, a 2-hexyl group, a tert-octyl group, a cyclopropyl group, a cyclobutyl group, a cyclopentyl group, a cyclohexyl group, and a 1-adamantyl group, preferred examples thereof are an n-hexyl group, an n-heptyl group, an n-octyl group, an n-nonyl group, an n-decyl group, an n-undecyl group, an n-dodecyl group, an isopropyl group, an isobutyl group, a sec-butyl group, a tert-butyl group, an isopentyl group, a tert-pentyl group, a neopentyl group, a 2-pentyl group, a 3-pentyl group, a 3-hexyl group, a 2-hexyl group, a tert-octyl group, a cyclopropyl group, a cyclobutyl group, a cyclopentyl group, a cyclohexyl group, and a 1-adamantyl group; and more preferred are, for instance, an isopropyl group, a tert-butyl group, a tert-octyl group, and a 1-adamantyl group. Moreover, the term "lower alkyl group" herein used means a linear, branched or cyclic alkyl group having 1 to 6 carbon atoms and preferably 1 to 3 carbon atoms and specific examples thereof include a methyl group, an ethyl group, an n-propyl group, an n-butyl group, an n-pentyl group, an n-hexyl group, an isopropyl group, an isobutyl group, a sec-butyl group, a tert-butyl group, an isopentyl group, a tert-pentyl group, a neopentyl group, a 2-pentyl group, a 3-pentyl group, a 3-hexyl group, a 2-hexyl group, a cyclopropyl group, a cyclobutyl group, a cyclopentyl group and a cyclohexyl group, with methyl and ethyl groups being preferably used herein.

The term "alkenyl group" used herein means a linear, branched or cyclic alkenyl group having 1 to 6 carbon atoms and specific examples thereof are a vinyl group, a 1-propenyl group, a 2-propenyl group, an isopropenyl group, a 1-butenyl group, a 2-butenyl group, and a 3-butenyl group.

The term "alkynyl group" herein used means a linear, branched or cyclic alkynyl group having 1 to 6 carbon atoms and specific examples thereof are an ethynyl group, a 1-propynyl group, 2-propynyl group, a 1-butynyl group, 2-butynyl group, and a 3-butynyl group.

The term "alkoxy group" herein used means an alkoxy group carrying a linear, branched or cyclic alkyl group having 1 to 18 and preferably 1 to 8 carbon atoms and specific examples thereof include a methoxy group, an ethoxy group, an n-propoxy group, an n-butoxy group, an n-pentyloxy group, an n-hexyloxy group, an n-heptyloxy group, an n-octyloxy group, an n-nonyloxy group, an n-decyloxy group, an n-undecyloxy group, an n-dodecyloxy group, an isopropoxy group, an isobutoxy group, a sec-butoxy group, a tert-butoxy group, a cyclo-propyloxy group, a cyclo-butoxy group, a cyclo-pentyloxy group, a cyclo-hexyloxy group, a cyclo-heptyloxy group, a 2-cyclohexyl-ethoxy group, a 1-adamantyloxy group, a 2-adamantyloxy group, a 1-adamantyl-methyloxy group, a 2-(1-adamantyl)-ethyloxy group, and a trifluoro-methoxy group, and preferred examples thereof are a methoxy group, an ethoxy group, an n-propoxy group, an isopropoxy group, an n-butoxy group, a tert-butoxy group, an n-pentyloxy group, and an n-hexyloxy group.

The term "alkylthio group" herein used means an alkylthio group carrying a linear, branched or cyclic alkyl group having 1 to 12 and preferably 1 to 6 carbon atoms and specific examples thereof include a methylthio group, an ethylthio group, an n-propylthio group, an isopropylthio group, an n-butylthio group, an isobutyl-thio group, a sec-butylthio group, a tert-butylthio group, a cyclo-propylthio group, a cyclo-butylthio group, a cyclo-pentylthio group, and a cyclo-butylthio group.

The term "alkylsulfonyl group" herein used means an alkylsulfonyl group carrying a linear, branched or cyclic alkyl group having 1 to 12 carbon atoms and specific examples thereof include a methanesulfonyl group, an ethane-sulfonyl group, a propane-sulfonyl group, a butane-sulfonyl group, a pentane-sulfonyl group, a hexane-sulfonyl group, a heptane-sulfonyl group, an octane-sulfonyl group, a nonane-sulfonyl group, a decane-sulfonyl group, an undecane-sulfonyl group, and a dodecane-sulfonyl group.

The term "acyl group" herein used means an acyl group carrying a linear, branched or cyclic alkyl group having 1 to 6 carbon atoms, or an acyl group carrying a linear, branched or cyclic alkenyl group having 1 to 6 carbon atoms, or an acyl group carrying a linear, branched or cyclic alkynyl group having 1 to 6 carbon atoms, or an acyl group carrying an aryl group which may be substituted with a substituent, and specific examples thereof include a formyl group, an acetyl group, a propionyl group, a butyryl group, an isobutyryl group, a valeryl group, an isovaleryl group, a pivaloyl group, a hexanoyl group, an acryloyl group, a methacryloyl group, a crotonoyl group, an isocrotonoyl group, a benzoyl group, and a naphthoyl group.

The term "acyloxy group" herein used means a formyl-oxy group or an acyloxy group carrying a linear, branched or cyclic alkyl group having 1 to 6 carbon atoms, or an acyloxy group carrying an aryl group which may be substituted with a substituent, and specific examples thereof include a formyl-oxy group, an acetyloxy group, a propionyl-oxy group, a butyryl-oxy group, an isobutyryl-oxy group, a valeryl-oxy group, an isovaleryl-oxy group, a pivaloyl-oxy group, a hexanoyl-oxy group, an acryloyl-oxy group, a methacryloyl-oxy group, a crotonoyl-oxy group, an isocrotonoyl-oxy group, a benzoyl-oxy group, and a naphthoyl-oxy group.

The term "mono- or di-alkylamino group" herein used means an amino group which is mono- or di-substituted with an alkyl group. In this respect, examples of the alkyl groups thereof may be the same as those listed above in connection with the foregoing "alkyl group". Specific examples thereof are an amino group, a methylamino group, an ethylamino group, a propylamino group, an isopropyl-amino group, a dimethylamino group, a diethylamino group, a dipropyl-amino group, a di-isopropyl-amino group, and a methyl ethyl-lamino group. Preferably, the alkyl groups thereof are those having 1 to 6 carbon atoms.

The term "alkoxycarbonyl group" herein used means an alkoxycarbonyl group carrying a linear, branched or cyclic alkyl group having 1 to 8 carbon atoms, and specific examples thereof are a methoxycarbonyl group, an ethoxycarbonyl group, a propoxy-carbonyl group, an isopropoxy-carbonyl group, an n-butoxy-carbonyl group, an isobutoxy-carbonyl group, a sec-butoxycarbonyl group, a tert-butoxycarbonyl group, and a benzyloxy-carbonyl group.

The term "carbamoyl group" herein used means a carbamoyl group which may have, on its nitrogen atom, a linear, branched or cyclic alkyl group having 1 to 6 carbon atoms, and specific examples thereof include a carbamoyl group, an N-methyl-carbamoyl group, an N-ethyl-carbamoyl group, an N,N-dimethyl-carbamoyl group, an N-pyrrolidyl-carbamoyl group, an N-piperidyl-carbamoyl group, and an N-morpholinyl-carbamoyl group. Moreover, the carbamoyl groups each of which may have a substituent(s) also include, for instance, those carrying, on the nitrogen atom, one or two substituents selected from the group consisting of linear, branched or cyclic alkyl groups each having 1 to 6 carbon atoms, aryl groups and heteroaryl groups and a specific example thereof is an N-methyl-N-pyridyl-carbamoyl group.

The term "alkylsulfonyl group" herein used means a sulfonyl group carrying, on its sulfur atom, a linear, branched or cyclic alkyl group having 1 to 6 carbon atoms and specific examples thereof are a methyl-sulfonyl group, an ethyl-sulfonyl group, a propyl-sulfonyl group and a butyl-sulfonyl group.

The term "heterocyclic group" herein used means a heterocyclic group comprising 1 to 3 rings each of which is a 5- to 7-membered ring constituted by, for instance, carbon atoms, and nitrogen, oxygen and/or sulfur atoms and specific examples of such heterocyclic rings are pyridine ring, dihydro-pyran ring, pyridazine ring, pyrimidine ring, pyrazine ring, pyrrole ring, furan ring, thiophene ring, oxazole ring, isoxazole ring, pyrazole ring, imidazole ring, thiazole ring, isothiazole ring, thiadiazole ring, pyrrolidine ring, piperidine ring, piperazine ring, indole ring, isoindole ring, benzofuran ring, iso-benzofuran ring, benzo-thiophene ring, benzo-pyrrole ring, benzopyrazole ring, benzimidazole ring, benzoxazole ring, benzo-dioxane ring, benzothiazole ring, purine ring, pyrazolo-pyrimidine ring, quinoline ring, isoquinoline ring, naphthyridine ring, quinazoline ring, benzodiazepine ring, carbazole ring, di-benzofuran ring, thiazolidine ring, morpholine ring, imidazo-thiazole ring, pyrrolo-pyridine ring, and dihydro-benzofuran ring and preferred are, for instance, pyridine ring, pyrimidine ring, pyridazine ring, pyrimidine ring, furan ring, and thiophene ring, with pyridine ring, pyrimidine ring, and thiophene ring being more preferred.

The term "aliphatic ring group" used herein denotes an aliphatic ring group consisting of single ring or two rings constituted by carbon atoms and specific examples thereof include cyclopropane ring, cyclobutene ring, cyclopentane ring, cyclohexane ring, cycloheptane ring, cyclo-octane ring, decalin ring, and norbornane ring, with cyclohexane ring being preferred.

The term "aryloxy group" used herein is an aryloxy group carrying an aryl group on its oxygen atom and specific examples of such aryl groups are those listed above in connection with the foregoing "aryl group". Specific examples thereof include phenoxy group, 1-naphthyloxy group, and 2-naphthyloxy group.

The term "arylamino group" used herein is an arylamino group substituted, on its nitrogen atom, with an aryl group, and specific examples of such aryl groups are those listed above in connection with the foregoing "aryl group". Specific examples thereof are phenylamino group and 1-naphthylamino group, and 2-naphthyl-amino group.

The term "aryl-vinyl group" used herein is a vinyl group which is substituted, on its 1- or 2-position, with an aryl group, and specific examples of such aryl groups are those listed above in connection with the foregoing "aryl group". Specific examples thereof include 1-phenylvinyl group and 2-phenylvinyl group.

The term "aryl-ethynyl group" used herein is an ethynyl group which is substituted with an aryl group at the 2-position thereof, and specific examples of such aryl groups are those listed above in connection with the foregoing "aryl group". Specific examples thereof include phenyl-ethynyl group or the like.

The term "heteroaryl group" used herein is a hetero-aromatic substituent comprising 1 to 3 rings each of which is a 5- to 7-membered ring constituted by carbon atoms, and nitrogen, oxygen and/or sulfur atoms and specific examples thereof include pyridyl group, pyridazinyl group, pyrimidinyl group, pyrazinyl group, pyrrolyl group, furanyl group, thienyl group, oxazolyl group, isoxazolyl group, pyrazolyl group, imidazolyl group, thiazolyl group, isothiazolyl group, thiadiazolyl group, indolyl group, iso-indolyl group, benzo-furyl group, isobenzo-furyl group, benzo-thienyl group, benzo-pyrazolyl group, benzimidazolyl group, benz-oxazolyl group, benzo-thiazolyl group, quinolyl group, isoquinolyl group, naphthyridinyl group, and quinazolyl group and preferred are, for instance, 2-pyridyl group, 3-pyridyl group, 4-pyridyl group, 1-pyrazolyl group and 2-pyrazinyl group.

The term "hetero-aryloxy group" used herein is a hetero-aryloxy group carrying, on its oxygen atom, a heteroaryl group, and examples of such heteroaryl groups include those listed above in connection with the foregoing "heteroaryl group". Specific examples thereof are 2-pyridyloxy group, 3-pyridyloxy group, 4-pyridyloxy group, and 2-pyrimidinyloxy group.

The term "heteroaryl-amino group" used herein is a heteroaryl-amino group carrying, on its nitrogen atom, a heteroaryl group, and examples of such heteroaryl groups include those listed above in connection with the foregoing "heteroaryl group". Specific examples thereof are 2-pyridylamino group, 3-pyridylamino group, 4-pyridylamino group, and 2-pyrimidinylamino group.

The term "which may have a substituent(s)" used herein means that a specific group may not have any substituent or may have at least one substituent. When such a specific group has a substituent, it may be substituted with at least one substituent such as those described above in connection with the general formula (I) or (IA) and when it has two or more substituents, they may be the same or different and the number of substituents and the positions thereof are not limited to any specific one. In this respect, the number of substituents is preferably 1, 2 or 3 and, in particular, it is preferably 1 or 2. More specifically, such substituents are, for instance, halogeno group, hydroxyl group, lower alkyl groups, mercapto groups, alkoxy groups each having 1 to 6 carbon atoms, alkylthio groups each having 1 to 6 carbon atoms, lower alkylsulfonyl groups, acyl groups each having 1 to 6 carbon atoms, acyloxy groups each having 1 to 6 carbon atoms, amino groups, alkylamino groups each having 1 to 6 carbon atoms, carboxyl group, alkoxycarbonyl groups each having 2 to 6 carbon atoms, benzyloxy-carbonyl group, carbamoyl groups, nitro group, cyano group, trifluoromethyl group, sulfonic acid group, sulfonamido group, sulfinamido group, aliphatic ring groups each having 1 to 6 carbon atoms, alkenyl groups each having 2 to 6 carbon atoms, alkynyl groups each having 2 to 6 carbon atoms, aryl groups each having 6 to 10 carbon atoms (such as phenyl group), or heterocyclic groups each having 3 to 9 carbon atoms, or a boronyl group.

In the present invention, the pyrazolo-pyrimidine compounds represented by the foregoing general formula (I) or pharmaceutically acceptable salts thereof are preferably those represented by the formula (I), in which $R^7$, $R^{22}$ and $R^{23}$ may be the same or different and preferably they each independently represent a hydrogen atom, a halogeno group, a hydroxyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, a sulfonamido group which may have a substituent(s), a sulfinamido group which may have a substituent(s), an aliphatic ring group which may have a substituent(s), an alkenyl group which may have a substituent(s), an alkynyl group which may have a substituent(s), a benzyloxy group which may have a substituent(s), an aryloxy group which may have a substituent(s), an arylvinyl group which may have a substituent(s), a hetero-aryloxy group which may have a substituent(s), an arylamino group which may have a substituent(s), a heteroaryl-amino group which may have a substituent(s), an aryl-ethynyl group which may have a substituent(s), an aryl group which may have a substituent(s), or a heterocyclic group which may have a substituent(s);

m is preferably 0, 1 or 2;

p is preferably 1;

U and V each independently represent a single bond, O, S, $NR^a$, $C(O)O$, $C(O)NR^a$, $OC(O)$, $NR^aC(O)$, $CR^{20}$=$CR^{21}$, or $C\equiv C$;

A is preferably an aryl group or a heterocyclic group;

$R^1$, $R^{18}$ and $R^{19}$ may be the same or different and preferably they each independently represent a hydrogen atom, a halogeno group, a hydroxyl group, an alkyl group which may have a substituent(s), an alkoxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, an aliphatic ring group which may have a substituent(s), an arylamino group which may have a substituent(s), a hetero-arylamino group which may have a substituent(s), an aryl group which may have a substituent(s), or a heterocyclic group which may have a substituent(s);

$R^2$ and $R^3$ may be the same or different and preferably they each independently represent a hydrogen atom, a halogeno group, a hydroxyl group, an alkyl group which may have a substituent(s), an alkoxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, an aliphatic ring group which may have a substituent(s), an arylamino group which may have a substituent(s), a hetero-arylamino group which may have a substituent(s), an aryl group which may have a substituent(s), or a heterocyclic group which may have a substituent(s);

$R^{20}$ and $R^{21}$ may be the same or different and preferably they each independently represent a hydrogen atom, a halogeno group, an alkyl group which may have a substituent(s), an alkoxy group which may have a substituent(s), a carboxyl group, an alkoxycarbonyl group which may have a substituent(s), a carbamoyl group which may have a substituent(s), a nitro group, a cyano group, a trifluoromethyl group, an aliphatic ring group which may have a substituent(s), an arylamino group which may have a substituent(s), a hetero-arylamino group which may have a substituent(s), an aryl group which may have a substituent(s), or a heterocyclic group which may have a substituent(s);

$R^4$ is preferably a group selected from the group consisting of a hydrogen atom, halogeno groups, aryl groups each of which may have a substituent(s), and heterocyclic groups which may have a substituent(s), with a hydrogen atom being particularly preferably used herein;

$R^{10}$ is preferably a hydrogen atom or a lower alkyl group which may have a substituent(s), with a hydrogen atom being particularly preferred.

$R^{14}$ is preferably $NR^cR^d$, an aliphatic ring group which may have a substituent(s) or a heterocyclic group which may have a substituent(s) and particularly preferably used herein is one represented by the following general formula:

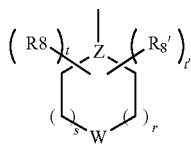
(III)

(In Formula (III), the substituents are the same as those specified above, and among them, preferably used herein are those represented by Formula (III), in which r is preferably 0, 1 or 2;
s is preferably 0, 1 or 2;

t is preferably 0, 1, 2, 3 or 4;
t is preferably 0, 1, 2, 3 or 4;
Z preferably represents N;
W preferably represents O, S, S(O), S(O$_2$), NR$^g$, C(O)NR$^g$, CR$^{20}$=CR$^{21}$, C≡C or NR$^g$C(O), with O being particularly preferred among others;

$R^8$ and $R^{8'}$ may be the same or different and preferably they each independently represent a hydrogen atom, a halogeno group, a hydroxyl group, an alkyl group which may have a substituent(s), an alkoxy group which may have a substituent(s), a trifluoromethyl group, an aryl group which may have a substituent(s), or a heterocyclic group which may have a substituent(s), and moreover, $R^8$ and $R^{8'}$ may be bonded together to form an aryl group which may have a substituent(s), a 3-o 7-membered aliphatic ring group which may have a substituent(s) or a 5- to 7-membered heterocyclic group which may have a substituent(s);

$R^{17}$ is preferably a hydrogen atom;

preferably, G represents a group selected from the group consisting of those represented by the following general formulas:

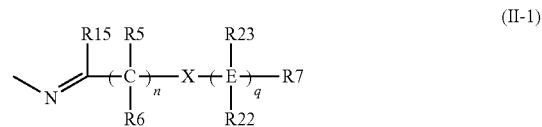
(II-1)

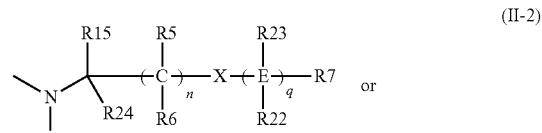
(II-2)

(II-3)

(in these general formulas, the substituents are the same as those specified above), with the group represented by the general formula (II-1) being particularly preferred;

furthermore, among those represented by the general formula (II-1), preferred are those of the general formula (II-1), in which n is preferably 0, 1 or 2, in particular, 0;
q is preferably 1;
$R^{15}$ and $R^{24}$ may be the same or different and preferably they each independently represent a hydrogen atom or an alkyl group which may have a substituent(s) and in particular, a hydrogen atom is preferable;
$R^5$ and $R^6$ may be the same or different and preferably they each independently represent a hydrogen atom, a halogeno group, a hydroxyl group, an alkyl group which may have a substituent(s), a mercapto group, an alkoxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, an aliphatic ring group which may have a substituent(s), an arylamino group which may have a substituent(s), a hetero-arylamino group which may have a substituent(s), an aryl group which may have a substituent(s), or a heterocyclic group which may have a substituent(s), with a hydrogen atom being particularly preferred;

X preferably represents a single bond, O, S, NR$^a$, C(O)O, C(O)NR$^a$, OC(O), NR$^a$C(O), CR$^{20}$=CR$^{21}$, or C≡C, with a single bond being particularly preferred;

E is preferably an aryl group or a heterocyclic group;

R$^7$, R$^{22}$ and R$^{23}$ may be the same or different and preferably, they each independently represent a hydrogen atom, a halogeno group, a hydroxyl group, a boronyl group, an alkyl group which may have a substituent(s), an alkoxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, an aliphatic ring group which may have a substituent(s), an arylamino group which may have a substituent(s), a hetero-arylamino group which may have a substituent(s), an aryl group which may have a substituent(s), or a heterocyclic group which may have a substituent(s).

In addition, among the foregoing groups, examples of the substituents represented by -(E(R$^{22}$)(R$^{23}$))$_q$—R$^7$ in the general formula (II-1) are m-tolyl group, 2-indolyl group, 3-indolyl group, 4-quinolinyl group, 2-benzofuranyl group, 3-benzofuranyl group, 5-indolyl group, 6-indolyl group, 5-benzofuranyl group, 3-vinylphenyl group, 3-acetylphenyl group, 2-benzothiophenyl group, and 3-benzothiophenyl group and these groups may further be substituted with one or two lower alkyl groups. Among them, preferred are m-tolyl group, 3-indolyl group, and 6-indolyl group are preferably used herein.

R$^a$ and R$^b$ may be the same or different and preferably, they each independently represent a hydrogen atom, an alkyl group which may have a substituent(s) or an acyl group which may have a substituent(s).

R$^{13}$ is preferably a hydrogen atom, an aryl group which may have a substituent(s), a heterocyclic group which may have a substituent(s) or an aliphatic ring group which may have a substituent(s).

R$^c$ and R$^d$ may be the same or different and preferably, they each independently represent an alkyl group which may have a substituent(s), an acyl group which may have a substituent(s), an alkoxycarbonyl group which may have a substituent(s), a carbamoyl group which may have a substituent(s), an aliphatic ring group which may have a substituent(s), or a heterocyclic group which may have a substituent(s).

R$^e$ is preferably a hydrogen atom, an alkyl group which may have a substituent(s), an acyl group which may have a substituent(s), an alkoxycarbonyl group which may have a substituent(s), or a carbamoyl group which may have a substituent(s).

In this respect, however, the substituents of the groups listed above are those selected from the group consisting of halogeno groups, hydroxyl group, lower alkyl groups, mercapto groups, alkoxy groups, alkylthio groups, alkylsulfonyl groups, acyl groups, acyloxy groups, amino groups, alkylamino groups, carboxyl group, alkoxycarbonyl groups, carbamoyl groups, nitro groups, cyano groups, trifluoromethyl group, aryl groups and heterocyclic groups.

Furthermore, the pyrazolo-pyrimidine compounds represented by the foregoing general formula (I) or pharmaceutically acceptable salts thereof preferably used in the present invention are those represented by Formula (I), in which R$^7$, R$^{22}$ and R$^{23}$ present in the general formula (I) may be the same or different and they each independently represent a hydrogen atom, a halogeno group, a hydroxyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, a sulfonamide group which may have a substituent(s), a sulfinamido group which may have a substituent(s), an aliphatic ring group which may have a substituent(s), an alkenyl group which may have a substituent(s), an alkynyl group which may have a substituent(s), a benzyloxy group which may have a substituent(s), an aryloxy group which may have a substituent(s), an arylvinyl group which may have a substituent(s), a hetero-aryloxy group which may have a substituent(s), an arylamino group which may have a substituent(s), a hetero-arylamino group which may have a substituent(s), an aryl-ethynyl group which may have a substituent(s), an aryl group which may have a substituent(s), or a heterocyclic group which may have a substituent(s).

Moreover, in the present invention, the pyrazolo-pyrimidine compounds represented by the foregoing general formula (I) or pharmaceutically acceptable salts thereof are preferably those represented by the general formula (I), which have the following combinations of the substituents thereof:

The substituent R$^{14}$ of the general formula (I) is one represented by the following general formula:

(III)

Further, in Formula (I), r=0, 1 or 2; s=0, 1 or 2; t=0, 1, 2, 3 or 4; t'=0, 1, 2, 3 or 4; and Z is N or CH;

W is O, S, S(O), S(O$_2$), NR$^g$, C(O)NR$^g$, CR$^{20}$=CR$^{21}$, C≡C or NR$^g$C(O);

R$^g$ is a hydrogen atom, a hydroxyl group, an alkyl group which may have a substituent(s), an alkoxy group which may have a substituent(s), an acyl group which may have a substituent(s), an alkoxycarbonyl group which may have a substituent(s), a carbamoyl group which may have a substituent(s), an aliphatic ring group which may have a substituent(s), an aryl group which may have a substituent(s), or a heterocyclic group which may have a substituent(s);

R$^8$ and R$^{8'}$ may be the same or different and preferably they each independently represent a hydrogen atom, a halogeno group, a hydroxyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, an aliphatic ring group which may have a substituent(s), an alkenyl group which may have a substituent(s), an alkynyl group which may have a substituent(s), a benzyloxy group which may have a substituent(s), an aryloxy group which may have a substituent(s), an arylvinyl group which may have a substituent(s), a heteroaryloxy group which may have a substituent(s), an arylamino group which may have a substituent(s), a hetero-arylamino group which may have a substituent(s), an aryl-ethynyl group which may have a substituent(s), an aryl group which may have a substituent(s), or a heterocyclic group which may have a substituent(s); or alternatively $R^8$ and $R^{8'}$ may be bonded together to form an aryl group which may have a substituent(s), a 3- to 7-membered aliphatic ring ring which may have a substituent(s) or a 5- to 7-membered heterocyclic ring which may have a substituent(s);

G is a group represented by the general formula (II-1).

In addition, in the present invention, the pyrazolo-pyrimidine compounds represented by the foregoing general formula (I) or pharmaceutically acceptable salts thereof are more preferably those represented by the general formula (I), which have the following combinations of the substituents thereof:

m is 0, 1 or 2; n is 0, 1 or 2;
$R^{10}$ is a hydrogen atom;
U and V each independently represent a single bond, O, S, $NR^a$, $CR^{20}$=$CR^{21}$, C≡C, $C(O)NR^a$, or $NR^aC(O)$;
X represents a single bond, O, S, $NR^a$, C(O)O, $C(O)NR^a$, OC(O), $NR^aC(O)$, $CR^{20}$=$CR^{21}$, or C≡C;
Z is N; r is 1; s is 1; and
W is O, S, S(O), $S(O_2)$ or $NR^g$.

Furthermore, in the present invention, the pyrazolo-pyrimidine compounds represented by the foregoing general formula (I) or pharmaceutically acceptable salts thereof are further preferably those represented by the general formula (I), which have the following combinations of the substituents thereof:

G is a group represented by the foregoing general formula (II-1); and in the same formula, n=0; q=1; and X represents a single bond.

In addition, in the present invention, the pyrazolo-pyrimidine compounds represented by the foregoing general formula (I) and set forth in claim 1 or pharmaceutically acceptable salts thereof are further preferably those represented by the general formula (I), which have the following combinations of the substituents thereof:

$R^{14}$ is a group represented by the foregoing general formula (III); and in the same formula, Z is N; W is O; t=0; and t'=0.

Moreover, in the present invention, the pyrazolo-pyrimidine compounds represented by the foregoing general formula (I) and set forth in claim 1 or pharmaceutically acceptable salts thereof are further preferably those represented by the general formula (I), which have the following combinations of the substituents thereof:

$R^4$ is a hydrogen atom; p=1; and
G is a group represented by the foregoing general formula (II-1); and in the same formula, n=0; q=1; and X represents a single bond; and
$R^{14}$ is a group represented by the foregoing general formula (III); and in the same formula, Z is N; W is O; t=0; and t'=0.

In addition, among them, especially preferred are those in which the substituent represented by -$(E(R^{22})(R^{23}))_q$—$R^7$ appearing in the general formula (II-1) represents an m-tolyl group or a 3-indolyl group.

Moreover, in the present invention, the pyrazolo-pyrimidine compounds represented by the foregoing general formula (I) and set forth in claim 1 or pharmaceutically acceptable salts thereof are further preferably those represented by the general formula (I), which have the following combinations of the substituents thereof:

$R^4$ is a hydrogen atom; p=1; m=0; U is a single bond; V is a single bond; G is a group represented by the foregoing general formula (II-1); and in the same formula, n=0; q=1; and X is a single bond; and $R^{14}$ is a group represented by the general formula (III); and in the same formula, Z is N; W is O; t=0; and t'=0.

Furthermore, among them, especially preferred are those in which the substituent represented by -$(E(R^{22})(R^{23}))_q$—$R^7$ appearing in the general formula (II-1) represents a 6-indolyl group, an m-tolyl group or a 3-indolyl group.

In addition, in the present invention, the pyrazolo-pyrimidine compounds represented by the foregoing general formula (I) or pharmaceutically acceptable salts thereof are likewise preferably those represented by the general formula (I), which have the following combinations of the substituents thereof:

$R^{10}$ is a hydrogen atom; m=0, 1 or 2; n=0, 1 or 2; and
U and V each independently represent a single bond, O, S, S(O), $S(O_2)$, C(O), C(O)O or OC(O).

Moreover, in the present invention, the pyrazolo-pyrimidine compounds represented by the foregoing general formula (I) or pharmaceutically acceptable salts thereof are further preferably those represented by the general formula (I), which have the following combinations of the substituents thereof:

G is a group represented by the foregoing general formula (II-1) or (II-2); and X is a single bond, $CR^{20}$=$CR^{21}$, or C≡C.

Furthermore, in the present invention, the pyrazolo-pyrimidine compounds represented by the foregoing general formula (I) or pharmaceutically acceptable salts thereof are further preferably those represented by the general formula (I), which have the following combinations of the substituents thereof:

The substituent $R^{14}$ of the compound of Formula (I) is $NR^cR^d$ or a group represented by the following general formula (III):

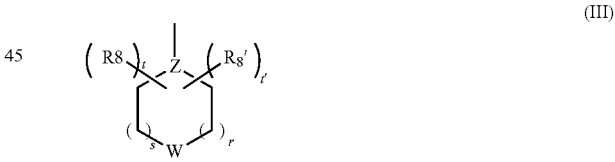

(III)

wherein r=0, 1 or 2; s=0, 1 or 2; t=0, 1, 2, 3 or 4; t'=0, 1, 2, 3 or 4;
Z is N or CH;
W is O, S, S(O), $S(O_2)$, $NR^g$, $CR^g$, $C(O)NR^g$, $CR^{20}$=$CR^{21}$, C≡C or $NR^gC(O)$;
$R^g$ is a hydrogen atom, a hydroxyl group, an alkyl group which may have a substituent(s), an alkoxy group which may have a substituent(s), an acyl group which may have a substituent(s), an alkoxycarbonyl group which may have a substituent(s), a carbamoyl group which may have a substituent(s), an aliphatic ring group which may have a substituent(s), an aryl group which may have a substituent(s), or a heterocyclic group which may have a substituent(s); and
$R^8$ and $R^{8'}$ may be the same or different and preferably they each independently represent a hydrogen atom, a halogeno group, a hydroxyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, an aliphatic ring group which may have a substituent(s), an alkenyl group which may have a substituent(s), an alkynyl group which may have a substituent(s), a benzyloxy group which may have a substituent(s), an aryloxy group which may have a substituent(s), an arylvinyl group which may have a substituent(s), a heteroaryloxy group which may have a substituent(s), an arylamino group which may have a substituent(s), a hetero-arylamino group which may have a substituent(s), an aryl-ethynyl group which may have a substituent(s), an aryl group which may have a substituent(s), or a heterocyclic group which may have a substituent(s); or alternatively $R^8$ and $R^{8'}$ may be bonded together to form an aryl group which may have a substituent(s), a 3- to 7-membered aliphatic ring ring which may have a substituent(s) or a 5- to 7-membered heterocyclic ring which may have a substituent(s).

In addition, in the present invention, the pyrazolo-pyrimidine compounds represented by the foregoing general formula (I) or pharmaceutically acceptable salts thereof are further preferably those represented by the general formula (I), which have the following combinations of the substituents thereof:

The substituent $R^{14}$ of the compound of the general formula (I) is $NR^cR^d$ or a group represented by the foregoing general formula (III); and in the same formula, Z is N; t=0; and t'=0.

Moreover, in the present invention, the pyrazolo-pyrimidine compounds represented by the foregoing general formula (I) are further preferably those prepared in Examples described later.

In the present invention, the compounds represented by the foregoing general formula (IA) are preferably those of the general formula (IA) carrying the substituents specified below:

The alkyl group is preferably one having 1 to 3 carbon atoms and, in particular, a methyl group or an ethyl group is preferable.

The alkoxy group is preferably one having 1 to 3 carbon atoms and, in particular, a methoxy group or an ethoxy group is preferable.

The mono- or di-alkylamino group is preferably a monoalkylamino group having 1 to 3 carbon atoms or a dialkylamino group having 2 to 6 carbon atoms and, in particular, a methylamino group, an ethylamino group, a dimethylamino group, or a diethylamino group is preferable.

When the alkyl group, alkoxy group, mono-alkylamino group or dialkylamino group has a substituent, the substituent is preferably an alkoxy group having 1 to 3 carbon atoms, a fluorine atom, a chlorine atom or a cyano group, and preferred also include a phenyl group.

When the carbamoyl group has a substituent, the substituent is preferably an alkyl group having 1 to 3 carbon atoms or a pyridyl group.

The aryl group is preferably a phenyl group or a naphthyl group, with a phenyl group being particularly preferred.

The heteroaryl group is preferably a 5- or 6-membered monocyclic heteroaryl group or a fused bicyclic heteroaryl group, wherein the 5- or 6-membered monocyclic heteroaryl group is particularly preferably a pyridyl group or a thienyl group, or alternatively a pyrazinyl group, a pyridazinyl group, an isoxazolyl group or a pyrimidinyl group. The fused bicyclic heteroaryl group is preferably a bicyclic group formed through the fusion of a 5- or 6-membered monocyclic ring with a 6-membered monocyclic ring and, in particular, an indolyl group is preferred. Moreover, preferably used herein also include, for instance, a benzo-furanyl group, a benzo-thiophenyl group and a pyrazolo[1,5-a]pyrimidinyl group.

When the aryl and heteroaryl groups each have a substituent, preferred examples of such substituents include alkyl groups each having 1 to 3 carbon atoms, alkoxy groups each having 1 to 3 carbon atoms, a fluorine atom, a chlorine atom, a bromine atom and amino groups each of which may have a substituent(s), provided that the substituents may likewise be bonded together to form a ring and an example of such substituent is an ethylene-dioxy group.

The heterocyclic group is preferably a piperidinyl group or a morpholinyl group.

When the heterocyclic group is a substituted one, preferred examples of such substituents are benzyloxy-carbonyl group, formyl group, and alkyl-carbonyl groups each having 1 to 3 carbon atoms.

The cyclic amino group is one formed from $NR^{48}R^{49}$ through the linkage of $R^{48}$ and $R^{49}$, wherein the ring may be formed through O, S or NH. The cyclic amino group is preferably a 5- or 6-membered cyclic amino group and specific examples thereof include 4-morpholinyl group, 1-piperidinyl group, 1-piperazinyl group and 1-pyrrolidinyl group, with 4-morpholinyl group being particularly preferred. When the cyclic amino group is a substituted one, the substituents thereof may be bonded together to form a ring and in this case, it is also preferred that the ring is a member selected from the group consisting of those represented by the following general formula:

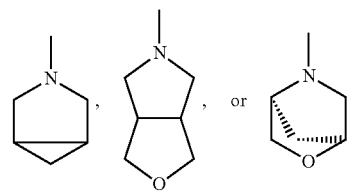

In particular, $m^4$ is preferably O.
In particular, $n^4$ is preferably O.
$R^{41}$ is preferably a hydrogen atom, a phenyl group which may have a substituent(s), or a 5- or 6-membered monocyclic heteroaryl group which may have a substituent(s) and, in particular, preferred are phenyl groups, pyridyl groups, thienyl groups, and pyrazinyl groups, which may have a substituent(s). Alternatively, also preferably used herein include piperidine rings, piperazine rings, and morpholine rings.

$R^{44}$ is preferably a hydrogen atom, a phenyl group or a bromine atom, with a hydrogen atom being particularly preferred.

$R^{42}$, $R^{43}$, $R^{45}$ and $R^{46}$ each preferably represent a hydrogen atom.

$R^{47}$ is preferably a phenyl group, a 5- or 6-membered monocyclic heteroaryl group, or a fused bicyclic heteroaryl group, which may have a substituent(s) and particularly preferably a phenyl group or a 3-indolyl group, which may be substituted with an alkyl group each having 1 to 3 carbon atoms. Also preferred are 6-indolyl group and phenyl groups each substituted with an alkylene group having 2 to 3 carbon atoms.

$R^{48}$ and $R^{49}$ each preferably represent an alkyl group having 1 to 3 carbon atoms and $NR^{48}R^{49}$ is preferably a 5- or 6-membered cyclic amino group, with 4-morpholinyl group being particularly preferred.

As the pyrazolo-pyrimidine compound represented by the general formula (IA), preferred are the compounds represented by Formula (IA) whose substituents are those specified below:

$m^4$ is O;

$n^4$ is O;

$R^{41}$ and $R^{44}$ each independently represent a hydrogen atom, a halogeno group, or a member selected from the group consisting of phenyl groups and 5- or 6-membered monocyclic heteroaryl groups, which may be substituted with a substituent selected from the group consisting of halogeno groups, alkyl groups having 1 to 3 carbon atoms, alkoxy groups having 1 to 3 carbon atoms, mono- or di-alkylamino groups each having 1 to 6 carbon atoms or a group represented by the following formula:

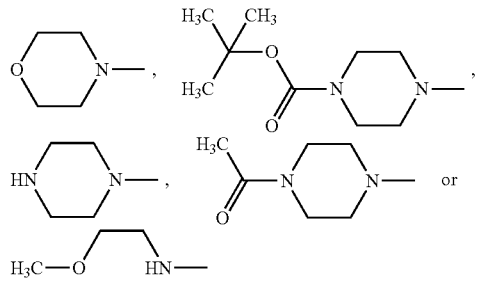

$R^{47}$ represents a group selected from the group consisting of phenyl groups, 5- or 6-membered monocyclic heteroaryl groups and fused bicyclic heteroaryl groups, each of which may be substituted with a substituent selected from the group consisting of halogeno groups, alkyl groups each having 1 to 3 carbon atoms and alkoxy groups each having 1 to 3 carbon atoms; and $NR^{48}R^{49}$ is a 5- or 6-membered cyclic amino group.

Moreover, preferred likewise include the compounds represented by Formula (IA) whose substituents are those specified below:

$R^{41}$ represents a halogeno group, an alkyl group having 1 to 3 carbon atoms, an alkoxy group having 1 to 3 carbon atoms, a mono- or di-alkylamino group having 1 to 6 carbon atoms, or a member selected from the group consisting of phenyl groups and 5- or 6-membered heteroaryl groups, each of which may be substituted with a substituent selected from the group consisting of those represented by the following formulas:

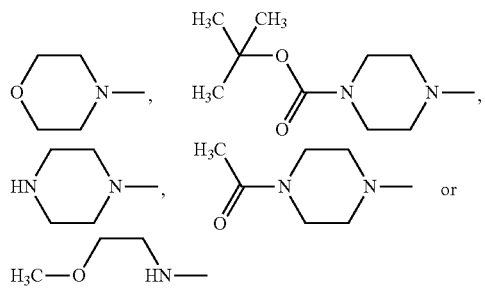

$R^{44}$ represents a hydrogen atom;

$NR^{48}R^{49}$ is a 4-morpholinyl group.

Furthermore, in the present invention, the pyrazolo-pyrimidine compounds represented by the foregoing general formula (I) or (IA), or pharmaceutically acceptable salts thereof are preferably those each including, in the molecule, a structure represented by the following formula:

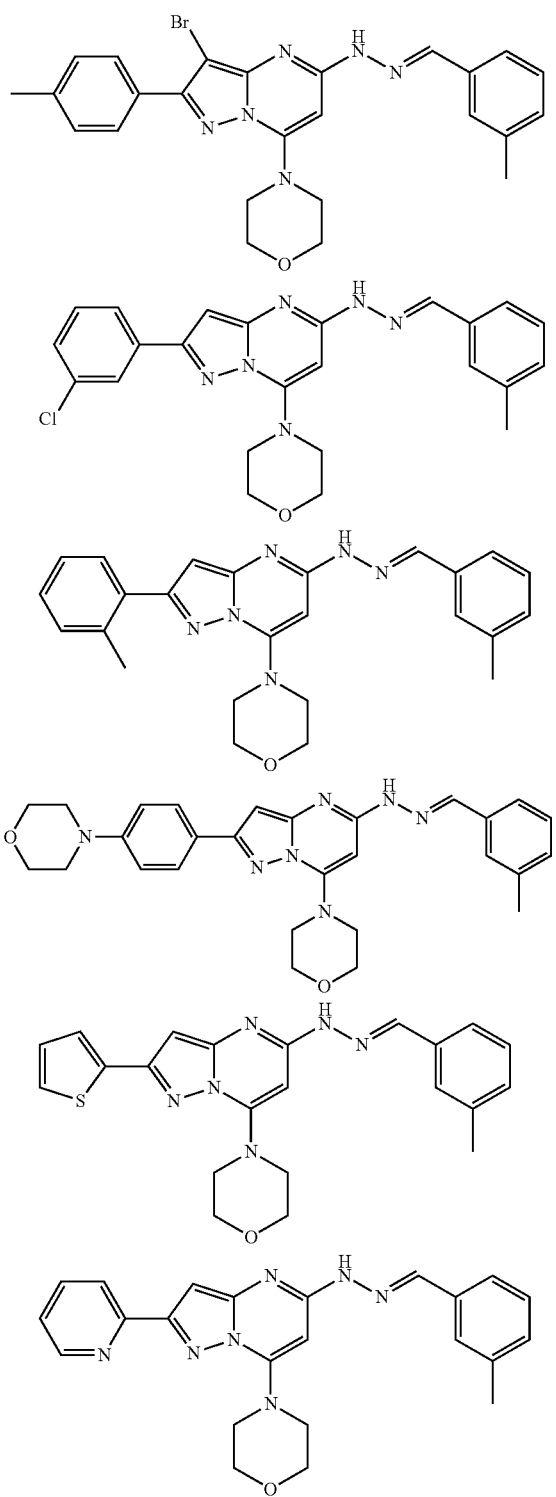

-continued

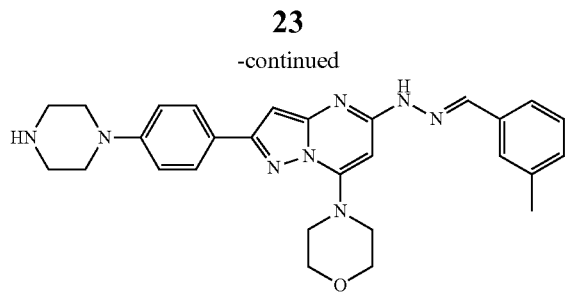

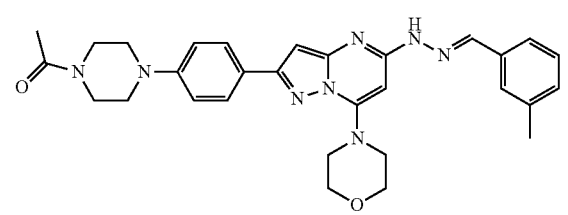

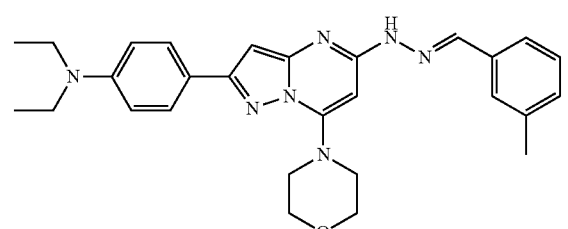

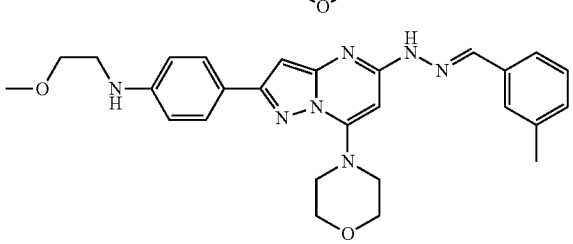

In addition, in the present invention, also preferred as the pyrazolo-pyrimidine compounds represented by the foregoing general formula (I) or (IA) include Compound Nos. 36, 38, 82, 83, 84, 85, 86, 90 and 93 and further Compound Nos. 117, 137, 138 and 142.

The method for the preparation of the compound (I) will be described below, while taking the compound (IA) as a typical example of the compound (I) according to the present invention. The compound (IA) of the present invention can be synthesized according to, for instance, the following method:

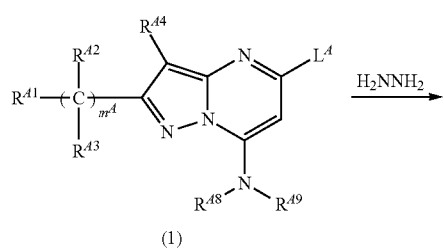

-continued

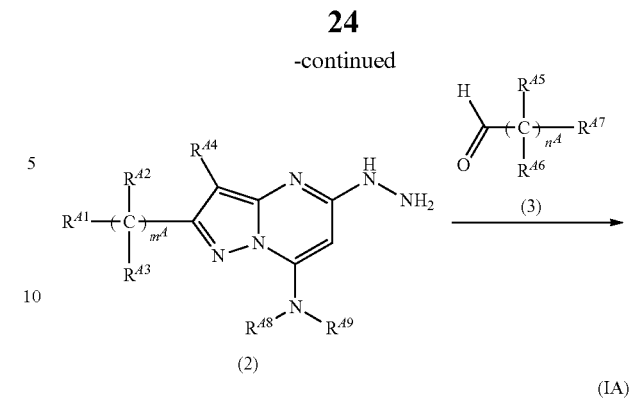

The foregoing compound (1) wherein $L^A$ represents a leaving group is reacted with hydrazine to form a compound (2) whose leaving group, $L^A$, is substituted with a hydrazinyl group, and subsequently an aldehyde (3) and the substituted hydrazine (2) can be subjected to a condensation reaction to thus form a compound (IA).

In this respect, the leaving group, $L^A$, may be, for instance, a chlorine atom. When the leaving group, $L^A$, is a chlorine atom, the foregoing substitution reaction with hydrazine is carried out, while heating at a temperature ranging from 50 to 250° C. for a reaction system comprising a mixture of the compound (1), a lower alcohol such as ethanol and hydrazine monohydrate. In this respect, the reaction system can be heated through the use of a water bath, a hot water bath or the application of microwaves.

In addition, the condensation reaction of the foregoing aldehyde with the substituted hydrazine can be carried out by combining the compound (2), the compound (3), a lower alcohol such as ethanol and, if desired, a catalytic amount of an acid such as acetic acid and then stirring the reaction system at room temperature.

The compound (1) can be prepared by, for instance, reacting the following compound (4) wherein $L^{A2}$ represents a leaving group with an amine (5):

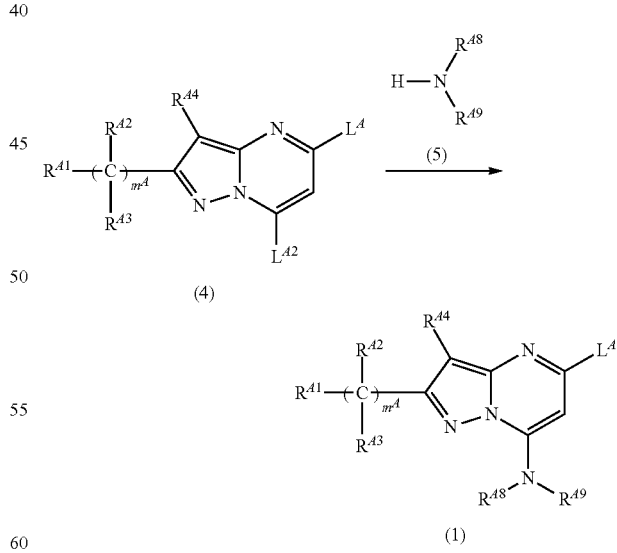

The leaving groups $L^A$ and $L^{A2}$ may be the same or different. When the leaving groups $L^A$ and $L^{A2}$ are both chlorine atoms, the substitution reaction with the foregoing amine can be carried out by stirring a mixture comprising the compound (4), the amine (5) and an ether solvent such as 1,4-dioxane at room temperature.

A compound (4-2) represented by the foregoing formula (4) in which $L^A$ and $L^{A2}$ are both chloride atoms can be prepared by reacting the following compound (6) with a substituted malonic acid diester in the presence of an appropriate base (such as sodium ethoxide or sodium methoxide) to give a compound (7) and further subjecting the resulting compound (7) to a reaction with a chlorination agent (such as phosphorus oxychloride).

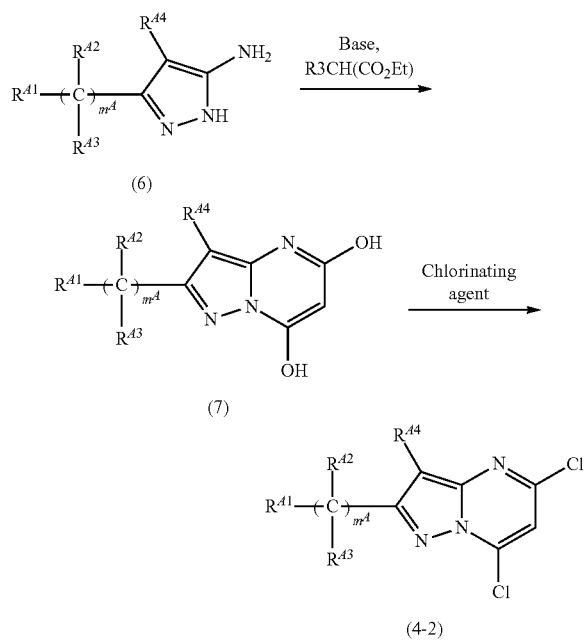

For instance, the compound (6-2) represented by the foregoing general formula (6) in which $R^{A4}$ is a hydrogen atom (H) can be synthesized by reacting the following compound (8) with hydrazine.

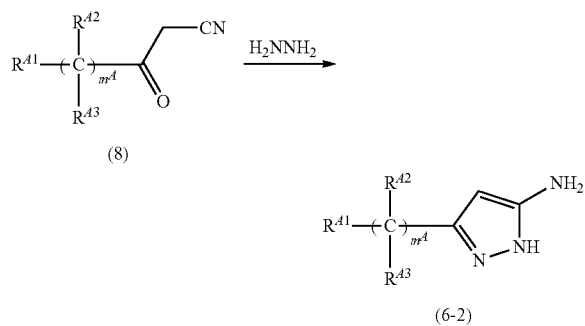

In the method for the preparation of the compound (IA) described above, the symbols such as $R^{A1}$ appearing in any synthetic intermediate are the same as those specified above in connection with the general formula (IA), provided that the synthetic method can be modified in such a manner that a protected group is used instead of a specific group and a deblocking reaction is added to the method at any appropriate stage thereof, or that a different group is used instead of a specific group and a substitute-transformation step is added to the method at any appropriate stage thereof.

Moreover, various modification, variation and/or addition, which are easy for one of ordinary skill in the art, can be made, if necessary, on the foregoing synthetic method and the procedures disclosed and used in the following Examples to thus form the compounds (1) according to the present invention.

The pyrazolo-pyrimidine compounds represented by the foregoing general formula (I) or (IA) or the pharmaceutically acceptable salts thereof can be purified by the use of the usual means such as the ion-exchange chromatography, the reversed phase high performance liquid chromatography, the affinity chromatography and the recrystallization technique. Such chemical synthesis method and the subsequent purification techniques are well-known in this art.

The pyrazolo-pyrimidine compound represented by the foregoing general formula (I) or (IA) may be in the form of a pharmaceutically acceptable salt thereof. More specifically, the term "pharmaceutically acceptable salt" herein used means, for the sufficiently acidic compounds of the present invention, an ammonium salt, an alkali metal salt (examples thereof include sodium and potassium salts and these salts are preferred in the present invention), an alkaline earth metal salt (examples thereof include calcium and magnesium salts and they are preferably used in the invention), and salts with organic bases such as dicyclo-hexylamine salts, benzathine salts, N-methyl-D-glucan salts, hydramine salts, and salts with amino acids such as alginine or lysine. In addition, examples of acid-addition salts of the sufficiently basic compounds according to the present invention include acid-addition salts with inorganic acids such as hydrochloric acid, sulfuric acid, nitric acid, and phosphoric acid; and acid-addition salts with organic acids such as acetic acid, lactic acid, citric acid, tartaric acid, maleic acid, fumaric acid, and monomethyl sulfuric acid. Moreover, these salts may optionally be water-containing products or hydrates.

Moreover, it would be construed that the present invention likewise embraces all of the isomers of the foregoing compounds of the present invention such as the optical isomers and the geometrical isomers, the hydrates, the solvates and the crystalline forms thereof.

The pyrazolo-pyrimidine compound and the pharmaceutically acceptable salt thereof according to the present invention can selectively inhibit the production of IL-12/IL-23, while they never significantly inhibit the production of TNF-α from the activated macrophage. More specifically, they can significantly inhibit IL-12/IL-23 without significantly inhibiting the production of TNF-α. Therefore, they can be used as agents for preventing or treating the IL-12/IL-23-excess production-related diseases with high selectivity and the use thereof is never accompanied by any danger of causing any side effect such as those observed for the compound which possesses a TNF-α production-inhibitory action.

Moreover, the IL-12/IL-23 production-inhibitory activity of the preferred pyrazolo-pyrimidine compounds or the pharmaceutically acceptable salts thereof according to the present invention are not considerably reduced even in the presence of human serum albumin (HAS) and α1-acidic glycoprotein (α1-AGP), which are proteins present in the human plasma. In general, in some cases, a compound as a candidate for a medicine shows an activity in vitro, but never shows any activity in vivo. The reason of this would be because the effect of the compound in vivo is reduced through the linkage thereof with the human serum albumin (HAS) and/or the α1-acidic glycoprotein (α1-AGP), which are proteins present in the human plasma. Contrary to this, the preferred pyrazolo-pyrimidine compounds or the pharmaceutically acceptable salts thereof according to the present invention can hold their excellent IL-12/IL-23 production-inhibitory activity even in the presence of HAS or α1-AGP. Accordingly, the pyrazolopyrimidine compounds or the pharmaceutically acceptable salts thereof according to the present invention can show quite excellent medical effect even when it is administered to human beings in the clinical practice.

In addition, the IL-12/IL-23 production-inhibitory activity of the preferred pyrazolo-pyrimidine compounds or the pharmaceutically acceptable salts thereof according to the present invention is not considerably reduced even in the whole blood and accordingly, they can show excellent medicinal effect or efficacy even when it is administered to human beings in the clinical practice.

The pharmaceutical composition or the agent for preventing or treating IL-12/IL-23-excess production-related diseases according to the present invention may comprise, as the pyrazolo-pyrimidine compounds or the pharmaceutically acceptable salts thereof according to the present invention, any pyrazolo-pyrimidine compounds or any pharmaceutically acceptable salts thereof, which are included in the group consisting of the pyrazolo-pyrimidine compounds represented by the foregoing general formula (I) or (IA) or the pharmaceutically acceptable salts thereof, alone or in any combination of at least two of them. Moreover, these compounds can likewise be used in combination with any pharmaceutically acceptable, physiologically acceptable and experimentally acceptable solid or liquid carrier, additives or the like.

Examples of the foregoing carriers include glucose, lactose, sucrose, starches, mannitol, dextrin, fatty acid glycerides, polyethylene glycol, hydroxyethyl starch, ethylene glycol, polyoxyethylene sorbitan fatty acid esters, gelatin, albumin, amino acids, water and physiological saline. In addition, if necessary, the commonly used additives such as a stabilizer, a wetting agent, an emulsifying agent, a binder and isotonicity can be incorporated into the pharmaceutical composition or the agent for preventing or treating IL-12/IL-23-excess production-related diseases according to the present invention, as the occasion may demand.

The foregoing additives are not restricted to particular ones inasmuch as they are commonly used depending on any particular purpose and specific examples thereof are perfumes, saccharides, sweetening agents, edible fibers, vitamins, amino acids such as sodium glutamate (MSG), nucleic acids such as inosine monophosphate (IMP), inorganic salts such as sodium chloride and water.

The pharmaceutical composition or the agent for preventing or treating IL-12/IL-23-excess production-related diseases according to the present invention can be used in any form such as dry powder, a paste and a solution without any restriction in the physical properties thereof.

The pharmaceutical composition or the agent for preventing or treating IL-12/IL-23-excess production-related diseases according to the present invention is not restricted in its administration methods and it can be administered through any invasive or non-invasive method such as the oral administration and the administration through injection and it may likewise be administered as a suppository or administered through the transdermal route.

The effective component can be administered as a commonly used pharmaceutical preparation together with a solid or liquid medicinal carrier which is adapted for the administration method such as the oral administration or the administration through injection. Examples of such pharmaceutical preparations are solid preparations such as tablets, granules, powders and capsules; liquid preparations such as solutions, suspensions and emulsions; and freeze-dried preparations. These preparations can be prepared according to the usual techniques for the preparation of the same. Furthermore, any pharmaceutically acceptable, physiologically acceptable solid or liquid carriers, additives or the like can be incorporated into the pharmaceutical composition or the agent for preventing or treating IL-12/IL-23-excess production-related diseases according to the present invention.

The amount, to be used, of the pharmaceutical composition or the agent for preventing or treating IL-12/IL-23-excess production-related diseases according to the present invention may appropriately be adjusted depending on each specific purpose. For instance, when orally administering the same to a subject, the pyrazolo-pyrimidine compound represented by the foregoing general formula (I) or (IA) or the pharmaceutically acceptable salt thereof is used in a dose preferably ranging from 0.0001 mg to 5 g per unit body weight (kg), more preferably 0.001 mg to 1 g per unit body weight (kg), and further preferably 0.01 mg to 10 mg per unit body weight (kg) as expressed in terms of the total amount of the effective component. The number of the administration thereof per day is not particularly restricted and it ranges from one to several times per day.

The content of the pyrazolo-pyrimidine compound represented by the general formula (I) or (IA) or the pharmaceutically acceptable salt thereof to be incorporated into the pharmaceutical composition or the agent for preventing or treating IL-12/IL-23-excess production-related diseases according to the present invention is not particularly restricted inasmuch as it falls within the range specified above and it preferably ranges from 0.000001 to 99.9999% by mass, more preferably 0.00001 to 99.999% by mass and particularly preferably 0.0001 to 99.99% by mass as expressed in terms of the dry weight of the composition or the agent.

The pharmaceutical composition or the agent for preventing or treating IL-12/IL-23-excess production-related diseases according to the present invention may further comprise one or at least two known substances which can show desired clinical effects.

The pharmaceutical composition or the agent for preventing or treating IL-12/IL-23-excess production-related diseases according to the present invention can be used for the prevention or treatment of any disease or condition on which the composition or the agent clinically shows desired preventive or therapeutic effects including the IL-12/IL-23-excess production-related diseases. Specific examples thereof include, but are not limited to, IL-12/IL-23-excess production-related diseases such as multiple sclerosis, systemic sclerosis, sepsis, myasthenia gravis, autoimmune neurosis, Guillain-Barre syndrome, autoimmune uveitis, autoimmune hemolytic anemia, pernicious anemia, autoimmune thrombocytopenia, temporal arteritis, anti-phospholipid syndrome, vasculitis, Wegener granulomatosis, Behcet disease, psoriasis, psoriatic arthritis, herpetic dermatitis, pemphigus vulgaris, leukoma, Crohn's disease, ulcerative colitis, interstitial pulmonary fibrosis, myelofibrosis, hepatic fibrosis, myocarditis, autoimmune thyroiditis (such as Grebs' disease and Hashimoto's disease), primary biliary cirrhosis, autoimmune hepatitis, immune-mediated diabetes mellitus, autoimmune ovaritis and orchitis, autoimmune adrenalitis, articular rheumatism, juvenile articular rheumatism, systemic lupus erythematosus, scleroderma, multiple myositis, dermatomyositis, spondyloarthropathy, rigid spondylitis, Sjogren's syndrome, and graft-versus-host disease.

The composition or the agent according to the present invention can more preferably be used for the prevention or treatment of the foregoing diseases and conditions, for instance, IL-12/IL-23-excess production-related diseases such as articular rheumatism, sepsis, Crohn's disease, ulcerative colitis, multiple sclerosis, psoriasis, and insulin-dependent diabetes mellitus. On the other hand, the composition or the agent according to the present invention can preferably be used for the prevention or treatment of the foregoing diseases and conditions, for instance, articular rheumatism, sepsis, Crohn's disease, ulcerative colitis, multiple sclerosis, psoriasis, and psoriatic arthritis.

EXAMPLE

The present invention will hereunder be described in more detail with reference to the following Examples, but these specific Examples never limit the scope of the present invention at all.

In this specification, the term "usual method" means the currently used means as chemical operations including separating, drying, filtration and concentration operations.

The procedures for preparing typical compounds of the present invention will further be described below with reference to the following Examples, but the compounds of the present invention are not restricted to those prepared in the following Examples at all.

In this connection, the term "room temperature" used in the following Reference Examples, Examples and Test Examples means the temperature ranging from 1 to 30° C. and the term "%" means "% by mass", unless otherwise specified.

In the following Reference Examples and Examples, the determination of $^1$H-NMR and the reaction which makes use of microwaves were carried out using the following apparatuses:

$^1$H-NMR: DPX300 (300 MHz) available from Bruker Company;

Microwave: Initiator 60EXP available from Biotage Company.

Example 1

Synthesis of N-(3-methyl-benzylidene)-N'-(2-phenyl-7-morpholin-4-yl-pyrazolo[1,5-a]pyrimidin-5-yl)-hydrazine (Compound 1)

(Step 1); Synthesis of 5,7-dichloro-2-phenyl-pyrazolo[1,5-a]pyrimidine

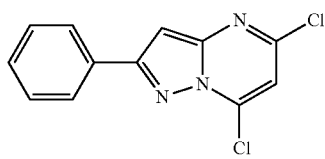

There was dissolved, in acetonitrile (20 mL), 3-amino-5-phenyl-pyrazole (1.00 g, 6.28 mM) in an argon gas atmosphere, malonyl chloride (672 µL, 6.91 mM) was added to the resulting solution with ice-cooling and the mixture was stirred for 2 hours. To this reaction liquid, there was further added malonyl chloride (210 µL, 2.15 mM) followed by stirring the mixture for one hour. This reaction liquid was diluted with water and then extracted with ethyl acetate. The resulting extracts were combined, dried over anhydrous sodium sulfate and the solvent was then distilled off. After the addition of phosphoryl chloride (10 mL) to the resulting solid with ice-cooling, the resulting suspension was stirred for 4 hours, while refluxing the same with heating. The phosphoryl chloride was distilled off from the reaction liquid, the residue thus obtained was diluted with water and then extracted with methylene chloride. The extracts thus obtained were combined, dried over anhydrous sodium sulfate, the solvent was distilled off and then the resulting residue was purified by the silica gel column chromatography (ethyl acetate/hexane=1: 10) to thus give the title compound (168 mg, yield: 10%).

$^1$H-NMR (300 MHz, CDCl$_3$): δ 6.95 (s, 1H), 7.00 (s, 1H), 7.43-7.52 (m, 3H), 8.00-8.03 (m, 2H); MS (ESI) m/z 264 (M+H)$^+$.

(Step 2): 5-Chloro-7-morpholin-4-yl-2-phenyl-pyrazolo[1,5-a]pyrimidine

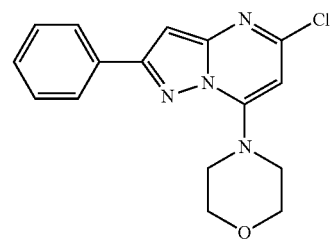

There was dissolved, in 1,4-dioxane (4 mL), 5,7-dichloro-2-phenyl-pyrazolo-[1,5-a]pyrimidine (168 mg, 0.637 mM), morpholine (111 µL, 1.27 mM) was added to the resulting solution and the mixture was stirred at room temperature for 15 minutes. The solvent was distilled off from the reaction mixture, the resulting residue was diluted with water and then extracted with methylene chloride. The extracts thus obtained were combined, dried over anhydrous sodium sulfate, the solvent was distilled off, and the resulting solid was washed with methanol to thus obtain the title compound (200 mg, yield: 100%).

$^1$H-NMR (300 MHz, CDCl$_3$): δ 3.85-3.88 (m, 4H), 3.98-4.01 (m, 4H), 6.07 (s, 1H), 6.79 (s, 1H), 7.40-7.48 (m, 3H), 7.93-7.96 (m, 2H); MS (ESI) m/z 315 (M+H)$^+$.

(Step 3): N-(3-Methyl-benzylidene)-N'-(2-phenyl-7-morpholin-4-yl-pyrazolo[1,5-a]-pyrimidin-5-yl)-hydrazine (Compound 1)

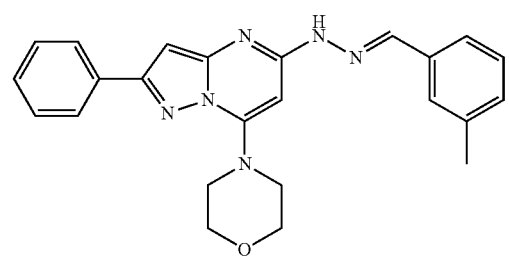

There was suspended, in ethanol (5 mL), 5-chloro-7-morpholin-4-yl-2-phenyl-pyrazolo[1,5-a]pyrimidine (144 mg, 0.457 mM), and then hydrazine monohydrate (222 µL, 4.57 mM) was added to the suspension. This suspension was stirred at 150° C. for 10 minutes under the irradiation with microwaves and it was further stirred at 120° C. for 10 minutes likewise under the irradiation with microwaves. This reaction liquid was diluted with water and then extracted with ethyl acetate. The extracts thus obtained were combined, dried over anhydrous sodium sulfate and then the solvent was distilled off.

The resulting residue was suspended in ethanol (2 mL), followed by the addition of acetic acid (2.0 μL, 0.035 mM) and 3-methyl-benzaldehyde (53.6 μL, 0.457 mM) and the stirring of the resulting mixture at room temperature for 30 minutes. This reaction mixture was filtered and then the resulting solid was purified by the silica gel column (High Flush Column Amino, available from YAMAZEN Co., Ltd.) chromatography (methylene chloride) to thus give the title compound (67.3 mg, overall yield for these two steps: 36%).

$^1$H-NMR (300 MHz, DMSO): δ 2.34 (s, 3H), 3.72-3.74 (m, 4H), 3.86-3.89 (m, 4H), 6.30 (s, 1H), 6.56 (s, 1H), 7.17 (m, 1H), 7.28-7.53 (m, 6H), 7.94 (d, 2H, J=7.3 Hz), 8.03 (s, 1H), 11.18 (s, 1H); MS (ESI) m/z 423 (M+H)$^+$.

Example 2

Synthesis of N-(1H-indol-3-yl-methylidene)-N'-(7-morpholin-4-yl-2-phenyl-pyrazolo[1,5-a]pyrimidin-5-yl)-hydrazine (Compound 2)

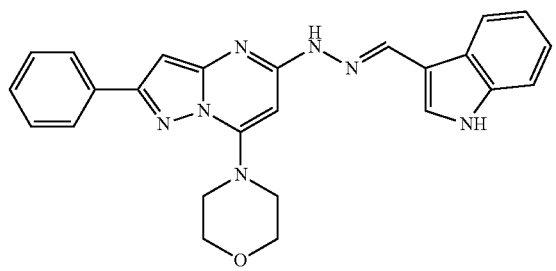

There was suspended, in ethanol (4 mL), 5-chloro-7-morpholin-4-yl-2-phenyl-pyrazolo[1,5-a]pyrimidine (100 mg, 0.318 mM), and then hydrazine monohydrate (77.1 μL, 1.59 mM) was added to the suspension. This suspension was stirred at 140° C. for 15 minutes under the irradiation with microwaves, hydrazine monohydrate (77.1 μL, 1.59 mM) was further added to the suspension and it was again stirred at 150° C. for 10 minutes likewise under the irradiation with microwaves. This reaction liquid was diluted with water and then extracted with ethyl acetate. The extracts thus obtained were combined, dried over anhydrous sodium sulfate and then the solvent was distilled off. The resulting residue was suspended in ethanol (2 mL), followed by the addition of acetic acid (2.0 μL, 0.035 mM) and indole-3-carboxy-aldehyde (46.5 mg, 0.318 mM) and the stirring of the resulting mixture at room temperature for an hour and a half. This reaction mixture was filtered and then the resulting solid was purified by the NH-silica gel column chromatography (methanol/methylene chloride=3:100) to thus give the title compound (39.1 mg, overall yield for these two steps: 28%).

$^1$H-NMR (300 MHz, DMSO): δ 2.34 (s, 3H), 3.74-3.77 (m, 4H), 3.89-3.92 (m, 4H), 6.36 (s, 1H), 6.49 (s, 1H), 7.12-7.22 (m, 2H), 7.34-7.47 (m, 4H), 7.72 (m, 1H), 7.93-7.96 (m, 2H), 8.23 (m, 1H), 8.27 (s, 1H), 10.89 (s, 1H), 11.45 (s, 1H); MS (ESI) m/z 438 (M+H)$^+$.

Example 3

Synthesis of N-(3-methyl-benzylidene)-N'-{2-(4-methylphenyl)-7-morpholin-4-yl-pyrazolo[1,5-a]pyrimidin-5-yl}-hydrazine (Compound 3)

(Step 1): 5,7-Dichloro-2-(4-methylphenyl)-pyrazolo[1,5-a]pyrimidine

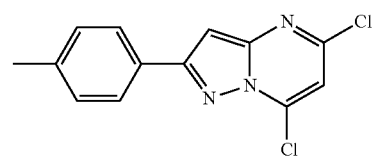

There was dissolved, in acetonitrile (40 mL), 5-amino-3-(4-methyl-phenyl)-pyrazole (2.00 g, 11.5 mM) in an argon gas atmosphere, malonyl chloride (1.34 mL, 13.8 mM) was added to the resulting solution with ice-cooling and the mixture was stirred at room temperature for 30 minutes. To this reaction liquid, there was added malonyl chloride (134 μL, 1.38 mM) followed by the further stirring of the mixture for 30 minutes. This reaction liquid was diluted with a 1M aqueous sodium hydroxide solution, washed with methylene chloride, and hydrochloric acid was added to the aqueous phase to make the same acidic (pH 2), followed by the extraction with ethyl acetate. The resulting extracts were combined and then concentrated, and the resulting solid was washed with diethyl ether. After the addition of phosphoryl chloride (5 mL) to the resulting solid with ice-cooling, the resulting suspension was stirred for 3 hours, while refluxing the same with heating. The phosphoryl chloride was distilled off from the reaction liquid, ethanol was added to the residue thus obtained with ice-cooling and then the mixture was stirred for 15 minutes. The reaction liquid was concentrated and then the resulting residue was purified by the silica gel column chromatography (ethyl acetate/hexane=1:10) to thus give the title compound (153 mg, overall yield of these two steps: 4%).

$^1$H-NMR (300 MHz, CDCl$_3$): δ 2.42 (s, 3H), 6.93 (s, 1H), 6.97 (s, 1H), 7.29 (d, 2H, J=8.1 Hz), 7.90 (d, 2H, J=8.1 Hz); MS (ESI) m/z 278 (M+H)$^+$.

(Step 2): 5-Chloro-2-(4-methylphenyl)-7-morpholin-4-yl-pyrazolo[1,5-a]pyrimidine

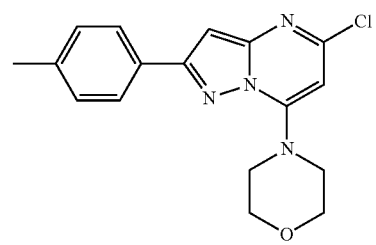

There was dissolved, in 1,4-dioxane (5 mL), 5,7-dichloro-2-(4-methylphenyl)-pyrazolo[1,5-a]pyrimidine (259 mg, 0.930 mM), morpholine (162 μL, 1.86 mM) was added to the resulting solution and then the mixture was stirred at room temperature for 15 minutes. The solvent was distilled off from the reaction mixture, the residue thus obtained was diluted with water and then extracted with methylene chloride. The extracts thus obtained were combined, dried over anhydrous sodium sulfate, the solvent was distilled off and the resulting solid was washed with methanol to thus give the title compound (274 mg, yield: 90%).

$^1$H-NMR (300 MHz, CDCl$_3$): δ 2.41 (s, 3H), 3.84-3.87 (m, 4H), 3.98-4.01 (m, 4H), 6.05 (s, 1H), 6.75 (s, 1H), 7.26 (d, 2H, J=8.1 Hz), 7.83 (d, 2H, J=8.1 Hz); MS (ESI) m/z 329 (M+H)$^+$.

(Step 3): N-(3-Methyl-benzylidene)-N'-{2-(4-methylphenyl)-7-morpholin-4-yl-pyrazolo[1,5-a]pyrimidin-5-yl}-hydrazine (Compound 3)

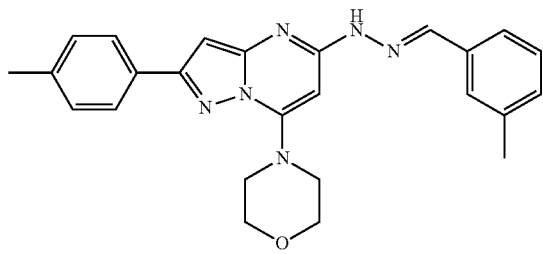

There was suspended, in ethanol (2 mL), 5-chloro-2-(4-methylphenyl)-7-morpholin-4-yl-pyrazolo[1,5-a]pyrimidine (50.0 mg, 0.152 mM) and then potassium carbonate (23.1 mg, 0.152 mM) and hydrazine monohydrate (36.9 μL, 0.760 mM) were added to the resulting suspension. This suspension was stirred at 150° C. for 20 minutes under the irradiation with microwaves, diluted with a saturated common salt aqueous solution and then extracted with ethyl acetate. The extracts thus obtained were combined, dried over anhydrous sodium sulfate and then the solvent was distilled off. The resulting residue was suspended in ethanol (2 mL), then acetic acid (5.0 μL, 0.087 mM) and 3-methyl-benzaldehyde (17.9 μL, 0.152 mM) were added to the suspension and then the resulting mixture was stirred at room temperature for one hour. This reaction mixture was filtered and then the resulting solid was purified by the NH-silica gel column chromatography (methylene chloride) to thus give the title compound (31.4 mg, overall yield of these two steps: 48%).

$^1$H-NMR (300 MHz, DMSO): δ 2.33 (s, 3H), 2.34 (s, 3H), 3.70-3.73 (m, 4H), 3.86-3.88 (m, 4H), 6.28 (s, 1H), 6.50 (s, 1H), 7.17 (m, 1H), 7.25 (d, 2H, J=8.2 Hz), 7.31 (m, 1H), 7.46 (m, 1H), 7.52 (m, 1H), 7.82 (d, 2H, J=8.2 Hz), 8.02 (s, 1H), 11.16 (s, 1H); MS (ESI) m/z 427 (M+H)$^+$.

Example 4

Synthesis of N-(1H-indol-3-yl-methylidene)-N'-{2-(4-methylphenyl)-7-morpholin-4-yl-pyrazolo[1,5-a]pyrimidin-5-yl}-hydrazine (Compound 4)

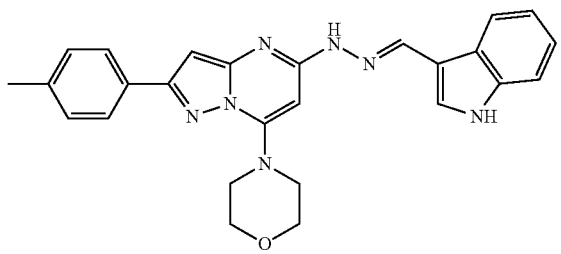

There was suspended, in ethanol (2 mL), 5-chloro-2-(4-methylphenyl)-7-morpholin-4-yl-pyrazolo[1,5-a]pyrimidine (50.0 mg, 0.152 mM) prepared in Example 3 (Step 2), then potassium carbonate (23.1 mg, 0.152 mM) and hydrazine monohydrate (36.9 μL, 0.760 mM) were added to the suspension. This suspension was stirred at 150° C. for 20 minutes under the irradiation with microwaves, diluted with a saturated aqueous common salt solution and then extracted with ethyl acetate. The extracts thus obtained were combined, dried over anhydrous sodium sulfate and then the solvent was distilled off. The resulting residue was suspended in ethanol (2 mL), then acetic acid (5.0 μL, 0.087 mM) and indole-3-carboxy-aldehyde (22.1 mg, 0.152 mM) were added to the suspension and then the mixture was stirred at room temperature for one hour. This reaction mixture was filtered and the resulting solid was purified by the NH-silica gel column chromatography (methanol/methylene chloride=3:100) to thus obtain the title compound (11.0 mg, overall yield of these two steps: 16%).

$^1$H-NMR (300 MHz, DMSO): δ 2.33 (s, 3H), 3.73-3.77 (m, 4H), 3.88-3.92 (m, 4H), 6.35 (s, 1H), 6.44 (s, 1H), 7.17-7.21 (m, 2H), 7.25 (d, 1H, J=7.9 Hz), 7.43 (m, 1H), 7.72 (d, 1H, J=2.6 Hz), 7.82 (d, 2H, J=7.9 Hz), 8.23 (m, 1H), 8.26 (s, 1H), 10.87 (s, 1H), 11.45 (s, 1H); MS (ESI) m/z 452 (M+H)$^+$.

Example 5

Synthesis of N-{3-bromo-2-(4-methylphenyl)-7-morpholin-4-yl-pyrazolo-[1,5-a]pyrimidin-5-yl}-N'-(3-methyl-benzylidene)-hydrazine (Compound 5)

(Step 1): 3-Bromo-5-chloro-2-(4-methylphenyl)-7-morpholin-4-yl-pyrazolo[1,5-a]-pyrimidine

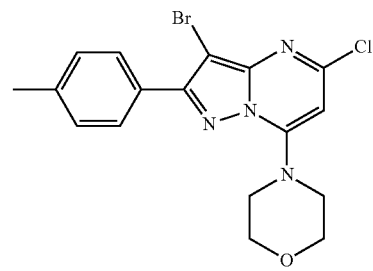

There was dissolved, in methylene chloride (2 mL), 5-chloro-2-(4-methyl-phenyl)-7-morpholin-4-yl-pyrazolo[1,5-a]pyrimidine (44.4 mg, 0.135 mM), then N-bromo-succinimide (27.1 mg, 0.152 mM) was added to the resulting solution and the mixture was stirred at room temperature for 40 minutes. This reaction liquid was diluted with a saturated aqueous ammonium chloride solution and then extracted with methylene chloride. The extracts thus obtained were combined, dried over anhydrous sodium sulfate, the solvent was then distilled off and the resulting residue was purified by the silica gel column chromatography (ethyl acetate/hexane=1:10) to thus obtain the title compound (27.6 mg, yield: 50%).

$^1$H-NMR (300 MHz, CDCl$_3$): δ 2.43 (s, 3H), 3.84-3.87 (m, 4H), 3.94-3.97 (m, 4H), 6.11 (s, 1H), 7.30 (d, 2H, J=8.1 Hz), 7.94 (d, 2H, J=8.1 Hz); MS (ESI) m/z 409 (M+H)$^+$.

(Step 2): N-{3-Bromo-2-(4-methylphenyl)-7-morpholin-4-yl-pyrazolo[1,5-a]-pyrimidin-5-yl}-N'-(3-methyl-benzylidene)-hydrazine (Compound 5)

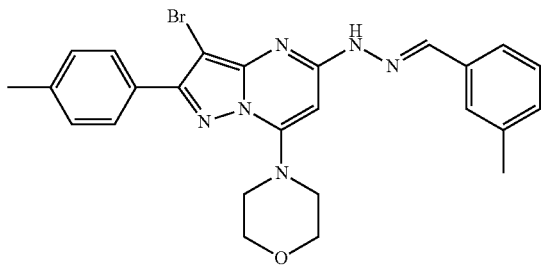

There was suspended, in ethanol (2 mL), 3-bromo-5-chloro-2-(4-methyl-phenyl)-7-morpholin-4-yl-pyrazolo[1,5-a]-pyrimidine (21.7 mg, 0.0532 mM) and then potassium carbonate (9.2 mg, 0.067 mM) and hydrazine monohydrate (13.0 μL, 0.268 mM) were added to the resulting suspension. This suspension was stirred at 150° C. for 10 minutes under the irradiation with microwaves, diluted with a saturated aqueous common salt solution and then extracted with ethyl acetate. The extracts thus obtained were combined, dried over anhydrous sodium sulfate and the solvent was then distilled off. The resulting residue was suspended in ethanol (2 mL), then acetic acid (5.0 μL, 0.087 mM) and 3-methyl-benzaldehyde (13.0 μL, 0.106 mM) were added to the suspension and the resulting mixture was stirred at room temperature for 2 hours. This reaction mixture was filtered and then the resulting solid was purified by the NH-silica gel column chromatography (methylene chloride) to thus give the title compound (6.3 mg, overall yield of these two steps: 23%).

$^1$H-NMR (300 MHz, DMSO): δ 2.34 (s, 3H), 2.36 (s, 3H), 3.70-3.73 (m, 4H), 3.82-3.86 (m, 4H), 6.38 (s, 1H), 7.18 (m, 1H), 7.28-7.33 (m, 3H), 7.47 (m, 1H), 7.53 (m, 1H), 7.84 (d, 2H, J=8.2 Hz), 8.05 (s, 1H), 11.60 (s, 1H); MS (ESI) m/z 507 (M+H)$^+$.

Example 6

Synthesis of N-(3-methyl-benzylidene)-N'-(7-morpholin-4-yl-3-phenyl-pyrazolo[1,5-a]pyrimidin-5-yl)-hydrazine (Compound 6)

(Step 1): 5,7-Dichloro-3-phenyl-pyrazolo[1,5-a]pyrimidine

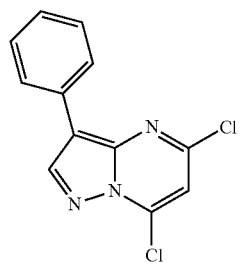

There was dissolved, in tetrahydrofuran (4 mL), 3-amino-4-phenyl-pyrazole (208 mg, 1.31 mM), then malonyl chloride (153 μL, 1.57 mM) was added to the solution with ice-cooling and the mixture was stirred at room temperature for 30 minutes. To the reaction solution, there was added malonyl chloride (15 μL, 0.16 mM) and the mixture was further stirred at room temperature for 30 minutes. This reaction liquid was diluted with a 1M aqueous sodium hydroxide solution, washed with ethyl acetate, the aqueous phase was acidified (pH 2) by the addition of hydrochloric acid and then it was extracted with ethyl acetate. The extracts thus obtained were combined, dried over anhydrous sodium sulfate, the solvent was then distilled off and the resulting solid was washed with diethyl ether. Phosphoryl chloride (4 mL) was added to the resulting solid with ice-cooling, and then the resulting suspension was stirred for 6 hours while refluxing the same with heating. The phosphoryl chloride was distilled off from the reaction liquid, ethanol was added to the resulting residue with ice-cooling and the mixture was stirred for 15 minutes. After the reaction liquid was concentrated, the concentrate was diluted with water and then extracted with methylene chloride. The extracts were combined, dried over anhydrous sodium sulfate, the solvent was distilled off and the resulting residue was purified by the silica gel column chromatography (ethyl acetate/hexane=1:10) to thus give the title compound (47.7 mg, overall yield of these two steps: 14%).

$^1$H-NMR (300 MHz, CDCl$_3$): δ 7/01 (s, 1H), 7.32 (m, 1H), 7.44-7.49 (m, 2H), 7.97-8.00 (m, 2H), 8.53 (s, H); MS (ESI) m/z 264 (M+H)$^+$.

(Step 2): 5-Chloro-7-morpholin-4-yl-3-phenyl-pyrazolo[1,5-a]pyrimidine

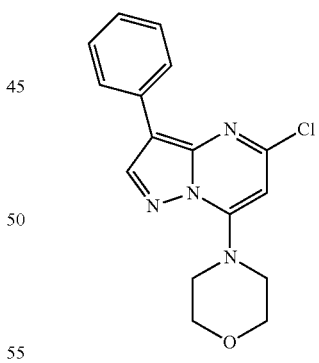

There was dissolved, in 1,4-dioxane (2 mL), 5,7-dichloro-3-phenyl-pyrazolo-[1,5-a]pyrimidine (47.7 mg, 0.181 mM), then morpholine (31.6 μL, 0.362 mM) was added to the solution and the resulting mixture was stirred at room temperature for 30 minutes. The solvent was distilled off from this reaction mixture, the resulting residue was diluted with water and extracted with methylene chloride. The extracts thus obtained were combined, dried over anhydrous sodium sulfate, the solvent was then distilled off, and the resulting solid was washed with methanol to thus obtain the title compound (46.8 mg, yield: 82%).

(Step 3): N-(3-Methyl-benzylidene)-N'-(7-morpholin-4-yl-3-phenyl-pyrazolo[1,5-a]-pyrimidin-5-yl-hydrazine (Compound 6)

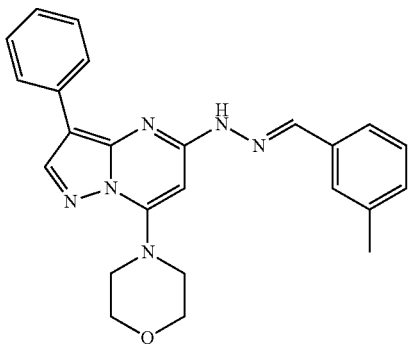

There was suspended, in ethanol (2 mL), 5-chloro-7-morpholin-4-yl-3-phenyl-pyrazolo[1,5-a]pyrimidine (42.1 mg, 0.134 mM) and then hydrazine monohydrate (65.0 μL, 1.34 mM) was added to the suspension. This suspension was stirred at 150° C. for 20 minutes under the irradiation with microwaves, the solvent was then distilled off, the resulting residue was diluted with a saturated aqueous common salt solution and extracted with ethyl acetate. The extracts thus obtained were combined, dried over anhydrous sodium sulfate, and the solvent was then distilled off. The resulting residue was suspended in ethanol (2 mL), then acetic acid (2.0 μL, 0.035 mM) and 3-methyl-benzaldehyde (15.8 μL, 0.134 mM) were added to the suspension and the mixture was stirred at room temperature for 2 hours and a half.

The solvent was then distilled off from the reaction mixture, and the resulting solid was washed with ethanol to thus give the title compound (12.1 mg, overall yield of these two steps: 22%).

$^1$H-NMR (300 MHz, CDCl$_3$): δ 2.41 (s, 3H), 3.75-3.78 (m, 4H), 4.00-4.03 (m, 4H), 6.44 (s, 1H), 7.18-7.22 (m, 2H), 7.31 (m, 1H), 7.38-7.43 (m, 2H), 7.48-7.50 (m, 2H), 7.73 (s, 1H), 7.98 (d, 2H, J=7.3 Hz), 8.22 (s, 1H), 8.56 (s, 1H); MS (ESI) m/z 423 (M+H)$^+$.

Example 7

Synthesis of N-benzylidene-N'-(7-morpholin-4-yl-2-phenyl-pyrazolo-[1,5-a]pyrimidin-5-yl)-hydrazine (Compound 7)

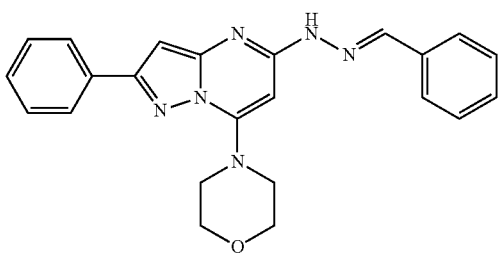

5-Chloro-7-morpholin-4-yl-2-phenyl-pyrazolo[1,5-a]pyrimidine (51.4 mg, 0.163 mM) was suspended in ethanol (1 mL) and then hydrazine monohydrate (15.8 μL, 0.326 mM) was added to the resulting suspension. This suspension was stirred for 2 hours and a half, while refluxing with heating, then hydrazine monohydrate (15.8 μL, 0.326 mM) was further added to the suspension, the mixture was stirred for additional 3 hours, hydrazine monohydrate (15.8 μL, 0.326 mM) was further added to the mixture and then the mixture was stirred for 18 hours. This reaction liquid was diluted with a saturated aqueous common salt solution and extracted with ethyl acetate. The extracts thus obtained were combined, dried over anhydrous sodium sulfate and the solvent was then distilled off. The resulting residue was suspended in ethanol (0.5 mL), then acetic acid (2.0 μL, 0.035 mM) and benzaldehyde (16.6 μL, 0.196 mM) were added to the suspension and the mixture was stirred at room temperature for 15 minutes. This reaction mixture was filtered and the resulting solid was purified by the NH-silica gel column chromatography (methylene chloride) to thus give the title compound (16.5 mg, overall yield of these two steps: 25%).

$^1$H-NMR (300 MHz, DMSO): δ 3.83-3.86 (m, 4H), 4.03-4.06 (m, 4H), 6.40 (s, 1H), 6.47 (s, 1H), 7.34-7.47 (m, 6H), 7.66-7.69 (m, 2H), 7.80 (s, 1H), 7.93-7.96 (m, 2H), 8.71 (br, 1H); MS (ESI) m/z 399 (M+H)$^+$.

Example 8

Synthesis of N-(7-morpholin-4-yl-2-phenyl-pyrazolo[1,5-a]pyrimidin-5-yl)-N'-pyridin-3-yl-methylidene-hydrazine (Compound 8)

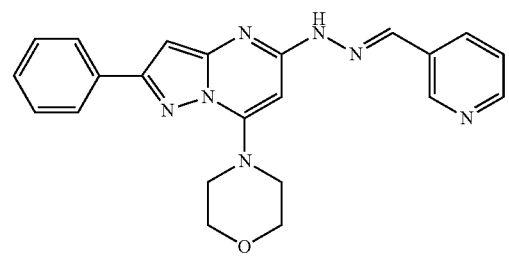

5-Chloro-7-morpholin-4-yl-2-phenyl-pyrazolo[1,5-a]pyrimidine (52.4 mg, 0.166 mM) was suspended in ethanol (1 mL) and then potassium carbonate (22.9 mg, 0.166 mM) and hydrazine monohydrate (40.3 μL, 0.830 mM) were added to the resulting suspension. This suspension was stirred at 150° C. for 15 minutes under the irradiation with microwaves, hydrazine monohydrate (40.3 μL, 0.830 mM) was then added to the suspension and the mixture was stirred at 150° C. for 10 minutes under the irradiation with microwaves. This reaction liquid was diluted with a saturated aqueous common salt solution and then extracted with ethyl acetate. The extracts thus obtained were combined together, dried over anhydrous sodium sulfate and thereafter the solvent was distilled off. The resulting residue was suspended in ethanol (1 mL), then acetic acid (2.0 μL, 0.035 mM) and pyridine-3-carboxy-aldehyde (17.1 μL, 0.183 mM) were added to the suspension and the mixture was stirred at room temperature for one hour. The reaction mixture was filtered to thus give the title compound (31.4 mg, overall yield of these two steps: 60%).

$^1$H-NMR (300 MHz, DMSO): δ 3.74-3.76 (m, 4H), 3.86-3.89 (m, 4H), 6.35 (s, 1H), 6.58 (s, 1H), 7.34-7.48 (m, 4H), 7.95 (d, 2H, J=7.0 Hz), 8.08 (s, 1H), 8.13 (m, 1H), 8.53 (dd, 1H, J=1.5, 4.8 Hz), 8.86 (d, 1H, J=1.5 Hz), 11.39 (s, 1H); MS (ESI) m/z 400 (M+H)⁺.

Example 9

Synthesis of N-(3-methyl-benzylidene)-N'-(7-morpholin-4-yl-pyrazolo-[1,5-a]pyrimidin-5-yl)-hydrazine (Compound 9)

(Step 1): 5,7-Dichloro-pyrazolo[1,5-a]pyrimidine

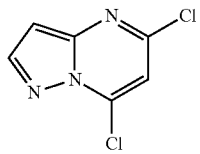

3-Amino-pyrazole (534 mg, 6.43 mM) was dissolved in sodium ethoxide (1M ethanol solution, 12.9 mL, 12.9 mM) and then diethyl malonate (1.07 mL, 7.07M) was added to the solution. This reaction liquid was stirred at 150° C. for 40 minutes under the irradiation with microwaves. This reaction mixture was diluted with water, acidified (pH 2) by the addition of hydrochloric acid and then extracted with ethyl acetate. The extracts were combined together, dried over anhydrous sodium sulfate and then the solvent was distilled off. Phosphoryl chloride (10 mL) was added to the resulting solid with ice-cooling and then the resulting suspension was stirred for 2 hours and a half, while refluxing the same with heating. The phosphoryl chloride was distilled off from this reaction liquid, ethanol was added to the resulting residue with ice-cooling and the mixture was subsequently stirred for 15 minutes. After the concentration of this reaction liquid, the latter was diluted with a saturated aqueous sodium bicarbonate solution and then extracted with methylene chloride. The extracts obtained were combined, dried over anhydrous sodium sulfate and then purified by the silica gel column chromatography (methylene chloride/hexane=3:1) to thus obtain the title compound (403 mg, overall yield of these two steps: 34%).
¹H-NMR (300 MHz, CDCl₃): δ 6.74 (d, 1H, J=2.3 Hz), 6.99 (s, 1H), 8.22 (d, 1H, J=2.3 Hz); MS (ESI) m/z 188 (M+H)⁺.

(Step 2): 5-Chloro-7-morpholin-4-yl-pyrazolo[1,5-a]pyrimidine

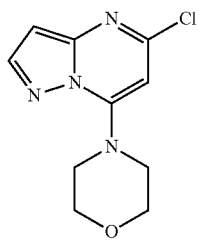

5,7-Dichloro-pyrazolo[1,5-a]pyrimidine (400 mg, 2.13 mM) was dissolved in 1,4-dioxane (8 mL), then morpholine (372 μL, 4.26 mM) was added to the solution and the mixture was stirred at room temperature for 30 minutes. The solvent was distilled off from the reaction mixture, the resulting residue was diluted with water and extracted with methylene chloride. The extracts thus obtained were combined, dried over anhydrous sodium sulfate and the solvent was then distilled off to give the title compound (461 mg, yield: 91%).
¹H-NMR (300 MHz, CDCl₃): δ 3.77-3.80 (m, 4H), 3.93-3.96 (m, 4H), 6.07 (s, 1H), 6.50 (d, 1H, J=2.2 Hz), 8.02 (d, 1H, J=2.2 Hz); MS (ESI) m/z 239 (M+H)⁺.

(Step 3): N-(3-methyl-benzylidene)-N'-(7-morpholin-4-yl-pyrazolo-[1,5-a]pyrimidin-5-yl)-hydrazine (Compound 9)

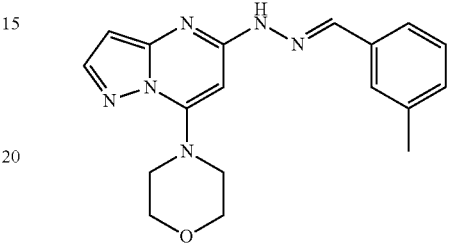

5-Chloro-7-morpholin-4-yl-pyrazolo[1,5-a]pyrimidine (52.0 mg, 0.218 mM) was suspended in ethanol (2 mL) and then potassium carbonate (33.1 mg, 0.240 mM) and hydrazine monohydrate (53.0 μL, 1.09 mM) were added to the suspension. This suspension was stirred at 150° C. for 15 minutes under the irradiation with microwaves. This reaction liquid was diluted with a saturated aqueous common salt solution and then extracted with ethyl acetate. The extracts thus obtained were combined, dried over anhydrous sodium sulfate and the solvent was then distilled off. The resulting residue was suspended in ethanol (2 mL), then acetic acid (5.0 μL, 0.087 mM) and 3-methyl-benzaldehyde (23.2 μL, 0.197 mM) were added to the suspension and then the reaction mixture was stirred at room temperature for one hour. This reaction mixture was filtered and the resulting solid was washed with methanol to thus obtain the title compound (35.1 mg, overall yield of these two steps: 48%).
¹H-NMR (300 MHz, DMSO): δ 2.34 (s, 3H), 3.64-3.67 (m, 4H), 3.80-3.83 (m, 4H), 6.05 (d, 1H, J=2.1 Hz), 6.29 (s, 1H), 7.16 (m, 1H), 7.30 (m, 1H), 7.46 (m, 1H), 7.51 (m, 1H), 7.88 (d, 1H, J=2.1 Hz), 8.01 (s, 1H), 11.14 (s, 1H); MS (ESI) m/z 337 (M+H)⁺.

Example 10

Synthesis of N-(1H-indol-3-yl-methylidene)-N'-(7-morpholin-4-yl-pyrazolo[1,5-a]pyrimidin-5-yl)-hydrazine (Compound 10)

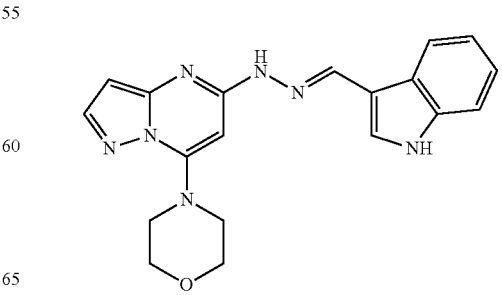

There was suspended, in ethanol (2 mL), 5-chloro-7-morpholin-4-yl-pyrazolo-[1,5-a]pyrimidine (52.0 mg, 0.218 mM) and then potassium carbonate (33.1 mg, 0.240 mM) and hydrazine monohydrate (53.0 μL, 1.09 mM) were added to the suspension. This suspension was stirred at 150° C. for 15 minutes under the irradiation with microwaves. This reaction liquid was diluted with a saturated aqueous common salt solution and then extracted with ethyl acetate. The extracts thus obtained were combined, dried over anhydrous sodium sulfate and the solvent was then distilled off. The resulting residue was suspended in ethanol (2 mL), then acetic acid (5.0 μL, 0.087 mM) and indole-3-carboxyaldehyde (28.3 mg, 0.193 mM) were added to the suspension and then the reaction mixture was stirred at room temperature for one hour. This reaction mixture was filtered and the resulting solid was washed with methanol to thus obtain the title compound (39.5 mg, overall yield of these two steps: 50%).

$^1$H-NMR (300 MHz, DMSO): δ 3.67-3.70 (m, 4H), 3.83-3.87 (m, 4H), 6.00 (d, 1H, J=2.1 Hz), 6.35 (s, 1H), 7.17-7.20 (m, 2H), 7.43 (m, 1H), 7.71 (d, 1H, J=2.3 Hz), 7.85 (d, 1H, J=2.1 Hz), 8.20 (s, 1H), 8.25 (s, 1H), 10.84 (s, 1H), 11.44 (s, 1H); MS (ESI) m/z 362 (M+H)$^+$.

Example 11

Synthesis of N-(3-bromo-7-morpholin-4-yl-pyrazolo[1,5-a]pyrimidin-5-yl)-N'-(3-methyl-benzylidene)-hydrazine (Compound 11)

(Step 1): 3-Bromo-5-chloro-7-morpholin-4-yl-pyrazolo[1,5-a]pyrimidine

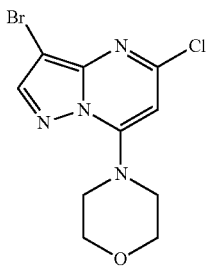

There was dissolved, in methylene chloride (2 mL), 5-chloro-7-morpholin-4-yl-pyrazolo[1,5-a]pyrimidine (100 mg, 0.419 mM), then N-bromo-succinimide (78.8 mg, 0.443 mM) was added to the solution and the mixture was stirred at room temperature for one hour. This reaction liquid was diluted with a saturated aqueous sodium bicarbonate solution and then extracted with ethyl acetate. The extracts thus obtained were combined, dried over anhydrous sodium sulfate and the solvent was then distilled off. The resulting residue was purified by the silica gel column chromatography (methylene chloride) to thus give the title compound (80.7 mg, yield: 61%).

$^1$H-NMR (300 MHz, CDCl$_3$): δ 3.77-3.80 (m, 4H), 3.93-3.96 (m, 4H), 6.11 (s, 1H), 8.00 (s, 1H); MS (ESI) m/z 319 (M+H)$^+$.

(Step 2): N-(3-bromo-7-morpholin-4-yl-pyrazolo[1,5-a]pyrimidin-5-yl)-N'-(3-methyl-benzylidene)-hydrazine (Compound 11)

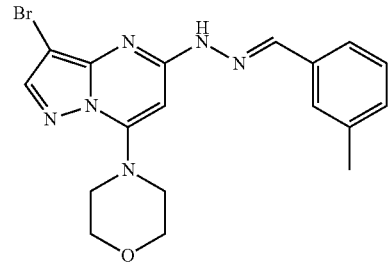

There was suspended, in ethanol (2 mL), 3-bromo-5-chloro-7-morpholin-4-yl-pyrazolo[1,5-a]pyrimidine (60.0 mg, 0.189 mM) and then potassium carbonate (26.2 mg, 0.190 mM) and hydrazine monohydrate (45.8 μL, 0.945 mM) were added to the suspension. This suspension was stirred at 150° C. for 10 minutes under the irradiation with microwaves. This reaction liquid was diluted with water and then extracted with ethyl acetate. The extracts thus obtained were combined, dried over anhydrous sodium sulfate and the solvent was then distilled off. The resulting residue was suspended in ethanol (2 mL), then acetic acid (10 μL, 0.174 mM) and 3-methyl-benzaldehyde (22.4 μL, 0.189 mM) were added to the suspension and then the mixture was stirred at room temperature for one hour. This reaction mixture was filtered and the resulting solid was washed with methanol to thus obtain the title compound (58.2 mg, overall yield of these two steps: 74%).

$^1$H-NMR (300 MHz, DMSO): δ 2.34 (s, 3H), 3.64-3.66 (m, 4H), 3.80-3.83 (m, 4H), 6.35 (s, 1H), 7.18 (m, 1H), 7.31 (m, 1H), 7.46 (m, 1H), 7.52 (m, 1H), 8.00 (s, 1H), 8.03 (s, 1H), 11.57 (s, 1H); MS (ESI) m/z 415 (M+H)$^+$.

Example 12

Synthesis of N-{2-(3-chloro-phenyl)-7-morpholin-4-yl-pyrazolo[1,5-a]-pyrimidin-5-yl}-N'-(3-methyl-benzylidene)-hydrazine (Compound 12)

(Step 1): 5,7-Dichloro-2-(3-chlorophenyl)-pyrazolo[1,5-a]pyrimidine

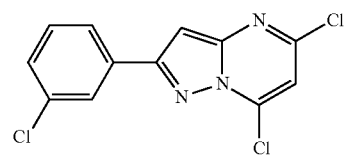

There was dissolved, in ethanol (7 mL), 3-amino-5-(3-chloro-phenyl)-pyrazole (600 mg, 3.10 mM) and then sodium ethoxide (2M ethanol solution, 3.32 mL, 6.64 mM) and diethyl malonate (517 μL, 3.41 mM) were added to the solution. This reaction liquid was stirred at 150° C. for 50 minutes under the irradiation with microwaves. This reaction mixture was filtered and the resulting solid was washed with methanol. After the addition of phosphoryl chloride (5 mL) to the resulting solid with ice-cooling, this suspension was stirred for 4 hours, while refluxing the same with heating. The phosphoryl chloride was distilled off from the reaction liquid, ethanol was added to the resulting residue with ice-cooling and the mixture was stirred for 15 minutes. This reaction liquid was concentrated and then the concentrate was purified by the silica gel column chromatography (methylene chloride) to thus give the title compound (496 mg, overall yield of these two steps: 54%).

$^1$H-NMR (300 MHz, CDCl$_3$): δ 6.98 (s, 1H), 6.99 (s, 1H), 7.40-7.42 (m, 2H), 7.88 (m, 1H), 8.01 (m, 1H); MS (ESI) m/z 298 (M+H)$^+$.

(Step 2): 5-Chloro-2-(3-chloro-phenyl)-7-morpholin-4-yl-pyrazolo[1,5-a]pyrimidine

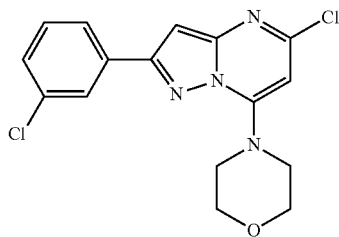

There was dissolved, in 1,4-dioxane (5 mL), 5,7-dichloro-2-(3-chlorophenyl)-pyrazolo[1,5-a]pyrimidine (200 mg, 0.670 mM), then morpholine (117 μL, 1.34 mM) was added to the solution and the mixture was stirred at room temperature for 30 minutes. The solvent was distilled off from the reaction mixture, the resulting residue was diluted with water and then extracted with methylene chloride. The extracts thus obtained were combined together and dried over anhydrous sodium sulfate, then the solvent was distilled off and the resulting solid was washed with methanol to give the title compound (222 mg, yield: 94%).

$^1$H-NMR (300 MHz, CDCl$_3$): δ 3.84-3.87 (m, 4H), 3.98-4.01 (m, 4H), 6.09 (s, 1H), 6.77 (s, 1H), 7.37-7.39 (m, 2H), 7.81 (m, 1H), 7.91 (m, 1H); MS (ESI) m/z 349 (M+H)$^+$.

(Step 3): N-{2-(3-Chlorophenyl)-7-morpholin-4-yl-pyrazolo[1,5-a]pyrimidin-5-yl}-N'-(3-methyl-benzylidene)-hydrazine (Compound 12)

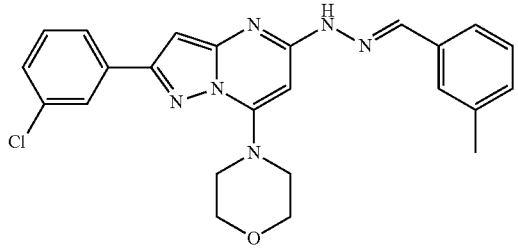

There was suspended, in ethanol (2 mL), 5-chloro-2-(3-chloro-phenyl)-7-morpholin-4-yl-pyrazolo[1,5-a]pyrimidine (50.5 mg, 0.145 mM) and then potassium carbonate (22.0 mg, 0.160 mM) and hydrazine monohydrate (35.2 μL, 0.725 mM) were added to the suspension. This suspension was stirred at 150° C. for 20 minutes under the irradiation with microwaves. This reaction liquid was diluted with a saturated aqueous common salt solution and then extracted with ethyl acetate. The extracts thus obtained were combined together and dried over anhydrous sodium sulfate and then the solvent was distilled off. The resulting residue was suspended in ethanol (2 mL), then acetic acid (5.0 μL, 0.087 mM) and 3-methyl-benzaldehyde (17.1 μL, 0.145 mM) were added to the suspension and the mixture was stirred at room temperature for one hour. This reaction mixture was filtered and the resulting solid was purified by the NH-silica gel column chromatography (methylene chloride) to give the title compound (42.8 mg, overall yield of these two steps: 66%).

$^1$H-NMR (300 MHz, DMSO): δ 2.34 (s, 3H), 3.71-3.73 (m, 4H), 3.86-3.88 (m, 4H), 6.32 (s, 1H), 6.66 (s, 1H), 7.17 (m, 1H), 7.31 (m, 1H), 7.41-7.53 (m, 4H), 7.92 (d, 2H, J=7.3 Hz), 7.96 (s, 1H); MS (ESI) m/z 447 (M+H)$^+$.

Example 13

Synthesis of N-{2-(4-chlorophenyl)-7-morpholin-4-yl-pyrazolo[1,5-a]-pyrimidin-5-yl}-N'-(3-methyl-benzylidene)-hydrazine (Compound 13)

(Step 1): 5,7-Dichloro-2-(4-chlorophenyl)-pyrazolo[1,5-a]pyrimidine

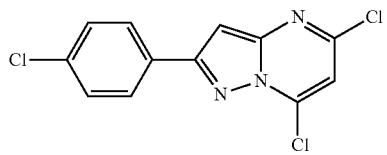

There was dissolved, in ethanol (5 mL), 3-amino-5-(4-chlorophenyl)-pyrazole (500 mg, 2.58 mM) and then sodium ethoxide (2M ethanol solution, 2.58 mL, 5.16 mM) and diethyl malonate (431 μL, 2.84 mM) were added to the solution. This reaction liquid was stirred at 150° C. for 50 minutes under the irradiation with microwaves. This reaction mixture was filtered and the resulting solid was washed with methanol. After the addition of phosphoryl chloride (5 mL) to the resulting solid with ice-cooling, the resulting suspension was stirred for 4 hours, while refluxing the same with heating. The phosphoryl chloride was distilled off from this reaction liquid, ethanol was then added to the resulting residue with ice-cooling and the mixture was stirred for 15 minutes. After the concentration of this reaction liquid, the resulting concentrate was purified by the silica gel column chromatography (methylene chloride) to give the title compound (406 mg, overall yield of these two steps: 53%).

$^1$H-NMR (300 MHz, CDCl$_3$): δ 6.97 (2s, each 1H), 7.45 (d, 2H, J=8.6 Hz), 7.95 (d, 2H, J=8.6 Hz); MS (ESI) m/z 298 (M+H)$^+$.

(Step 2): 5-Chloro-2-(4-chlorophenyl)-7-morpholin-4-yl-pyrazolo[1,5-a]pyrimidine

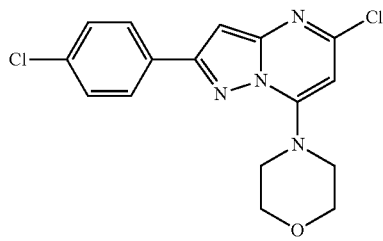

There was dissolved, in 1,4-dioxane (5 mL), 5,7-dichloro-2-(4-chlorophenyl)-pyrazolo[1,5-a]pyrimidine (200 mg, 0.670 mM), then morpholine (117 μL, 1.34 mM) was added to the solution and the mixture was stirred at room temperature for 30 minutes. The solvent was distilled off from the reaction mixture and the resulting residue was diluted with water and extracted with methylene chloride. The extracts thus obtained were combined, dried over anhydrous sodium sulfate, the solvent was distilled off and then the resulting solid was washed with methanol to give the title compound (222 mg, yield: 94%).

$^1$H-NMR (300 MHz, CDCl$_3$): δ 3.83-3.87 (m, 4H), 3.98-4.01 (m, 4H), 6.08 (s, 1H), 6.75 (s, 1H), 7.42 (d, 2H, J=8.6 Hz), 7.87 (d, 2H, J=8.6 Hz); MS (ESI) m/z 349 (M+H)$^+$.

(Step 3): N-{2-(4-Chlorophenyl)-7-morpholin-4-yl)-pyrazolo[1,5-a]pyrimidin-5-yl}-N'-(3-methyl-benzylidene)-hydrazine (Compound 13)

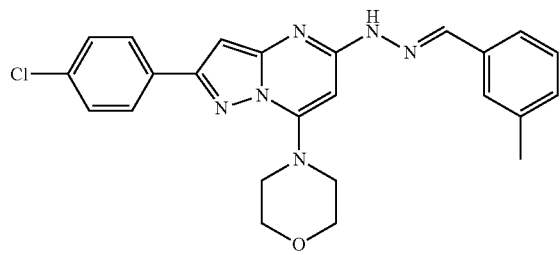

There was suspended, in ethanol (2 mL), 5-chloro-2-(4-chloro-phenyl)-7-morpholin-4-yl-pyrazolo[1,5-a]pyrimidine (50.0 mg, 0.143 mM) and then potassium carbonate (21.7 mg, 0.157 mM) and hydrazine monohydrate (69.4 μL, 1.43 mM) were added to the suspension. This suspension was stirred at 150° C. for 20 minutes, while applying microwaves to the same. This reaction liquid was diluted with a saturated aqueous common salt solution and then extracted with ethyl acetate. The extracts thus obtained were combined together and then dried over anhydrous sodium sulfate and the solvent was distilled off. The resulting residue was suspended in ethanol (2 mL), then acetic acid (5.0 μL, 0.087 mM) and 3-methyl-benzaldehyde (17.0 μL, 0.144 mM) were added to the suspension and the mixture was stirred at room temperature for one hour. This reaction liquid was filtered and the resulting solid was purified by the NH-silica gel column chromatography (methylene chloride) to give the title compound (36.8 mg, overall yield of these two steps: 58%).

$^1$H-NMR (300 MHz, DMSO): δ 2.34 (s, 3H), 3.71-3.73 (m, 4H), 3.86-3.88 (m, 4H), 6.31 (s, 1H), 6.59 (s, 1H), 7.17 (m, 1H), 7.31 (m, 1H), 7.47-7.53 (m, 4H), 7.96 (d, 2H, J=8.5 Hz), 8.03 (s, 1H), 11.20 (s, 1H); MS (ESI) m/z 447 (M+H)$^+$.

Example 14

Synthesis of N-(3-methyl-benzylidene)-N'-{2-(2-methyl-phenyl)-7-morpholin-4-yl-pyrazolo[1,5-a]pyrimidin-5-yl}-hydrazine (Compound 14)

(Step 1): 5,7-Dichloro-2-(2-methyl-phenyl)-pyyrazolo[1,5-a]pyrimidine

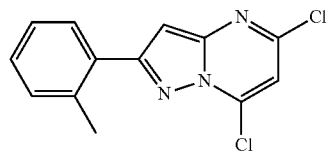

There was dissolved, in ethanol (7 mL), 3-amino-5-(2-methyl-phenyl)-pyrazole (500 mg, 2.87 mM) and then sodium ethoxide (2M ethanol solution, 2.87 mL, 5.74 mM) and diethyl malonate (479 μL, 3.16 mM) were added to the solution. This reaction liquid was stirred at 150° C. for 50 minutes under the irradiation with microwaves, then sodium ethoxide (2M ethanol solution, 2.50 mL, 5.00 mM) and diethyl malonate (450 μL, 2.96 mM) were added and then the mixture was stirred at 150° C. for 50 minutes under the irradiation with microwaves. This reaction mixture was filtered and the resulting solid was washed with methanol. Phosphoryl chloride (5 mL) was added to the resulting solid with ice-cooling, and then this suspension was stirred for 2 hours while refluxing the same with heating. The phosphoryl chloride was distilled off from this reaction liquid, then ethanol was added to the resulting residue with ice-cooling and the mixture was stirred for 15 minutes. The reaction liquid was concentrated and then the resulting concentrate was purified by the silica gel column chromatography (methylene chloride) to thus give the title compound (159 mg, overall yield of these two steps: 20%).

$^1$H-NMR (300 MHz, CDCl$_3$): δ 2.54 (s, 3H), 6.88 (s, 1H), 6.98 (s, 1H), 7.29-7.34 (m, 3H), 7.67 (m, 1H); MS (ESI) m/z 280 (M+H)$^+$.

(Step 2): 5-Chloro-2-(2-methyl-phenyl)-7-morpholin-4-yl-pyrazolo[1,5-a]pyrimidine

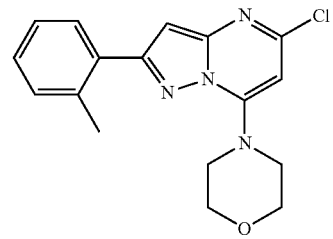

There was dissolved, in 1,4-dioxane (2 mL), 5,7-dichloro-2-(2-methyl-phenyl)-pyrazolo[1,5-a]pyrimidine (74.4 mg, 0.267 mM), then morpholine (46.6 μL, 0.534 mM) was added to the solution and the mixture was stirred at room temperature for one hour. The solvent was distilled off from this reaction mixture, the resulting residue was diluted with water and then extracted with methylene chloride. The extracts thus obtained were combined, dried over anhydrous sodium sulfate, the solvent was distilled off and the resulting solid was washed with methanol to give the title compound (75.3 mg, yield: 86%).

$^1$H-NMR (300 MHz, CDCl$_3$): δ 3.84-3.87 (m, 4H), 3.93-3.97 (m, 4H), 6.08 (s, 1H), 6.68 (s, 1H), 7.29-7.32 (m, 3H), 7.65 (m, 1H); MS (ESI) m/z 329 (M+H)$^+$.

(Step 3): N-(3-Methyl-benzylidene)-N'-{2-(2-methyl-phenyl)-7-morpholin-4-yl-pyrazolo[1,5-a]pyrimidin-5-yl}-hydrazine (Compound 14)

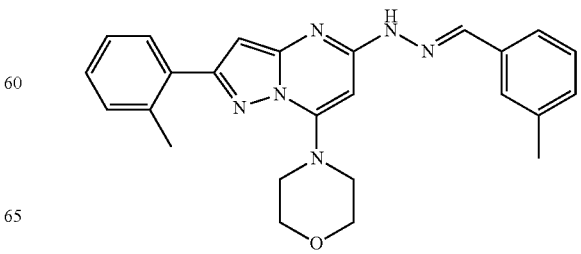

There was suspended, in ethanol (2 mL), 5-chloro-2-(2-methyl-phenyl)-7-morpholin-4-yl-pyrazolo[1,5-a]pyrimidine (72.1 mg, 0.219 mM) and then potassium carbonate (32.8 mg, 0.241 mM) and hydrazine monohydrate (106 μL, 2.19 mM) were added to the suspension. This suspension was stirred at 150° C. for 20 minutes under the irradiation with microwaves. This reaction liquid was diluted with a saturated aqueous common salt solution and then extracted with ethyl acetate. The extracts thus obtained were combined together and then dried over anhydrous sodium sulfate and the solvent was distilled off. The resulting residue was suspended in ethanol (2 mL), then acetic acid (5.0 μL, 0.087 mM) and 3-methyl-benzaldehyde (25.4 μL, 0.219 mM) were added to the suspension and the mixture was stirred at room temperature for one hour. This reaction mixture was filtered and the resulting solid was purified by the NH-silica gel column chromatography (methylene chloride) to give the title compound (11.2 mg, overall yield of these two steps: 12%).

$^1$H-NMR (300 MHz, DMSO): δ 2.34 (s, 3H), 2.52 (s, 3H), 3.71-3.72 (m, 4H), 3.82-3.84 (m, 4H), 6.31 (s, 1H), 6.35 (s, 1H), 7.17 (m, 1H), 7.25-7.33 (m, 4H), 7.47 (m, 1H), 7.52 (m, 1H), 7.65 (m, 1H), 8.03 (s, 1H), 11.18 (s, 1H); MS (ESI) m/z 427 (M+H)$^+$.

Example 15

Synthesis of N-{2-(4-methoxy-phenyl)-7-morpholin-4-yl-pyrazolo[1,5-a]pyrimidin-5-yl}-N'-(3-methyl-benzylidene)-hydrazine (Compound 15)

(Step 1): 5,7-Dichloro-2-(4-methoxy-phenyl)-pyrazolo[1,5-a]pyrimidine

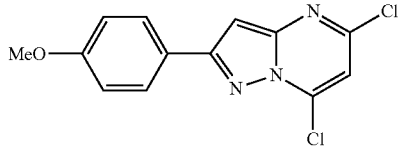

There was dissolved, in ethanol (5 mL), 3-amino-5-(4-methoxy-phenyl)-pyrazole (500 mg, 2.64 mM) and then sodium ethoxide (2M ethanol solution, 2.64 mL, 5.28 mM) and diethyl malonate (441 μL, 2.90 mM) were added to the solution. This reaction liquid was stirred at 150° C. for 50 minutes under the irradiation with microwaves, then sodium ethoxide (2M ethanol solution, 1.00 mL, 2.00 mM) and diethyl malonate (200 μL, 1.32 mM) were added to the liquid and the mixture was stirred at 150° C. for 50 minutes under the irradiation with microwaves. This reaction mixture was filtered to obtain a solid. Phosphoryl chloride (5 mL) was added to the resulting solid with ice-cooling and then the suspension was stirred for 5 hours, while refluxing the same with heating. The phosphoryl chloride was distilled off from the reaction liquid, ethanol was added to the resulting residue with ice-cooling and then the mixture was stirred for 15 minutes. After the concentration of the reaction liquid, the resulting concentrate was purified by the silica gel column chromatography (methylene chloride) to give the title compound (415 mg, overall yield of these two steps: 53%).

$^1$H-NMR (300 MHz, CDCl$_3$): δ 3.87 (s, 3H), 6.92 (2s, each 1H), 7.00 (d, 2H, J=9.1 Hz), 7.95 (d, 2H, J=9.1 Hz); MS (ESI) m/z 294 (M+H)$^+$.

(Step 2): 5-Chloro-2-(4-methoxy-phenyl)-7-morpholin-4-yl-pyrazolo[1,5-a]pyrimidine

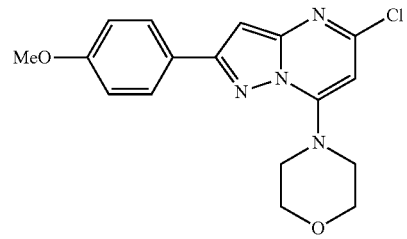

There was dissolved, in 1,4-dioxane (5 mL), 5,7-dichloro-2-(4-methoxy-phenyl)-pyrazolo[1,5-a]pyrimidine (202 mg, 0.688 mM), then morpholine (120 μL, 1.38 mM) was added to the solution and the mixture was stirred at room temperature for one hour. The solvent was distilled off from this reaction mixture, the resulting residue was diluted with water and then extracted with methylene chloride. The extracts thus obtained were combined together and then dried over anhydrous sodium sulfate, the solvent was distilled off and the resulting solid was washed with methanol to give the title compound (235 mg, yield: 99%).

$^1$H-NMR (300 MHz, CDCl$_3$): δ 3.84-3.87 (m, 4H), 3.87 (s, 3H), 3.98-4.01 (m, 4H), 6.05 (s, 1H), 6.71 (s, 1H), 6.98 (d, 2H, J=8.8 Hz), 7.88 (d, 2H, J=8.8 Hz); MS (ESI) m/z 345 (M+H)$^+$.

(Step 3): N-{2-(4-methoxy-phenyl)-7-morpholin-4-yl-pyrazolo[1,5-a]pyrimidin-5-yl}-N'-(3-methyl-benzylidene)-hydrazine (Compound 15)

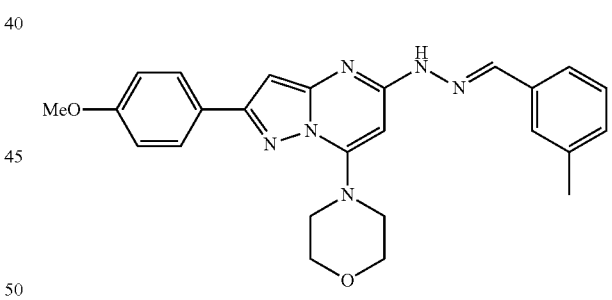

There was suspended, in ethanol (2 mL), 5-chloro-2-(4-methoxy-phenyl)-7-morpholin-4-yl-pyrazolo[1,5-a]pyrimidine (64.8 mg, 0.188 mM) and then potassium carbonate (28.6 mg, 0.198 mM) and hydrazine monohydrate (91.2 μL, 1.88 mM) were added to the suspension. This suspension was stirred at 150° C. for 25 minutes under the irradiation with microwaves. This reaction liquid was diluted with a saturated aqueous common salt solution and then extracted with ethyl acetate. The extracts thus obtained were combined, dried over anhydrous sodium sulfate and the solvent was then distilled off. The resulting residue was suspended in ethanol (2 mL), then acetic acid (5.0 μL, 0.087 mM) and 3-methyl-benzaldehyde (22.1 μL, 0.188 mM) were added to the suspension and the mixture was stirred at room temperature for one hour. This reaction mixture was filtered and the resulting solid was purified by the NH-silica gel column chromatography (methylene chloride) to thus give the title compound (54.6 mg, overall yield of these two steps: 66%).

$^1$H-NMR (300 MHz, DMSO): δ 2.34 (s, 3H), 3.72-3.73 (m, 4H), 3.79 (s, 3H), 3.85-3.87 (m, 4H), 6.27 (s, 1H), 6.46 (s, 1H), 7.00 (d, 2H, J=8.8 Hz), 7.17 (m, 1H), 7.31 (m, 1H), 7.46 (m, 1H), 7.51 (m, 1H), 7.87 (d, 2H, J=8.8 Hz), 8.02 (s, 1H), 11.16 (s, 1H); MS (ESI) m/z 443 (M+H)$^+$.

Example 16

Synthesis of N-{2-(4-bromo-phenyl)-7-morpholin-4-yl-pyrazolo[1,5-a]-pyrimidin-5-yl}-N'-(3-methyl-benzylidene)-hydrazine (Compound 16)

(Step 1): 2-(4-Bromo-phenyl)-5,7-dichloro-pyrazolo[1,5-a]pyrimidine

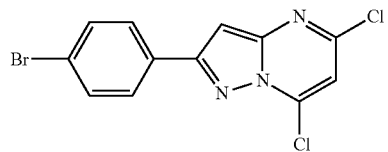

There was dissolved, in ethanol (5 mL), 3-amino-5-(4-bromo-phenyl)-pyrazole (500 mg, 2.10 mM) and then sodium ethoxide (2M ethanol solution, 2.10 mL, 4.20 mM) and diethyl malonate (351 μL, 2.31 mM) were added to the solution. This reaction liquid was stirred at 150° C. for 50 minutes under the irradiation with microwaves. This reaction mixture was filtered and the solid thus obtained was washed with diethyl ether. After the addition of phosphoryl chloride (5 mL) to the resulting solid with ice-cooling, the suspension was stirred for 7 hours while refluxing the same with heating. The phosphoryl chloride was distilled off from the reaction liquid, ethanol was added to the resulting residue with ice-cooling and the mixture was then stirred for 15 minutes. After the concentration of the reaction liquid, the resulting concentrate was purified by the silica gel column chromatography (methylene chloride) to thus give the title compound (315 mg, overall yield of these two steps: 44%).

$^1$H-NMR (300 MHz, CDCl$_3$): δ 6.97 (s, 1H), 6.97 (s, 1H), 7.61 (d, 2H, J=8.5 Hz), 7.88 (d, 2H, J=8.5 Hz); MS (ESI) m/z 344 (M+H)$^+$.

(Step 2): 2-(4-Bromo-phenyl)-5-chloro-7-morpholin-4-yl-pyrazolo[1,5-a]pyrimidine

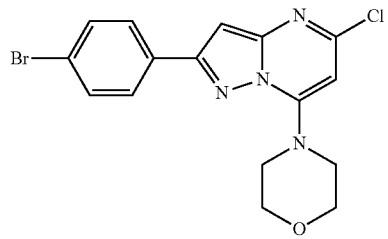

There was dissolved, in 1,4-dioxane (5 mL), 2-(4-bromo-phenyl)-5,7-dichloro-pyrazolo[1,5-a]pyrimidine (217 mg, 0.633 mM), then morpholine (110 μL, 1.27 mM) was added to the solution and the mixture was stirred at room temperature for one hour. The solvent was distilled off from this reaction mixture and the residue thus obtained was diluted with water and then extracted with methylene chloride. The extracts obtained were combined together, dried over anhydrous sodium sulfate, the solvent was distilled off and then the resulting solid was washed with methanol to thus give the title compound (240 mg, yield: 96%).

$^1$H-NMR (300 MHz, CDCl$_3$): δ 3.83-3.87 (m, 4H), 3.98-4.01 (m, 4H), 6.09 (s, 1H), 6.76 (s, 1H), 7.58 (d, 2H, J=8.6 Hz), 7.81 (d, 2H, J=8.6 Hz); MS (ESI) m/z 395 (M+H)$^+$.

(Step 3): N-{2-(4-Bromo-phenyl)-7-morpholin-4-yl-pyrazolo[1,5-a]-pyrimidin-5-yl}-N'-(3-methyl-benzylidene)-hydrazine (Compound 16)

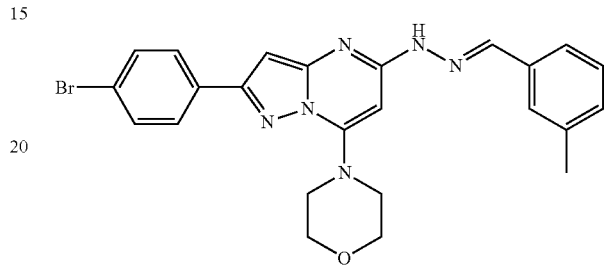

There was suspended, in ethanol (2 mL), 2-(4-bromo-phenyl)-5-chloro-7-morpholin-4-yl-pyrazolo[1,5-a]pyrimidine (59.3 mg, 0.179 mM) and then potassium carbonate (27.2 mg, 0.197 mM) and hydrazine monohydrate (86.8 μL, 1.79 mM) were added to the suspension. This suspension was stirred at 150° C. for 20 minutes under the irradiation with microwaves. This reaction liquid was diluted with a saturated aqueous common salt solution and then extracted with ethyl acetate. The extracts thus obtained were combined together, dried over anhydrous sodium sulfate and the solvent was then distilled off. The resulting residue was suspended in ethanol (2 mL), then acetic acid (5.0 μL, 0.087 mM) and 3-methyl-benzaldehyde (21.1 μL, 0.179 mM) were added to the suspension and the mixture was stirred at room temperature for one hour. This reaction mixture was filtered and the resulting solid was purified by the NH-silica gel column chromatography (methylene chloride) to thus give the title compound (30.7 mg, overall yield of these two steps: 35%).

$^1$H-NMR (300 MHz, DMSO): δ 2.34 (s, 3H), 3.71-3.73 (m, 4H), 3.85-3.87 (m, 4H), 6.31 (s, 1H), 6.59 (s, 1H), 7.17 (m, 1H), 7.31 (m, 1H), 7.47 (m, 1H), 7.52 (m, 1H), 7.64 (d, 2H, J=8.4 Hz), 7.90 (d, 2H, J=8.4 Hz), 8.03 (s, 1H), 11.20 (s, 1H); MS (ESI) m/z 491 (M+H)$^+$.

Example 17

Synthesis of N-(3-methyl-benzylidene)-N'-{7-morpholin-4-yl-2-(4-morpholin-4-yl-phenyl)-pyrazolo[1,5-a]pyrimidin-5-yl}-hydrazine (Compound 17)

(Step 1): 5-Chloro-7-morpholin-4-yl-2-(4-morpholin-4-yl-phenyl)-pyrazolo[1,5-a]-pyrimidine

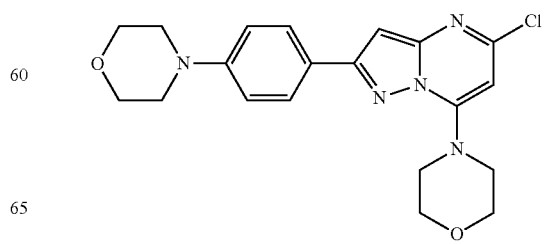

There was dissolved, in toluene (2 mL), 2-(4-bromo-phenyl)-5-chloro-7-morpholin-4-yl-pyrazolo[1,5-a]pyrimidine (41.7 mg, 0.106 mM) in an argon gas atmosphere and then there were added, to the resulting solution, sodium t-butoxide (15.3 mg, 0.159 mM), tris(dibenzylidene acetone) di-palladium (4.9 mg, 0.0053 mM), 2-biphenyl-di-t-butyl phosphine (4.7 mg, 0.016 mM) and morpholine (13.9 μL, 0.159 mM), followed by the stirring of the resulting mixture at 70° C. for 3 hours and the further stirring of the same at 90° C. for one hour. This reaction liquid was diluted with water and then extracted with ethyl acetate. The extracts thus obtained were combined, they were dried over anhydrous sodium sulfate, the solvent was distilled off and the resulting residue was purified by the silica gel column chromatography (ethyl acetate/hexane=1:4) to thus give the title compound (15.6 mg, yield: 39%).

$^1$H-NMR (300 MHz, CDCl$_3$): δ 3.22-3.25 (m, 4H), 3.83-3.90 (m, 8H), 6.03 (s, 1H), 6.70 (s, 1H), 6.97 (d, 2H, J=8.8 Hz), 7.85 (d, 2H, J=8.8 Hz); MS (ESI) m/z 400 (M+H)$^+$.

(Step 2): N-(3-methyl-benzylidene)-N'-{7-morpholin-4-yl-2-(4-morpholin-4-yl-phenyl)-pyrazolo[1,5-a]pyrimidin-5-yl}-hydrazine (Compound 17)

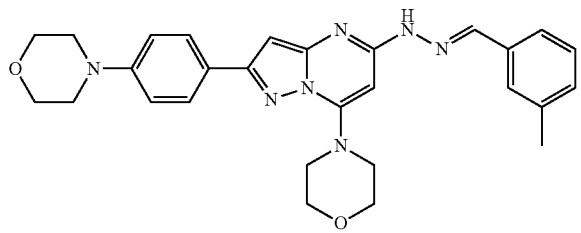

There was suspended, in ethanol (2 mL), 5-chloro-7-morpholin-4-yl-2-(4-morpholin-4-yl-phenyl)-pyrazolo[1,5-a]-pyrimidine (36.3 mg, 0.0908 mM) and then potassium carbonate (13.8 mg, 0.0999 mM) and hydrazine monohydrate (44.0 μL, 0.908 mM) were added to the suspension. This suspension was stirred at 150° C. for 20 minutes under the irradiation with microwaves. This reaction liquid was diluted with a saturated aqueous common salt solution and then extracted with ethyl acetate. The extracts thus obtained were combined, dried over anhydrous sodium sulfate and then the solvent was distilled off. The resulting residue was suspended in ethanol (2 mL), then acetic acid (5.0 μL, 0.087 mM) and 3-methyl-benzaldehyde (10.7 μL, 0.0908 mM) were added to the suspension and the mixture was stirred at room temperature for one hour. This reaction mixture was filtered and the resulting solid was purified by the NH-silica gel column chromatography (methylene chloride) to give the title compound (23.8 mg, overall yield of these two steps: 49%).

$^1$H-NMR (300 MHz, DMSO): δ 2.34 (s, 3H), 3.14-3.17 (m, 4H), 3.70-3.76 (m, 8H), 3.85-3.88 (m, 4H), 6.26 (s, 1H), 6.42 (s, 1H), 7.00 (d, 2H, J=8.8 Hz), 7.17 (m, 1H), 7.30 (m, 1H), 7.46 (m, 1H), 7.51 (m, 1H), 7.79 (d, 2H, J=8.8 Hz), 8.01 (s, 1H), 11.13 (s, 1H); MS (ESI) m/z 498 (M+H)$^+$.

Example 18

Synthesis of N-(3-methyl-benzylidene)-N'-(7-morpholin-4-yl-2-thiophen-2-yl-pyrazolo[1,5-a]pyrimidin-5-yl)-hydrazine (Compound 18)

(Step 1): 5,7-Dichloro-2-thiophen-2-yl-pyrazolo[1,5-a]pyrimidine

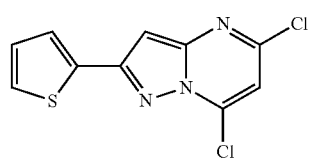

There was dissolved, in ethanol (5 mL), 3-amino-5-thiophen-2-yl-pyrazole (500 mg. 3.03 mM) and then sodium ethoxide (2M ethanol solution, 3.03 mL, 6.06 mM) and diethyl malonate (552 μL, 3.64 mM) were added to the solution. This reaction liquid was stirred at 150° C. for 50 minutes under the irradiation with microwaves. This reaction mixture was filtered and the resulting solid was washed with diethyl ether. After the addition of phosphoryl chloride (5 mL) to the resulting solid with ice-cooling, the resulting suspension was stirred for 2 hours, while refluxing the same with heating. The phosphoryl chloride was distilled off from the reaction liquid, ethanol was then added to the resulting residue with ice-cooling and the mixture was stirred for 15 minutes. After the concentration of the reaction liquid, the resulting concentrate was purified by the silica gel column chromatography (ethyl acetate/hexane=1:10) to thus give the title compound (378 mg, overall yield of these two steps: 46%).

$^1$H-NMR (300 MHz, CDCl$_3$): δ 6.88 (s, 1H), 6.93 (s, 1H), 7.14 (dd, 1H, J=3.5, 5.0 Hz), 7.43 (dd, 1H, J=1.2, 5.0 Hz), 7.61 (dd, 1H, J=1.2, 3.5 Hz); MS (ESI) m/z 266 (M+H)$^+$.

(Step 2): 5-Chloro-7-morpholin-4-yl-2-thiophen-2-yl-pyrazolo[1,5-a]pyrimidine

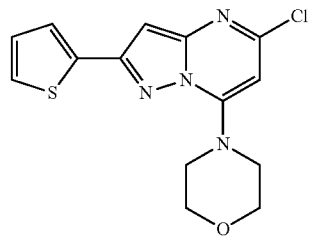

There was dissolved, in 1,4-dioxane (4 mL), 5,7-dichloro-2-thiophen-2-yl-pyrazolo[1,5-a]pyrimidine (184 mg, 0.679 mM), then morpholine (118 μL, 1.36 mM) was added to the solution and the mixture was stirred at room temperature for 2 hours. The solvent was distilled off from the reaction mixture, the residue was diluted with water and then extracted with methylene chloride. The extracts thus obtained were combined, dried over anhydrous sodium sulfate, the solvent was then distilled off and the resulting solid was washed with methanol to thus give the title compound (114 mg, yield: 52%).

¹H-NMR (300 MHz, CDCl₃): δ 3.82-3.85 (m, 4H), 3.96-4.00 (m, 4H), 6.05 (s, 1), 6.67 (s, 1H), 7.11 (dd, 1H, J=3.5, 5.0 Hz), 7.36 (dd, 1H, J=1.2, 5.0 Hz), 7.52 (dd, 1H, J=1.2, 3.5 Hz); MS (ESI) m/z 321 (M+H)⁺.

(Step 3): N-(3-methyl-benzylidene)-N'-(7-morpholin-4-yl-2-thiophen-2-yl-pyrazolo-[1,5-a]pyrimidin-5-yl)-hydrazine (Compound 18)

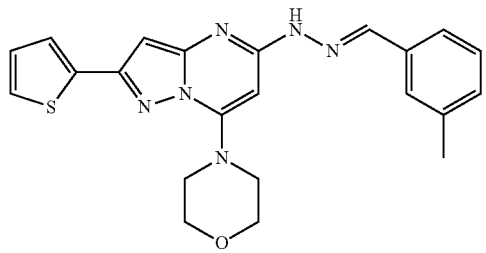

There was suspended, in ethanol (2 mL), 5-chloro-7-morpholin-4-yl-2-thiophen-2-yl-pyrazolo[1,5-a]pyrimidine (52.7 mg, 0.164 mM) and then potassium carbonate (24.9 mg, 0.180 mM) and hydrazine monohydrate (79.6 μL, 1.64 mM) were added to the suspension. This suspension was stirred at 150° C. for 20 minutes under the irradiation with microwaves. This reaction liquid was diluted with a saturated aqueous common salt solution and then extracted with ethyl acetate. The extracts thus obtained were combined, dried over anhydrous sodium sulfate and then the solvent was distilled off. The resulting residue was suspended in ethanol (2 mL), then acetic acid (5.0 μL, 0.087 mM) and 3-methyl-benzaldehyde (19.3 μL, 0.179 mM) were added to the suspension and the mixture was stirred at room temperature for one hour. The reaction mixture was filtered and the resulting solid was purified by the NH-silica gel column chromatography (methylene chloride) and the resulting solid was washed with methanol to thus give the title compound (41.4 mg, overall yield of these two steps: 60%).

¹H-NMR (300 MHz, DMSO): δ 2.34 (s, 3H), 3.67-3.70 (m, 4H), 3.84-3.87 (m, 4H), 6.29 (s, 1H), 6.43 (s, 1H), 7.13 (dd, 1H, J=3.5, 5.0 Hz), 7.17 (m, 1H), 7.31 (m, 1H), 7.46 (m, 1H), 7.52 (m, 1H), 7.54 (dd, 1H, J=0.9, 5.0 Hz), 7.57 (dd, 1H, J=0.9, 3.5 Hz), 8.02 (s, 1H), 11.21 (s, 1H); MS (ESI) m/z 419 (M+H)⁺.

Example 19

Synthesis of N[2-{4-(4-t-butoxycarbonyl-piperazin-1-yl)-phenyl}-7-morpholin-4-yl-pyrazolo[1,5-a]pyrimidin-5-yl]-N'-(3-methyl-benzylidene)-hydrazine (Compound 19)

(Step 1): 2-{4-(4-t-Butoxycarbonyl-piperazin-1-yl)-phenyl}-5-chloro-7-morpholin-4-yl-pyrazolo[1,5-a]pyrimidine

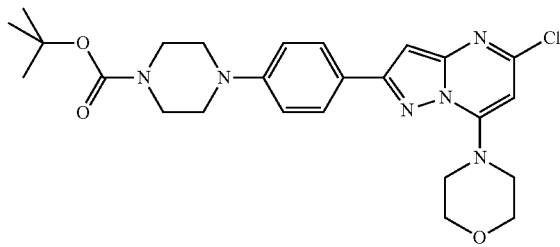

There was dissolved, in toluene (3 mL), 2-(4-bromo-phenyl)-5-chloro-7-morpholin-4-yl-pyrazolo[1,5-a]pyrimidine (56.2 mg, 0.143 mM) in an argon gas atmosphere, then there were added, to the resulting solution, a solution of sodium t-butoxide (20.6 mg, 0.215 mM), tris(dibenzylidene acetone) di-palladium (7.2 mg, 0.0079 mM) and tri-t-butyl phosphine (4.7 μL, 0.023 mM) in toluene (0.30 mL) and t-butyl 1-piperazine carboxylate (39.9 mg, 0.215 mM) and the resulting mixture was stirred at 90° C. for 30 minutes. This reaction liquid was diluted with a saturated aqueous common salt solution and then extracted with ethyl acetate. The extracts thus obtained were combined, dried over anhydrous sodium sulfate, then the solvent was distilled off and the resulting residue was purified by the silica gel column chromatography (ethyl acetate/hexane=1:3) to thus give the title compound (40.5 mg, yield: 57%).

¹H-NMR (300 MHz, CDCl₃): δ 1.41 (3s, each 3H), 3.20-3.24 (m, 4H), 3.58-3.62 (m, 4H), 3.83-3.86 (m, 4H), 3.97-4.00 (m, 4H), 6.03 (s, 1H), 6.69 (s, 1H), 6.97 (d, 2H, J=8.8 Hz), 7.84 (d, 2H, J=8.8 Hz); MS (ESI) m/z 499 (M+H)⁺.

(Step 2): N-[2-{4-(4-t-butoxycarbonyl-piperazin-1-yl)-phenyl}-7-morpholin-4-yl-pyrazolo[1,5-a]pyrimidin-5-yl]-N'-(3-methyl-benzylidene)-hydrazine (Compound 19)

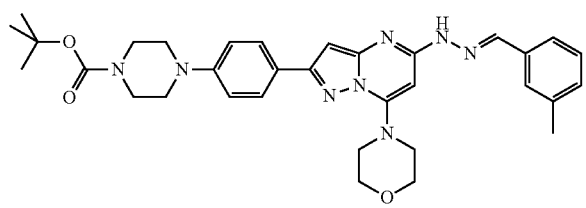

There was suspended, in ethanol (2 mL), 2-{4-(4-t-butoxycarbonyl-piperazin-1-yl)-phenyl}-5-chloro-7-morpholin-4-yl-pyrazolo[1,5-a]pyrimidine (33.7 mg, 0.0675 mM) and then potassium carbonate (10.3 mg, 0.743 mM) and hydrazine mono-hydrate (33.0 μL, 0.675 mM) were added to the suspension. This suspension was stirred at 150° C. for 35 minutes under the irradiation with microwaves. This reaction liquid was diluted with a saturated aqueous common salt solution and then extracted with ethyl acetate. The extracts thus obtained were combined, dried over anhydrous sodium sulfate and the solvent was distilled off.

The resulting residue was suspended in ethanol (2 mL), acetic acid (5.0 μL, 0.087 mM) and 3-methyl-benzaldehyde (8.0 μL, 0.068 mM) were added to the suspension and the mixture was then stirred at room temperature for one hour. This reaction mixture was filtered and the resulting solid was washed with methanol to thus give the title compound (14.1 mg, overall yield of these two steps: 35%).

¹H-NMR (300 MHz, DMSO): δ 1.41 (3s, each 3H), 2.34 (s, 3H), 3.15-3.18 (m, 4H), 3.44-3.48 (m, 4H), 3.70-3.74 (m, 4H), 3.84-3.88 (m, 4H), 6.26 (s, 1H), 6.42 (s, 1H), 7.01 (d, 2H, J=8.8 Hz), 7.17 (m, 1H), 7.30 (m, 1H), 7.46 (m, 1H), 7.51 (m, 1H), 7.89 (d, 2H, J=8.8 Hz), 8.01 (s, 1H), 11.13 (s, 1H); MS (ESI) m/z 597 (M+H)⁺.

Example 20

Synthesis of N-(3-methyl-benzylidene)-N'-(7-morpholin-4-yl-2-pyridin-2-yl-pyrazolo[1,5-a]pyrimidin-5-yl)-hydrazine (Compound 20)

(Step 1): 5,7-Dichloro-2-pyridin-2-yl-pyrazolo[1,5-a]pyrimidine

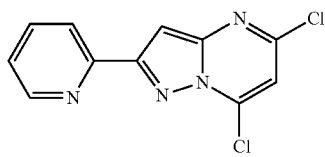

There were dissolved, in ethanol (10 mL), 3-oxo-3-pyridin-2-yl-propane-nitrile (500 mg, 3.42 mM) and hydrazine monohydrate (199 μL, 4.10 mM) and the solution was stirred at 150° C. for 10 minutes under the irradiation with microwaves. The solvent was distilled off from this reaction liquid, the resulting residue was dissolved in ethanol (8 mL) and then sodium ethoxide (2M ethanol solution, 3.76 mL, 7.52 mM) and diethyl malonate (623 μL, 4.10 mM) were added to the solution. This reaction liquid was stirred at 150° C. for 50 minutes under the irradiation with microwaves. This reaction mixture was filtered and the resulting solid was washed with diethyl ether. Phosphoryl chloride (5 mL) was added to the resulting solid and the resulting suspension was stirred for 2 hours while refluxing the same with heating. The phosphoryl chloride was distilled off from this reaction liquid, ethanol was then added to the residue with ice-cooling and the mixture was stirred for 15 minutes. After the concentration of the reaction liquid, the resulting concentrate was purified by the silica gel column chromatography (methanol/methylene chloride=1:50 to 1:5) to thus give the title compound (378 mg, overall yield of these three steps: 34%).

$^1$H-NMR (300 MHz, CD$_3$OD): δ 7.62 (s, 1H), 7.65 (s, 1H), 8.10 (m, 1H), 8.72-8.74 (m, 2H), 8.89 (m, 1H); MS (ESI) m/z 265 (M+H)$^+$.

(Step 2): 5-Chloro-7-morpholin-4-yl-2-pyridin-2-yl-pyrazolo[1,5-a]pyrimidine

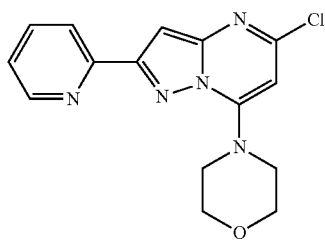

There was suspended, in 1,4-dioxane (5 mL), 5,7-dichloro-2-pyridin-2-yl-pyrazolo[1,5-a]pyrimidine (348 mg, 1.31 mM), then morpholine (230 μL, 2.64 mM) was added to the suspension and the mixture was stirred at room temperature for 20 minutes. The solvent was distilled off from the reaction mixture, the residue obtained was diluted with water and then extracted with ethyl acetate. The extracts thus obtained were combined, dried over anhydrous sodium sulfate, the solvent was distilled off and the resulting solid was washed with diethyl ether to thus give the title compound (312 mg, yield: 75%). $^1$H-NMR (300 MHz, CDCl$_3$): δ 3.84-3.87 (m, 4H), 3.99-4.02 (m, 4H), 6.12 (s, 1H), 7.16 (s, 1H), 7.30 (ddd, 1H, J=1.2, 5.0, 7.7 Hz), 7.78 (dt, 1H, J=1.8, 7.7 Hz), 8.11 (d, 1H, J=7.7 Hz), 8.70 (m, 1H); MS (ESI) m/z 316 (M+H)$^+$.

(Step 3): N-(3-Methyl-benzylidene)-N'-(7-morpholin-4-yl-2-pyridin-2-yl-pyrazolo-[1,5-a]pyrimidin-5-yl)-hydrazine (Compound 20)

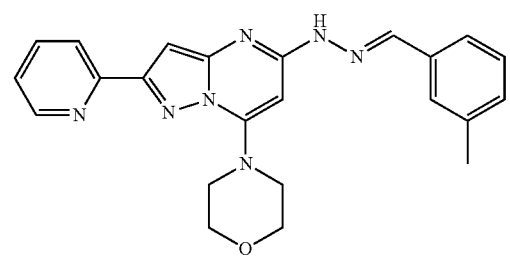

There was suspended, in ethanol (2 mL), 5-chloro-7-morpholin-4-yl-2-pyridin-2-yl-pyrazolo[1,5-a]pyrimidine (53.1 mg, 0.168 mM) and then potassium carbonate (25.5 mg, 0.185 mM) and hydrazine monohydrate (81.5 μL, 1.68 mM) were added to the suspension. This suspension was stirred at 150° C. for 20 minutes under the irradiation with microwaves. This reaction liquid was diluted with a saturated aqueous common salt solution and then extracted with ethyl acetate. The extracts thus obtained were combined, dried over anhydrous sodium sulfate and then the solvent was distilled off. The resulting residue was suspended in ethanol (2 mL), then acetic acid (5.0 μL, 0.087 mM) and 3-methyl-benzaldehyde (19.8 μL, 0.168 mM) were added to the suspension and the mixture was stirred at room temperature for 30 minutes. This reaction mixture was filtered and the resulting solid was purified by the NH-silica gel column chromatography (methanol/methylene chloride=1:50 to 1:20) to thus give the title compound (21.3 mg, overall yield of these two steps: 31%).

$^1$H-NMR (300 MHz, DMSO): δ 2.34 (s, 3H), 3.72-3.74 (m, 4H), 3.87-3.90 (m, 4H), 6.35 (s, 1H), 6.60 (s, 1H), 7.18 (m, 1H), 7.31 (m, 1H), 7.48 (m, 1H), 7.52 (m, 1H), 7.88 (dt, 1H, J=1.8, 7.9 Hz), 8.02 (s, 1H), 8.08 (m, 1H), 8.73 (m, 1H), 11.24 (s, 1H); MS (ESI) m/z 414 (M+H)$^+$.

Example 21

Synthesis of N-(3-methyl-benzylidene)-N'-{7-morpholin-4-yl-2-(4-piperazin-1-yl-phenyl)-pyrazolo[1,5-a]pyrimidin-5-yl}-hydrazine (Compound 21)

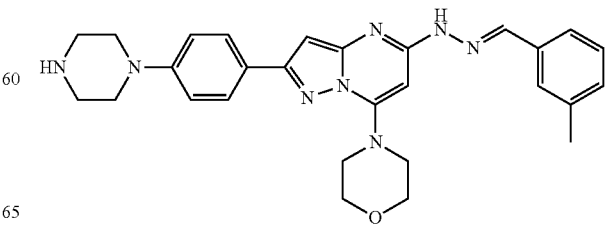

There was dissolved, in methylene chloride (1 mL), N[2-{4-(4-t-butoxy-carbonyl-piperazin-1-yl)-phenyl}-7-morpholin-4-yl-pyrazolo[1,5-a]pyrimidin-5-yl]-N'-(3-methyl-benzylidene)-hydrazine (44.4 mg, 0.0744 mM), then trifluoroacetic acid (TFA, 1 mL) was added to the solution and the mixture was stirred at room temperature for 20 minutes. This reaction liquid was concentrated and the resulting residue was purified by the reversed phase HPLC (C-18 ODS Column) to thus give the trifluoroacetic acid salt of the title compound (38.1 mg, yield: 71%).

$^1$H-NMR (300 MHz, DMSO): δ2.35 (s, 3H), 3.22-3.28 (m, 4H), 3.40-3.44 (m, 4H), 3.74-3.78 (m, 4H), 3.84-3.88 (m, 4H), 6.19 (br, 1H), 6.49 (s, 1H), 7.06 (d, 2H, J=8.8 Hz), 7.19 (m, 1H), 7.32 (m, 1H), 7.54 (m, 1H), 7.83 (d, 2H, J=8.8 Hz), 8.05 (s, 1H), 8.73 (br, 2H), 11.32 (br, 1H); MS (ESI) m/z 497 (M+H)$^+$.

Example 22

Synthesis of N-[2-{4-(4-acetyl-piperazin-1-yl)-phenyl}-7-morpholin-4-yl-pyrazolo[1,5-a]pyrimidin-5-yl]-N'-(3-methyl-benzylidene)-hydrazine (Compound 22)

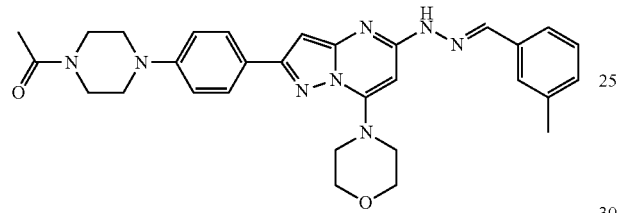

There was dissolved, in methylene chloride (0.75 mL), N[2-{4-(4-t-butoxy-carbonyl-piperazin-1-yl)-phenyl}-7-morpholin-4-yl-pyrazolo[1,5-a]pyrimidin-5-yl]-N'-(3-methyl-benzylidene)-hydrazine (23.8 mg, 0.0399 mM), then trifluoroacetic acid (0.75 mL) was added to the solution and the mixture was stirred at room temperature for one hour. This reaction liquid was concentrated, the resulting residue was dissolved in pyridine (0.75 mL) and acetic anhydride (0.75 mL) was added to the solution. After stirring this reaction liquid at room temperature for one hour, the liquid was then concentrated and the resulting residue was purified by the reversed phase HPLC to thus give the trifluoroacetic acid salt of the title compound (9.1 mg, yield: 30%).

$^1$H-NMR (300 MHz, DMSO): δ 2.04 (s, 3H), 2.35 (s, 3H), 3.18-3.24 (m, 4H), 3.56-3.58 (m, 4H), 3.80-3.88 (m, 8H), 6.07 (br, 1H), 6.53 (s, 1H), 7.03 (d, 2H, J=8.8 Hz), 7.22 (m, 1H), 7.34 (m, 1H), 7.56-7.62 (m, 2H), 7.80 (d, 2H, J=8.8 Hz), 8.09 (s, 1H); MS (ESI) m/z 539 (M+H)$^+$.

Example 23

Synthesis of N-{2-(4-diethyl-amino-phenyl)-7-morpholin-4-yl-pyrazolo-[1,5-a]pyrimidin-5-yl}-N'-(3-methyl-benzylidene)-hydrazine (Compound 23)

(Step 1): 2-(4-Diethyl-amino-phenyl)-5-chloro-7-morpholin-4-yl-pyrazolo[1,5-a]-pyrimidine

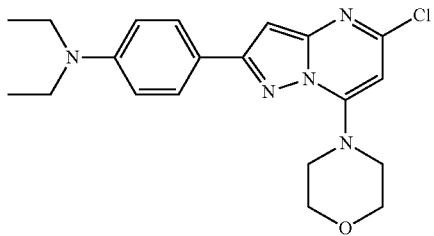

There was dissolved, in toluene (3 mL), 2-(4-bromo-phenyl)-5-chloro-7-morpholin-4-yl-pyrazolo[1,5-a]pyrimidine (69.2 mg, 0.176 mM) in an argon gas atmosphere, then there were added, to the resulting solution, a solution of sodium t-butoxide (40.6 mg, 0.442 mM), tris(dibenzylidene acetone) di-palladium (8.1 mg, 0.0088 mM) and tri-t-butyl phosphine (12.8 μL, 0.0528 mM) in toluene (0.30 mL) and diethylamine hydrochloride (23.1 mg, 0.211 mM) and the resulting mixture was stirred at 80° C. for 4 hours and a half. This reaction liquid was diluted with a saturated aqueous common salt solution and then extracted with ethyl acetate.

The extracts thus obtained were combined, dried over anhydrous sodium sulfate, then the solvent was distilled off and the resulting residue was purified by the reversed phase HPLC to thus give the trifluoroacetic acid salt of the title compound (31.9 mg, yield: 32%).

$^1$H-NMR (300 MHz, CDCl$_3$): δ 1.18 (2t, each 3H, J=7.2 Hz), 3.56 (2q, each 2H, J=7.2 Hz), 3.84-3.87 (m, 4H), 3.98-4.01 (m, 4H), 6.11 (s, 1H), 6.80 (s, 1H), 7.53 (d, 2H, J=8.8 Hz), 8.06 (d, 2H, J=8.8 Hz); MS (ESI) m/z 386 (M+H)$^+$.

(Step 2): N-{2-(4-diethyl-amino-phenyl)-7-morpholin-4-yl-pyrazolo[1,5-a]pyrimidin-5-yl}-N'-(3-methyl-benzylidene)-hydrazine (Compound 23)

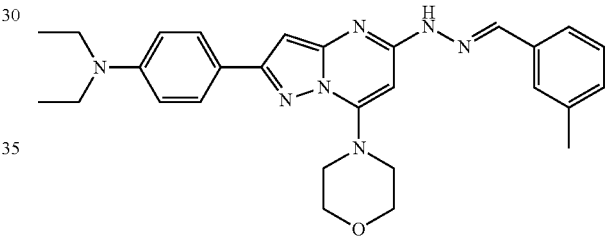

There was suspended, in ethanol (2 mL), trifluoroacetic acid salt of 2-(4-diethyl-amino-phenyl)-5-chloro-7-morpholin-4-yl-pyrazolo[1,5-a]-pyrimidine (24.3 mg, 0.0396 mM) and then potassium carbonate (6.0 mg, 0.044 mM9 and hydrazine monohydrate (19.2 μL, 0.396 mM) were added to the suspension. After this suspension was stirred at 150° C. for 20 minutes under the irradiation with microwaves, hydrazine monohydrate (19.2 μL, 0.396 mM) was added thereto, and then the mixture was stirred at 150° C. for 20 minutes under the irradiation with microwaves. This reaction liquid was diluted with a saturated aqueous common salt solution and then extracted with ethyl acetate. The extracts thus obtained were combined, dried over anhydrous sodium sulfate and then the solvent was distilled off. The resulting residue was suspended in ethanol (2 mL), then acetic acid (5.0 μL, 0.087 mM) and 3-methyl-benzaldehyde (4.7 μL, 0.040 mM) were added to suspension and the mixture was stirred at room temperature for 20 minutes. This reaction mixture was filtered, the resulting solid was washed with methanol to thus give the title compound (13.2 mg. overall yield of these two steps: 69%).

$^1$H-NMR (300 MHz, DMSO): δ 1.10 (2t, each 3H, J=7.0 Hz), 2.34 (s, 3H), 3.36 (2q, each 2H, J=7.0 Hz), 3.70-3.73 (m, 4H), 3.85-3.88 (m, 4H), 6.23 (s, 1H), 6.33 (s, 1H), 6.70 (d, 2H, J=8.8 Hz), 7.16 (m, 1H), 7.30 (m, 1H), 7.46 (m, 1H), 7.51 (m, 1H), 7.71 (d, 2H, J=8.8 Hz), 8.01 (s, 1H), 11.10 (s, 1H); MS (ESI) m/z 484 (M+H)$^+$.

Example 24

Synthesis of N-[2-{4-(2-methoxy-ethyl-amino)-phenyl}-7-morpholin-4-yl-pyrazolo[1,5-a]pyrimidin-5-yl]-N'-(3-methyl-benzylidene)-hydrazine (Compound 24)

(Step 1): 5-Chloro-2-{4-(2-methoxy-ethyl-amino)-phenyl}-7-morpholin-4-yl-pyrazolo-[1,5-a]pyrimidine

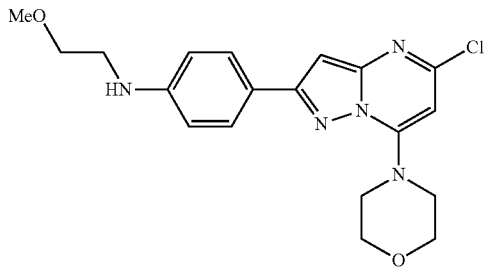

There was dissolved, in toluene (3 mL), 2-(4-bromo-phenyl)-5-chloro-7-morpholin-4-yl-pyrazolo[1,5-a]pyrimidine (59.3 mg, 0.151 mM) in an argon gas atmosphere, then there were added, to the resulting solution, a solution of sodium t-butoxide (58.0 mg, 0.604 mM), tris(dibenzylidene acetone) di-palladium (6.9 mg, 0.0076 mM) and tri-t-butyl phosphine (11.0 μL, 0.0453 mM) in toluene (0.556 mL) and 2-methoxy-ethylamine (26.3 μL, 0.302 mM) and the resulting mixture was stirred at 80° C. for 4 hours and a half. This reaction liquid was diluted with a saturated aqueous common salt solution and then extracted with ethyl acetate. The extracts thus obtained were combined, dried over anhydrous sodium sulfate, then the solvent was distilled off and the resulting residue was purified by the silica gel column chromatography (ethyl acetate//hexane=1:4 to 2:3) to thus give the title compound (34.2 mg, yield: 58%).

$^1$H-NMR (300 MHz, CDCl$_3$): δ 3.33-3.38 (m, 2H), 3.41 (s, 3H), 3.64 (dd, 2H, J=5.0, 5.6 Hz), 3.83-3.86 (m, 4H), 3.97-4.00 (m, 4H), 4.24 (m, 1H), 6.01 (s, 1H), 6.66 (s, 1H), 6.69 (d, 2H, J=8.8 Hz), 7.77 (d, 2H, J=8.8); MS (ESI) m/z 388 (M+H)$^+$.

(Step 2): N-[2-{4-(2-Methoxy-ethyl-amino)-phenyl}-7-morpholin-4-yl-pyrazolo[1,5-a]pyrimidin-5-yl]-N'-(3-methyl-benzylidene)-hydrazine (Compound 24)

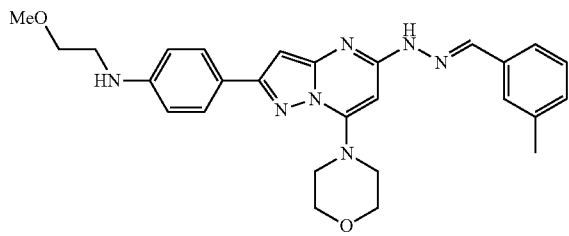

There was suspended, in ethanol (2 mL), 5-chloro-2-{4-(2-methoxy-ethyl-amino)-phenyl}-7-morpholin-4-yl-pyrazolo[1,5-a]pyrimidine (32.6 mg, 0.0841 mM) and then potassium carbonate (12.8 mg, 0.0925 mM) and hydrazine monohydrate (40.8 μL, 0.841 mM) were added to the suspension. This suspension was stirred at 150° C. for 30 minutes under the irradiation with microwaves. This reaction liquid was diluted with a saturated aqueous common salt solution and then extracted with ethyl acetate. The extracts thus obtained were combined, dried over anhydrous sodium sulfate and then the solvent was distilled off. The resulting residue was suspended in ethanol (2 mL), then acetic acid (5.0 μL, 0.087 mM) and 3-methyl-benzaldehyde (9.9 μL, 0.0841 mM) were added to the suspension and then the mixture was stirred at room temperature for 30 minutes. This reaction mixture was filtered and the resulting solid was purified by the NH-silica gel column chromatography (methylene chloride) and further the resulting solid was washed with methanol to thus give the title compound (10.6 mg, overall yield of these two steps: 26%).

$^1$H-NMR (300 MHz, DMSO): δ 2.34 (s, 3H), 3.22 (m, 2H), 3.28 (s, 3H), 3.49 (dd, 2H, J=5.3, 5.9 Hz), 3.69-3.73 (m, 4H), 3.84-3.88 (m, 4H), 5.84 (m, 1H), 6.23 (s, 1H), 6.32 (s, 1H), 6.64 (d, 2H, J=8.5 Hz), 7.16 (m, 1H), 7.30 (m, 1H), 7.46 (m, 1H), 7.51 (m, 1H), 7.65 (d, 2H, J=8.5 Hz), 8.01 (s, 1H), 11.09 (s, 1H); MS (ESI) m/z 486 (M+H)$^+$.

Example 25

Synthesis of N-(2-chloro-benzylidene)-N'-(7-morpholin-4-yl-2-phenyl-pyrazolo[1,5-a]pyrimidin-5-yl)-hydrazine (Compound 25)

There was dissolved, in ethanol (2 mL), trifluoroacetic acid salt of (7-morpholin-4-yl-2-phenyl-pyrazolo[1,5-a]pyrimidin-5-yl)-hydrazine (30.3 mg, 0.0563 mM), then 2-chloro-benzaldehyde (6.3 μL, 0.056 mM) was added to the solution and the mixture was stirred at room temperature for one hour. This reaction liquid was filtered and the resulting solid was purified by the NH-silica gel column chromatography (methylene chloride) to thus give the title compound (4.3 mg, yield: 18%).

$^1$H-NMR (300 MHz, DMSO): δ 3.72-3.75 (m, 4H), 3.86-3.88 (m, 4H), 6.33 (s, 1H), 6.57 (s, 1H), 7.34-7.50 (m, 6H), 7.93-7.96 (m, 2H), 8.06-8.09 (m, 1H), 8.44 (s, 1H), 11.45 (s, 1H); MS (ESI) m/z 433 (M+H)$^+$.

Example 26

Synthesis of N-(3-chloro-benzylidene)-N'-(7-morpholin-4-yl-2-phenyl-pyrazolo[1,5-a]pyrimidin-5-yl)-hydrazine (Compound 26)

There was dissolved, in ethanol (2 mL), trifluoroacetic acid salt of (7-morpholin-4-yl-2-phenyl-pyrazolo[1,5-a]pyrimidin-5-yl)-hydrazine (30.8 mg, 0.0572 mM), then 3-chloro-benzaldehyde (6.5 μL, 0.057 mM) was added to the solution and the mixture was stirred at room temperature for one hour. This reaction liquid was filtered and the resulting solid was purified by the NH-silica gel column chromatography (methylene chloride) to thus give the title compound (9.6 mg, yield: 34%).

$^1$H-NMR (300 MHz, DMSO): δ 3.74-3.75 (m, 4H), 3.86-3.88 (m, 4H), 6.31 (s, 1H), 6.58 (s, 1H), 7.27-7.47 (m, 5H), 7.68 (m, 1H), 7.73 (m, 1H), 7.93-7.96 (m, 2H), 8.04 (s, 1H), 11.34 (s, 1H); MS (ESI) m/z 433 (M+H)$^+$.

Example 27

Synthesis of N-(4-chloro-benzylidene)-N'-(7-morpholin-4-yl-2-phenyl-pyrazolo[1,5-a]pyrimidin-5-yl)-hydrazine (Compound 27)

There was dissolved, in ethanol (2 mL), trifluoroacetic acid salt of (7-morpholin-4-yl-2-phenyl-pyrazolo[1,5-a]pyrimidin-5-yl)-hydrazine (28.5 mg, 0.0529 mM), then 4-chlorobenzaldehyde (7.4 mg, 0.053 mM) was added to the solution and the mixture was stirred at room temperature for one hour. This reaction liquid was filtered, the resulting solid was diluted with a saturated aqueous sodium bicarbonate solution and then the solution was extracted with methylene chloride. The extracts thus obtained were combined, dried over anhydrous sodium sulfate, then the solvent was distilled off and the resulting solid was washed with diethyl ether to thus give the title compound (13.0 mg, yield: 57%).

$^1$H-NMR (300 MHz, DMSO): δ 3.73-3.74 (m, 4H), 3.86-3.88 (m, 4H), 6.31 (s, 1H), 6.57 (s, 1H), 7.34-7.49 (m, 5H), 7.73 (d, 2H, J=8.8 Hz), 7.93-7.96 (m, 2H), 8.04 (s, 1H), 11.28 (s, 1H); MS (ESI) m/z 433 (M+H)$^+$.

Example 28

Synthesis of N-(2-methoxy-benzylidene)-N'-(7-morpholin-4-yl-2-phenyl-pyrazolo[1,5-a]pyrimidin-5-yl)-hydrazine (Compound 28)

There was dissolved, in ethanol (2 mL), trifluoroacetic acid salt of (7-morpholin-4-yl-2-phenyl-pyrazolo[1,5-a]pyrimidin-5-yl)-hydrazine (24.1 mg, 0.0448 mM), then 2-methoxybenzaldehyde (6.0 μL, 0.049 mM) was added to the solution and the mixture was stirred at room temperature for one hour. This reaction liquid was filtered and the resulting solid was washed with methanol to thus give the trifluoroacetic acid salt of the title compound (21.2 mg, yield: 87%).

$^1$H-NMR (300 MHz, DMSO): δ 3.76-3.81 (m, 4H), 3.85 (s, 3H), 3.85-3.87 (m, 4H), 6.17 (br, 1H), 6.60 (s, 1H), 7.00-7.10 (m, 2H), 7.36-7.49 (m, 5H), 7.93-7.99 (m, 3H), 8.44 (s, 1H); MS (ESI) m/z 429 (M+H)$^+$.

Example 29

Synthesis of N-(3-methoxy-benzylidene)-N'-(7-morpholin-4-yl-2-phenyl-pyrazolo[1,5-a]pyrimidin-5-yl)-hydrazine (Compound 29)

There was dissolved, in ethanol (2 mL), trifluoroacetic acid salt of (7-morpholin-4-yl-2-phenyl-pyrazolo[1,5-a]pyrimidin-5-yl)-hydrazine (23.0 mg, 0.0427 mM), then 3-methoxybenzaldehyde (5.7 μL, 0.047 mM) was added to the solution and the mixture was stirred at room temperature for one hour. This reaction liquid was filtered and the resulting solid was washed with methanol to thus give the trifluoroacetic acid salt of the title compound (21.2 mg, yield: 92%).

$^1$H-NMR (300 MHz, DMSO): δ 3.78-3.81 (m, 4H), 3.81 (s, 3H), 3.86-3.88 (m, 4H), 6.19 (br, 1H), 6.62 (s, 1H), 6.97 (m, 1H), 7.32-7.49 (m, 6H), 7.94-7.97 (m, 3H), 8.08 (s, 1H); MS (ESI) m/z 429 (M+H)$^+$.

Example 30

Synthesis of N-(4-methoxy-benzylidene)-N'-(7-morpholin-4-yl-2-phenyl-pyrazolo[1,5-a]pyrimidin-5-yl)-hydrazine (Compound 30)

There was dissolved, in ethanol (2 mL), trifluoroacetic acid salt of (7-morpholin-4-yl-2-phenyl-pyrazolo[1,5-a]pyrimidin-5-yl)-hydrazine (24.6 mg, 0.0457 mM), then 4-methoxybenzaldehyde (6.1 μL, 0.050 mM) was added to the solution and the mixture was stirred at room temperature for one hour. This reaction liquid was filtered and the resulting solid was washed with methanol to thus give the trifluoroacetic acid salt of the title compound (24.8 mg, yield: quantitative).

$^1$H-NMR (300 MHz, DMSO): δ 3.76-3.81 (m, 4H), 3.80 (s, 3H), 3.86-3.87 (m, 4H), 6.14 (br, 1H), 6.61 (s, 1H), 7.01 (d, 2H, J=8.8 Hz), 7.37-7.49 (m, 3H), 7.71-7.74 (m, 3H), 7.94-7.97 (m, 2H), 8.07 (s, 1H); MS (ESI) m/z 429 (M+H)$^+$.

Example 31

Synthesis of N-(3-methyl-benzylidene)-N'-{7-morpholin-4-yl-2-[4-(1-oxo-pentan-1-yl)piperazin-1-yl-phenyl]-pyrazolo[1,5-a]pyrimidin-5-yl}-hydrazine (Compound 31)

There was dissolved, in methylene chloride (1 mL), N-{2-(4-t-butoxycarbonyl-piperazin-1-yl-phenyl)-7-morpholin-4-yl-pyrazolo[1,5-a]pyrimidin-5-yl}-N'-(3-methyl-benzylidene)-hydrazine (42.4 mg, 0.0711 mM), then trifluoroacetic acid (1 mL) was added to the solution and the mixture was stirred at room temperature for 20 minutes. This reaction liquid was concentrated, the resulting concentrate was diluted with a saturated aqueous solution of sodium bicarbonate and then the solution was extracted with ethyl acetate. The extracts thus obtained were combined, dried over anhydrous sodium sulfate and the solvent was distilled off. The resulting solid was dissolved in methylene chloride (3 mL), valeryl chloride (8.5 mL, 0.0712 mM) was added to the solution and the mixture was stirred at room temperature for 2 hours. The solvent was then distilled off from the reaction liquid and the resulting residue was purified by the reversed phase HPLC to thus give the trifluoroacetic acid salt of the title compound (27.2 mg, overall yield of these two steps: 47%).

$^1$H-NMR (300 MHz, DMSO): δ 0.87 (t, 3H, J=7.2 Hz), 1.24-1.36 (m, 2H), 1.44-1.53 (m, 2H), 2.32-2.36 (m, 5H), 3.18-3.23 (m, 4H), 3.70-3.87 (m, 12H), 6.10 (br, 1H), 6.50 (s, 1H), 7.02 (d, 2H, J=8.8 Hz), 7.21 (m, 1H), 7.33 (m, 1H); MS (ESI) m/z 581 (M+H)$^+$.

Example 32

Synthesis of N-{2-[4-bis-(2-methoxy-ethyl-amino)-phenyl]-7-morpholin-4-yl-pyrazolo[1,5-a]pyrimidin-5-yl}-N'-(3-methyl-benzylidene)-hydrazine (Compound 32)

(Step 1): 5-Chloro-2-[4-bis-(2-methoxy-ethyl)-amino-phenyl]-7-morpholin-4-yl-pyrazolo[1,5-a]pyrimidine The following reactions were carried out in an argon gas atmosphere. There was dissolved, in toluene (3 mL), 2-(4-bromo-phenyl)-5-chloro-7-morpholin-4-yl-pyrazolo[1,5-a]pyrimidine (59.0 mg, 0.150 mM), there were then added, to the solution, a solution of sodium t-butoxide (21.6 mg, 0.225 mM), tris(dibenzylidene acetone) di-palladium (6.9 mg, 0.0076 mM) and tri-t-butyl phosphine (10.9 µL, 0.0453 mM) in toluene (0.556 mL) and bis-(2-methoxyethyl)-amine (33.2 µL, 0.225 mM) and the resulting mixture was stirred at 80° C. for 4 hours and a half. This reaction liquid was diluted with a saturated aqueous common salt solution and then extracted with ethyl acetate. The extracts thus obtained were combined, dried over anhydrous sodium sulfate, then the solvent was distilled off and the resulting residue was purified by the silica gel column chromatography (ethyl acetate//hexane=1:4 to 2:3) to thus give the title compound (42.0 mg, yield: 63%).

$^1$H-NMR (300 MHz, CDCl$_3$): δ 3.37 (2s each 3H), 3.55-3.64 (m, 8H), 3.83-3.86 (m, 4H), 3.97-4.00 (m, 4H), 6.10 (s, 1H), 6.65 (s, 1H), 6.78 (d, 2H, J=8.5 Hz), 7.79 (d, 2H, J=8.5 Hz); MS (ESI) m/z 446 (M+H)$^+$.

(Step 2): N-{2-[4-bis-(2-methoxy-ethyl-amino)-phenyl]-7-morpholin-4-yl-pyrazolo-[1,5-a]pyrimidin-5-yl}-N'-(3-methyl-benzylidene)-hydrazine (Compound 32)

There was suspended, in ethanol (2 mL), 5-chloro-2-[4-bis-(2-methoxy-ethyl)-amino-phenyl]-7-morpholin-4-yl-pyrazolo[1,5-a]pyrimidine (33.3 mg, 0.0747 mM) and then potassium carbonate (11.4 mg, 0.0822 mM) and hydrazine monohydrate (36.2 µL, 0.747 mM) were added to the suspension. This suspension was stirred at 150° C. for 30 minutes under the irradiation with microwaves. This reaction liquid was diluted with a saturated aqueous common salt solution and then extracted with ethyl acetate. The extracts thus obtained were combined, dried over anhydrous sodium sulfate and the solvent was then distilled off. The resulting residue was suspended in ethanol (2 mL), then acetic acid (5.0 µL, 0.087 mM) and 3-methyl-benzaldehyde (8.8 µL, 0.0747 mM) were added to the suspension and then the mixture was stirred at room temperature for 30 minutes. The solvent was distilled off from this reaction mixture and the resulting residue was purified by the reversed phase HPLC to thus give the trifluoroacetic acid salt of the title compound (10.6 mg, overall yield of these two steps: 25%).

$^1$H-NMR (300 MHz, CDCl$_3$): δ 2.40 (s, 3H), 3.37 (2s, each 3H), 3.58-3.63 (m, 8H), 4.00-4.11 (m, 8H), 6.19 (s, 1H), 6.53 (s, 1H), 6.77 (d, 2H, J=8.8 Hz), 7.22-7.34 (m, 3H), 7.52-7.56 (m, 2H), 7.71 (d, 2H, J=8.8 Hz), 8.22 (s, 1H); MS (ESI) m/z 544 (M+H)$^+$.

Example 33

Synthesis of N-(2-furan-2-yl-7-morpholin-4-yl-pyrazolo[1,5-a]-pyrimidin-5-yl)-N-(3-methyl-benzylidene)-hydrazine (Compound 33)

(Step 1): 5,7-Dichloro-2-furan-2-yl-pyrazolo[1,5-a]pyrimidine

There was dissolved, in ethanol (4 mL), 3-amino-5-furan-2-yl-pyrazole (502 mg, 3.35 mM) and then sodium ethoxide (2M ethanol solution, 4.19 mL, 8.38 mM) and diethyl malonate (610 µL, 4.02 mM) were added to the solution. This reaction liquid was stirred at 150° C. for 50 minutes under the irradiation with microwaves. This reaction mixture was filtered and the resulting solid was washed with diethyl ether. Phosphoryl chloride (20 mL) was added to the resulting solid with ice-cooling and then the resulting suspension was stirred for 8 hours, while refluxing the same with heating. The phosphoryl chloride was distilled off from this reaction liquid, ethanol was then added to the residue with ice-cooling and the mixture was stirred for 15 minutes. After the concentration of this reaction liquid, the resulting concentrate was purified by the silica gel column chromatography (methylene chloride) to thus give the title compound (167 mg, overall yield of these two steps: 20%).

$^1$H-NMR (300 MHz, CDCl$_3$): δ 6.56 (dd, 1H, J=1.8, 3.5 Hz), 6.91 (s, 1H), 6.95 (s, 1H), 7.02 (dd, 1H, J=0.6, 3.5 Hz), 7.58 (dd, 1H, J=0.6, 1.8 Hz); MS (ESI) m/z 254 (M+H)$^+$.

(Step 2): 5-Chloro-2-furan-2-yl-7-morpholin-4-yl-pyrazolo[1,5-a]pyrimidine

There was dissolved, in 1,4-dioxane (4 mL), 5,7-dichloro-2-furan-2-yl-pyrazolo[1,5-a]pyrimidine (167 mg, 0.657 mM), then morpholine (115 µL, 1.31 mM) was added to the solution and the mixture was stirred at room temperature for one hour. The solvent was distilled off from this reaction mixture, the resulting residue was diluted with water and then extracted with methylene chloride. The extract thus obtained were combined, dried over anhydrous sodium sulfate, the solvent was distilled off and the resulting solid was washed with methanol to thus give the title compound (186 mg, yield: 93%).

$^1$H-NMR (300 MHz, CDCl$_3$): δ 3.81-3.84 (m, 4H), 3.96-3.99 (m, 4H), 6.07 (s, 1H), 6.52 (dd, 1H, J=1.8, 3.5 Hz), 6.70 (s, 1H), 6.89 (dd, 1H, J=0.9, 3.5 Hz), 7.54 (dd, 1H, J=0.9, 1.8 Hz); MS (ESI) m/z 305 (M+H)$^+$.

(Step 3): N-(2-furan-2-yl-7-morpholin-4-yl-pyrazolo[1,5-a]-pyrimidin-5-yl)-N'-(3-methyl-benzylidene)-hydrazine (Compound 33)

There was suspended, in ethanol (2 mL), 5-chloro-2-furan-2-yl-7-morpholin-4-yl-pyrazolo[1,5-a]pyrimidine (51.1 mg, 0.168 mM) and then potassium carbonate (25.5 mg, 0.185 mM) and hydrazine monohydrate (81.5 µL, 1.68 mM) were added to the suspension. This suspension was stirred at 150° C. for 20 minutes under the irradiation with microwaves. This reaction liquid was diluted with a saturated aqueous common salt solution and then extracted with ethyl acetate. The extracts thus obtained were combined, dried over anhydrous sodium sulfate and the solvent was then distilled off. The resulting residue was suspended in ethanol (2 mL), then acetic acid (5.0 µL, 0.087 mM) and 3-methyl-benzaldehyde (19.3 µL, 0.179 mM) were added to the suspension and the mixture was stirred at room temperature for one hour. This reaction mixture was filtered, the resulting solid was purified by the NH-silica gel column chromatography (methylene chloride) and then the resulting solid was washed with methanol to thus give the title compound (34.5 mg, overall yield of these two steps: 51%).

$^1$H-NMR (300 MHz, DMSO): δ 2.34 (s, 3H), 3.67-3.70 (m, 4H), 3.84-3.86 (m, 4H), 6.30 (s, 1H), 6.32 (s, 1H), 6.61 (dd, 1H, J=1.8, 3.5 Hz), 6.91 (m, 1H), 7.17 (m, 1H), 7.31 (m, 1H), 7.47 (m, 1H), 7.52 (m, 1H), 7.78 (m, 1H), 8.02 (s, 1H). 11.21 (s, 1H); MS (ESI) m/z 403 (M+H)$^+$.

Example 34

Synthesis of N-(3-methyl-benzyl)-N'-(7-morpholin-4-yl-2-phenyl-pyrazolo[1,5-a]pyrimidin-5-yl)-hydrazine (Compound 34)

There was dissolved in, THF (5 ml), N-(3-methyl-benzylidene)-N'-(7-morpholin-4-yl-2-phenyl-pyrazolo[1,5-a]pyrimidin-5-yl)-hydrazine (50.0 mg, 0.121 mM), then lithium boron hydride (26.4 mg 1.21 mM) was added to the solution and the mixture was stirred at room temperature for 30 hours. The solvent was distilled off from the reaction liquid, the resulting residue was diluted with water and then extracted with methylene chloride. The extracts thus obtained were combined, dried over anhydrous sodium sulfate, the solvent was then distilled off, the resulting solid was purified by the NH-silica gel column chromatography (methylene chloride) and then trifluoroacetic acid salt of the title compound (8.7 mg, yield: 11%) was prepared using 0.1% THF-acetonitrile.

$^1$H-NMR (300 MHz, DMSO): δ 2.29 (s, 3H), 3.71-3.73 (m, 4H), 3.80-3.84 (m, 4H), 4.00 (s, 2H), 5.65 (s, 1), 6.63 (s, 1H), 7.09 (m, 1H), 7.21-7.26 (m, 3H), 7.41-7.50 (m, 3H), 7.91-7.94 (m, 2H); MS (ESI) m/z 415 (M+H)$^+$.

Example 35

Synthesis of N-(6-methyl-pyridin-2-yl-methylidene)-N'-(7-morpholin-4-yl-2-pyridin-2-yl-pyrazolo[1,5-a]pyrimidin-5-yl)-hydrazine (Compound 35)

There was suspended, in 1,4-dioxane (2 mL), 5-chloro-7-morpholin-4-yl-2-pyridin-2-yl-pyrazolo[1,5-a]pyrimidine (51.0 mg, 0.162 mM), then potassium carbonate (24.6 mg, 0.178 mM) and hydrazine monohydrate (157 μL, 1.62 mM) were added to the suspension and the suspension was then stirred at 150° C. for 20 minutes under the irradiation with microwaves. After the completion of the stirring operation, the reaction liquid was diluted with a saturated aqueous common salt solution and extracted with ethyl acetate. The resulting extracts were combined, dried over anhydrous sodium sulfate and the solvent was then distilled off.

The resulting residue was suspended in ethanol (2 mL), then acetic acid (5.0 μL, 0.087 mM) and 6-methyl-pyridine-2-carboxaldehyde (196.mg, 0.162 mM) were added to the suspension and then the mixture was stirred at room temperature for one hour. The solvent was distilled off from this reaction liquid and the resulting residue was purified by the NH-silica gel column chromatography (methanol/methylene chloride=1:50 to 1:20) to thus give the title compound (28.9 mg, overall yield of these two steps: 25%).

$^1$H-NMR (300 MHz, DMSO): δ 2.46 (s, 3H), 3.73-3.76 (m, 4H), 3.86-3.89 (m, 4H), 6.38 (s, 1H), 6.64 (s, 1H), 7.19 (d, 1H, J=7.3 Hz), 7.38 (ddd, 1H, J=1.2, 4.7, 7.3 Hz), 7.72 (t, 1H, J=7.3 Hz), 7.84 (d, 1H, J=7.3 Hz), 7.89 (dt, 1H, J=1.8, 7.9 Hz), 8.04 (m, 1H), 8.09 (d, 1H, J=7.9 Hz), 8.63 (m, 1H), 11.51 (s, 1H); MS (ESI) m/z 415 (M+H)$^+$.

Example 36

Synthesis of (N-(1H-indol-3-yl-methylidene)-N'-(7-morpholin-4-yl-2-pyridin-2-yl-pyrazolo[1,5-a]pyrimidin-5-yl)-hydrazine (Compound 36)

There was suspended, in ethanol (2 mL), 5-chloro-7-morpholin-4-yl-2-pyridin-2-yl-pyrazolo[1,5-a]pyrimidine (51.0 mg, 0.162 mM), then potassium carbonate (24.6 mg, 0.178 mM) and hydrazine monohydrate (78.5 μL, 1.62 mM) were added to the suspension. The suspension was then stirred at 150° C. for 20 minutes under the irradiation with microwaves. The reaction liquid was diluted with a saturated aqueous common salt solution and extracted with ethyl acetate. The resulting extracts were combined, dried over anhydrous sodium sulfate and the solvent was then distilled off. The resulting residue was suspended in ethanol (2 mL), then acetic acid (4.6 μL, 0.081 mM) and indole-3-carboxaldehyde (23.5 mg, 0.162 mM) were added to the suspension and then the mixture was stirred at room temperature for 30 minutes.

The reaction mixture was filtered and the resulting solid was purified by the NH-silica gel column chromatography (methanol/methylene chloride=1:50 to 1:20) to thus give the title compound (32.9 mg, overall yield of these two steps: 46%).

$^1$H-NMR (300 MHz, DMSO): δ 3.76-3.78 (m, 4H), 3.90-3.92 (m, 4H), 6.41 (s, 1H), 6.55 (s, 1H), 7.12-7.22 (m, 2H), 7.35-7.45 (m, 2H), 7.73 (d, 1H, J=2.7 Hz), 7.88 (m, 1H), 8.08 (m, 1H), 8.22 (m, 1H), 8.23 (s, 1H), 8.63 (m, 1H), 10.96 (s, 1H), 11.46 (s, 1H); MS (ESI) m/z 439 (M+H)$^+$.

Example 37

Synthesis of N-(3-methyl-benzylidene)-N'-[7-morpholin-4-yl-2-(2-phenoxy-ethoxy)-pyrazolo[1,5-a]pyrimidin-5-yl]-hydrazine (Compound 37)

(Step 1): 5-(2-Phenoxy-ethoxy)-2H-pyrazol-3-yl-amine

There was suspended, in 2-phenoxy ethanol (25 g, 180 mM), 5-amino-1H-pyrazol-3-ol (4.00 g, 41.4 mM), then p-toluenesulfonic acid monohydrate (15.4 g, 80.8 mM) was added to the suspension and the mixture was stirred at 130° C. for 5 hours under reduced pressure. This reaction liquid was diluted with acetonitrile, the solid precipitated out of the liquid was filtered off and washed with acetonitrile. The resulting solid was suspended in a 6% aqueous sodium bicarbonate solution (250 mL), the suspension was stirred at room temperature and the solid was then filtered off. The resulting solid was dissolved in ethyl acetate, dried over anhydrous sodium sulfate and then the solvent was distilled off to thus give the title compound (2.90 g, yield: 33%).

$^1$H-NMR (300 MHz, CD$_3$OD): δ 4.22-4.25 (m, 2H), 4.30-4.34 (m, 2H), 4.98 (s, 1H), 6.89-6.95 (m, 3H), 7.23-7.28 (m, 2H); MS (ESI) m/z 220 (M+H)$^+$.

(Step 2): 5,7-Dichloro-2-(2-phenoxy-ethoxy)-pyrazole[1,5-a]pyrimidine

There was dissolved, in ethanol (4 mL), 5-(2-phenoxy-ethoxy)-2H-pyrazol-3-yl-amine (1.00 g, 4.56 mM) and then sodium ethoxide (2M ethanol solution, 5.02 mL, 10.0 mM) and diethyl malonate (830 μL, 5.47 mM) were added to the solution. This reaction liquid was stirred at 150° C. for 50 minutes under the irradiation with microwaves. This reaction mixture was filtered and the resulting solid was washed with diethyl ether. To the resulting solid, there was added phosphoryl chloride (20 mL) with ice-cooling and then this suspension was stirred for 2 hours while refluxing the same with heating. The phosphoryl chloride was distilled off from this reaction liquid, ethanol was then added to the resulting residue with ice-cooling and the mixture was stirred for 15 minutes. This reaction liquid was concentrated and the resulting concentrate was purified by the silica gel column chromatography (methanol/methylene chloride=1:20) to thus give the title compound (167 mg, overall yield of these two steps: 45%).

$^1$H-NMR (300 MHz, CDCl$_3$): δ 4.35-4.39 (m, 2H), 4.71-4.74 (m, 2H), 6.14 (s, 1H), 6.83 (s, 1H), 6.94-6.99 (m, 4H), 7.27-7.32 (m, 2H); MS (ESI) m/z 324 (M+H)$^+$.

(Step 3): 5-Chloro-7-morpholin-4-yl-2-(2-phenoxy-ethoxy)-pyrazolo[1,5-a]pyrimidine There was dissolved, in 1,4-dioxane (5 mL), 5,7-dichloro-2-(2-phenoxy-ethoxy)-pyrazole[1,5-a]pyrimidine (300 mg, 0.925 mM), morpholine (161 μL, 1.85 mM) was added to the solution and the mixture was stirred at room temperature for one hour. The solvent was distilled off from this reaction mixture, the resulting residue was diluted with water and extracted with methylene chloride. The resulting extracts were combined, dried over anhydrous sodium sulfate, the solvent was then distilled off and the resulting solid was washed with methanol to thus give the title compound (304 mg, yield: 88%).

$^1$H-NMR (300 MHz, CDCl$_3$): δ 3.72-3.76 (m, 4H), 3.90-3.93 (m, 4H), 4.34-4.37 (m, 2H), 4.60-4.63 (m, 2H), 5.94 (s, 1H), 6.00 (s, 1H), 6.93-7.00 (m, 3H), 7.27-7.32 (m, 2H).

(Step 4): N-(3-methyl-benzylidene)-N-[7-morpholin-4-yl-2-(2-phenoxy-ethoxy)-pyrazolo[1,5-a]pyrimidin-5-yl]-hydrazine (Compound 37)

There was suspended, in ethanol (2 mL), 5-chloro-7-morpholin-4-yl-2-(2-phenoxy-ethoxy)-pyrazolo[1,5-a]pyrimidine (50.4 m, 0.134 mM) and then potassium carbonate (20.4 mg, 0.147 mM) and hydrazine monohydrate (65.0 μL, 1.34 mM) were added to the suspension. This suspension was stirred at 150° C. for 20 minutes under the irradiation with microwaves. This reaction liquid was diluted with a saturated aqueous common salt solution and then extracted with ethyl acetate. The resulting extracts were combined, dried over anhydrous sodium sulfate and the solvent was distilled off. The resulting residue was suspended in ethanol (2 mL), then acetic acid (5.0 μL, 0.087 mM) and 3-methyl-benzaldehyde (15.8 μL, 0.134 mM) were added to the suspension and the mixture was stirred at room temperature for one hour. This reaction mixture was filtered and the resulting solid was washed with methanol to thus give the title compound (43.1 mg, yield: 68%).

$^1$H-NMR (300 MHz, DMSO): δ 2.33 (s, 3H), 3.59-3.62 (m, 4H), 3.78-3.81 (m, 4H), 4.29-4.32 (m, 2H), 4.48-4.51 (m, 2H), 5.56 (s, 1H), 6.17 (s, 1H), 6.91-6.98 (m, 3H), 7.45 (m, 1H), 7.50 (m, 1H), 8.00 (s, 1H), 11.07 (s, 1H); MS (ESI) m/z 473 (M+H)$^+$.

Example 38

Synthesis of N-(3-methyl-benzylidene)-N'-(7-morpholin-4-yl-2-pyridin-3-yl-pyrazolo[1,5-a]pyrimidin-5-yl)-hydrazine (Compound 38)

(Step 1): 5-Chloro-7-morpholin-4-yl-2-pyridin-3-yl-pyrazolo[1,5-a]pyrimidine

There was dissolved, in ethanol (10 mL), 3-oxo-3-pyridin-3-yl-propionitrile (600 mg, 4.11 mM), then hydrazine monohydrate (239 μL, 4.93 mM) was added to the solution and the mixture was stirred at 150° C. for 10 minutes under the irradiation with microwaves. The solvent was distilled off from the reaction liquid and then the residue was dried under reduced pressure. The resulting solid was dissolved in ethanol (10 mL) and then sodium ethoxide (2M ethanol solution, 4.52 mL, 9.04 mM) and diethyl malonate (749 μL, 4.93 mM) were added to the solution. This reaction liquid was stirred at 150° C. for 50 minutes under the irradiation with microwaves. This reaction mixture was filtered and the resulting solid was washed with diethyl ether.

After the addition of phosphoryl chloride (10 mL) to the resulting solid with ice-cooling, the resulting suspension was stirred for 8 hours while refluxing the same with heating. The phosphoryl chloride was removed from the reaction liquid through distillation, ethanol was added to the residue with ice-cooling and then the mixture was stirred for 15 minutes. After the reaction liquid was concentrated, the resulting concentrate was purified by the silica gel column chromatography (methylene chloride) to thus give the title compound (138 mg, overall yield of these two steps: 9.0%).

$^1$H-NMR (300 MHz, CDCl$_3$): δ 3.85-3.88 (m, 4H), 3.98-4.01 (m, 4H), 6.11 (s, 1H), 6.82 (s, 1H), 7.39 (m, 1H), 8.19 (m, 1H), 8.64 (m, 1H), 9.20 (m, 1H); MS (ESI) m/z 316 (M+H)$^+$.

(Step 2): N-(3-methyl-benzylidene)-N'-(7-morpholin-4-yl-2-pyridin-3-yl-pyrazolo-[1,5-a]pyrimidin-5-yl)-hydrazine (Compound 38)

There was suspended, in 1,4-dioxane (2 mL), 5-chloro-7-morpholin-4-yl-2-pyridin-3-yl-pyrazolo[1,5-a]pyrimidine (52.4 mg, 0.166 mM), then hydrazine mono-hydrate (80.5 μL, 1.66 mM) was added to the suspension and the mixture was stirred for 10 hours while refluxing the same with heating. After the stirring of the mixture, the reaction liquid was diluted with water and then extracted with ethyl acetate. The resulting extracts were combined, dried over anhydrous sodium sulfate and the solvent was distilled off.

The resulting residue was suspended in ethanol (2 mL), then acetic acid (4.8 μL, 0.083 mM) and 3-methyl-benzaldehyde (21.5 μL, 0.183 mM) were added to the suspension and the resulting mixture was stirred at room temperature for one hour. After the stirring of the suspension, it was filtered and then the resulting solid was washed with diethyl ether to thus give the title compound (43.7 mg, yield: 64%).

$^1$H-NMR (300 MHz, DMSO): δ 2.34 (s, 3H), 3.71-3.74 (m, 4H), 3.86-3.88 (m, 4H), 6.33 (s, 1H), 6.68 (s, 1H), 7.18 (m, 1H), 7.31 (m, 1H), 7.46-7.54 (m, 3H), 8.04 (s, 1H), 8.29 (m, 1H), 8.57 (m, 1H), 9.15 (m, 1H), 11.22 (s, 1H); MS (ESI) m/z 414 (M+H)$^+$.

Example 39

Synthesis of N-(3-carboxy-benzylidene)-N'-(7-morpholin-4-yl-2-phenyl-pyrazolo[1,5-a]pyrimidin-5-yl)-hydrazine (Compound 39)

There was dissolved, in ethanol (2 mL), trifluoroacetic acid salt of (7-morpholin-4-yl-2-phenyl-pyrazolo[1,5-a]pyrimidin-5-yl)-hydrazine (20.3 mg, 0.0377 mM), then 3-carboxy-benzaldehyde (5.7 mg, 0.038 mM) was added to the solution and the mixture was stirred at room temperature for one hour. This reaction liquid was filtered and the resulting solid was washed with methanol to thus give the title compound (14.0 mg, yield: 84%).

$^1$H-NMR (300 MHz, DMSO): δ 3.74-3.76 (m, 4H), 3.86-3.88 (m, 4H), 6.26 (s, 1H), 6.60 (s, 1H), 7.35-7.48 (m, 3H), 7.56 (m, 1H), 7.90-7.97 (m, 3H), 8.02 (d, 1H, J=7.9 Hz), 8.16 (d, 2H, J=9.1 Hz), 11.38 (br, 1H); MS (ESI) m/z 443 (M+H)$^+$.

Example 40

Synthesis of N-(2-methoxy-5-methyl-benzylidene)-N'-(7-morpholin-4-yl-2-phenyl-pyrazolo[1,5-a]pyrimidin-5-yl)-hydrazine (Compound 40)

There was dissolved, in ethanol (2 mL), trifluoroacetic acid salt of (7-morpholin-4-yl-2-phenyl-pyrazolo[1,5-a]pyrimidin-5-yl)-hydrazine (21.4 mg, 0.0397 mM), then 2-methoxy-5-methyl-benzaldehyde (5.5 μL, 0.040 mM) was added to the solution and the mixture was stirred at room temperature for one hour. This reaction liquid was filtered and the resulting solid was washed with methanol to thus give the trifluoroacetic acid salt of the title compound (18.2 mg, yield: 82%).

$^1$H-NMR (300 MHz, DMSO): δ 2.30 (s, 3H), 3.76-3.80 (m, 4H), 3.82 (s, 3H), 3.86-3.88 (m, 4H), 6.12 (br, 1H), 6.63 (s, 1H), 6.98 (d, 2H, J=8.5 Hz), 7.20 (m, 1H), 7.37-7.49 (m, 3H), 7.77 (s, 1H), 7.95 (d, 2H, J=8.5 Hz), 7.96 (s, 1H), 8.42 (s, 1H); MS (ESI) m/z 443 (M+H)$^+$.

Example 41

Synthesis of N-(cyclohexyl-methylidene)-N'-(7-morpholin-4-yl-2-phenyl-pyrazolo[1,5-a]pyrimidin-5-yl)-hydrazine (Compound 41)

There was dissolved, in ethanol (2 mL), trifluoroacetic acid salt of (7-morpholin-4-yl-2-phenyl-pyrazolo[1,5-a]pyrimidin-5-yl)-hydrazine (21.2 mg, 0.0394 mM), then cyclohexane-carboxy-aldehyde (4.8 μL, 0.039 mM) was added to the solution and the mixture was stirred at room temperature for one hour. This reaction liquid was filtered and the resulting solid was washed with diethyl ether to thus give the trifluoroacetic acid salt of the title compound (18.5 mg, yield: 91%).

$^1$H-NMR (300 MHz, DMSO): δ 1.16-1.32 (m, 5H), 1.62-1.80 (m, 5H), 2.26 (m, 1H), 3.72-3.76 (m, 4H), 3.83-3.86 (m, 4H), 5.95 (br, 1H), 6.56 (s, 1H), 7.34-7.48 (m, 4H), 7.92 (d, 2H, J=7.0 Hz); MS (ESI) m/z 405 (M+H)$^+$.

Example 42

Synthesis of N-(7-morpholin-4-yl-2-phenyl-pyrazolo[1,5-a]pyrimidin-5-yl)-N'-(3-phenyl-propylidene)-hydrazine (Compound 42)

There was dissolved, in ethanol (2 mL), trifluoroacetic acid salt of (7-morpholin-4-yl-2-phenyl-pyrazolo[1,5-a]pyrimidin-5-yl)-hydrazine (22.5 mg, 0.0418 mM), then 3-phenyl-propionaldehyde (5.5 μL, 0.042 mM) was added to the solution and the mixture was stirred at room temperature for one hour. This reaction liquid was filtered and the resulting solid was washed with methanol to thus give the trifluoroacetic acid salt of the title compound (22.4 mg, yield: quantitative).

$^1$H-NMR (300 MHz, DMSO): δ 2.58-2.64 (m, 2H), 2.83-2.88 (m, 2H), 3.70-3.74 (m, 4H), 3.81-3.85 (m, 4H), 5.94 (br, 1H), 6.55 (s, 1H), 7.18 (m, 1H), 7.25-7.32 (m, 4H), 7.36-7.48 (m, 4H); MS (ESI) m/z 427 (M+H)$^+$.

Example 43

Synthesis of N-[7-(3-hydroxy-azetidin-1-yl)-2-phenyl-pyrazolo[1,5-a]-pyrimidin-5-yl]-N'-(3-methyl-benzylidene)-hydrazine (Compound 43)

(Step 1): 5-Chloro-7-(3-hydroxy-azetidin-1-yl)-2-phenyl-pyrazolo[1,5-a]pyrimidine There was dissolved, in 1,4-dioxane (2 mL), 5,7-dichloro-2-phenyl-pyrazolo-[1,5-a]pyrimidine (64.5 mg, 0.244 mM), then 3-hydroxy-azetidine hydrochloride (29.4 mg, 0.268 mM) and potassium carbonate (74.2 mg, 0.537 mM) were added to the solution and the mixture was stirred at room temperature for 3 hours. The solvent was removed from this reaction mixture through distillation, the resulting residue was diluted with water and then extracted with methylene chloride. The resulting extracts were combined, dried over anhydrous sodium sulfate, the solvent was distilled off and the resulting solid was washed with diethyl ether to thus give the title compound (42.4 mg, yield: 58%).

$^1$H-NMR (300 MHz, CDCl$_3$): δ 2.41 (m, 1H), 4.43-4.49 (m, 2H), 4.85-4.91 (m, 3H), 5.55 (s, 1H), 6.63 (s, 1H), 7.37-7.46 (m, 3H), 7.89-7.92 (m, 2H); MS (ESI) m/z 301 (M+H)$^+$.

(Step 2): N-[7-(3-hydroxy-azetidin-1-yl)-2-phenyl-pyrazolo[1,5-a]-pyrimidin-5-yl]-N'-(3-methyl-benzylidene)-hydrazine (Compound 43)

There was suspended, in ethanol (2 mL), 5-chloro-7-(3-hydroxy-azetidin-1-yl)-2-phenyl-pyrazolo[1,5-a]-pyrimidine (40.0 mg, 0.133 mM) and then potassium carbonate (20.2 mg, 0.146 mM) and hydrazine monohydrate (64.5 μL, 1.33 mM) were added to the suspension. This suspension was stirred at 150° C. for 15 minutes under the irradiation with microwaves. This reaction liquid was diluted with water and then extracted with ethyl acetate. The resulting extracts were combined, dried over anhydrous sodium sulfate and the solvent was distilled off.

The resulting residue was suspended in ethanol (2 mL), then acetic acid (3.8 μL, 0.067 mM) and 3-methyl-benzaldehyde (15.7 μL, 0.133 mM) were added to the suspension and the mixture was stirred at room temperature for one hour. The solvent was distilled off from this reaction mixture and the resulting residue was purified by the reversed phase HPLC to thus give the trifluoroacetic acid salt of the title compound (19.4 mg, yield: 28%).

$^1$H-NMR (300 MHz, DMSO): a 2.36 (s, 3H), 4.31 (br, 2H), 4.68 (m, 2H), 4.83 (m, 1H), 5.40 (br, 1H), 6.61 (s, 1H), 7.25 (d, 1H, J=7.3 Hz), 7.33-7.50 (m, 3H), 7.64 (m, 2H), 7.95 (d, 2H, J=7.6 Hz), 8.10 (s, 1H); MS (ESI) m/z 399 (M+H)$^+$.

Example 44

Synthesis of N-(3-methyl-benzylidene)-N'-(2-phenyl-7-piperazin-1-yl-pyrazolo[1,5-a]pyrimidin-5-yl)-hydrazine (Compound 44)

(Step 1): 7-(4-Tert-butoxy-carbonyl-piperazin-1-yl)-5-chloro-2-phenyl-pyrazolo[1,5-a]pyrimidine There was dissolved, in 1,4-dioxane (3 mL), 5,7-dichloro-2-phenyl-pyrazolo-[1,5-a]pyrimidine (86.0 mg, 0.326 mM), then 1-(tert-butoxy-carbonyl)-piperazine (121 mg, 0.652 mM) was added to the solution and the mixture was stirred at room temperature for one hour. The solvent was distilled off from this reaction mixture, the resulting residue was diluted with water and then extracted with methylene chloride. The resulting extracts were combined, dried over anhydrous sodium sulfate, the solvent was distilled off and the resulting solid was washed with methanol to thus give the title compound (105 mg, yield: 78%).

$^1$H-NMR (300 MHz, CDCl$_3$): δ 1.51 (3s, each 3H), 3.70-3.75 (m, 4H), 3.81-3.82 (m, 4H), 6.07 (s, 1H), 6.79 (s, 1H), 7.40-7.50 (m, 3H), 7.94-7.97 (m, 2H); MS (ESI) m/z 414 (M+H)$^+$.

(Step 2): N-[7-(4-Tert-butoxy-carbonyl-piperazin-1-yl)-2-phenyl-pyrazolo[1,5-a]-pyrimidin-5-yl]-N'-(3-methyl-benzylidene)-hydrazine There was suspended, in ethanol (2 mL), 7-(4-tert-butoxy-carbonyl-piperazin-1-yl)-5-chloro-2-phenyl-pyrazolo[1,5-a]pyrimidine (103 mg, 0.250 mM) and then potassium carbonate (38.0 mg, 0.275 mM) and hydrazine monohydrate (145 μL, 2.50 mM) were added to the suspension. This suspension was stirred at 150° C. for 15 minutes under the irradiation with microwaves. This reaction liquid was diluted with water and then extracted with ethyl acetate. The resulting extracts were combined, dried over anhydrous sodium sulfate, the solvent was then distilled off.

The resulting residue was suspended in ethanol (2 mL), then acetic acid (7.6 μL, 0.125 mM) and 3-methyl-benzaldehyde (29.4 μL, 0.250 mM) were added to the suspension and the mixture was stirred at room temperature for one hour. This reaction mixture was filtered and then the resulting solid was washed with methanol to thus give the title compound (78.9 mg, overall yield of these two steps: 62%).

$^1$H-NMR (300 MHz, DMSO): δ 1.44 (3s, each 3H), 2.35 (s, 3H), 3.61-3.63 (m, 4H), 3.68-3.70 (m, 4H), 6.32 (s, 1H), 6.56 (s, 1H), 7.17 (d, 1H, J=7.6 Hz), 7.28-7.48 (m, 5H), 7.53 (d, 1H, J=7.6 Hz), 7.95-7.98 (m, 2H), 8.02 (s, 1H), 11.19 (s, 1H); MS (ESI) m/z 512 (M+H)$^+$.

(Step 3): N-(3-methyl-benzylidene)-N'-(2-phenyl-7-piperazin-1-yl-pyrazolo[1,5-a]-pyrimidin-5-yl)-hydrazine (Compound 44)

There was dissolved, in a 1:1 mixture of trifluoroacetic acid/methylene chloride (2 mL), N-[7-(4-tert-butoxy-carbonyl-piperazin-1-yl)-2-phenyl-pyrazolo-[1,5-a]pyrimidin-5-yl]-N'-(3-methyl-benzylidene)-hydrazine (17.2 mg, 0.0336 mM) and the solution was stirred at room temperature for 30 minutes. After the reaction liquid was concentrated, the resulting concentrate was purified by the reversed phase HPLC to thus give the trifluoroacetic acid salt of the title compound (13.6 mg, yield: 80%).

$^1$H-NMR (300 MHz, DMSO): δ 2.35 (s, 3H), 3.39-3.45 (m, 4H), 3.94-3.98 (m, 4H), 6.34 (s, 1H), 6.61 (s, 1H), 7.19 (d, 1H, J=7.6 Hz), 7.29-7.56 (m, 6H), 7.97-7.99 (m, 2H), 8.06 (s, 1H), 8.95 (br, 2H), 11.35 (br, 1H); MS (ESI) m/z 412 (M+H)$^+$.

Example 45

Synthesis of N-[7-(2-hydroxy-ethyl)-methyl-amino-2-phenyl-pyrazolo-[1,5-a]pyrimidin-5-yl]-N'-(3-methyl-benzylidene)-hydrazine (Compound 45)

(Step 1): 5-Chloro-7-(2-hydroxy-ethyl)-methyl-amino-2-phenyl-pyrazolo[1,5-a]-pyrimidine There was dissolved, in 1,4-dioxane (2 mL), 5,7-dichloro-2-phenyl-pyrazolo-[1,5-a]pyrimidine (52.6 mg, 0.199 mM), then 2-methylamino-ethanol (32.0 μL, 0.398 mM) was added to the solution and then the solution was stirred at room temperature for one hour. The solvent was distilled off from the reaction mixture, the resulting residue was diluted with water and then extracted with ethyl acetate. The resulting extracts were combined, dried over anhydrous sodium sulfate, the solvent was distilled off and the resulting solid was washed with diethyl ether to thus give the title compound (53.4 mg, yield: 89%).

$^1$H-NMR (300 MHz, CDCl$_3$): δ 3.18 (s, 3H), 4.04-4.09 (m, 2H), 4.16-4.20 (m, 2H), 5.04 (t, 1H, J=4.4 Hz), 6.07 (s, 1H), 6.75 (s, 1H), 7.41-7.51 (m, 3H), 7.88-7.91 (m, 2H); MS (ESI) m/z 303 (M+H)$^+$.

(Step 2): N-[7-(2-Hydroxy-ethyl)-methyl-amino-2-phenyl-pyrazolo[1,5-a]pyrimidin-5-yl]-N'-(3-methyl-benzylidene)-hydrazine (Compound 45)

There was suspended, in ethanol (2 mL), 5-chloro-7-(2-hydroxyethyl)-methyl-amino-2-phenyl-pyrazolo[1,5-a]-pyrimidine (50.5 mg, 0.167 mM) and then potassium carbonate (25.4 mg, 0.184 mM) and hydrazine monohydrate (81.0 μL, 1.67 mM) were added to the suspension. This suspension was stirred at 150° C. for 20 minutes under the irradiation with microwaves. This reaction liquid was diluted with water and then extracted with ethyl acetate. The resulting extracts were combined, dried over anhydrous sodium sulfate and the solvent was distilled off.

The resulting residue was suspended in ethanol (2 mL), then acetic acid (4.8 μL, 0.084 mM) and 3-methyl-benzaldehyde (19.7 μL, 0.167 mM) were added to the suspension and the mixture was stirred at room temperature for one hour. The solvent was distilled off from the reaction mixture and the resulting solid was purified by the reversed phase HPLC to thus give the trifluoroacetic acid salt of the title compound (20.6 mg, yield: 24%).

$^1$H-NMR (300 MHz, DMSO): δ 2.36 (s, 3H), 3.33 (s, 3H), 3.80 (t, 2H, J=5.6 Hz), 4.20 (m, 2H), 5.87 (br, 1H), 6.66 (s, 1H), 7.24 (d, 1H, J=7.6 Hz), 7.33-7.51 (m, 5H), 7.61-7.67 (m, 2H), 7.96 (d, 2H, J=7.0 Hz), 8.11 (s, 1H); MS (ESI) m/z 401 (M+H)$^+$.

Example 46

Synthesis of N-(3-methyl-benzylidene)-N'-(2-phenyl-7-thiazolidin-3-yl-pyrazolo[1,5-a]pyrimidin-5-yl)-hydrazine (Compound 46)

(Step 1): 5-Chloro-2-phenyl-7-thiazolidin-3-yl-pyrazolo[1,5-a]pyrimidine

There was dissolved, in 1,4-dioxane (2 mL), 5,7-dichloro-2-phenyl-pyrazolo-[1,5-a]pyrimidine (51.4 mg, 0.195 mM), then thiazolidine (30.7 μL, 0.390 mM) was added to the solution and then the mixture was stirred at room temperature for one hour. The solvent was distilled off from this reaction mixture, the resulting residue was diluted with water and then extracted with ethyl acetate. The resulting extracts were combined, dried over anhydrous sodium sulfate, the solvent was distilled off and the resulting solid was washed with methanol to thus give the title compound (48.5 mg, yield: 78%).

$^1$H-NMR (300 MHz, CDCl$_3$): δ 3.21 (t, 2H, J=6.2 Hz), 4.15 (t, 2H, J=6.2 Hz), 5.29 (s, 2H), 5.91 (s, 1H), 6.71 (s, 1H), 7.39-7.48 (m, 3H), 7.92-7.95 (m, 2H); MS (ESI) m/z 317 (M+H)$^+$.

(Step 2): N-(3-Methyl-benzylidene)-N'-(2-phenyl-7-thiazolidin-3-yl-pyrazolo[1,5-a]-pyrimidin-5-yl)-hydrazine (Compound 46)

There was suspended, in ethanol (2 mL), 5-chloro-7-thiazolidin-3-yl-2-phenyl-pyrazolo[1,5-a]pyrimidine (77.3 mg, 0.244 mM) and then potassium carbonate (37.1 mg, 0.268 mM) and hydrazine monohydrate (118 μL, 2.44 mM) were added to the suspension. This suspension was stirred at 150° C. for 20 minutes under the irradiation with microwaves. This reaction liquid was diluted with water and then extracted with ethyl acetate. The resulting extracts were combined, dried over anhydrous sodium sulfate and the solvent was distilled off.

The resulting residue was suspended in ethanol (2 mL), then acetic acid (7.0 μL, 0.122 mM) and 3-methyl-benzaldehyde (28.7 μL, 0.244 mM) were added to the suspension and the mixture was stirred at room temperature for one hour. This reaction mixture was filtered and the resulting solid was purified by the NH-silica gel column chromatography (methylene chloride) to thus give the title compound (48.1 mg, yield: 48%).

¹H-NMR (300 MHz, DMSO): δ 2.34 (s, 3H), 3.19 (t, 2H, J=6.2 Hz), 4.13 (t, 2H, J=6.2 Hz), 5.13 (s, 2H), 6.25 (s, 1H), 6.52 (s, 1H), 7.17 (d, 1H, J=7.3 Hz), 7.28-7.54 (m, 7H), 7.95-7.9 (m, 2H), 8.01 (s, 1H), 11.10 (s, 1H); MS (ESI) m/z 415 (M+H)⁺.

Example 47

Synthesis of N-(3-hydroxy-benzylidene)-N'-(7-morpholin-4-yl-2-phenyl-pyrazolo[1,5-a]pyrimidin-5-yl)-hydrazine (Compound 47)

There was dissolved, in ethanol (2 mL), trifluoroacetic acid salt of (7-morpholin-4-yl-2-phenyl-pyrazolo[1,5-a]pyrimidin-5-yl)-hydrazine (25.0 mg, 0.0464 mM), then 3-hydroxy-benzaldehyde (6.2 mg, 0.051 mM) was added to the solution and the mixture was stirred at room temperature for one hour. This reaction liquid was filtered and the resulting solid was purified by the NH-silica gel column chromatography (methanol/methylene chloride=1/20) to thus give the title compound (19.2 mg, yield: quantitative).
¹H-NMR (300 MHz, DMSO): δ 3.71-3.74 (m, 4H), 3.86-3.90 (m, 4H), 6.28 (s, 1H), 6.55 (s, 1H), 6.76 (m, 1H), 7.07-7.10 (m, 2H), 7.21 (t, 1H, J=7.8 Hz), 7.37-7.48 (m, 3H), 7.93-7.97 (m, 3H), 9.55 (s, 1H), 11.15 (s, 1H); MS (ESI) m/z 415 (M+H)⁺.

Example 48

Synthesis of N-(4-hydroxy-benzylidene)-N'-(7-morpholin-4-yl-2-phenyl-pyrazolo[1,5-a]pyrimidin-5-yl)-hydrazine (Compound 48)

There was dissolved, in ethanol (2 mL), trifluoroacetic acid salt of (7-morpholin-4-yl-2-phenyl-pyrazolo[1,5-a]pyrimidin-5-yl)-hydrazine (25.0 mg, 0.0464 mM), then 4-hydroxy-benzaldehyde (6.2 mg, 0.051 mM) was added to the solution and the mixture was stirred at room temperature for one hour. This reaction liquid was filtered and the resulting solid was purified by the NH-silica gel column chromatography (methanol/methylene chloride=1/20) to thus give the title compound (19.2 mg, yield: quantitative).
¹H-NMR (300 MHz, DMSO): δ 3.70-3.73 (m, 4H), 3.86-3.89 (m, 4H), 6.28 (s, 1H), 6.51 (s, 1H), 6.81 (d, 2H, J=8.5 Hz), 7.34-7.54 (m, 5H), 7.92-7.96 (m, 3H), 9.77 (s, 1H), 10.98 (s, 1H); MS (ESI) m/z 415 (M+H)⁺.

Example 49

Synthesis of N-(2-cyano-benzylidene)-N'-(7-morpholin-4-yl-2-phenyl-pyrazolo[1,5-a]pyrimidin-5-yl)-hydrazine (Compound 49)

There was dissolved, in ethanol (2 mL), trifluoroacetic acid salt of (7-morpholin-4-yl-2-phenyl-pyrazolo[1,5-a]pyrimidin-5-yl)-hydrazine (30.0 mg, 0.0557 mM), then 2-cyano-benzaldehyde (6.7 mg, 0.061 mM) was added to the solution and the mixture was stirred at room temperature for one hour. This reaction liquid was filtered and the resulting solid was purified by the NH-silica gel column chromatography (methanol/methylene chloride=1/20) to thus give the title compound (22.2 mg, yield: 94%).
¹H-NMR (300 MHz, DMSO): δ 3.74-3.78 (m, 4H), 3.84-3.87 (m, 4H), 6.54 (s, 1H), 6.62 (s, 1H), 7.35-7.54 (m, 4H), 7.74 (t, 1H J=7.6 Hz), 7.88 (d, 2H, J=7.9 Hz), 7.95 (d, 2H, J=7.0 Hz), 8.24 (s, 1H), 11.58 (s, 1H); MS (ESI) m/z 424 (M+H)⁺.

Example 50

Synthesis of N-(3-cyano-benzylidene)-N'-(7-morpholin-4-yl-2-phenyl-pyrazolo[1,5-a]pyrimidin-5-yl)-hydrazine (Compound 50)

There was dissolved, in ethanol (2 mL), trifluoroacetic acid salt of (7-morpholin-4-yl-2-phenyl-pyrazolo[1,5-a]pyrimidin-5-yl)-hydrazine (30.0 mg, 0.0557 mM), then 3-cyano-benzaldehyde (6.7 mg, 0.061 mM) was added to the solution and the mixture was stirred at room temperature for one hour. This reaction liquid was filtered and the resulting solid was purified by the NH-silica gel column chromatography (methanol/methylene chloride=1/20) to thus give the title compound (23.6 mg, yield: quantitative).
¹H-NMR (300 MHz, DMSO): δ 3.75-3.77 (m, 4H), 3.87-3.90 (m, 4H), 6.34 (s, 1H), 6.59 (s, 1H), 7.35-7.48 (m, 3H), 7.62 (t, 1H, J=7.8 Hz), 7.80 (td, 1H, J=1.2, 7.8 Hz), 7.94-7.97 (m, 2H), 8.05-8.12 (m, 3H), 11.42 (s, 1H); MS (ESI) m/z 424 (M+H)⁺.

Example 51

Synthesis of N-(4-cyano-benzylidene)-N'-(7-morpholin-4-yl-2-phenyl-pyrazolo[1,5-a]pyrimidin-5-yl)-hydrazine (Compound 51)

There was dissolved, in ethanol (2 mL), trifluoroacetic acid salt of (7-morpholin-4-yl-2-phenyl-pyrazolo[1,5-a]pyrimidin-5-yl)-hydrazine (30.0 mg, 0.0557 mM), then 4-cyano-benzaldehyde (6.7 mg, 0.061 mM) was added to the solution and the mixture was stirred at room temperature for one hour. This reaction liquid was filtered and the resulting solid was purified by the NH-silica gel column chromatography (methanol/methylene chloride=1/20) to thus give the title compound (23.6 mg, yield: quantitative).
¹H-NMR (300 MHz, DMSO): δ 3.73-3.76 (m, 4H), 3.87-3.89 (m, 4H), 6.34 (s, 1H), 6.61 (s, 1H), 7.35-7.48 (m, 3H), 7.84-7.97 (m, 6H), 8.09 (s, 1H), 11.51 (s, 1H); MS (ESI) m/z 424 (M+H)⁺.

Example 52

Synthesis of N-(4-dimethylamino-benzylidene)-N'-(7-morpholin-4-yl-2-phenyl-pyrazolo[1,5-a]pyrimidin-5-yl)-hydrazine (Compound 52)

There was dissolved, in ethanol (2 mL), trifluoroacetic acid salt of (7-morpholin-4-yl-2-phenyl-pyrazolo[1,5-a]pyrimidin-5-yl)-hydrazine (21.4 mg, 0.0397 mM), then 4-dimethylamino-benzaldehyde (7.2 mg, 0.051 mM) was added to the solution and the mixture was stirred at room temperature for one hour. This reaction liquid was filtered and the resulting solid was washed with methanol to thus give the trifluoroacetic acid salt of the title compound (26.8 mg, yield: 86%).
¹H-NMR (300 MHz, DMSO): δ 2.98 (2s, each 3H), 3.78-3.89 (m, 8H), 6.02 (br, 1H), 6.62 (br, 1H), 6.76 (d, 2H, J=8.7 Hz), 7.38-7.50 (m, 3H), 7.62-7.64 (m, 2H), 7.95 (d, 2H, J=8.7 Hz), 8.02 (s, 1H); MS (ESI) m/z 424 (M+H)⁺.

Example 53

Synthesis of N-(furan-2-yl-methylidene)-N'-(7-morpholin-4-yl-2-phenyl-pyrazolo[1,5-a]pyrimidin-5-yl)-hydrazine (Compound 53)

There was dissolved, in ethanol (2 mL), trifluoroacetic acid salt of (7-morpholin-4-yl-2-phenyl-pyrazolo[1,5-a]pyrimidin-5-yl)-hydrazine (25.0 mg, 0.0464 mM), then furan-2-carbaldehyde (4.2 μL, 0.051 mM) was added to the solution and the mixture was stirred at room temperature for one hour. This reaction liquid was filtered and the resulting solid was washed with diethyl ether to thus give the trifluoroacetic acid salt of the title compound (22.1 mg, yield: 89%).

$^1$H-NMR (300 MHz, DMSO): δ 3.72-3.77 (m, 4H), 3.85-3.87 (m, 4H), 6.11 (s, 1H), 6.60 (s, 1H), 6.62 (m, 1H), 6.87 (m, 1H), 7.36-7.48 (m, 3H), 7.82 (s, 1H), 7.93-8.00 (m, 3H); MS (ESI) m/z 389 (M+H)$^+$.

Example 54

Synthesis of N-(5-methyl-furan-2-yl-methylidene)-N'-(7-morpholin-4-yl-2-phenyl-pyrazolo[1,5-a]pyrimidin-5-yl)-hydrazine (Compound 54)

There was dissolved, in ethanol (2 mL), trifluoroacetic acid salt of (7-morpholin-4-yl-2-phenyl-pyrazolo[1,5-a]pyrimidin-5-yl)-hydrazine (25.0 mg, 0.0464 mM), then 5-methyl-furan-2-carbaldehyde (5.1 μL, 0.051 mM) was added to the solution and the mixture was stirred at room temperature for one hour. This reaction liquid was filtered and the resulting solid was washed with diethyl ether to thus give the trifluoroacetic acid salt of the title compound (21.4 mg, yield: 89%).

$^1$H-NMR (300 MHz, DMSO): δ 2.35 (s, 3H), 3.75-3.79 (m, 4H), 3.86-3.88 (m, 4H), 6.04 (br, 1H), 6.26 (d, 1H, J=2.3 Hz), 6.61 (s, 1H), 6.78 (br, 1H), 7.37-7.49 (m, 3H), 7.93-7.96 (m, 3H); MS (ESI) m/z 403 (M+H)$^+$.

Example 55

Synthesis of N-(4,5-dimethyl-furan-2-yl-methylidene)-N'-(7-morpholin-4-yl-2-phenyl-pyrazolo[1,5-a]pyrimidin-5-yl)-hydrazine (Compound 55)

There was dissolved, in ethanol (2 mL), trifluoroacetic acid salt of (7-morpholin-4-yl-2-phenyl-pyrazolo[1,5-a]pyrimidin-5-yl)-hydrazine (25.0 mg, 0.0464 mM), then 4,5-dimethyl-furan-2-carbaldehyde (6.2 μL, 0.051 mM) was added to the solution and the mixture was stirred at room temperature for one hour. This reaction liquid was filtered and the resulting solid was washed with diethyl ether to thus give the trifluoroacetic acid salt of the title compound (20.1 mg, yield: 82%).

$^1$H-NMR (300 MHz, DMSO): δ 1.94 (s, 3H), 2.26 (s, 1H), 3.74-3.79 (m, 4H), 3.86-3.89 (m, 4H), 6.02 (br, 1H), 6.61 (s, 1H), 6.70 (s, 1H), 7.37-7.49 (m, 3H), 7.89-7.96 (m, 3H); MS (ESI) m/z 417 (M+H)$^+$.

Example 56

Synthesis of N-{7-[1-(2-hydroxyethyl)-piperazin-4-yl]-pyrazolo[1,5-a]-pyrimidin-5-yl}-N'-(3-methyl-benzylidene)-hydrazine (Compound 56)

(Step 1): 5-Chloro-7-[1-(2-hydroxyethyl)-piperazin-4-yl]-2-phenyl-pyrazolo[1,5-a]-pyrimidine There was dissolved, in 1,4-dioxana (3 mL), 5,7-dichloro-2-phenyl-pyrazolo-[1,5-a]pyrimidine (50.4 mg, 0.191 mM), then 1-(2-hydroxyethyl)-piperazine (46 μL, 0.382 mM) was added to the solution and the mixture was stirred at room temperature for one hour. The solvent was distilled off from this reaction mixture and the resulting solid was washed with ethyl acetate to thus give the title compound in a quantitative yield.

MS (ESI) m/z 358 (M+H)$^+$.

(step 2): N-{7-[1-(2-Hydroxyethyl)-piperazin-4-yl]-pyrazolo[1,5-a]-pyrimidin-5-yl}-N'-(3-methyl-benzylidene)-hydrazine (Compound 56)

There was suspended, in ethanol (2 mL), 5-chloro-7-[1-(2-hydroxyethyl)-piperazin-4-yl]-2-phenyl-pyrazolo[1,5-a]-pyrimidine (68.2 mg, 0.191 mM) and then potassium carbonate (29.0 mg, 0.210 mM) and hydrazine monohydrate (92.6 μL, 1.91 mM) were added to the suspension. This suspension was stirred at 150° C. for 20 minutes under the irradiation with microwaves. This reaction liquid was diluted with water and then the mixture was extracted with ethyl acetate. The resulting extracts were combined, dried over anhydrous sodium sulfate and the solvent was distilled off.

The resulting residue was suspended in ethanol (2 mL), then acetic acid (10 μL, 0.171 mM) and 3-methyl-benzaldehyde (22.5 μL, 0.191 mM) were added to the suspension and the mixture was stirred at room temperature for one hour. This reaction mixture was filtered and the resulting solid was washed with diethyl ether to thus give the title compound (19.1 mg, overall yield of these two steps: 22%).

$^1$H-NMR (300 MHz, DMSO): δ 2.35 (s, 3H), 2.50 (m, 2H), 2.68-2.73 (m, 4H), 3.57 (m, 2H), 3.70-3.75 (m, 4H), 4.46 (t, 1H, J=5.1 Hz), 6.29 (s 1H), 6.54 (s, 1H), 7.17 (d, 1H, J=7.6 Hz), 7.28-7.52 (m, 6H), 7.94 (d, 2H, J=7.0 Hz), 8.02 (s, 1H), 11.15 (s, 1H); MS (ESI) m/z 456 (M+H)$^+$.

Example 57

Synthesis of N-(2-methyl-benzylidene)-N'-(7-morpholin-4-yl-2-phenyl-pyrazolo[1,5-a]pyrimidin-5-yl)-hydrazine (Compound 57)

(Step 1): (7-Morpholin-4-yl-2-phenyl-pyrazolo[1,5-a]pyrimidin-5-yl)-hydrazine

There was suspended, in ethanol (5 mL), 5-chloro-7-morpholin-4-yl-2-phenyl-pyrazolo[1,5-a]pyrimidine (206 mg, 0.654 mM) and then potassium carbonate (99.4 mg, 0.719 mM) and hydrazine monohydrate (317 μL, 4.57 mM) were added to the suspension. This suspension was stirred at 150° C. for 20 minutes under the irradiation with microwaves. This reaction liquid was diluted with a saturated aqueous common salt solution and then extracted with ethyl acetate. The resulting extracts were combined, dried over anhydrous sodium sulfate, the solvent was distilled off and the resulting residue was purified by the reversed phase HPLC to thus give the trifluoroacetic acid salt of the title compound (192 mg, yield: 55%).

MS (ESI) m/z 311 (M+H)$^+$ (Step 2): N-(2-Methyl-benzylidene)-N'-(7-morpholin-4-yl-2-phenyl-pyrazolo[1,5-a]-pyrimidin-5-yl)-hydrazine (Compound 57)

There was dissolved, in ethanol (2 mL), trifluoroacetic acid salt of (7-morpholin-4-yl-2-phenyl-pyrazolo[1,5-a]pyrimidin-5-yl)-hydrazine (20.0 mg, 0.0371 mM), then 2-methyl-benzaldehyde (5.5 μL, 0.045 mM) was added to the solution and the mixture was stirred at room temperature for one hour. This reaction liquid was filtered and the resulting solid was washed with methanol to thus give the trifluoroacetic acid salt of the title compound (19.1 mg, yield: 98%).

¹H-NMR (300 MHz, DMSO): δ 2.45 (s, 3H), 3.77-3.81 (m, 4H), 3.85-3.89 (m, 4H), 6.19 (br, 1H), 6.62 (s, 1H), 7.23-7.30 (m, 3H), 7.37-7.49 (m, 3H), 7.90-7.97 (m, 3H), 8.38 (s, 1H); MS (ESI) m/z 413 (M+H)⁺.

Example 58

Synthesis of N-(4-methyl-benzylidene)-N'-(7-morpholin-4-yl-2-phenyl-Pyrazolo[1,5-a]pyrimidin-5-yl)-hydrazine (Compound 58)

There was dissolved, in ethanol (2 mL), trifluoroacetic acid salt of (7-morpholin-4-yl-2-phenyl-pyrazolo[1,5-a]pyrimidin-5-yl)-hydrazine (20.0 mg, 0.0371 mM), then 4-methyl-benzaldehyde (5.1 μL, 0.045 mM) was added to the solution and the mixture was stirred at room temperature for one hour. This reaction liquid was filtered and the resulting solid was washed with methanol to thus give the trifluoroacetic acid salt of the title compound (19.2 mg, yield: 98%).

¹H-NMR (300 MHz, DMSO): δ 2.34 (s, 3H), 3.78-3.83 (m, 4H), 3.86-3.89 (m, 4H), 6.14 (br, 1H), 6.62 (s, 1H), 7.26 (d, 2H, J=7.9 Hz), 7.37-7.49 (m, 4H), 7.67 (d, 2H, J=7.3 Hz), 7.94-7.97 (m, 2H), 8.09 (s, 1H); MS (ESI) m/z 413 (M+H)⁺.

Example 59

Synthesis of N-(3-trifluoromethyl-benzylidene)-N'-(7-morpholin-4-yl-2-phenyl-pyrazolo[1,5-a]pyrimidin-5-yl)-hydrazine (Compound 59)

There was dissolved, in ethanol (2 mL), trifluoroacetic acid salt of (7-morpholin-4-yl-2-phenyl-pyrazolo[1,5-a]pyrimidin-5-yl)-hydrazine (20.0 mg, 0.0371 mM), then 3-trifluoro-benzaldehyde (5.9 μL, 0.045 mM) was added to the solution and the mixture was stirred at room temperature for one hour. This reaction liquid was filtered and the resulting solid was washed with methanol to thus give the trifluoroacetic acid salt of the title compound (21.6 mg, yield: 94%).

¹H-NMR (300 MHz, DMSO): δ 3.79-3.89 (m, 8H), 6.21 (br, 1H), 6.66 (s, 1H), 7.37-7.49 (m, 3H), 7.65-7.75 (m, 2H), 7.95-7.98 (m, 2H), 8.06-8.12 (m, 2H), 8.19 (s, 1H); MS (ESI) m/z 467 (M+H)⁺.

Example 60

Synthesis of N-(3H-imidazol-4-yl-methylidene)-N'-(7-morpholin-4-yl-2-phenyl-pyrazolo[1,5-a]pyrimidin-5-yl)-hydrazine (Compound 60)

There was dissolved, in ethanol (2 mL), trifluoroacetic acid salt of (7-morpholin-4-yl-2-phenyl-pyrazolo[1,5-a]pyrimidin-5-yl)-hydrazine (20.0 mg, 0.0371 mM), then 3H-imidazole-4-carboxy-aldehyde (4.3 mg, 0.046 mM) was added to the solution and the mixture was stirred at room temperature for one hour. This reaction liquid was filtered and the resulting solid was washed with diethyl ether to thus give the trifluoroacetic acid salt of the title compound (9.1 mg, yield: 49%).

¹H-NMR (300 MHz, DMSO): δ 3.73-3.77 (m, 4H), 3.87-3.91 (m, 4H), 6.45 (s, 1H), 6.59 (s, 1H), 7.35-7.48 (m, 3H), 7.91 (m, 3H), 8.01 (s, 1H), 11.49 (br, 1H); MS (ESI) m/z 389 (M+H)⁺.

Example 61

Synthesis of N-(7-morpholin-4-yl-2-phenyl-pyrazolo[1,5-a]pyrimidin-5-yl)-N'-(thiophen-2-yl-methylidene)-hydrazine (Compound 61)

There was dissolved, in ethanol (2 mL), trifluoroacetic acid salt of (7-morpholin-4-yl-2-phenyl-pyrazolo[1,5-a]pyrimidin-5-yl)-hydrazine (20.0 mg, 0.0371 mM), then thiophene-2-carboxy-aldehyde (4.1 μL, 0.046 mM) was added to the solution and the mixture was stirred at room temperature for one hour. This reaction liquid was filtered and the resulting solid was washed with methanol to thus give the trifluoroacetic acid salt of the title compound (18.3 mg, yield: 95%).

¹H-NMR (300 MHz, DMSO): δ 3.75-3.79 (m, 4H), 3.86-3.87 (m, 4H), 6.09 (br, 1H), 6.61 (s, 1H), 7.12 (dd, 1H, J=3.8, 4.7 Hz), 7.46-7.49 (m, 4H), 7.61 (d, 1H, J=4.7 Hz), 7.95 (d, 2H, J=7.0 Hz), 8.29 (s, 1H), 11.49 (br, 1H); MS (ESI) m/z 405 (M+H)⁺.

Example 62

Synthesis of N-(3-methyl-thiophen-2-yl-methylidene)-N'-(7-morpholin-4-yl-2-phenyl-pyrazolo[1,5-a]pyrimidin-5-yl)-hydrazine (Compound 62)

There was dissolved, in ethanol (2 mL), trifluoroacetic acid salt of (7-morpholin-4-yl-2-phenyl-pyrazolo[1,5-a]pyrimidin-5-yl)-hydrazine (20.0 mg, 0.0371 mM), then thiophene-2-carboxy-aldehyde (4.7 μL, 0.046 mM) was added to the solution and the mixture was stirred at room temperature for one hour. This reaction liquid was filtered and the resulting solid was washed with methanol to thus give the trifluoroacetic acid salt of the title compound (11.6 mg, yield: 59%).

¹H-NMR (300 MHz, DMSO): δ 2.30 (s, 3H), 3.73-3.77 (m, 4H), 3.86-3.87 (m, 4H), 6.08 (br, 1H), 6.60 (s, 1H), 6.95 (d, 1H, J=5.0 Hz), 7.36-7.52 (m, 4H), 7.94 (d, 2H, J=7.0 Hz), 8.33 (s, 1H); MS (ESI) m/z 419 (M+H)⁺.

Example 63

Synthesis of N-(2-methyl-3-phenyl-alkylidene)-N'-(7-morpholin-4-yl-2-phenyl-pyrazolo[1,5-a]pyrimidin-5-yl)-hydrazine (Compound 63)

There was dissolved, in ethanol (2 mL), trifluoroacetic acid salt of (7-morpholin-4-yl-2-phenyl-pyrazolo[1,5-a]pyrimidin-5-yl)-hydrazine (20.0 mg, 0.0371 mM), then 2-methyl-3-phenyl-propenal (6.2 μL, 0.046 mM) was added to the solution and the mixture was stirred at room temperature for one hour. This reaction liquid was filtered and the resulting solid was washed with methanol to thus give the trifluoroacetic acid salt of the title compound (20.5 mg, yield: quantitative).

¹H-NMR (300 MHz, DMSO): δ 2.20 (s, 3H), 3.74-3.79 (m, 4H), 3.85-3.88 (m, 4H), 6.11 (br, 1H), 6.61 (s, 1H), 6.81 (s, 1H), 7.30 (m, 1H), 7.37-7.49 (m, 7H), 7.92-7.96 (m, 3H); MS (ESI) m/z 439 (M+H)⁺.

Example 64

Synthesis of N-(2-methyl-3-ethyl-allylidene)-N'-(7-morpholin-4-yl-2-phenyl-pyrazolo[1,5-a]pyrimidin-5-yl)-hydrazine (Compound 64)

There was dissolved, in ethanol (2 mL), trifluoroacetic acid salt of (7-morpholin-4-yl-2-phenyl-pyrazolo[1,5-a]pyrimidin-5-yl)-hydrazine (20.0 mg, 0.0371 mM), then 2-methyl-2-pentenal (5.1 μL, 0.046 mM) was added to the solution and the mixture was stirred at room temperature for one hour. This reaction liquid was filtered and the resulting solid was washed with methanol to thus give the trifluoroacetic acid salt of the title compound (16.1 mg, yield: 86%).

¹H-NMR (300 MHz, DMSO): δ 1.00 (t, 3H, J=7.5 Hz), 1.89 (s, 3H), 2.22 (m, 1H), 3.73-3.78 (m, 4H), 3.84-3.86 (m,

4H), 5.84 (m, 1H), 6.03 (br, 1H), 6.58 (s, 1H), 7.36-7.48 (m, 3H), 7.74 (s, 1H), 7.93 (d, 2H, J=6.7 Hz); MS (ESI) m/z 391 (M+H)$^+$.

Example 65

Synthesis of N-(7-morpholin-4-yl-2-phenyl-pyrazolo [1,5-a]pyrimidin-5-yl)-N'-(oct-2-yn-1-ylidene)-hydrazine (Compound 65)

There was dissolved, in ethanol (2 mL), trifluoroacetic acid salt of (7-morpholin-4-yl-2-phenyl-pyrazolo[1,5-a]pyrimidin-5-yl)-hydrazine (20.0 mg, 0.0371 mM), then oct-2-ynal (5.5 μL, 0.041 mM) was added to the solution and the mixture was stirred at room temperature for one hour. This reaction liquid was filtered and the resulting solid was washed with diethyl ether to thus give the trifluoroacetic acid salt of the title compound (14.6 mg, yield: 74%).
$^1$H-NMR (300 MHz, DMSO): δ 0.85-0.91 (m, 3H), 1.29-1.41 (m, 4H), 1.47-1.61 (m, 2H), 2.41 (m, 1H), 2.55 (m, 1H), 3.71-3.79 (m, 4H), 3.83-3.85 (m, 4H), 6.02 (s, 0.5H), 6.23 (s, 0.5H), 6.60 (s, 0.5H), 6.65 (s, 0.5H), 6.81 (s, 0.5H), 7.32 (s, 0.5H), 7.38-7.49 (m, 3H), 7.93-7.97 (m, 2H); MS (ESI) m/z 417 (M+H)$^+$.

Example 66

Synthesis of N-benzyl-N-methyl-N'-(7-morpholin-4-yl-2-phenyl-pyrazolo[1,5-a]pyrimidin-5-yl)-hydrazine (Compound 66)

To a solution obtained by dissolving, in toluene (2.0 mL), 5-chloro-7-morpholin-4-yl-2-phenyl-pyrazolo[1,5-a]pyrimidine (35 mg, 0.11 mM), there were, in order, added sodium tert-butoxide (32 mg, 0.33 mM), 2-(2'-di-tert-butylphosphine)-biphenyl palladium (II) acetate (7.7 mg, 0.017 mM), N-benzyl-N-methylhydrazine (47 μL, 0.33 mM) and then the mixture was stirred at 90° C. for 14 hours. The reaction mixture was cooled down to room temperature, then concentrated under reduced pressure, and thereafter the resulting residue was subjected to the reversed phase high performance chromatography using, as the loading material, chemically bonded octadodecyl group-containing silica gel, while eluting with a mixed water/acetonitrile solvent containing trifluoroacetic acid in a concentration of 0.1% (v/v) and then the fractions containing the intended compound was lyophilized to thus give the trifluoroacetic acid salt of the title compound (12 mg, yield: 17%).
$^1$H-NMR (300 MHz, CDCl$_3$) δ 2.79 (3H, s), 3.80-3.96 (10H, m), 5.70 (1H, s), 6.52 (1H, s), 7.24-7.46 (8H, m), 7.80-7.83 (2H, m), 11.38 (1H, s); MS (ESI) m/z (M+H)$^+$ 415

Example 67

Synthesis of N-(2-methyl-1H-indol-7-yl-methylidene)-N'-(7-morpholin-4-yl-2-phenyl-pyrazolo[1,5-a]pyrimidin-5-yl)-hydrazine (Compound 67)

(Step 1): 7-Morpholin-4-yl-2-phenyl-pyrazolo[1,5-a] pyrimidin-5-yl-hydrazine

To a solution of 5-chloro-7-morpholin-4-yl-2-phenyl-pyrazolo[1,5-a]pyrimidine (150 mg, 0.48 mM) in 1,4-dioxane (5.0 mL), there was added hydrazine monohydrate (0.23 mL, 4.8 mM) and the mixture was stirred at 90° C. for 14 hours. The reaction mixture was cooled down to room temperature, then water was added thereto and the mixture was extracted with ethyl acetate. The organic phase thus obtained was dried over anhydrous magnesium sulfate and then concentrated under reduced pressure to thus give the title compound (133 mg, yield: 90%). MS (ESI) m/z (M+H)$^+$ 311

(Step 2): N-(2-methyl-1H-indol-7-yl-methylidene)-N'-(7-morpholin-4-yl-2-phenyl-pyrazolo[1,5-a]pyrimidin-5-yl)-hydrazine (Compound 67)

To a solution of the compound prepared in the foregoing step 1 (17 mg, 0.055 mM) in absolute ethanol (2.0 mL), there were added 2-methyl-7-formyl-indole (7.5 mg, 0.047 mM) and acetic acid (2.0 μL) and then the mixture was stirred at room temperature for 3 hours. The precipitated solid was filtered off and then washed with ethanol to thus give the title compound (12 mg, yield: 49%).
$^1$H-NMR (300 MHz, DMSO): δ 3.88 (11H, m), 6.28 (2H, s), 6.68 (1H, s), 7.05 (1H, J=7.5 Hz, t), 7.26 (1H, s), 7.38-7.54 (5H, m), 7.97 (1H, s), 8.00 (1H, s), 8.37 (1H, s), 10.67 (1H, s); MS (ESI) m/z (M+H)$^+$ 452

Example 68

Synthesis of N-(3-methyl-benzylidene)-N'-{7-morpholin-4-yl-2-(morpholin-4-yl-phenylamino)-pyrazolo[1,5-a]pyrimidin-5-yl}-hydrazine (Compound 68)

(Step 1): 5-Chloro-7-morpholin-4-yl-2-(morpholin-4-yl-phenylamino)-pyrazolo-[1,5-a]pyrimidine To a solution of 2-(4-bromophenyl)-5-chloro-7-morpholin-4-yl-pyrazolo[1,5-a]-pyrimidine (100 mg, 0.25 mM) in toluene (7.0 mL), there were, in order, added sodium tert-butoxide (49 mg, 0.51 mM), tris(dibenzylidene-acetone) dipalladium (12 mg, 0.013 mM), tri-tert-butyl-phosphine (25 μL, 0.10 mM) and N-amino-morpholine (39 mg, 0.38 mM) and the mixture was stirred at 90° C. for 4 hours. After cooling the mixture to room temperature, water was added thereto and the mixture was extracted with ethyl acetate. The organic phase thus obtained was washed with a saturated aqueous common salt solution, dried over anhydrous magnesium sulfate and then concentrated under reduced pressure. The resulting residue was washed with methanol to thus give the title compound (62 mg, yield: 60%).
MS (ESI) m/z (M+H)$^+$ 415

(Step 2): N-(3-methyl-benzylidene)-N'-{7-morpholin-4-yl-2-(morpholin-4-yl-phenyl-amino)-pyrazolo [1,5-a]pyrimidin-5-yl}-hydrazine (Compound 68)

To a solution of the compound (60 mg, 0.14 mM) prepared in the foregoing step 1 in 1,4-dioxane (5.0 mL), there was added hydrazine monohydrate (70 μL, 1.4 mM) and then the mixture was stirred at 90° C. for 14 hours. The mixture was cooled down to room temperature, water was added thereto and the mixture was extracted with ethyl acetate. The resulting organic phase was washed with a saturated aqueous common salt solution, dried over anhydrous magnesium sulfate and then concentrated under reduced pressure. The resulting residue was subjected to a slurry-washing treatment (methylene chloride/diethyl ether) and the resulting solid was dissolved in ethanol (2.0 mL). Metatolualdehyde (9.5 μL, 0.080 mM) and acetic acid (2 μL) were added to this solution and then the mixture was stirred at room temperature for 4 hours.

The precipitated solid was filtered off and then washed with ethanol to thus give the title compound (20 mg, overall yield of these two steps: 27%).
$^1$H-NMR (300 MHz, CDCl$_3$): δ 2.36 (3H, s), 2.71 (4H, s), 3.67-3.73 (8H, m), 3.88 (4H, m), 6.26 (1H, s), 6.36 (1H, s), 6.82 (1H, s), 6.86 (1H, s), 6.89 (1H, s), 7.18 (1H, J=7.5 Hz, d), 7.32 (1H, J=7.5 Hz, d), 7.48-7.54 (2H, m), 7.69 (1H, s), 7.72 (1H, s), 8.03 (1H, s), 11.13 (1H, s); MS (ESI) m/z (M+H)÷ 513

Example 69

Synthesis of N-(3-methyl-benzylidene)-N'-{7-morpholin-4-yl-2-(4-thiomorpholin-4-yl-phenyl)-pyrazolo[1,5-a]pyrimidin-5-yl}-hydrazine (Compound 69)

(Step 1): 5-Chloro-7-morpholin-4-yl-2-(4-thiomorpholin-4-yl-phenyl)-pyrazolo-[1,5-a]pyrimidine To a solution of 2-(4-bromophenyl)-5-chloro-7-morpholin-4-yl-pyrazolo[1,5-a]-pyrimidine (100 mg, 0.25 mM) in toluene (7.0 mL), there were, in order, added sodium tert-butoxide (49 mg, 0.51 mM), tris(dibenzylidene-acetone)dipalladium (12 mg, 0.013 mM), tri-tert-butyl-phosphine (25 μL, 0.10 mM) and thio-morpholine (38 μL, 0.38 mM) and the mixture was stirred at 90° C. for 4 hours. After cooling the mixture to room temperature, water was added thereto and the mixture was extracted with ethyl acetate. The organic phase thus obtained was washed with a saturated aqueous common salt solution, dried over anhydrous magnesium sulfate and then concentrated under reduced pressure. The resulting residue was washed with methanol to thus give the title compound (60 mg, yield: 57%).
MS (ESI) m/z (M+H)$^+$ 416

(Step 2): N-(3-methyl-benzylidene)-N'-{7-morpholin-4-yl-2-(4-thiomorpholin-4-yl-phenyl)-pyrazolo[1,5-a]pyrimidin-5-yl}-hydrazine (Compound 69)

To a solution of the compound (60 mg, 0.14 mM) prepared in the foregoing step 1 in 1,4-dioxane (5.0 mL), there was added hydrazine monohydrate (0.2 mL, 4.1 mM) and then the mixture was stirred at 90° C. for 14 hours. The mixture was cooled down to room temperature, water was then added thereto and the mixture was extracted with ethyl acetate. The resulting organic phase was washed with a saturated aqueous common salt solution, dried over anhydrous magnesium sulfate and then concentrated under reduced pressure. The resulting residue was subjected to a slurry-washing treatment (methylene chloride/diethyl ether) and the resulting crude product of a hydrazine-adduct was dissolved in ethanol (2.0 mL). Metatolualdehyde (17 μL, 0.14 mM) and acetic acid (2 μL) were added to this solution and then the mixture was stirred at room temperature for 4 hours. The precipitated solid was filtered off and then washed with ethanol to thus give the title compound (7.0 mg, overall yield of these two steps: 10%).
$^1$H-NMR (300 MHz, CDCl$_3$): δ 2.35 (3H, s), 2.66 (4H, s), 3.61 (4H, s), 3.72 (4H, s), 3.87 (4H, s), 6.26 (1H, s), 6.42 (1H, s), 6.98 (2H, m), 7.17 (1H, m), 7.31 (1H, J=6.9 Hz, t), 7.47-7.53 (2H, m), 7.78 (2H, m), 8.02 (1H, s), 11.14 (1H, s); MS (ESI) m/z (M+H)$^+$ 514

Example 70

Synthesis of N-(2-methyl-benzofuran-7-yl-methylidene)-N'-(7-morpholin-4-yl-2-phenyl-pyrazolo[1,5-a]pyrimidin-5-yl)-hydrazine (Compound 70)

To a solution of 7-morpholin-4-yl-2-phenyl-pyrazolo[1,5-a]pyrimidin-5-yl-hydrazine (25 mg, 0.081 mM) in absolute ethanol (2.0 mL), there were added 2-methyl-7-formyl-benzofuran (19 mg, 0.12 mM) and acetic acid (2.0 μL) and the mixture was stirred at room temperature for 3 hours. The precipitated solid was recovered through filtration and washed with ethanol to thus give the title compound (28 mg, yield: 78%).
$^1$H-NMR (300 MHz, DMSO): δ 2.47 (3H, s), 3.76-3.77 (4H, m), 3.87-3.89 (4H, m), 6.46 (1H, s), 6.58 (1H, s), 6.63 (1H, s), 7.24 (1H, J=7.2 Hz, t), 7.35-7.53 (4H, m), 7.60 (1H, J=7.2 Hz, d), 7.94 (1H, s), 7.96 (1H, s), 8.40 (1H, s), 11.35 (1H, s); MS (ESI) m/z (M+H)$^+$ 453

Example 71

Synthesis of N-(2,2-dimethyl-2,3-dihydro-benzofuran-7-yl-methyl-idene)-N'-(7-morpholin-4-yl-2-phenyl-pyrazolo[1,5-a]pyrimidin-5-yl)-hydrazine (Compound 71)

To a solution of 7-morpholin-4-yl-2-phenyl-pyrazolo[1,5-a]pyrimidin-5-yl-hydrazine (20 mg, 0.065 mM) in absolute ethanol (2.0 mL), there were added 2,2-dimethyl-2,3-dihydro-benzofuran (17 mg, 0.097 mM) and acetic acid (2.0 μL) and the mixture was stirred at room temperature for 3 hours. Water was added to the mixture, the mixture was then extracted with ethyl acetate and then the resulting organic phase was washed with a saturated aqueous common salt solution. After the drying of the organic phase over anhydrous magnesium sulfate, the organic phase was concentrated under reduced pressure. The resulting residue was purified by the NH-silica gel column chromatography (ethyl acetate:hexane=1:2) to thus give the title compound (18 mg, yield: 60%).
$^1$H-NMR (300 MHz, CDCl$_3$): δ 1.52 (3H, s), 1.55 (3H, s), 3.03 (2H, s), 3.80-3.84 (4H, m), 4.02-4.05 (4H, m), 6.40 (1H, s), 6.46 (1H, s), 6.87 (1H, J=7.4 Hz, t), 7.13 (1H, J=1.2, 7.4 Hz, dd), 7.36-7.46 (3H, m), 7.67 (1H, J=7.8 Hz, d), 7.93-7.96 (3H, m), 8.33 (1H, s);
MS (ESI) m/z (M+H)$^+$ 469

Example 72

Synthesis of N-(1H-indol-4-yl-methylidene)-N'-(7-morpholin-4-yl-2-phenyl-pyrazolo[1,5-a]pyrimidin-5-yl)-hydrazine (Compound 72)

To a solution of 7-morpholin-4-yl-2-phenyl-pyrazolo[1,5-a]pyrimidin-5-yl-hydrazine (15 mg, 0.048 mM) in absolute ethanol (2.0 mL), there were added 4-formyl-indole (11 mg, 0.076 mM) and acetic acid (2.0 μL) and the mixture was stirred at room temperature for 3 hours. The precipitated solid was filtered off and then washed with ethanol to thus give the title compound (12 mg, yield: 58%).
$^1$H-NMR (300 MHz, DMSO): δ 3.77 (4H, m), 3.91 (4H, m), 6.39 (1H, s), 6.57 (1H, s), 7.06-7.23 (3H, m), 7.40-7.52 (5H, m), 7.95 (1H, s), 7.97 (1H, s), 8.35 (1H, s), 11.16 (1H, s), 11.34 (1H, s); MS (ESI) m/z (M+H)$^+$ 438

Example 73

Synthesis of N-(1H-indol-7-yl-methylidene)-N'-(7-morpholin-4-yl-2-phenyl-pyrazolo[1,5-a]pyrimidin-5-yl)-hydrazine (Compound 73)

There was dissolved, in ethanol (2 mL), (7-morpholin-4-yl-2-phenyl-pyrazolo-[1,5-a]pyrimidin-5-yl)-hydrazine (14.8 mg, 0.0477 mM) and then indole-7-carboxy-aldehyde (7.6 mg, 0.052 mM) was added to the solution and the mixture was stirred at room temperature for 2 hours. This reaction liquid was filtered and then the resulting solid was purified by the NH-silica gel column chromatography (methylene chloride) to thus give the title compound (9.3 mg, yield: 44%).

$^1$H-NMR (300 MHz, DMSO): δ 3.79-3.82 (m, 4H), 3.87-3.90 (m, 4H), 6.34 (s, 1H), 6.56 (m, 1H), 6.61 (s, 1H), 7.09 (t, 1H, J=7.5 Hz), 7.28 (d, 1H, J=7.5 Hz), 7.35-7.51 (m, 4H), 7.62 (d, 1H, J=7.6 Hz), 7.96 (d, 2H, J=7.3 Hz), 8.35 (s, 1H), 10.88 (s, 1H), 11.24 (s, 1H);

MS (ESI) m/z 438 (M+H)$^+$.

Example 74

Synthesis of N-(2-methoxy-benzothiazol-4-yl-methylidene)-N'-(7-morpholin-4-yl-2-phenyl-pyrazolo[1,5-a]pyrimidin-5-yl)-hydrazine (Compound 74)

There was dissolved, in ethanol (2 mL), (7-morpholin-4-yl-2-phenyl-pyrazolo-[1,5-a]pyrimidin-5-yl)-hydrazine (15.1 mg, 0.0487 mM) and then 2-methoxy-benzo-thiazole-4-carbaldehyde (10.4 mg, 0.054 mM) was added to the solution and the mixture was stirred at room temperature for one hour. This reaction liquid was filtered and then the resulting solid was washed with diethyl ether to thus give the title compound (20.1 mg, yield: 85%).

$^1$H-NMR (300 MHz, DMSO): δ 3.73-3.75 (m, 4H), 3.87-3.89 (m, 4H), 4.21 (s, 3H), 6.37 (s, 1H), 6.58 (s, 1H), 7.32-7.48 (m, 4H), 7.88 (dd, 1H, J=1.2, 7.9 Hz), 7.97 (d, 2H, J=7.0 Hz), 8.02 (d, 1H, J=7.6 Hz), 8.77 (s, 1H), 11.37 (s, 1H); MS (ESI) m/z 486 (M+H)$^+$.

Example 75

Synthesis of N-(6-methy-imidazo[2,1-b]thiazole-5-methylidene)-N'-(7-morpholin-4-yl-2-phenyl-pyrazolo[1,5-a]pyrimidin-5-yl)-hydrazine (Compound 75)

There was dissolved, in ethanol (2 mL), (7-morpholin-4-yl-2-phenyl-pyrazolo-[1,5-a]pyrimidin-5-yl)-hydrazine (15.1 mg, 0.0487 mM) and then 6-methylimidazo-[2,1-b]thiazole-5-carbaldehyde (8.9 mg, 0.054 mM) was added to the solution and the mixture was stirred at room temperature for one hour. This reaction liquid was filtered and then the resulting solid was washed with diethyl ether to thus give the title compound (10.2 mg, yield: 46%).

$^1$H-NMR (300 MHz, DMSO) δ 2.34 (s, 3H), 3.73-3.76 (m, 4H), 3.87-3.90 (m, 4H), 6.15 (s, 1H), 6.54 (s, 1H), 7.34-7.47 (m, 4H), 7.94 (d, 2H, J=7.0 Hz), 8.21 (d, 1H, J=2.4 Hz), 8.23 (s, 1H), 11.08 (s, 1H); MS (ESI) m/z 459 (M+H)$^+$.

Example 76

Synthesis of N-(6-chloro-imidazo[2,1-b]thiazole-5-methylidene)-N'-(7-morpholin-4-yl-2-phenyl-pyrazolo[1,5-a]pyrimidin-5-yl)-hydrazine (Compound 76)

There was dissolved, in ethanol (2 mL), (7-morpholin-4-yl-2-phenyl-pyrazolo-[1,5-a]pyrimidin-5-yl)-hydrazine (15.0 mg, 0.0483 mM) and then 6-chloro-imidazo-[2,1-b]thiazole-5-carbaldehyde (9.9 mg, 0.053 mM) was added to the solution and the mixture was stirred at room temperature for one hour. This reaction liquid was filtered and then the resulting solid was washed with diethyl ether to thus give the title compound (20.8 mg, yield: 90%).

$^1$H-NMR (300 MHz, DMSO) δ 3.75-3.78 (m, 4H), 3.87-3.90 (m, 4H), 6.15 (s, 1H), 6.58 (s, 1H), 7.34-7.47 (m, 3H), 7.62 (d, 1H, J=4.7 Hz), 7.94 (d, 2H, J=7.0 Hz), 8.18 (s, 1H), 8.25 (d, 1H, J=4.4 Hz), 11.28 (s, 1H); MS (ESI) m/z 479 (M+H)$^+$.

Example 77

Synthesis of N-(3-methyl-1H-indol-7-yl-methylidene)-N'-(7-morpholin-4-yl-2-phenyl-pyrazolo[1,5-a]pyrimidin-5-yl)-hydrazine (Compound 77)

There was dissolved, in ethanol (2 mL), (7-morpholin-4-yl-2-phenyl-pyrazolo-[1,5-a]pyrimidin-5-yl)-hydrazine (15.3 mg, 0.0493 mM) and then 3-methyl-indole-7-carboxyaldehyde (8.6 mg, 0.054 mM) was added to the solution and the mixture was stirred at room temperature for 2 hours. This reaction liquid was filtered and then the resulting solid was washed with methanol to thus give the title compound (16.0 mg, yield: 72%).

$^1$H-NMR (300 MHz, DMSO): δ 2.30 (s, 3H), 3.78-3.84 (m, 4H), 3.87-3.91 (m, 4H), 6.33 (s, 1H), 6.59 (s, 1H), 7.08 (t, 1H, J=7.5 Hz), 7.25-7.27 (m, 2H), 7.35-7.48 (m, 3H), 7.56 (d, 1H, J=7.5 Hz), 7.96 (d, 2H, J=7.0 Hz), 8.33 (s, 1H), 10.54 (s, 1H), 11.20 (s, 1H); MS (ESI) m/z 452 (M+H)$^+$.

Example 78

Synthesis of N-(2-methyl-1H-indol-3-yl-methylidene)-N'-(7-morpholin-4-yl-2-phenyl-pyrazolo[1,5-a]pyrimidin-5-yl)-hydrazine (Compound 78)

There was dissolved, in ethanol (2 mL), (7-morpholin-4-yl-2-phenyl-pyrazolo-[1,5-a]pyrimidin-5-yl)-hydrazine (15.5 mg, 0.0499 mM) and then 2-methyl-indole-3-carboxyaldehyde (8.6 mg, 0.052 mM) was added to the solution and the mixture was stirred at room temperature for 2 hours. This reaction liquid was filtered and then the resulting solid was washed with methanol to thus give the title compound (12.1 mg, yield: 54%).

$^1$H-NMR (300 MHz, DMSO): δ 2.49 (s, 3H), 3.74-3.77 (m, 4H), 3.89-3.91 (m, 4H), 6.35 (s, 1H), 6.49 (s, 1H), 7.09-7.16 (m, 2H), 7.31-7.47 (m, 4H), 7.94 (d, 2H, J=7.0 Hz), 8.12 (m, 1H), 8.34 (s, 1H), 10.76 (s, 1H), 11.36 (s, 1H); MS (ESI) m/z 452 (M+H)$^+$.

Example 79

Synthesis of N-(3-methyl-benzylidene)-N'-(2-methyl-7-morpholin-4-yl-pyrazolo[1,5-a]pyrimidin-5-yl)-hydrazine (Compound 79)

(Step 1)
5,7-Dichloro-2-methyl-pyrazolo[1,5-a]pyrimidine

There was dissolved, in ethanol (100 mL), 3-amino-5-methyl-pyrazole (3.00 mg, 30.9 mM) and then sodium ethoxide (4.21 g, 61.8 mM) and diethyl malonate (5.63 mL, 37.1 mM) were added to the solution and this reaction liquid was stirred for 2 hours, while refluxing the same with heating. This reaction mixture was filtered and then the resulting solid was washed with diethyl ether. After the addition of phosphoryl chloride (20 mL) to the resulting solid with ice-cooling, the resulting suspension was stirred for 2 hours, while refluxing the same with heating. The phosphoryl chloride was distilled off from this reaction liquid, ethanol was then added to the residue thus obtained with ice-cooling and then the mixture was stirred for 15 minutes. After the concentration of this reaction liquid, the resulting concentrate was purified by the silica gel column chromatography (methylene chloride) to thus give the title compound (3.09 g, overall yield of these two steps: 50%).

$^1$H-NMR (300 MHz, CDCl$_3$): δ 2.55 (s, 3H), 6.51 (s, 1H), 6.88 (s, 1H); MS (ESI) m/z 201 (M+H)$^+$.

(Step 2): 5-Chloro-2-methyl-7-morpholin-4-yl-pyrazolo[1,5-a]pyrimidine

There was dissolved, in 1,4-dioxane (20 mL), 5,7-dichloro-2-methyl-pyrazolo-[1,5-a]pyrimidine (1.00 g, 4.95 mM), then morpholine (863 μL, 9.90 mM) was added to the solution and the mixture was stirred at room temperature for one hour. The solvent was then distilled off from this reaction mixture, the resulting residue was diluted with water and the mixture was extracted with methylene chloride. The resulting extracts were combined, dried over anhydrous sodium sulfate, the solvent was distilled off and the resulting solid was washed with methanol to thus give the title compound (927 mg, yield: 74%).

$^1$H-NMR (300 MHz, CDCl$_3$): δ 2.46 (s, 3H), 3.75-3.78 (m, 4H), 3.93-3.96 (m, 4H), 6.00 (s, 1H), 6.28 (s, 1H).

(Step 3): (2-Methyl-7-morpholin-4-yl-pyrazolo[1,5-a]pyrimidin-5-yl)-hydrazine

There was dissolved, in 1,4-dioxane (3 mL), 5-chloro-2-methyl-7-morpholin-4-yl-pyrazolo[1,5-a]pyrimidine (179 mg, 0.708 mM), then hydrazine monohydrate (343 μL, 7.08 mM) was added to the solution, and the mixture was stirred at 90° C. overnight. This reaction liquid was then diluted with water and the mixture was extracted with ethyl acetate. The resulting extracts were combined, dried over anhydrous sodium sulfate, the solvent was distilled off and the resulting solid was washed with diethyl ether to thus give the title compound (88.7 mg, yield: 51%).

$^1$H-NMR (300 MHz, DMSO): δ 2.22 (s, 3H), 3.44-3.47 (m, 4H), 3.75-3.78 (m, 4H), 4.21 (br, 2H), 5.59 (s, 1H), 5.73 (s, 1H), 7.89 (s, 1H); MS (ESI) m/z 249 (M+H)$^+$.

(Step 4): N-(3-Methyl-benzylidene)-N'-(2-methyl-7-morpholin-4-yl-pyrazolo[1,5-a]-pyrimidin-5-yl)-hydrazine (Compound 79)

There was dissolved, in ethanol (2 mL), (2-methyl-7-morpholin-4-yl-pyrazolo-[1,5-a]pyrimidin-5-yl)-hydrazine (24.7 mg, 0.0995 mM), then acetic acid (5.0 μL, 0.087 mM) and 3-methyl-benzaldehyde (12.9 μL, 0.109 mM) were added to the solution and the resulting mixture was stirred at room temperature for 2 hours. This reaction liquid was filtered and the resulting solid was washed with methanol to thus give the title compound (29.6 mg, yield: 85%).

$^1$H-NMR (300 MHz, DMSO): δ 2.29 (s, 3H), 2.33 (s, 3H), 3.62-3.65 (m, 4H), 3.79-3.83 (m, 4H), 5.86 (s, 1H), 6.20 (s, 1H), 7.16 (d, 1H, J=7.6 Hz), 7.29 (t, 1H, J=7.6 Hz), 7.45 (s, 1H), 7.50 (d, 1H, J=7.6 Hz), 7.99 (s, 1H), 11.06 (s, 1H); MS (ESI) m/z 351 (M+H)$^+$.

Example 80

Synthesis of N-(1H-indol-3-yl-methylidene)-N'-(2-methyl-7-morpholin-4-yl-pyrazolo[1,5-a]pyrimidin-5-yl)-hydrazine (Compound 80)

There was dissolved, in ethanol (2 mL), (2-methyl-7-morpholin-4-yl-pyrazolo-[1,5-a]pyrimidin-5-yl)-hydrazine (24.5 mg, 0.0988 mM) and then acetic acid (5.0 μL, 0.087 mM) and indole-3-carboxyaldehyde (15.8 mg, 0.109 mM) were added to the solution and the mixture was stirred at room temperature for 2 hours. This reaction liquid was filtered and then the resulting solid was washed with methanol to thus give the title compound (26.4 mg, yield: 71%).

$^1$H-NMR (300 MHz, DMSO): δ 2.27 (s, 3H), 3.65-3.68 (m, 4H), 3.83-3.86 (m, 4H), 5.80 (s, 1H), 6.27 (s, 1H), 7.16-7.19 (m, 2H), 7.42 (m, 1H), 7.70 (d, 1H, J=2.6 Hz), 8.20 (m, 1H), 8.24 (s, 1H), 10.76 (s, 1H), 11.42 (s, 1H); MS (ESI) m/z 376 (M+H)$^+$.

Example 81

Synthesis of N-(2-ethoxycarbonyl-7-morpholin-4-yl-pyrazolo[1,5-a]-pyrimidin-5-yl)-N'-(3-methyl-benzylidene)-hydrazine (Compound 81)

(Step 1): Ethyl 5-amino-1H-pyrazole-3-carboxylate

To a solution of diethyl oxalate (10.0 g, 68.4 mM) in THF (10 mL), there were added 18-crown-6 (1.80 mg, 6.84 mM) and potassium tert-butoxide (1M THF solution, 71.6 mL, 71.6 mM), then acetonitrile (3.99 mL, 75.2 mM) was further added to the mixture at 0° C. and the resulting mixture was stirred for 10 minutes. The temperature of this solution was raised up to 70° C. and it was stirred for 30 minutes at that temperature. The resulting suspension was filtered and the solid was washed with diethyl ether.

The resulting solid was suspended in ethanol (100 mL), followed by the addition of water (20 mL), and then concentrated hydrochloric acid (3.0 mL) and methyl carbazinate (3.61 g, 39.7 mM) with ice-cooling and the stirring of the resulting mixture at room temperature for 20 hours. After the completion of the stirring operation, potassium carbonate (2.74 g, 19.8 mM) was added to this suspension and the latter was stirred at 90° C. for 30 minutes. This reaction liquid was concentrated under reduced pressure, the resulting concentrate was diluted with water and the mixture was extracted with ethyl acetate. The resulting extracts were combined, dried over anhydrous sodium sulfate, the solvent was distilled off and then the resulting solid was sufficiently washed with diethyl ether to thus give the title compound (5.34 g, yield: 50%).

$^1$H-NMR (300 MHz, DMSO): δ 1.23 (t, 3H, J=6.9 Hz), 4.19 (q, 2H, J=6.9 Hz), 4.74-5.12 (br, 2H), 5.64-5.89 (br, 1H), 12.09-12.53 (br, 1H); MS (ESI) m/z 156 (M+H)$^+$.

(Step 2): 5,7-Dichloro-2-ethoxycarbonyl-4-yl-pyrazolo[1,5-a]pyrimidine

There was dissolved, in ethanol (3 mL), ethyl 5-amino-1H-pyrazole-3-carboxylate (201 mg, 1.30 mM) and then sodium ethoxide (195 g, 2.86 mM) and diethyl malonate (217 μL, 1.43 mM) were added to the solution. This reaction liquid was stirred for 8 hours, while refluxing the same with heating. This reaction mixture was filtered and then the resulting solid was washed with diethyl ether. After the addition of phosphoryl chloride (10 mL) to the resulting solid with ice-cooling, the resulting suspension was stirred for 3 hours, while refluxing the same with heating. The phosphoryl chloride was distilled off from the reaction liquid, ethanol was then added to the residue with ice-cooling and then the mixture was stirred for 15 minutes. After the concentration of this reaction liquid, the resulting concentrate was purified by the silica gel column chromatography (methanol/methylene chloride=1:100) to thus give the title compound (49.5 mg, overall yield of these two steps: 15%).

$^1$H-NMR (300 MHz, CDCl$_3$): δ 1.45 (t, 3H, J=7.2 Hz), 4.50 (q, 2H, J=7.2 Hz), 7.11 (s, 1H), 7.23 (s, 1H); MS (ESI) m/z 259 (M+H)$^+$.

(Step 3): 5-Chloro-2-ethoxycarbonyl-7-morpholin-4-yl)-pyrazolo[1,5-a]pyrimidine

There was dissolved, in 1,4-dioxane (2 mL), 5,7-dichloro-2-ethoxycarbonyl-4-yl-pyrazolo[1,5-a]pyrimidine (49.5 mg, 0.195 mM), then morpholine (33.1 μL, 0.390 mM) was added to the solution and the mixture was stirred at room temperature for one hour. The solvent was distilled off from this reaction mixture, the residue was diluted with water and then the mixture was extracted with methylene chloride. The resulting extracts were combined, dried over anhydrous sodium sulfate, the solvent was distilled off and then the resulting solid was washed with methanol to thus give the title compound (47.4 mg, yield: 80%).

$^1$H-NMR (300 MHz, CDCl$_3$): δ 1.43 (t, 3H, J=7.2 Hz), 3.82-3.85 (m, 4H), 3.95-3.98 (m, 4H), 4.45 (q, 2H, J=7.2 Hz), 6.17 (s, 1H), 6.98 (s, 1H); MS (ESI) m/z 311 (M+H)$^+$.

(Step 4): N-(2-ethoxycarbonyl-7-morpholin-4-yl-pyrazolo[1,5-a]-pyrimidin-5-yl)-N'-(3-methyl-benzylidene)-hydrazine (Compound 81)

There was suspended, in 1,4-dioxane (2 mL), 5-chloro-2-ethoxycarbonyl-7-morpholin-4-yl-pyrazolo[1,5-a]pyrimidine (46.3 mg, 0.149 mM), then hydrazine monohydrate (12.7 μL, 0.447 mM) was added to the suspension and the mixture was stirred for 20 hours, while refluxing the same with heating. After the completion of the stirring operation, the reaction liquid was diluted with water and the mixture was extracted with ethyl acetate. The resulting extracts were combined, dried over anhydrous sodium sulfate and the solvent was distilled off.

The resulting residue was suspended in ethanol (2 mL), then acetic acid (5.0 μL, 0.087 mM) and 3-methyl-benzaldehyde (19.3 μL, 0.164 mM) were added to the suspension and the mixture was stirred at room temperature for one hour. After the stirring operation, the suspension was filtered, the resulting solid was purified by the reversed phase HPLC and then subjected to a desalting operation to thus give the title compound (14.2 mg, overall yield of these two steps: 23%).

$^1$H-NMR (300 MHz, DMSO): δ 1.30 (t, 3H, J=7.2 Hz), 2.34 (s, 3H), 3.64-3.68 (m, 4H), 3.82-3.85 (m, 4H), 4.31 (q, 2H, J=7.2 Hz), 6.42 (s, 1H), 6.48 (s, 1H), 7.18 (d, 1H, J=7.3 Hz), 7.31 (t, 1H, J=7.3 Hz), 7.47 (s, 1H), 7.52 (d, 1H, J=7.3 Hz), 8.03 (s, 1H), 11.32 (s, 1H); MS (ESI) m/z 409 (M+H)$^+$.

Example 82

Synthesis of N-(1H-indol-3-yl-methylidene)-N'-(7-morpholin-4-yl-2-pyridin-3-yl-pyrazolo[1,5-a]pyrimidin-5-yl)-hydrazine (Compound 82)

There was suspended, in 1,4-dioxane (2 mL), 5-chloro-7-morpholin-4-yl-2-pyridin-3-yl-pyrazolo[1,5-a]pyrimidine (78.2 mg, 0.248 mM), then hydrazine monohydrate (120 μL, 2.48 mM) was added to the suspension and the mixture was stirred for 20 hours, while refluxing the same with heating. After the completion of the stirring operation, the reaction liquid was diluted with water and the mixture was extracted with ethyl acetate. The resulting extracts were combined, dried over anhydrous sodium sulfate and the solvent was distilled off.

The resulting residue was suspended in ethanol (5 mL), then acetic acid (20 μL, 0.349 mM) and indole-3-carboxyaldehyde (39.6 mg, 0.273 mM) were added to the suspension and the mixture was stirred at room temperature for 2 hours. After the stirring operation, the suspension was filtered, the resulting solid was purified by the reversed phase HPLC and then subjected to a desalting operation to thus give the title compound (53.2 mg, yield: 48%).

$^1$H-NMR (300 MHz, DMSO): δ 3.73-3.77 (m, 4H), 3.88-3.92 (m, 4H), 6.38 (s, 1H), 6.61 (s, 1H), 7.20 (m, 1H), 7.46 (m, 2H), 7.72 (s, 1H), 8.21 (m, 1H), 8.28-8.34 (m, 2H), 8.55 (m, 1H), 9.14 (m, 1H), 10.90 (s, 1H), 11.45 (s, 1H); MS (ESI) m/z 439 (M+H)$^+$.

Example 83

Synthesis of N-(3-methyl-benzylidene)-N'-(7-morpholin-4-yl-2-pyridin-4-yl-pyrazolo[1,5-a]pyrimidin-5-yl)-hydrazine (Compound 83)

(Step 1): 5-Pyridin-4-yl-2H-pyrazol-3-yl-amine

Acetonitrile (2.09 mL, 39.7 mM) was added to a solution of 18-crown-6 (875 mg, 3.31 mM) and potassium tert-butoxide (1M THF solution, 36.4 mL, 36.4 mM) in THF (10 mL) at 60° C. and then the mixture was stirred for 5 minutes. To this solution, there was added ethyl isonicotinate (5.00 g, 33.1 mM) and the mixture was then stirred for 30 minutes. This suspension was filtered and the resulting solid was washed with diethyl ether.

The resulting solid was suspended in ethanol (60 mL), then concentrated hydrochloric acid (3.0 mL) and methyl carbazinate (3.61 g, 39.7 mM) were added to the suspension with ice-cooling and the mixture was stirred at room temperature for 20 hours. After the stirring operation, potassium carbonate (2.74 g, 19.8 mM) was added to this suspension and the mixture was stirred at 90° C. for one hour. This reaction solution was concentrated under reduced pressure, the concentrate was diluted with water and the mixture was then extracted with ethyl acetate. The resulting extracts were combined, dried over anhydrous sodium sulfate, the solvent was distilled off and the resulting solid was sufficiently washed with diethyl ether to thus give the title compound (1.33 g, yield: 25%).

$^1$H-NMR (300 MHz, DMSO): δ 4.65-5.16 (br, 2H), 5.81 (br, 1H), 7.59-7.61 (m, 2H), 8.50-8.52 (m, 2H), 11.80 (br, 1H); MS (ESI) m/z 161 (M+H)$^+$.

(Step 2): 5.7-Dichloro-4-yl-2-pyridin-4-yl-pyrazolo[1,5-a]pyrimidine

To a solution of 5-pyridin-4-yl-2H-pyrazol-3-yl-amine (1.29 g, 8.05 mM) in ethanol (20 mL), there were added sodium ethoxide (1.21 mL, 17.7 mM) and diethyl malonate (1.34 mL, 8.86 mM) and the mixture was stirred for 9 hours, while refluxing the same with heating. After the stirring operation, the reaction liquid was filtered and the resulting solid was washed with diethyl ether.

After the addition of phosphoryl chloride (15 mL) to the resulting solid, the resulting suspension was stirred for 4 hours, while refluxing the same with heating. The phosphoryl chloride was distilled off from this reaction liquid, ethanol was then added to the residue with ice-cooling and the mixture was stirred for 15 minutes. After the concentration of the reaction liquid, the residues obtained was purified by the silica gel column chromatography (methanol/methylene chloride=1:50 to 1:20) to thus give the title compound (380 mg, yield: 18%).

$^1$H-NMR (300 MHz, DMSO): δ 7.79 (s, 1H), 7.84 (s, 1H), 8.41 (d, 2H, J=6.6 Hz), 8.97 (d, 2H, J=6.6 Hz); MS (ESI) m/z 265 (M+H)$^+$.

(Step 3): 5-Chloro-7-morpholin-4-yl-2-pyridin-4-yl-pyrazolo[1,5-a]pyrimidine

There was dissolved, in 1,4-dioxane (3 mL), 5.7-dichloro-4-yl-2-pyridin-4-yl-pyrazolo[1,5-a]pyrimidine (380 mg, 1.43 mM), then morpholine (249 μL, 2.86 mM) was added to the solution and the mixture was stirred at room temperature for one hour. After the completion of the reaction, the suspension was concentrated, the concentrate was diluted with water and then the mixture was extracted with ethyl acetate. The resulting extracts were combined, dried over anhydrous sodium sulfate, the solvent was distilled off and the resulting solid was washed with diethyl ether to thus give the title compound (306 mg, yield: 68%).

$^1$H-NMR (300 MHz, DMSO): δ 3.83-3.85 (m, 4H), 3.89-3.91 (m, 4H), 6.50 (s, 1H), 7.35 (s, 1H), 8.21 (d, 2H, J=6.2 Hz), 8.81 (d, 2H, J=6.2 Hz); MS (ESI) m/z 316 (M+H)$^+$.

(Step 4): N-(3-methyl-benzylidene)-N'-(7-morpholin-4-yl-2-pyridin-4-yl-pyrazolo-[1,5-a]pyrimidin-5-yl)-hydrazine (Compound 83)

There was suspended, in 1,4-dioxane (2 mL), 5-chloro-7-morpholin-4-yl-2-pyridin-4-yl-pyrazolo[1,5-a]pyrimidine (84.0 mg, 0.266 mM), then hydrazine monohydrate (129 μL, 2.66 mM) was added to the suspension and the suspension was stirred for 10 hours while refluxing the same with heating. After the stirring operation, the reaction liquid was diluted with water and then extracted with ethyl acetate. The resulting extracts were combined, dried over anhydrous sodium sulfate and then the solvent was distilled off.

The resulting residue was suspended in ethanol (2 mL), then acetic acid (5.0 μL, 0.087 mM) and 3-methyl-benzaldehyde (31.3 μL, 0.266 mM) were added to the suspension and the mixture was stirred at room temperature for one hour. After the stirring operation, the suspension was filtered and the resulting solid was purified by the reversed phase HPLC and then subjected to a desalting operation to thus give the title compound (36.2 mg, overall yield of these two steps: 33%).

$^1$H-NMR (300 MHz, DMSO): δ 2.35 (s, 3H), 3.71-7.75 (m, 4H), 3.87-3.90 (m, 4H), 6.36 (s, 1H), 6.74 (s, 1H), 7.18 (d, 1H, J=7.6 Hz), 7.32 (t, 1H, J=7.6 Hz), 7.48 (s, 1H), 7.53 (d, 1H, J=7.6 Hz), 7.90 (d, 2H, J=4.8 Hz), 8.04 (s, 1H), 8.64 (d, 2H, J=4.8 Hz), 11.27 (s, 1H); MS (ESI) m/z 414 (M+H)$^+$.

Example 84

Synthesis of N-(1H-indol-3-yl-methylidene)-N'-(7-morpholin-4-yl-2-pyridin-4-yl-pyrazolo[1,5-a]pyrimidin-5-yl)-hydrazine (Compound 84)

There was suspended, in 1,4-dioxane (2 mL), 5-chloro-7-morpholin-4-yl-2-pyridin-4-yl-pyrazolo[1,5-a]pyrimidine (84.0 mg, 0.266 mM), then hydrazine monohydrate (129 μL, 2.66 mM) was added to the suspension and the suspension was stirred for 20 hours while refluxing the same with heating. After the stirring operation, the reaction liquid was diluted with water and then extracted with ethyl acetate. The resulting extracts were combined, dried over anhydrous sodium sulfate and the solvent was distilled off.

The resulting residue was suspended in ethanol (5 mL), then acetic acid (5.0 μL, 0.087 mM) and indole-3-carboxyaldehyde (38.0 mg, 0.266 mM) were added to the suspension and the mixture was stirred at room temperature for 2 hours. After the stirring operation, the suspension was filtered, the resulting solid was purified by the reversed phase HPLC and then subjected to a desalting operation to thus give the title compound (40.4 mg, overall yield of these two steps: 35%).

$^1$H-NMR (300 MHz, DMSO): δ 3.74-3.77 (m, 4H), 3.90-3.93 (m, 4H), 6.42 (s, 1H), 6.68 (s, 1H), 7.18-7.23 (m, 2H), 7.43 (m, 1H), 7.74 (s, 1H), 7.90 (d, 2H, J=6.9 Hz), 8.22 (m, 1H), 8.29 (s, 1H), 8.64 (d, 2H, J=6.0 Hz), 10.98 (s, 1H), 11.47 (s, 1H); MS (ESI) m/z 439 (M+H)$^+$.

Example 85

Synthesis of N-(3-methyl-benzylidene)-N'-[7-morpholin-4-yl-2-(6-morpholin-4-yl-pyridin-3-yl)-pyrazolo[1,5-a]pyrimidin-5-yl]-hydrazine (Compound 85)

(Step 1): 5-Chloro-7-morpholin-4-yl-2-(6-morpholin-4-yl-pyridin-3-yl)-pyrazolo[1,5-a]pyrimidine There was dissolved, in methanol (50 mL), methyl 6-chloro-nicotinate (4.00 g, 23.3 mM), then morpholine (6.10 mL, 69.9 mM) was added to the solution and the solution was stirred for 14 hours while refluxing the same with heating. The solvent was distilled off from this reaction liquid, the resulting residue was diluted with water and then extracted with ethyl acetate. The resulting extracts were combined, dried over anhydrous sodium sulfate, the solvent was distilled off to thus obtain methyl 6-(morpholin-4-yl)-nicotinate (4.07 g, yield: 79%). Subsequently, acetonitrile (1.61 mL, 30.6 mM) was added to a solution of 18-crown-6 (476 mg, 1.80 mM) and potassium tert-butoxide (1M THF solution, 27.0 mL, 27.0 mM) in THF (10 mL) at 60° C. and then the mixture was stirred for 5 minutes. To this solution, there was added the methyl 6-(morpholin-4-yl)-nicotinate (4.00 g, 18.0 mM) prepared above and the mixture was stirred for 30 minutes. This suspension was filtered and the resulting solid was washed with diethyl ether.

The resulting solid was suspended in ethanol (60 mL), then concentrated hydrochloric acid (3.0 mL) and methyl carbazinate (3.61 g, 39.7 mM) were added to the suspension and the mixture was stirred at room temperature for 20 hours. After the stirring operation, potassium carbonate (2.74 g, 19.8 mM) was added to the suspension and the mixture was stirred at 90° C. for one hour. This reaction solution was concentrated under reduced pressure, the concentrate was diluted with water and then extracted with ethyl acetate. The resulting extracts were combined, dried over anhydrous sodium sulfate, the solvent was distilled off and the resulting solid was sufficiently washed with diethyl ether to thus give 5-(6-morpholin-4-yl-pyridin-3-yl)-2H-pyrazol-3-yl-amine.

The resulting 5-(6-morpholin-4-yl-pyridin-3-yl)-2H-pyrazol-3-yl-amine (720 mg, 2.93 mM) was dissolved in ethanol (20 mL), then sodium ethoxide (440 mg, 6.45 mM) and diethyl malonate (491 mL, 3.22 mM) were added to the solution. This reaction liquid was stirred for 6 hours, while refluxing the same with heating. This reaction mixture was filtered and the resulting solid was washed with diethyl ether. Phosphoryl chloride (20 mL) was added to the resulting solid with ice-cooling, and the suspension was stirred for 2 hours while refluxing the same with heating. The phosphoryl chloride was distilled off from this reaction liquid, ethanol was added to the resulting residue with ice-cooling and the mixture was stirred for 15 minutes. This reaction liquid was concentrated and then the concentrate was purified by the silica gel column chromatography (methanol/methylene chloride=1:20) to thus give 5,7-dichloro-2-(6-morpholin-4-yl-pyridin-3-yl)-pyrazolo[1,5-a]-pyrimidine.

The resulting 5,7-dichloro-2-(6-morpholin-4-yl-pyridin-3-yl)-pyrazolo[1,5-a]-pyrimidine was dissolved in 1,4-dioxane (4 mL), morpholine (500 μL, 5.74 mM) was added to the solution and then the mixture was stirred at room temperature for one hour. The solvent was distilled off from this reaction mixture, the residue obtained was diluted with water, the precipitated solid was recovered through filtration and then dried under reduced pressure to thus give the title compound (59.6 mg, overall yield of these three steps: 5.1%).

$^1$H-NMR (300 MHz, CDCl$_3$): δ 3.58-3.61 (m, 4H), 3.83-3.87 (m, 8H), 3.96-3.99 (m, 4H), 6.06 (s, 1H), 6.69 (s, 1H), 6.70 (d, 1H, J=8.0 Hz), 8.01 (dd, 1H, J=2.1, 8.8 Hz), 8.80 (d, 1H, J=2.1 Hz); MS (ESI) m/z 401 (M+H)$^+$.

(Step 2): N-(3-methyl-benzylidene)-N'-[7-morpholin-4-yl-2-(6-morpholin-4-yl-pyridin-3-yl)-pyrazolo[1,5-a]pyrimidin-5-yl]-hydrazine (Compound 85)

There was suspended, in 1,4-dioxane (3 mL), 5-chloro-7-morpholin-4-yl-2-(6-morpholin-4-yl-pyridin-3-yl)-pyrazolo[1,5-a]pyrimidine (28.9 mg, 0.0720 mM) and then hydrazine monohydrate (34.8 μL, 0.720 mM) was added to the suspension. After stirring this suspension at 60° C. overnight, it was stirred at 150° C. for 10 minutes under the irradiation with microwaves. Hydrazine monohydrate (40 μL, 0.82 mM) was added to this reaction liquid and then it was stirred at 150° C. for 15 minutes under the irradiation with microwaves. This reaction liquid was diluted with a saturated aqueous common salt solution and then extracted with ethyl acetate. The resulting extracts were combined, dried over anhydrous sodium sulfate and the solvent was distilled off. The resulting residue was suspended in ethanol (2 mL), then acetic acid (5.0 μL, 0.087 mM) and 3-methyl-benzaldehyde (8.5 μL, 0.072 mM) were added to the suspension and the mixture was stirred at room temperature for one hour. The solvent was distilled off from the reaction mixture, the resulting residue was purified by the reversed phase HPLC and then subjected to a desalting operation to thus give the title compound (14.3 mg, overall yield of these two steps: 40%).

$^1$H-NMR (300 MHz, DMSO): δ 2.34 (s, 3H), 3.49-3.51 (m, 4H), 3.69-3.72 (m, 8H), 3.85-3.88 (m, 4H), 6.27 (s, 1H), 6.48 (s, 1H), 6.91 (d, 1H, J=9.1 Hz), 7.17 (d, 1H, J=7.6 Hz), 7.31 (t, 1H, J=7.6 Hz), 7.47 (s, 1H), 7.52 (d, 1H, J=7.6 Hz), 8.02 (s, 1H), 8.06 (dd, 1H, J=2.3, 9.1 Hz), 8.71 (d, 1H, J=2.3 Hz), 11.16 (s, 1H); MS (ESI) m/z 499 (M+H)$^+$.

Example 86

Synthesis of N-(1H-indol-3-yl-methylidene)-N'-[7-morpholin-4-yl-2-(6-morpholin-4-yl-pyridin-3-yl)-pyrazolo[1,5-a]pyrimidin-5-yl]-hydrazine (Compound 86)

There was suspended, in 1,4-dioxane (3 mL), 5-chloro-7-morpholin-4-yl-2-(6-morpholin-4-yl-pyridin-3-yl)-pyrazolo[1,5-a]pyrimidine (28.9 mg, 0.0720 mM) and then hydrazine monohydrate (34.8 μL, 0.720 mM) was added to the suspension. After stirring this suspension at 60° C. overnight, it was stirred at 150° C. for 10 minutes under the irradiation with microwaves. Hydrazine monohydrate (40 μL, 0.82 mM) was added to this reaction liquid and then it was stirred at 150° C. for 15 minutes under the irradiation with microwaves. This reaction liquid was diluted with a saturated aqueous common salt solution and then extracted with ethyl acetate. The resulting extracts were combined, dried over anhydrous sodium sulfate and the solvent was distilled off. The resulting residue was suspended in ethanol (2 mL), then acetic acid (5.0 μL, 0.087 mM) and indole-3-carboxy-aldehyde (10.5 μL, 0.072 mM) were added to the suspension and the mixture was stirred at room temperature for one hour. The solvent was distilled off from the reaction mixture, the resulting residue was purified by the reversed phase HPLC and then subjected to a desalting operation to thus give the title compound (10.0 mg, overall yield of these two steps: 27%).

$^1$H-NMR (300 MHz, DMSO): δ 3.48-3.52 (m, 4H), 3.69-3.74 (m, 8H), 3.89-3.92 (m, 4H), 6.33 (s, 1H), 6.42 (s, 1H), 6.91 (d, 1H, J=8.8 Hz), 7.18-7.21 (m, 2H), 7.43 (m, 1H), 7.73 (s, 1H), 8.06 (dd, 1H, J=2.3, 8.8 Hz), 8.22 (m, 1H), 8.27 (s, 1H), 8.71 (d, 1H, J=2.3 Hz), 10.78 (s, 1H), 11.45 (s, 1H); MS (ESI) m/z 524 (M+H)$^+$.

Example 87

N-(3-methyl-benzylidene)-N'-(7-morpholin-4-yl-3-pyridin-2-yl-pyrazolo[1,5-a]pyrimidin-5-yl)-hydrazine (Compound 87)

(Step 1): 3-Amino-4-pyridin-2-yl-pyrazole

To a solution of 2-pyridine-acetonitrile (500 mg, 4.2 mM) in trifluoromethyl benzene (1.5 mL), there were added dimethylformamide dimethylacetal (0.75 mL) and N,N-dimethylformamide (0.75 mL) and the mixture was stirred at 140° C. for 15 minutes under the irradiation with microwaves. After concentrating the reaction solution under reduced pressure, the resulting residue was purified by the reversed phase HPLC to thus give the trifluoroacetic acid salt of the title compound (600 mg, yield: 57%).

MS (ESI) m/z (M+H)$^+$ 161

(Step 2): 5,7-Dichloro-3-pyridin-2-yl-pyrazolo[1,5-a]pyrimidine

To a solution of the compound (1.2 g, 2.4 mM) prepared in the foregoing step 1 in ethanol (15 mL), there were added sodium ethoxide (0.81 g, 12 mM) and diethyl malonate (0.44 mL, 2.9 mM) and then the mixture was stirred at 80° C. for 14 hours. After cooling the mixture to room temperature, the precipitated solid was recovered through filtration and the solid was washed with ethanol to thus give a crude product in the form of a bis-sodium salt. This crude product was suspended in phosphorus oxychloride (10 mL) and then the suspension was stirred at 90° C. for 5 hours. After cooling the suspension to room temperature, it was concentrated under reduced pressure and then the resulting residue was purified by the NH-silica gel column chromatography (methanol:methylene chloride=1:99) to thus give the title compound (193 mg, overall yield of these two steps: 30%).

MS (ESI) m/z (M+H)$^+$ 266

(Step 3): (7-Morpholin-4-yl-3-pyridin-2-yl-pyrazolo[1,5-a]pyrimidin-5-yl)-hydrazine To a solution of the compound (193 mg, 0.73 mM) prepared in the foregoing step 2 in 1,4-dioxane (7.0 mL), there was added morpholine (0.13 mL, 1.5 mM) and the mixture was stirred at room temperature for 4 hours. Water was added to the mixture and the mixture was extracted with ethyl acetate and the organic phase was washed with a saturated aqueous common salt solution. After drying the organic phase over anhydrous magnesium sulfate, the organic phase was concentrated under reduced pressure, the residue obtained was dissolved in 1,4-dioxane (5.0 mL) and then hydrazine monohydrate (0.35 mL, 7.3 mM) was added to the solution. After stirring the mixture at 90° C. for 5 hours, it was then cooled to room temperature and water was added thereto. The mixture was extracted with ethyl acetate, the resulting organic phase was dried over anhydrous magnesium sulfate and then concentrated under reduced pressure to give a crude product of the title compound (151 mg, overall yield of these two steps: 67%).

$^1$H-NMR (300 MHz, DMSO): δ 3.52-3.55 (4H, m), 3.62-3.82 (4H, m), 4.47-4.53 (2H, br), 5.81 (1H, br), 7.05 (1H, J=0.9, 4.8, 7.2 Hz, ddd), 7.71 (1H, J=1.8, 7.8 Hz, dt), 8.25-8.53 (4H, m); MS (ESI) m/z (M+H)$^+$ 312

(Step 4): N-(3-methyl-benzylidene)-N'-(7-morpholin-4-yl-3-pyridin-2-yl-pyrazolo-[1,5-a]pyrimidin-5-yl)-hydrazine (Compound 87)

To a solution of the compound (25 mg, 0.080 mM) prepared in the foregoing step 3 in ethanol (1.0 mL), there were added metatolualdehyde (14 μL, 0.12 mM) and acetic acid (3 μL) and then the mixture was stirred at room temperature for 3 hours. The precipitated solid was recovered through filtration and then washed with ethanol to thus give the title compound (15 mg, yield: 45%).

$^1$H-NMR (300 MHz, DMSO): δ 2.37 (3H, s), 3.44 (4H, s), 3.85 (4H, m), 6.41 (1H, s), 7.12 (1H, J=1.2, 6.0 Hz, dt), 7.21 (1H, J=7.5 Hz, d), 7.34 (1H, J=7.5 Hz, t), 7.51 (1H, s), 7.57 (1H, J=7.5 Hz, d), 7.77 (1H, J=2.1, 7.5 Hz, dt), 8.14 (1H, s), 8.48-8.53 (3H, m), 11.44 (1H, s); MS (ESI) m/z (M+H)$^+$ 414

Example 88

Synthesis of N-(1H-indol-3-yl-methylidene)-N'-(7-morpholin-4-yl-3-pyridin-2-yl-pyrazolo[1,5-a]pyrimidin-5-yl)-hydrazine (Compound 88)

To a solution of (7-morpholin-4-yl-3-pyridin-2-yl-pyrazolo[1,5-a]pyrimidin-5-yl)-hydrazine (25 mg, 0.080 mM) in ethanol (1.5 mL), there were added 3-formyl-indole (18 mg, 0.12 mM) and acetic acid (3 μL) and then the mixture was stirred at room temperature for 3 hours. The precipitated solid was recovered through filtration and then washed with ethanol to thus give the title compound (18 mg, yield: 51%).

$^1$H-NMR (300 MHz, DMSO): δ 3.74 (4H, s), 3.88-3.93 (4H, m), 6.45 (1H, br), 7.12 (1H, J=7.5 Hz, t), 7.20-7.26 (2H, m), 7.43-7.48 (1H, m), 7.73-7.80 (2H, m), 8.29-8.52 (5H, m), 11.16 (1H, s), 11.51 (1H, s); MS (ESI) m/z (M+H)$^+$ 439

Example 89

Synthesis of N-(2-carboxy-7-morpholin-4-yl-pyrazolo[1,5-a]pyrimidin-5-yl)-N'-(3-methyl-benzylidene)-hydrazine (Compound 89)

There was suspended, in 1,4-dioxane (2 mL), 5-chloro-2-ethoxycarbonyl-7-morpholin-4-yl-pyrazolo[1,5-a]pyrimidine (203 mg, 0.653 mM), then hydrazine monohydrate (317 μL, 6.53 mM) was added to the suspension and the suspension was stirred for 20 hours while refluxing the same with heating. After the stirring operation, the reaction liquid was diluted with water and then extracted with ethyl acetate. The resulting extracts were combined, dried over anhydrous sodium sulfate and the solvent was then distilled off.

The resulting residue was suspended in ethanol (2 mL), then acetic acid (18.7 μL, 0.327 mM) and 3-methyl-benzaldehyde (76.9 μL, 0.653 mM) were added to the suspension, the mixture was stirred at room temperature for one hour, the suspension was filtered and the resulting solid was washed with diethyl ether. The resulting solid was dissolved in THF (2 mL), a 1M aqueous solution of sodium hydroxide (2 mL) was added to the solution and the mixture was stirred at room temperature overnight. The solvent was distilled off from this reaction liquid, the residue was purified by the reversed phase HPLC and then subjected to a desalting operation to thus give the title compound (29.7 mg, yield: 12%).

$^1$H-NMR (300 MHz, DMSO): δ 2.34 (s, 3H), 3.66-3.69 (m, 4H), 3.82-3.85 (m, 4H), 6.38 (s, 1H), 6.45 (s, 1H), 7.19 (d, 1H, J=7.6 Hz), 7.31 (t, 1H, J=7.6 Hz), 7.49 (m, 1H), 7.53 (d, 1H, J=7.6 Hz), 8.04 (s, 1H), 11.37 (s, 1H); MS (ESI) m/z 381 (M+H)$^+$.

Example 90

Synthesis of N-(3-methyl-benzylidene)-N'-(7-morpholin-4-yl-2-pyrazin-2-yl-pyrazolo[1,5-a]pyrimidin-5-yl)-hydrazine (Compound 90)

(Step 1): 3-Amino-5-pyrazin-2-yl-pyrazole

To a solution of 18-crown-6 (0.57 g, 2.2 mM) in tetrahydrofuran (10 mL), there was added a 1.0M potassium tert-butoxide/tetrahydrofuran solution (24 mL, 24 mM) and then the mixture was heated up to 60° C. Acetonitrile (1.3 mL, 24 mM) was then added to the mixture at that temperature, followed by the stirring of the same for 5 minutes and the subsequent addition of 2-methoxycarbonyl-pyrazine (3 g, 22 mM). After stirring the mixture at 60° C. for 30 minutes, it was cooled to room temperature, the precipitated solid was recovered through filtration and washed with tetrahydrofuran. The resulting solid was dried in vacio, suspended in ethanol (60 mL) and then methyl carbazinate (2.7 g, 30 mM) was added thereto. Concentrated hydrochloric acid (2.2 mL) was added to the suspension with ice-cooling and the mixture was stirred for 14 hours at that temperature. There were added, to the mixture, potassium carbonate (2.4 g, 17 mM) and water (10 mL) and the mixture was stirred at 90° C. for one hour. After cooling the mixture to room temperature, it was concentrated under reduced pressure and then water was added thereto. The mixture was extracted with ethyl acetate, the organic phase thus obtained was dried over anhydrous magnesium sulfate and then concentrated under reduced pressure to thus give a crude product of the title compound (627 mg, yield: 18%).

MS (ESI) m/z (M+H)$^+$ 162

(Step 2): 5,7-Dichloro-2-pyrazin-2-yl-pyrazolo[1,5-a]pyrimidine

To a solution of the compound (627 mg, 3.9 mM) prepared in the foregoing step 1 in ethanol (15 mL), there were added diethyl malonate (0.71 mL, 4.7 mM) and sodium ethoxide (0.53 g, 7.8 mM) and the mixture was stirred at 80° C. for 14 hours. After cooling the mixture to room temperature, the precipitated solid was recovered through filtration and then washed with ethanol. The resulting solid was suspended in phosphorus oxychloride (10 mL) and the suspension was stirred at 90° C. for 5 hours. After the suspension was cooled to room temperature, it was concentrated under reduced pressure and then the resulting residue was purified by the NH-silica gel column chromatography (methanol:methylene chloride=1:99) to thus give the title compound (204 mg, overall yield of these two steps: 20%).

$^1$H-NMR (300 MHz, DMSO): δ 7.46 (1H, s), 7.79 (1H, s), 8.75 (1H, J=2.4 Hz, d), 8.81 (1H, J=1.5, 2.4 Hz, dd), 9.37 (1H, J=1.5 Hz, d); MS (ESI) m/z (M+H)$^+$ 266

(Step 3): (7-Morpholin-4-yl-2-pyrazin-2-yl-pyrazolo [1,5-a]pyrimidin-5-yl)-hydrazine To a solution of the compound (204 mg, 0.77 mM) obtained in the foregoing step 2 in 1,4-dioxane (5.0 mL), there was added morpholine (0.13 mL, 1.5 mM) and the mixture was stirred at room temperature for 4 hours. Water was added to the mixture, the latter was extracted with ethyl acetate and the resulting organic phase was washed with a saturated aqueous common salt solution. After drying the organic phase over anhydrous magnesium sulfate, it was concentrated under reduced pressure, the residue obtained was dissolved in 1,4-dioxane (5.0 mL) and then hydrazine monohydrate (0.37 mL, 7.7 mM) was added thereto. After stirring the mixture at 90° C. for 5 hours, it was cooled to room temperature and water was then added thereto. The mixture was extracted with ethyl acetate, the resulting organic phase was dried over anhydrous magnesium sulfate and then concentrated under reduced pressure to thus give a crude product of the title compound (175 mg, overall yield of these two steps: 73%).

MS (ESI) m/z (M+H)$^+$ 313

(Step 4): N-(3-methyl-benzylidene)-N'-(7-morpholin-4-yl-2-pyrazin-2-yl-pyrazolo-[1,5-a]pyrimidin-5-yl)-hydrazine (Compound 90)

To a solution of the compound (8.7 mg, 0.028 mM) prepared in the foregoing step 3 in ethanol (1.0 mL), there were added metatolualdehyde (10 µL, 0.084 mM) and acetic acid (3 µL) and the mixture was stirred at room temperature for 3 hours. The precipitated solid was recovered through filtration and then washed with ethanol to thus give the title compound (5.6 mg, yield: 49%).

$^1$H-NMR (300 MHz, DMSO): δ 2.36 (3H, s), 3.75 (4H, s), 3.90 (4H, m), 6.40 (1H, s), 6.68 (1H, s), 7.20 (1H, J=7.5 Hz, d), 7.33 (1H, J=7.5 Hz, d), 7.50 (1H, s), 7.55 (1H, J=7.5 Hz, d), 8.05 (1H, s), 8.65 (1H, J=2.4 Hz, d), 8.72 (1H, J=1.2 Hz, t), 9.33 (1H, J=1.2 Hz, d), 11.31 (1H, s); MS (ESI) m/z (M+H)$^+$ 415

Example 91

Synthesis of N-(7-morpholin-4-yl-2-pyridin-4-yl-pyrazolo[1,5-a]-pyrimidin-5-yl)-N'-thiophen-3-yl-methylidene-hydrazine (Compound 91)

There was suspended, in 1,4-dioxane (3 mL), 5-chloro-7-morpholin-4-yl-2-pyridin-4-yl-pyrazolo[1,5-a]pyrimidine (110 mg, 0.35 mM), then hydrazine monohydrate (170 µL, 3.5 mM) was added to the suspension and the mixture was stirred for 18 hours while refluxing the same with heating. After the stirring operation, the reaction liquid was concentrated, the concentrate was diluted with water and then extracted with ethyl acetate. The resulting extracts were combined, dried over anhydrous sodium sulfate and the solvent was distilled off.

The resulting residue was suspended in ethanol (5 mL), then acetic acid (8.7 µL, 0.015 mM) and 3-thiophene-aldehyde (36 µL, 0.33 mM) were added to the suspension and the mixture was stirred at room temperature for one hour. After the stirring operation, the residue thus obtained was purified by the reversed phase HPLC, the purified product was basified by the addition of a 6N aqueous sodium hydroxide solution and then it was stirred. It was then extracted with ethyl acetate to thus give the title compound (23.0 mg, yield: 16.3%).

$^1$H-NMR (300 MHz, DMSO-d6); δ 3.73 (bs, 4H), 3.89 (bs, 4H), 6.36 (s, 1H), 6.74 (s, 1H), 7.57-7.64 (m, 2H), 7.82 (d, 1H, J=1.8 Hz), 7.91 (d, 2H, J=5.7 Hz), 8.13 (s, 1H), 8.66 (d, 2H, J=6 Hz), 11.2 (s, 1H); MS (ESI) m/z 406 (M+H)$^+$.

Example 92

Synthesis of N-(4-methoxy-3-methyl-benzylidene)-N'-(7-morpholin-4-yl-2-pyridin-4-yl-pyrazolo[1,5-a] pyrimidin-5-yl)-hydrazine (Compound 92)

There was suspended, in 1,4-dioxane (3 mL), 5-chloro-7-morpholin-4-yl-2-pyridin-4-yl-pyrazolo[1,5-a]pyrimidine (110 mg, 0.35 mM), then hydrazine monohydrate (170 µL, 3.5 mM) was added to the suspension and the mixture was stirred for 18 hours while refluxing the same with heating. After the stirring operation, the reaction liquid was concentrated, the concentrate was diluted with water and then extracted with ethyl acetate. The resulting extracts were combined, dried over anhydrous sodium sulfate and the solvent was distilled off.

The resulting residue was suspended in ethanol (5 mL), then acetic acid (8.4 µL, 0.015 mM) and 3-methyl-p-anisaldehyde (47 µL, 0.32 mM) were added to the suspension and the mixture was stirred at room temperature for one hour. After the stirring operation, the residue obtained was purified by the reversed phase HPLC and then subjected to a desalting operation to thus give the title compound (20 mg, yield: 15.2%).

$^1$H-NMR (300 MHz, DMSO-d6); δ 2.20 (s, 3H), 3.73 (bs, 4H), 3.83 (s, 3H), 3.88 (bs, 4H), 6.36 (s, 1H), 6.73 (s, 1H), 7.00 (d, 1H, J=9.3 Hz), 7.51 (d, 1H, J=6.9 Hz), 7.91 (d, 2H, J=3 Hz), 8.01 (s, 1H), 8.66 (d, 2H, J=3 Hz), 11.1 (s, 1H); MS (ESI) m/z 444 (M+H)$^+$.

Example 93

Synthesis of N-(1H-indol-3-yl-methylidene)-N'-(7-morpholin-4-yl-2-pyrazin-2-yl-pyrazolo[1,5-a]pyrimidin-5-yl)-hydrazine (Compound 93)

To a solution of (7-Morpholin-4-yl-2-pyrazin-2-yl-pyrazolo[1,5-a]pyrimidin-5-yl)-hydrazine (20 mg, 0.064 mM) in ethanol (2.0 mL), there were added 3-formyl-indole (19 mg, 0.13 mM) and acetic acid (5 µL) and the mixture was stirred at room temperature for 3 hours. The precipitated solid was recovered through filtration and then washed with ethanol to thus give the title compound (15 mg, yield: 54%).

$^1$H-NMR (300 MHz, DMSO): δ 3.76 (4H, s), 3.91 (4H, m), 6.44 (1H, s), 6.60 (1H, s), 7.17-7.22 (2H, m), 7.42-7.45 (1H, m), 7.74 (1H, J=2.4 Hz, d), 8.21 (1H, J=3.3, 5.7 Hz, dd), 8.28

(1H, s), 8.62 (1H, J=2.4 Hz, d), 8.70 (1H, m), 9.11 (1H, J=1.5 Hz, d), 11.00 (1H, s), 11.47 (1H, s); MS (ESI) m/z (M+H)+ 440

Example 94

Synthesis of N-(3-methyl-benzylidene)-N-(7-morpholin-4-yl-2-pyridazin-4-yl-pyrazolo[1,5-a]pyrimidin-5-yl)-hydrazine (Compound 94)

(Step 1): Synthesis of methyl 5-amino-3-pyridazin-4-yl-pyrazole-1-carboxylate

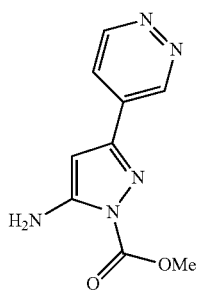

To a solution of 18-crown-6 (0.48 g, 1.8 mM) in tetrahydrofuran (10 mL), there was added a 1.0M potassium tert-butoxide/tetrahydrofuran solution (20 mL, 20 mM) and then the mixture was warmed up to 60° C. Acetonitrile (1.0 mL, 20 mM) was added to the mixture at that temperature, the mixture was stirred for 10 minutes and 4-methoxycarbonyl-pyridazine (2.5 g, 18 mM) was then added thereto. After stirring the mixture at 60° C. for 30 minutes, it was cooled to room temperature, the precipitated solid was recovered through filtration and then washed with tetrahydrofuran. After drying the resulting solid in vacuo, it was suspended in ethanol (50 mL) and then methyl carbazinate (2.3 g, 26 mM) was added thereto. Concentrated hydrochloric acid (1.5 mL) was added to the suspension with ice-cooling and the mixture was stirred at that temperature for 14 hours. The reaction liquid was concentrated under reduced pressure and the excess hydrochloric acid was neutralized by the addition of a saturated sodium bicarbonate aqueous solution. The reaction liquid was extracted with ethyl acetate, the organic phase thus obtained was dried over anhydrous magnesium sulfate and concentrated under reduced pressure to thus give a crude product of the title compound (0.50 g, yield: 13%).
MS (ESI) m/z (M+H)+ 220

(Step 2): Synthesis of 5,7-dichloro-2-pyridazin-4-yl-pyrazolo[1,5-a]pyrimidine

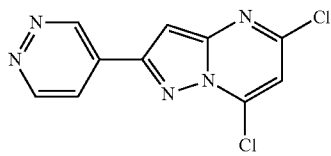

To a solution of the compound (0.50 g, 2.3 mM) obtained in the step 1 in ethanol (10 mL), there were added diethyl malonate (0.69 mL, 4.6 mM) and sodium ethoxide (0.53 g, 7.8 mM) and the mixture was stirred at 80° C. for 14 hours. After cooling the mixture to room temperature, the precipitated solid was recovered through filtration and then washed with ethanol to thus give a crude product in the form of a bis-sodium salt thereof. Phosphorus oxychloride (5.0 mL) was added to the crude product and then the mixture was stirred at 90° C. for 5 hours. After the mixture was cooled to room temperature, it was concentrated under reduced pressure and the resulting residue was purified by the reversed phase high performance liquid chromatography which made use of the chemically bonded octadodesyl group-containing silica gel as a loading material to thus give the title compound (49 mg, yield: 8%).
MS (ESI) m/z (M+H)+ 266

(Step 3): Synthesis of (7-Morpholin-4-yl-2-pyridazin-4-yl-pyrazolo[1,5-a]pyrimidin-5-yl)-hydrazine

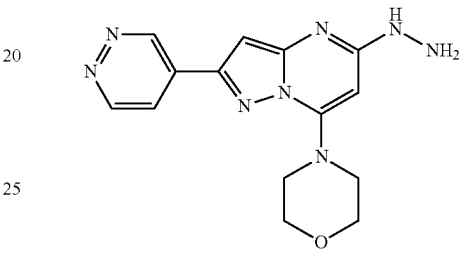

To a solution of the compound (49 mg, 0.18 mM) obtained in the foregoing step 2 in 1,4-dioxane (2.0 mL), there was added morpholine (32 μL, 0.37 mM) and then the mixture was stirred at room temperature for 4 hours. Water was added to the mixture, followed by the extraction of the mixture with ethyl acetate and the subsequent washing of the resulting organic phase with a saturated aqueous common salt solution. After drying the organic phase over anhydrous magnesium sulfate, it was concentrated under reduced pressure, the residue obtained was dissolved in 1,4-dioxane (4.0 mL) and then hydrazine monohydrate (45 μL, 0.92 mM) was added thereto. After stirring the mixture at 90° C. for 14 hours, it was cooled to room temperature, and then water was added thereto. The mixture was extracted with ethyl acetate, the resulting organic phase was dried over anhydrous magnesium sulfate and then concentrated under reduced pressure to thus give a crude product of the title compound (40 mg, overall yield of these two steps: 69%).
MS (ESI) m/z (M+H)+ 313

(Step 4): Synthesis of N-(3-methyl-benzylidene)-N-(7-morpholin-4-yl-2-pyridazin-4-yl-pyrazolo[1,5-a]pyrimidin-5-yl)-hydrazine (Compound 94)

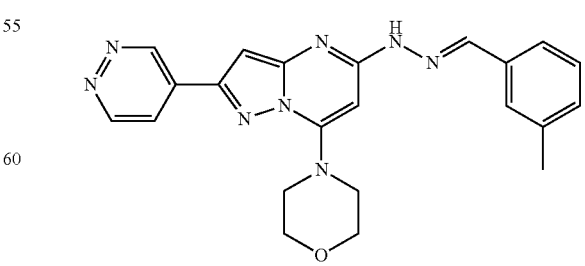

To a solution of the compound (15 mg, 0.048 mM) obtained in the foregoing step 3 in ethanol (2.0 mL), there were added metatolualdehyde (11 μL, 0.096 mM) and acetic acid (5.0 μL) and the mixture was stirred at room temperature for 3 hours. The precipitated solid was filtered off and then subjected to a slurry-washing treatment (methanol, dichloromethane) to thus give the title compound (10 mg, yield: 50%).

¹H-NMR (300 MHz, DMSO): δ 2.36 (3H, s), 3.71-3.77 (4H, m), 3.87-3.91 (4H, m), 6.40 (1H, J=1.8 Hz, d), 6.91 (1H, s), 7.20 (1H, J=6.9 Hz, d), 7.33 (1H, J=7.8 Hz, t), 7.50 (1H, s), 7.55 (1H, J=6.9 Hz, d), 8.07 (1H, s), 8.15 (1H, J=2.1, 5.4 Hz, dd), 9.31 (1H, J=4.2 Hz, d), 9.79 (1H, J=1.8 Hz, d), 11.32 (1H, J=2.7 Hz, d)

MS (ESI) m/z (M+H)⁺ 415

Example 95

Synthesis of N-benzofuran-3-yl-methylidene-N'-(7-morpholin-4-yl-2-pyridin-4-yl-pyrazolo[1,5-a]-hydrazine (Compound 95)

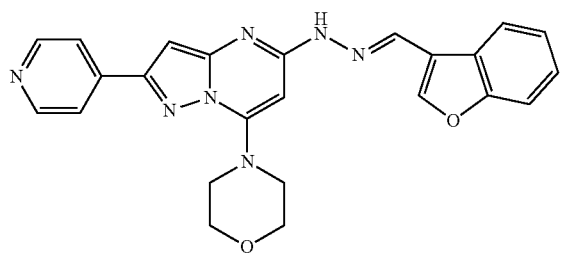

There was suspended, in ethanol (3.0 mL), 5-chloro-7-morpholin-4-yl-2-pyridin-4-yl-pyrazolo[1,5-a]pyrimidine (82 mg, 0.26 mM), then acetic acid (7.5 μL, 0.13 mM) and benzofuran 3-carboxy-aldehyde (42 mg, 0.29 mM) were added to the suspension and the mixture was stirred at room temperature for one hour. This reaction liquid was filtered, washed with ethanol and then with diethyl ether to thus give the title compound (8.5 mg, yield: 7.4%).

¹H-NMR (300 MHz, DMSO-d6); δ 3.78 (bs, 4H), 3.90 (bs, 4H), 6.39 (s, 1H), 6.75 (s, 1H), 7.42-7.45 (m, 2H), 7.61-7.67 (m, 1H), 7.91 (d, 2H, J=6.3 Hz), 8.24-8.25 (m, 1H), 8.28 (s, 1H), 8.42 (s, 1H), 8.64 (d, 2H, J=5.7 Hz), 11.3 (s, 1H); MS (ESI) m/z 440 (M+H)⁺.

Example 96

Synthesis of N-benzofuran-2-yl-methylidene-N'-(7-morpholin-4-yl-2-pyridin-4-yl-pyrazolo[1,5-a]-hydrazine (Compound 96)

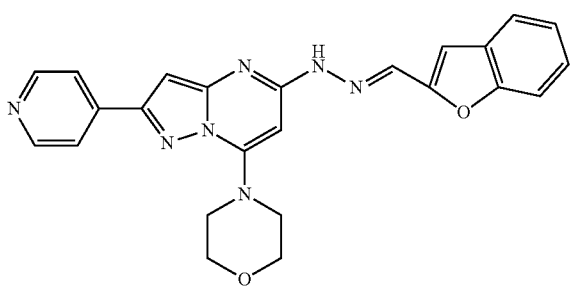

There was suspended, in ethanol (1.8 mL), 5-chloro-7-morpholin-4-yl-2-pyridin-4-yl-pyrazolo[1,5-a]pyrimidine (40 mg, 0.13 mM), then acetic acid (3.7 μL, 0.026 mM) and benzofuran 2-carboxy-aldehyde (21 mg, 0.14 mM) were added to the suspension and the mixture was stirred at room temperature for one hour. This reaction liquid was filtered, washed with ethanol and then with diethyl ether to thus give the title compound (22 mg, yield: 50%).

¹H-NMR (300 MHz, DMSO-d6); δ 3.74 (bs, 4H), 3.88 (bs, 4H), 6.31 (s, 1H), 6.79 (s, 1H), 7.23-7.40 (m, 3H), 7.61-7.67 (m, 2H), 7.91 (d, 2H, J=6 Hz), 8.10 (s, 1H), 8.64 (d, 2H, J=6 Hz), 11.5 (s, 1H); MS (ESI) m/z 440 (M+H)⁺.

Example 97

Synthesis of N-(1H-indol-3-yl-methylidene)-N-(7-morpholin-4-yl-2-pyridazin-4-yl-pyrazolo[1,5-a]pyrimidin-5-yl)-hydrazine (Compound 97)

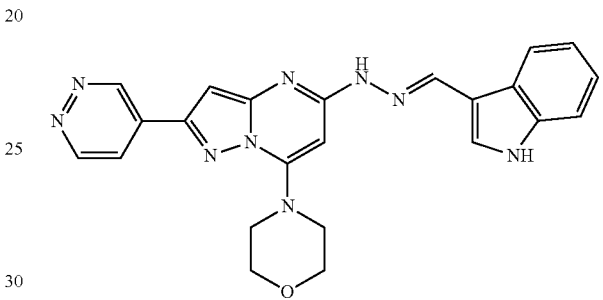

To a solution of (7-morpholin-4-yl-2-pyridazin-4-yl-pyrazolo[1,5-a]pyrimidin-5-yl)-hydrazine (20 mg, 0.064 mM) in ethanol (3.0 mL), there were added 3-formyl-indole (19 mg, 0.13 mM) and acetic acid (5.0 μL) and the mixture was stirred at room temperature for 3 hours. The precipitated solid was recovered through filtration and then subjected to a slurry-washing treatment (methanol, dichloromethane) to thus give the title compound (20 mg, yield: 71%).

¹H-NMR (300 MHz, DMSO): δ 3.76-3.80 (4H, m), 3.93-3.96 (4H, m), 6.46 (1H, s), 6.85 (1H, s), 7.19-7.24 (2H, m), 7.44-7.47 (1H, m), 7.76 (1H, J=2.7 Hz, d), 8.15 (1H, J=2.4, 5.4 Hz, dd), 8.22-8.25 (1H, m), 8.31 (1H, s), 9.31 (1H, J=5.4 Hz, d), 9.79 (1H, J=2.4 Hz, d), 11.05 (1H, s), 11.49 (1H, s)

MS (ESI) m/z (M+H)⁺ 440

Example 98

Synthesis of N-(3-methyl-benzylidene)-N'-[2-(5-methylisoxazol-3-yl)-7-morpholin-4-yl-pyrazolo[1,5-a]pyrimidin-5-yl]-hydrazine (Compound 98)

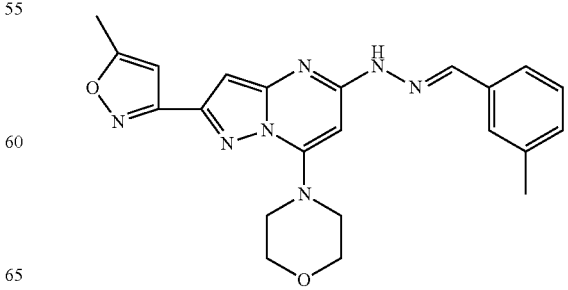

(Step 1): 5-Chloro-2-(5-methylisoxazol-3-yl)-7-morpholin-4-yl-pyrazolo[1,5-a]-pyrimidine There was added, to 18-crown-6 (0.94 g, 3.5 mM), a 1.0M potassium tert-butoxide/tetrahydrofuran solution (43 mL, 42 mM) and the mixture was warmed up to 60° C. Acetonitrile (2.1 mL, 39 mM) was added to the mixture at that temperature, the mixture was stirred for 5 minutes, and then there was added, to the mixture, 5-methyl-isoxazole 4-carboxylic acid methyl ester (5.0 g, 35 mM). After stirring the mixture at 60° C. for one hour, it was cooled to room temperature, the precipitated solid was filtered and washed with tetrahydrofuran and diethyl ether. The resulting solid was dried in vacuo, then suspended in ethanol (140 mL) and concentrated hydrochloric acid (4.0 mL) was added to the suspension with ice-cooling. Subsequently, methyl carbazinate (6.4 g, 70 mM) was added to the suspension at room temperature, followed by the stirring of the same for 16 hours. The suspension was concentrated under reduced pressure, water was added to the concentrate, the mixture was extracted with ethyl acetate, the resulting organic phase was dried over anhydrous magnesium sulfate and then concentrated under reduced pressure. After the resulting solid was dried in vacuo, then suspended in ethanol (80 mL), sodium ethoxide (2.0 g, 29 mM) was added to the suspension, the mixture was stirred at room temperature for one hour, then diethyl malonate (8.0 mL, 53 mM) and sodium ethoxide (5.2 g, 76 mM) were added to the mixture, followed by the stirring of the same at 90° C. for 9 hours. After cooling the reaction liquid to room temperature, the precipitated solid was recovered through filtration and then washed with diethyl ether.

The resulting solid was dried in vacuo, suspended in phosphorus oxychloride (64 mL) and the suspension was stirred at 90° C. for 2 hours. After cooling the suspension to room temperature, it was concentrated under reduced pressure and the concentrate was suspended in ethanol (28 mL). Morpholine (28 mL, 32 mM) was added to this suspension and the mixture was stirred at room temperature for 3 hours. After the mixture was concentrated under reduced pressure, water (400 mL) was added to the resulting residue and the precipitated solid was recovered through filtration. The resulting solid was purified by the silica gel column chromatography (dichloromethane) to thus give a crude product of the title compound (820 mg, overall yield of these five steps: 7.3%).
MS (ESI) m/z (M+H)+ 320

(Step 2): [2-(5-methylisoxazol-3-yl)-7-morpholin-4-yl-pyrazolo[1,5-a]pyrimidin-5-yl]-hydrazine There was suspended, in 1,4-dioxane (20 mL), 5-chloro-2-(5-methylisoxazol-3-yl)-7-morpholin-4-yl-pyrazolo[1,5-a]-pyrimidine (0.82 g, 2.6 mM) prepared in the foregoing step 1, then hydrazine monohydrate (1.3 mL, 26 mM) was added to the suspension and the suspension was stirred for 3 hours while refluxing the same with heating. After the stirring operation, the reaction liquid was concentrated, the concentrate was then diluted with water and extracted with ethyl acetate. The resulting extracts were combined, dried over anhydrous sodium sulfate and the solvent was distilled off to thus give a crude product of the title compound (210 mg, yield: 26%). MS (ESI) m/z (M+H)+ 316.

(Step 3): N-(3-methyl-benzylidene)-N'-[2-(5-methyl-isoxazol-3-yl)-7-morpholin-4-yl-pyrazolo[1,5-a]pyrimidin-5-yl]-hydrazine There was suspended, in ethanol (10 mL), [2-(5-methyl-isoxazol-3-yl)-7-morpholin-4-yl-pyrazolo[1,5-a]pyrimidin-5-yl]-hydrazine (110 mg, 0.34 mM) prepared in the preceding step 2, then acetic acid (9 μL, 0.17 mM) and metatolualdehyde (44 μL, 0.37 mM) were added to the suspension and the mixture was stirred at room temperature for 4 hours. The precipitated solid was filtered, washed with diethyl ether and then purified by the reversed phase HPLC (C-18 ODS Column) to thus give the trifluoroacetic acid (TFA) salt of the title compound (18 mg, yield: 10%).
1H-NMR (300 MHz, DMSO-d6); δ 2.36 (s, 3H), δ 3.73 (bs, 4H), 3.87 (bs, 4H), 6.33 (bs, 1H), 6.48 (s, 1H), 6.69 (s, 1H), 7.21 (d, 1H, J=4.2 Hz), 7.34 (t, 1H, J=7.5 Hz), 7.52-7.58 (m, 2H), 8.07 (s, 1H), 11.4 (s, 1H); MS (ESI) m/z 418 (M+H)+

Example 99

Synthesis of N-(1H-indol-3-yl-methylidene)-N'-[2-(5-methylisoxazol-3-yl)-7-morpholin-4-yl-pyrazolo[1,5-a]pyrimidin-5-yl]-hydrazine (Compound 99)

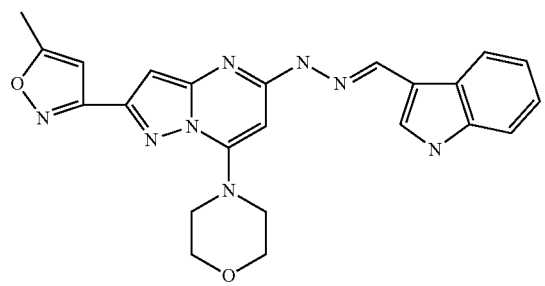

There was suspended, in ethanol (10 mL), [2-(5-methyl-isoxazol-3-yl)-7-morpholin-4-yl-pyrazolo[1,5-a]pyrimidin-5-yl]-hydrazine (97 mg, 0.31 mM), then acetic acid (8.8 μL, 0.16 mM) and indole-3-carboxyaldehyde (50 mg, 0.34 mM) were added to the suspension and the mixture was stirred at room temperature for 4 hours. The precipitated solid was filtered, washed with diethyl ether and then purified by the reversed phase HPLC (C-18 ODS Column) to thus give the trifluoroacetic acid (TFA) salt of the title compound (6.1 mg, yield: 3.5%).
1H-NMR (300 MHz, DMSO-d6); δ3.77 (bs, 4H), 3.88 (bs, 4H), 6.45 (br, 2H), 6.68 (s, 1H), 7.17-7.22 (m, 2H), 7.43-7.46 (m, 1H), 7.81 (bs, 1H), 8.26-8.32 (m, 2H), 11.1 (bs, 1H), 11.5 (bs, 1H); MS (ESI) m/z 443 (M+H)+

Example 100

Synthesis of N-(3-methyl-benzylidene)-N-(7-morpholin-4-yl-2-piperidin-1-yl-pyrazolo[1,5-a]pyrimidin-5-yl)-hydrazine (Compound 100)

(Step 1): Synthesis of methyl 5-amino-3-piperidin-1-yl-pyrazole-1-carboxylate

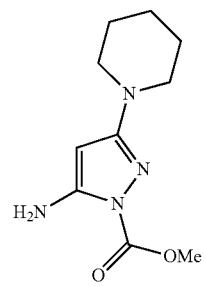

To a solution of 1-cyanoacetyl-piperidine (0.75 g, 4.9 mM) in dichloromethane (12 mL), there was added phosphorus oxychloride (0.47 mL, 5.2 mM) and the mixture was stirred at 100° C. for 15 minutes under the irradiation with microwaves. Methyl carbazinate (580 mg, 6.4 mM) was added to the reaction liquid and the mixture was stirred at 100° C. for 20 minutes under the irradiation with microwaves. The reaction solution was concentrated under reduced pressure and the concentrate was neutralized by the addition of a saturated aqueous sodium bicarbonate solution. The neutralized concentrate was extracted with ethyl acetate, the resulting organic phase was dried over anhydrous magnesium sulfate and then concentrated under reduced pressure to thus give a crude product of the title compound (0.57 g, yield: 52%).

MS (ESI) m/z (M+H)+ 225

(Step 2): Synthesis of methyl 5-(ethoxycarbonyl-acetylamino)-3-piperidin-1-yl-pyrazole-1-carboxylate

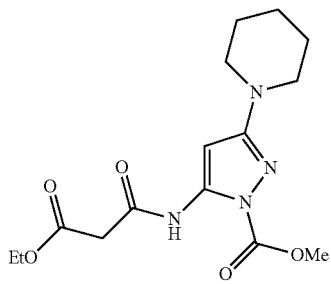

To a solution of the compound (1.1 g, 5.1 mM) prepared in the foregoing step 1 in dichloromethane (40 mL), there were, in order, added ethyl malonyl chloride (0.78 mL, 6.1 mM) and triethylamine (0.85 mL, 6.1 mM) and then the mixture was stirred at room temperature for 3 hours. The reaction solution was then concentrated under reduced pressure and water was added thereto. The mixture was extracted with ethyl acetate, the resulting organic phase was dried over anhydrous magnesium sulfate, concentrated under reduced pressure and then subjected to a slurry-washing treatment (dichloromethane, diethyl ether) to thus give the title compound (1.6 g, yield: 92%).

$^1$H-NMR (300 MHz, DMSO): δ 1.32 (3H, J=7.2 Hz, t), 1.53-1.61 (6H, m), 3.28-3.30 (4H, m), 3.52 (2H, s), 4.04 (3H, s), 4.29 (2H, J=7.2 Hz, q), 6.57 (1H, s), 11.44 (1H, s)

MS (ESI) m/z (M+H)+ 339

(Step 3): Synthesis of 5,7-dichloro-2-piperidin-1-yl-pyrazolo[1,5-a]pyrimidine

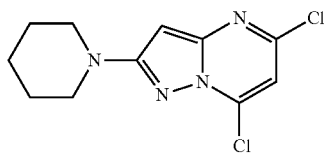

To a solution of the compound (2.3 g, 6.8 mM) prepared in the preceding step 2 in ethanol (50 mL), there was added a 28% methanol solution of sodium methoxide (3 mL, 15 mM) and the mixture was stirred at 70° C. for one hour. After cooling the mixture to room temperature, the precipitated solid was filtered and then washed with ethanol to thus give a crude product in the form of a bis-sodium salt thereof. To the crude product, there were added phosphorus oxychloride (10 mL) and pyridine (0.6 mL) and the mixture was stirred at 90° C. for 5 hours. After cooling the mixture to room temperature, it was concentrated under reduced pressure and the concentrate was neutralized with a saturated aqueous sodium bicarbonate solution. The neutralized concentrate was extracted with dichloromethane, the resulting organic phase was dried over anhydrous magnesium sulfate, then concentrated under reduced pressure and thereafter the resulting residue was purified by the silica gel column chromatography (SiO$_2$, methanol: dichloromethane=1:9) to thus give the title compound (633 mg, overall yield of these two steps: 34%%).

$^1$H-NMR (300 MHz, DMSO): δ 1.66 (6H, br), 3.40-3.42 (4H, m), 5.94 (1H, s), 6.65 (1H, s)

MS (ESI) m/z (M+H)+ 271

(Step 4): Synthesis of (7-morpholin-4-yl-2-piperidin-1-yl-pyrazolo[1,5-a]-pyrimidin-5-yl)-hydrazine

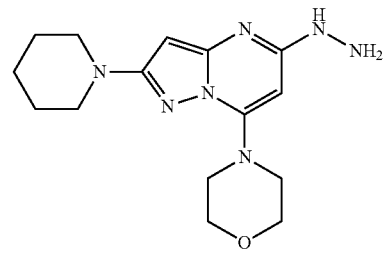

To a solution of the compound (0.63 g, 2.3 mM) prepared in the foregoing step 3 in 1,4-dioxane (15 mL), there was added morpholine (0.4 mL, 4.7 mM) and then the mixture was stirred at room temperature for 4 hours. Water was added thereto, the mixture was extracted with ethyl acetate and the resulting organic phase was washed with a saturated aqueous common salt solution. After drying the organic phase over anhydrous magnesium sulfate, it was concentrated under reduced pressure, the resulting residue was dissolved in 1,4-dioxane (15 mL) and then hydrazine monohydrate (1.1 mL, 23 mM) was added thereto. The mixture was stirred at 90° C. for 14 hours, then cooled to room temperature and water was added thereto. The mixture was extracted with ethyl acetate, the resulting organic phase was dried over anhydrous magnesium sulfate and then concentrated under reduced pressure to thus give a crude product of the title compound (0.51 g, overall yield of these two steps: 69%).

MS (ESI) m/z (M+H)+ 318

(Step 5): Synthesis of N-(3-methyl-benzylidene)-N-(7-morpholin-4-yl-2-piperidin-1-yl-pyrazolo[1,5-a]pyrimidin-5-yl)-hydrazine (Compound 100)

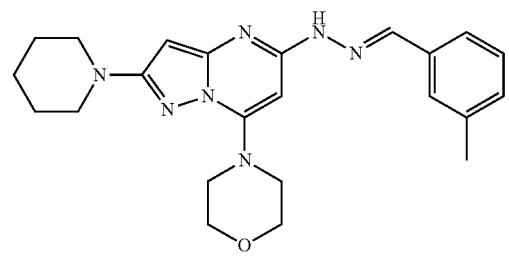

To a solution of the compound (50 mg, 0.16 mM) prepared in the preceding step 4 in ethanol (2.0 mL), there were added metatolualdehyde (37 μL, 0.32 mM) and acetic acid (5.0 μL) and the mixture was stirred at room temperature for 3 hours. The precipitated solid was recovered through filtration and then washed with ethanol to thus give the title compound (22 mg, yield: 33%).

$^1$H-NMR (300 MHz, DMSO): δ 1.57 (6H, s), 2.35 (3H, s), 3.23 (4H, s), 3.63 (4H, s), 3.81 (4H, s), 5.51 (1H, s), 6.07 (1H, s), 7.17 (1H, J=7.5 Hz, d), 7.31 (1H, J=7.5 Hz, t), 7.45 (1H, s), 7.49 (1H, J=7.5 Hz, d), 7.98 (1H, s), 10.96 (1H, s)

MS (ESI) m/z (M+H)$^+$ 420

Example 101

Synthesis of N-(1H-indol-3-yl-methylidene)-N-(7-morpholin-4-yl-2-piperidin-1-yl-pyrazolo[1,5-a]pyrimidin-5-yl)-hydrazine (Compound 101)

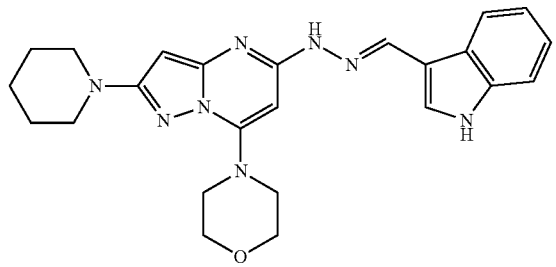

To a solution of (7-morpholin-4-yl-2-piperidin-1-yl-pyrazolo[1,5-a]pyrimidin-5-yl)-hydrazine (50 mg, 0.16 mM) in ethanol (3.0 mL), there were added 3-formyl-indole (46 mg, 0.32 mM) and acetic acid (5.0 μL) and the mixture was stirred at room temperature for 3 hours. The precipitated solid was recovered through filtration and then washed with ethanol to thus give the title compound (30 mg, yield: 43%).

$^1$H-NMR (300 MHz, DMSO): δ 1.57 (6H, s), 3.19-3.23 (4H, m), 3.67-3.68 (4H, m), 3.83-3.86 (4H, m), 5.46 (1H, s), 6.13 (1H, s), 7.15-7.22 (2H, m), 7.42-7.45 (1H, m), 7.70 (1H, J=2.7 Hz, d), 8.19-8.23 (2H, m), 10.65 (1H, s), 11.42 (1H, s)

MS (ESI) m/z (M+H)$^+$ 445

Example 102

Synthesis of N-(1H-indol-5-yl-methylidene)-N-(7-morpholin-4-yl-2-piperidin-1-yl-pyrazolo[1,5-a]pyrimidin-5-yl)-hydrazine (Compound 102)

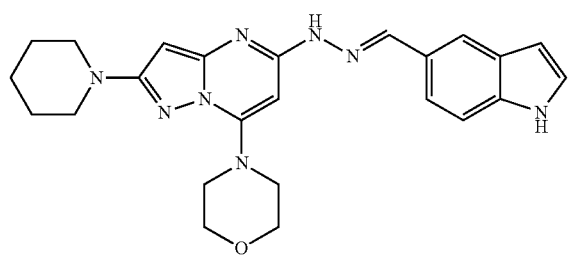

To a solution of (7-morpholin-4-yl-2-piperidin-1-yl-pyrazolo[1,5-a]pyrimidin-5-yl)-hydrazine (50 mg, 0.16 mM) in ethanol (3.0 mL), there were added 5-formyl-indole (46 mg, 0.32 mM) and acetic acid (5.0 μL) and the mixture was stirred at room temperature for 3 hours. The precipitated solid was recovered through filtration and then washed with ethanol to thus give the title compound (22 mg, yield: 31%).

$^1$H-NMR (300 MHz, DMSO): δ 1.57 (6H, m), 3.23 (4H, m), 3.64 (4H, s), 3.82 (4H, s), 5.48 (1H, s), 5.76 (1H, s), 6.09 (1H, s), 6.48 (1H, s), 7.37 (1H, J=2.7 Hz, t), 7.43 (1H, J=8.4 Hz, d), 7.57 (1H, J=8.4 Hz, d), 7.73 (1H, s), 8.09 (1H, s), 10.76 (1H, s), 11.24 (1H, s)

MS (ESI) m/z (M+H)$^+$ 445

Example 103

Synthesis of N-(1H-indol-5-yl-methylidene)-N-(7-morpholin-4-yl-2-pyridin-3-yl-pyrazolo[1,5-a]pyrimidin-5-yl)-hydrazine (Compound 103)

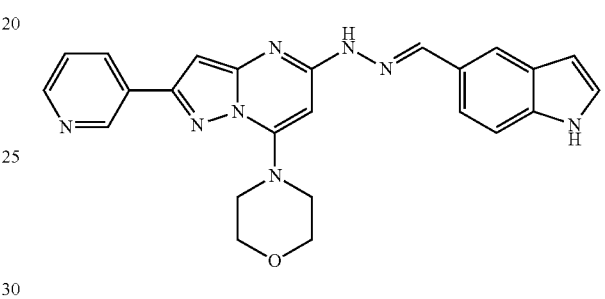

To a solution of (7-morpholin-4-yl-2-pyridin-3-yl-pyrazolo[1,5-a]pyrimidin-5-yl)-hydrazine (30 mg, 0.096 mM) in ethanol (3.0 mL), there were added 5-formyl-indole (21 mg, 0.14 mM) and acetic acid (5.0 μL) and the mixture was stirred at room temperature for 3 hours. The precipitated solid was recovered through filtration and then washed with ethanol to thus give the title compound (30 mg, yield: 71%).

$^1$H-NMR (300 MHz, DMSO): δ 3.74 (4H, m), 3.89 (4H, m), 6.37 (1H, s), 6.50 (1H, s), 6.66 (1H, s), 7.39 (1H, J=2.7 Hz, t), 7.44-7.52 (2H, m), 7.61 (1H, J=7.2 Hz, d), 7.78 (1H, s), 8.17 (1H, s), 8.31 (1H, J=2.1, 8.1 Hz, dt), 8.58 (1H, J=4.8 Hz, d), 9.16 (1H, s), 11.05 (1H, s), 11.26 (1H, s)

MS (ESI) m/z (M+H)$^+$ 439

Example 104

Synthesis of N-(1H-indol-5-yl-methylidene)-N-(7-morpholin-4-yl-2-piperidin-4-yl-pyrazolo[1,5-a]pyrimidin-5-yl)-hydrazine (Compound 104)

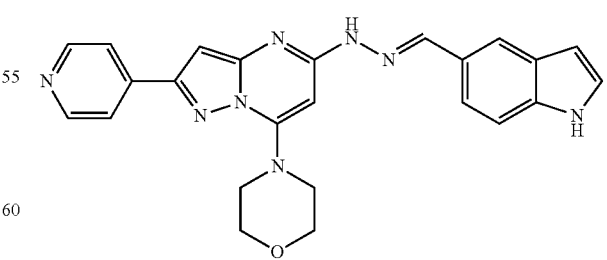

To a solution of (7-morpholin-4-yl-2-pyridin-4-yl-pyrazolo[1,5-a]pyrimidin-5-yl)-hydrazine (25 mg, 0.080 mM) in ethanol (3.0 mL), there were added 5-formyl-indole (18 mg, 0.12 mM) and acetic acid (5.0 μL) and the mixture was stirred

Example 105

Synthesis of N-(2,3-dimethyl-1H-indol-5-yl-methylidene)-N-(7-morpholin-4-yl-2-pyridin-3-yl-pyrazolo[1,5-a]pyrimidin-5-yl)-hydrazine (Compound 105)

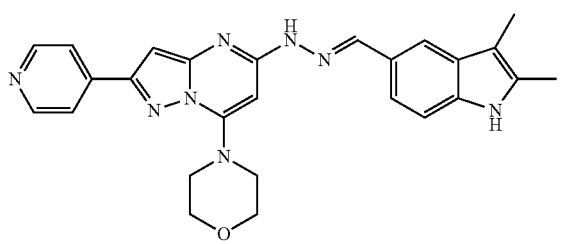

To a solution of (7-morpholin-4-yl-2-pyridin-3-yl-pyrazolo[1,5-a]pyrimidin-5-yl)-hydrazine (30 mg, 0.096 mM) in ethanol (3.0 mL), there were added 5-formyl-2,3-dimethylindole (25 mg, 0.14 mM) and acetic acid (5.0 µL) and the mixture was stirred at room temperature for 3 hours. The precipitated solid was recovered through filtration and then washed with ethanol to thus give the title compound (33 mg, yield: 73%).

$^1$H-NMR (300 MHz, DMSO): δ 2.25 (3H, s), 2.42 (3H, s), 3.82 (4H, m), 3.87-3.89 (4H, m), 6.39 (1H, s), 6.70 (1H, s), 7.03 (1H, J=6.9 Hz, t), 7.17 (1H, J=6.9 Hz, d), 7.43-7.51 (2H, m), 8.30-8.33 (2H, m), 8.57 (1H, J=1.5, 4.8 Hz, dd), 9.16 (1H, s), 10.34 (1H, s), 11.28 (1H, s)

MS (ESI) m/z (M+H)$^+$ 467

Example 106

Synthesis of N-(2,3-dimethyl-1H-indol-5-yl-methylidene)-N-(7-morpholin-4-yl-2-pyridin-4-yl-pyrazolo[1,5-a]pyrimidin-5-yl)-hydrazine (Compound 106)

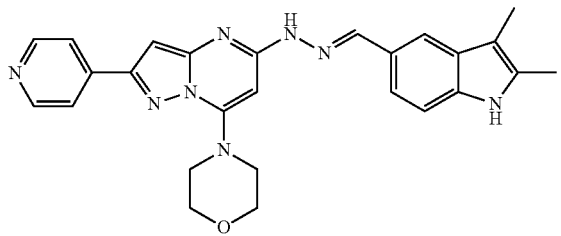

To a solution of (7-morpholin-4-yl-2-pyridin-4-yl-pyrazolo[1,5-a]pyrimidin-5-yl)-hydrazine (29 mg, 0.093 mM) in ethanol (3.0 mL), there were added 5-formyl-2,3-dimethylindole (24 mg, 0.14 mM) and acetic acid (5.0 µL) and the mixture was stirred at room temperature for 3 hours. The precipitated solid was recovered through filtration and then washed with ethanol to thus give the title compound (29 mg, yield: 67%).

$^1$H-NMR (300 MHz, DMSO): δ 2.19 (3H, s), 2.42 (3H, s), 3.80-3.82 (4H, m), 3.87-3.89 (4H, m), 6.42 (1H, s), 6.75 (1H, s), 7.03 (1H, J=7.5 Hz, t), 7.17 (1H, J=7.5 Hz, d), 7.44 (1H, J=7.5 Hz, d), 7.90-7.95 (2H, m), 8.30 (1H, s), 8.63 (1H, J=1.5 Hz, d), 8.65 (1H, J=1.5 Hz, d), 10.34 (1H, s), 11.30 (1H, s)

MS (ESI) m/z (M+H)$^+$ 467

Example 107

Synthesis of N-(2,3-dimethyl-1H-indol-5-yl-methylidene)-N-(7-morpholin-4-yl-2-pyrazin-2-yl-pyrazolo[1,5-a]pyrimidin-5-yl)-hydrazine (Compound 107)

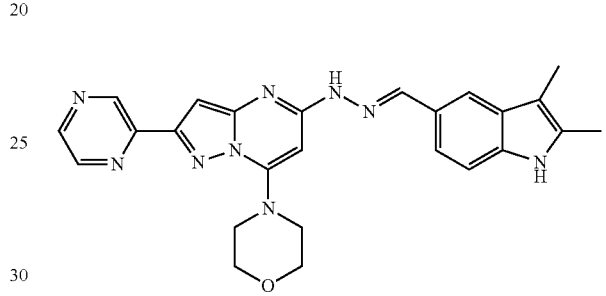

To a solution of (7-morpholin-4-yl-2-pyrazin-2-yl-pyrazolo[1,5-a]pyrimidin-5-yl)-hydrazine (23 mg, 0.074 mM) in ethanol (3.0 mL), there were added 5-formyl-2,3-dimethylindole (19 mg, 0.11 mM) and acetic acid (5.0 µL) and the mixture was stirred at room temperature for 3 hours. The precipitated solid was recovered through filtration and then washed with ethanol to thus give the title compound (21 mg, yield: 68%).

$^1$H-NMR (300 MHz, DMSO): δ 2.20 (3H, s), 2.43 (3H, s), 3.84 (4H, s), 3.88-3.90 (4H, m), 6.70 (1H, s), 7.04 (1H, J=7.5 Hz, t), 7.20 (1H, J=7.5 Hz, d), 7.46 (1H, J=7.5 Hz, d), 8.32 (1H, s), 8.64 (1H, J=2.4 Hz, d), 8.72 (1H, J=2.4 Hz, d), 9.33 (1H, s)

MS (ESI) m/z (M+H)$^+$ 468

Example 108

Synthesis of N-benzo[b]thiophen-2-yl-methylidene-N'-(7-morpholin-4-yl-2-pyridin-4-yl-pyrazolo[1,5-a]pyrimidin-5-yl)-hydrazine (Compound 108)

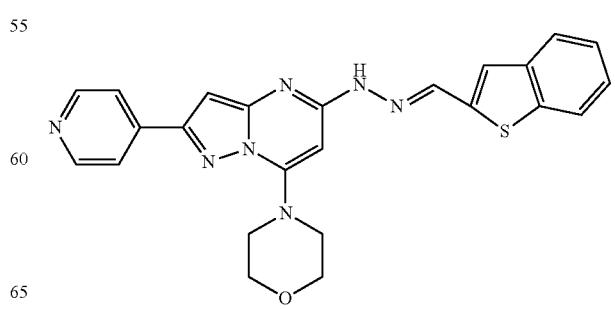

There was suspended, in ethanol (3.0 mL), 5-chloro-7-morpholin-4-yl-2-pyridin-4-yl-pyrazolo[1,5-a]pyrimidine (80 mg, 0.26 mM), then acetic acid (7.4 μL, 0.13 mM) and thianaphthene-3-carboxy-aldehyde (46 mg, 0.29 mM) were added to the suspension and the mixture was stirred at room temperature for one hour. This reaction liquid was filtered and the resulting solid was washed with ethanol and then with diethyl ether to thus give the title compound (2.6 mg, yield: 2.2%).

$^1$H-NMR (300 MHz, DMSO-d6); δ 3.74 (bs, 4H), 3.92 (bs, 4H), 6.30 (s, 1H), 6.80 (s, 1H), 7.40 (m, 2H), 7.68 (s, 1H), 7.80-7.95 (m, 4H), 8.38 (s, 1H), 8.67 (d, 2H, J=6.3 Hz), 11.5 (s, 1H); MS (ESI) m/z 456 (M+H)$^+$.

Example 109

Synthesis of N-benzo[b]thiophen-3-yl-methylidene-N'-(7-morpholin-4-yl-2-pyridin-4-yl-pyrazolo[1,5-a]pyrimidin-5-yl)-hydrazine (Compound 109)

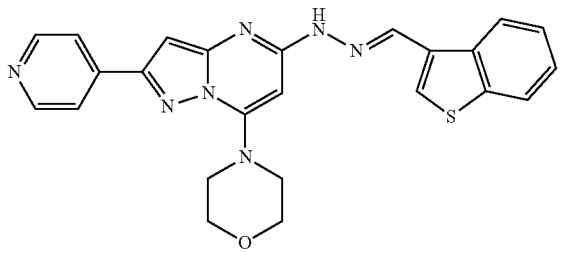

There was suspended, in ethanol (3.0 mL), 5-chloro-7-morpholin-4-yl-2-pyridin-4-yl-pyrazolo[1,5-a]pyrimidine (80 mg, 0.26 mM), then acetic acid (7.4 μL, 0.13 mM) and thianaphthene-2-carboxy-aldehyde (46 mg, 0.29 mM) were added to the suspension and the mixture was stirred at room temperature for one hour. This reaction liquid was filtered and the resulting solid was washed with ethanol and then with diethyl ether to thus give the title compound (3.4 mg, yield: 2.9%).

$^1$H-NMR (300 MHz, DMSO-d6); δ 3.80 (bs, 4H), 3.94 (bs, 4H), 6.41 (s, 1H), 6.78 (s, 1H), 7.49 (t, 1H, J=6.9 Hz), 7.59 (t, 1H, J=6.9 Hz), 7.93 (d, 2H, J=6.3 Hz), 8.08 (d, 1H, J=7.8 Hz), 8.14 (s, 1H), 8.41 (s, 1H), 8.67 (d, 2H, J=6 Hz), 8.74 (d, 2H, J=7.8 Hz); MS (ESI) m/z 456 (M+H)$^+$.

Example 110

Synthesis of N-(3-methyl-benzylidene)-N'-[2-(6-methyl-pyridin-3-yl)-7-morpholin-4-yl-pyrazolo[1,5-a]pyrimidin-5-yl]-hydrazine (Compound 110)

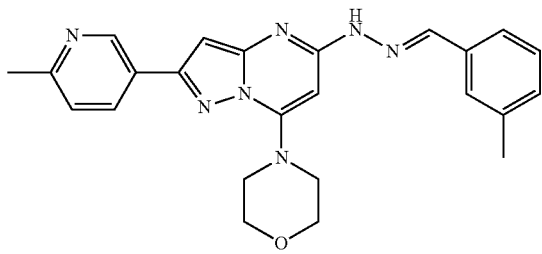

(Step 1): 5-Chloro-2-(6-methyl-pyridin-3-yl)-7-morpholin-4-yl-pyrazolo[1,5-a]-pyrimidine To 18-crown-6 (0.44 g, 1.7 mM), there was added a 1.0M potassium tert-butoxide/tetrahydrofuran solution (20 mL, 20 mM), then the mixture was stirred, acetonitrile (1.0 mL, 18 mM) was added to the mixture and the resulting reaction liquid was stirred for 5 minutes. To the reaction liquid, there was added methyl-6-methyl nicotinate (2.5 g, 17 mM), the temperature of the mixture was raised up to 60° C. and it was stirred for one hour. Then it was cooled down to room temperature and the precipitated solid was recovered through filtration and washed with tetrahydrofuran and diethyl ether. The resulting solid was dried in vacuo, suspended in ethanol (42 mL) and concentrated hydrochloric acid (1.5 mL) was added to the suspension with ice-cooling. Subsequently, methyl carbazinate (1.8 g, 20 mM) was added thereto at room temperature, and then the mixture was stirred for 16 hours. It was concentrated under reduced pressure, water was added to the resulting concentrate, the mixture was extracted with ethyl acetate, the resulting organic phase was dried over anhydrous magnesium sulfate and then concentrated under reduced pressure. The resulting oil was dried under a vacuum, then suspended in ethanol (31 mL), sodium ethoxide (0.9 g, 13 mM) was added to the suspension and the mixture was stirred at room temperature for one hour. Then diethyl malonate (3.2 mL, 21 mM) and sodium ethoxide (2.0 g, 29 mM) were added to the suspension and the resulting mixture was stirred at 90° C. for 24 hours. The reaction liquid was cooled down to room temperature, the precipitated solid was recovered through filtration and washed with diethyl ether.

The resulting solid was dried under a vacuum, then suspended in phosphorus oxychloride (25 mL) and stirred at 90° C. for 3 hours. After cooling the suspension to room temperature, it was concentrated under reduced pressure and the resulting concentrate was suspended in ethanol (22 mL). Morpholine (22 mL, 250 mM) was added to this suspension and the mixture was stirred at room temperature for 20 hours. After the concentration of the mixture under reduced pressure, water (400 mL) was added to the resulting residue, the precipitated solid was recovered through filtration to thus give a crude product of the title compound (790 mg, overall yield of these five steps: 15%).

MS (ESI) m/z (M+H)$^+$ 330

(Step 2): [2-(6-Methyl-pyridin-3-yl)-7-morpholin-4-yl-pyrazolo[1,5-a]pyrimidin-5-yl]-hydrazine There was suspended, in 1,4-dioxane (24 mL), 5-chloro-2-(6-methyl-pyridin-3-yl)-7-morpholin-4-yl-pyrazolo[1,5-a]-pyrimidine (0.79 g, 2.4 mM) prepared in the preceding step 1, then hydrazine monohydrate (1.2 mL, 24 mM) was added to the suspension and the mixture was stirred for 15 hours, while refluxing the same with heating. After the stirring operation, the reaction liquid was concentrated, the concentrate was diluted with water and then extracted with ethyl acetate. The resulting extracts were combined, dried over anhydrous sodium sulfate and then the solvent was distilled off to thus give a crude product of the title compound (210 mg, yield: 27%).

MS (ESI) m/z (M+H)$^+$ 326

(Step 3): N-(3-methyl-benzylidene)-N'-[2-(6-methyl-pyridin-3-yl)-7-morpholin-4-yl-pyrazolo[1,5-a]pyrimidin-5-yl]-hydrazine There was suspended, in ethanol (3 mL), [2-(6-methyl-pyridin-3-yl)-7-morpholin-4-yl-pyrazolo[1,5-a]pyrimidin- 5-yl]-hydrazine (70 mg, 0.22 mM) prepared in the preceding step 2, then acetic acid (6.3 µL, 0.11 mM) and metatolualdehyde (28 µL, 0.24 mM) were added to the suspension and the mixture was stirred at room temperature for 16 hours. The precipitated solid was recovered through filtration and then washed with diethyl ether to thus give the title compound (50.2 mg, yield: 53%).

$^1$H-NMR (300 MHz, CDCl$_3$); δ 2.40 (s, 3H), 2.61 (s, 3H), 3.82 (bs, 4H), 4.04 (bs, 4H), 6.41 (s, 1H), 6.45 (s, 1H), 7.18-7.33 (m, 3H), 7.46-7.51 (m, 2H), 7.78 (s, 1H), 8.08 (dd, 1H, J=8.1, 2.1 Hz), 8.70 (bs, 1H), 9.60 (bs, 1H), MS (ESI) m/z 428 (M+H)$^+$

Example 111

Synthesis of N-benzofuran-3-yl-methylidene-N'-[2-(6-methyl-pyridin-3-0)-7-morpholin-4-yl-pyrazolo[1,5-a]pyrimidin-5-yl]-hydrazine (Compound 111)

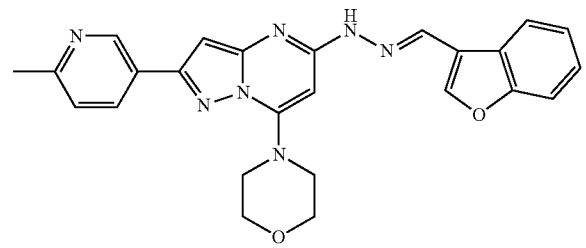

There was suspended, in ethanol (3.0 mL), [2-(6-methyl-pyridin-3-yl)-7-morpholin-4-yl-pyrazolo[1,5-a]pyrimidin-5-yl]-hydrazine (70 mg, 0.22 mM), then acetic acid (6.3 µL, 0.11 mM) and 1-benzofuran-3-carbaldehyde (35 mg, 0.24 mM) were added to the suspension and the mixture was stirred at room temperature for 16 hours. The precipitated solid was recovered through filtration and then washed with diethyl ether to thus give the title compound (4.5 mg, yield: 4.5%).

$^1$H-NMR (300 MHz, DMSO-d6); δ 3.79 (bs, 4H), 3.93 (bs, 4H), 6.37 (s, 1H), 6.65 (s, 1H), 7.36 (d, 1H, J=9.6 Hz), 7.44-7.46 (m, 2H), 7.63-7.72 (m, 1H), 8.17-8.29 (m, 3H), 8.43 (s, 1H), 9.03 (d, 1H, J=2.1 Hz), 11.3 (s, 1H), MS (ESI) m/z 454 (M+H)+_

Example 112

Synthesis of N-(1H-indol-3-yl-methylidene)-N'-[2-(6-methyl-pyridin-3-yl)-7-morpholin-4-yl-pyrazolo[1,5-a]pyrimidin-5-yl]-hydrazine (Compound 112)

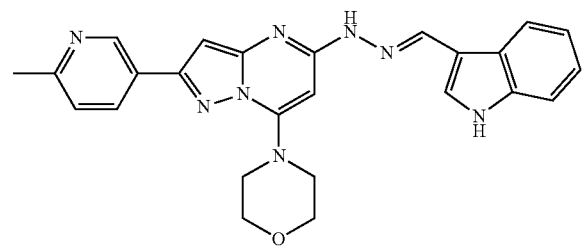

There was suspended, in ethanol (3.0 mL), [2-(6-methyl-pyridin-3-yl)-7-morpholin-4-yl-pyrazolo[1,5-a]pyrimidin-5-yl]-hydrazine (70 mg, 0.22 mM), then acetic acid (6.3 µL, 0.11 mM) and indole-3-carboxy-aldehyde (35 mg, 0.24 mM) were added to the suspension and the mixture was stirred at room temperature for 16 hours. The precipitated solid was recovered through filtration and then washed with diethyl ether to thus give the title compound (46 mg, yield: 47%).

$^1$H-NMR (300 MHz, DMSO-d6); δ 3.77 (bs, 4H), 3.93 (bs, 4H), 6.39 (s, 1H), 6.58 (s, 1H), 7.20-7.23 (m, 2H), 7.35 (d, 1H, J=8.4 Hz), 7.44-7.46 (m, 1H), 7.59 (d, 1H, J=2.7), 8.17-8.29 (m, 3H), 9.02 (d, 1H, J=1.8 Hz), 10.9 (s, 1H), 11.5 (s, 1H), MS (ESI) m/z 453 (M+H)$^+$

Example 113

Synthesis of N-(2,3-dihydro-benzo[1,4]dioxin-6-yl-methylidene)-N'-(7-morpholin-4-yl-2-pyridin-4-yl-pyrazolo[1,5-a]pyrimidin-5-yl)-hydrazine (Compound 113)

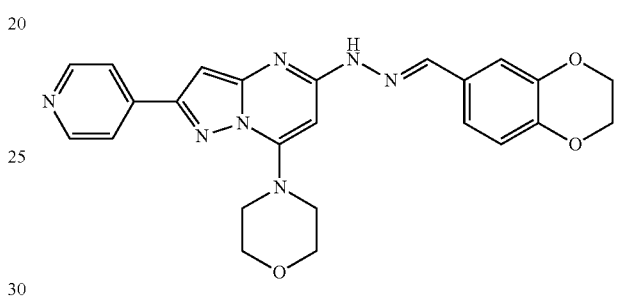

There was suspended, in ethanol (3.0 mL), 5-chloro-7-morpholin-4-yl-2-pyridin-4-yl-pyrazolo[1,5-a]pyrimidine (70 mg, 0.22 mM), then acetic acid (6.3 µL, 0.11 mM) and 2,3-dihydro-benzo[1,4]dioxin-6-carbaldehyde (43 mg, 0.24 mM) were added to the suspension and the mixture was stirred at room temperature for 2 hours. This reaction liquid was filtered, the resulting solid was washed with ethanol and then with diethyl ether and then purified by the reversed phase HPLC (C-18 ODS Column) to thus give the trifluoroacetic acid (TFA) salt of the title compound (7.0 mg, yield: 1.5%).

$^1$H-NMR (300 MHz, DMSO-d6); δ 3.73 (bs, 4H), 3.88 (bs, 4H), 4.28 (s, 4H), 6.36 (s, 1H), 6.87 (s, 1H), 6.92 (d, 1H, J=8.1 Hz), 7.19-7.24 (m, 2H), 7.99 (s, 1H), 8.15 (d, 2H, J=6.3 Hz), 8.77 (d, 2H, J=6.3 Hz); MS (ESI) m/z 458 (M+H)$^+$.

Example 114

Synthesis of N-(3-methyl-benzofuran-2-yl-methylidene)-N'-(7-morpholin-4-yl-2-pyridin-4-yl-pyrazolo[1,5-a]pyrimidin-5-yl)-hydrazine (Compound 114)

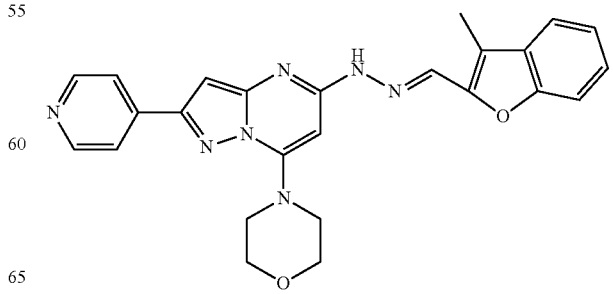

There was suspended, in ethanol (3.0 mL), 5-chloro-7-morpholin-4-yl-2-pyridin-4-yl-pyrazolo[1,5-a]pyrimidine (70 mg, 0.22 mM), then acetic acid (6.3 μL, 0.11 mM) and 3-methyl-benzofuran-2-carbaldehyde (39 mg, 0.24 mM) were added to the suspension and the mixture was stirred at room temperature for 2 hours. This reaction liquid was filtered and the resulting solid was washed with ethanol and then with diethyl ether to thus give the title compound (42 mg, yield: 9.3%).

$^1$H-NMR (300 MHz, DMSO-d6); δ 2.42 (s, 3H), 3.75 (bs, 4H), 3.91 (bs, 4H), 6.32 (s, 1H), 6.80 (s, 1H), 7.30-7.40 (m, 2H), 7.59 (d, 1H, J=8.1 Hz), 7.67 (d, 1H, J=7.2 Hzz), 7.93 (d, 2H, J=6 Hz), 8.24 (s, 1H), 8.67 (d, 2H, J=6 Hz), 11.4 (s, 1H); MS (ESI) m/z 454 (M+H)$^+$.

Example 115

Synthesis of N-(3-ethyl-benzylidene)-N-(7-morpholin-4-yl-2-pyridazin-3-yl-pyrazolo[1,5-a]pyrimidin-5-yl)-hydrazine (Compound 115)

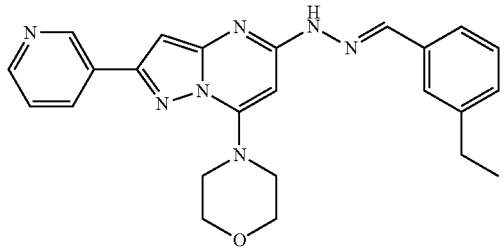

There was suspended, in ethanol (3.0 mL), (7-morpholin-4-yl-2-pyridin-3-yl-pyrazolo[1,5-a]pyrimidin-5-yl)-hydrazine (24 mg, 0.077 mM), then 3-ethyl-benz-aldehyde (16 mg, 0.12 mM) and acetic acid (5.0 μL) were added to the suspension and the mixture was stirred at room temperature for 3 hours. The precipitated solid was filtered and washed with ethanol to thus give the title compound (18 mg, yield: 55%).

$^1$H-NMR (300 MHz, DMSO): δ 1.20 (3H, J=7.8 Hz, t), 2.64 (2H, J=7.8 Hz, q), 3.72 (4H, s), 3.86-3.87 (4H, m), 6.33 (1H, s), 6.67 (1H, s), 7.21 (1H, J=7.8 Hz, d), 7.33 (1H, J=7.8 Hz, t), 7.46-7.50 (2H, m), 7.55 (1H, J=7.8 Hz, d), 8.05 (1H, s), 8.28 (1H, J=1.8, 7.8 Hz, dt), 8.56 (1H, J=1.2, 4.5 Hz, dd), 9.14 (1H, J=1.2 Hz, d), 11.23 (1H, s)
MS (ESI) m/z (M+H)$^+$ 428

Example 116

Synthesis of N-(3-ethyl-benzylidene)-N-(7-morpholin-4-yl-2-pyrazin-2-yl-pyrazolo[1,5-a]pyrimidin-5-yl)-hydrazine (Compound 116)

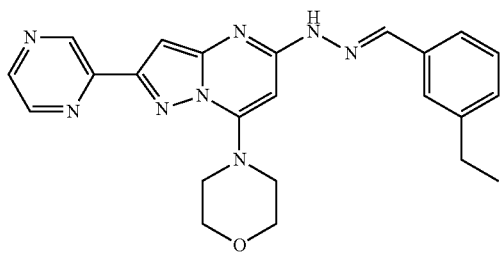

To a solution of (7-morpholin-4-yl-2-pyrazin-2-yl-pyrazolo[1,5-a]pyrimidin-5-yl)-hydrazine (26 mg, 0.083 mM) in ethanol (3.0 mL), there were added 3-ethyl-benz-aldehyde (17 mg, 0.12 mM) and acetic acid (5.0 μL) and the mixture was stirred at room temperature for 3 hours. The precipitated solid was filtered and washed with ethanol to thus give the title compound (21 mg, yield: 58%).

$^1$H-NMR (300 MHz, DMSO): δ 1.20 (3H, J=7.8 Hz, t), 2.64 (2H, J=7.8 Hz, q), 3.73 (4H, s), 3.87-3.88 (4H, m), 6.37 (1H, s), 6.65 (1H, s), 7.21 (1H, J=7.8 Hz, d), 7.33 (1H, J=7.8 Hz, t), 7.49 (1H, s), 7.55 (1H, J=7.8 Hz, d), 8.04 (1H, s), 8.63 (1H, J=2.7 Hz, d), 8.70 (1H, m), 9.31 (1H, J=1.2 Hz, d), 11.29 (1H, s)
MS (ESI) m/z (M+H)$^+$ 429

Example 117

Synthesis of N-(1H-indol-6-yl-methylidene)-N'-(7-morpholin-4-yl-2-pyridin-4-yl-pyrazolo[1,5-a]pyrimidin-5-yl)-hydrazine (Compound 117)

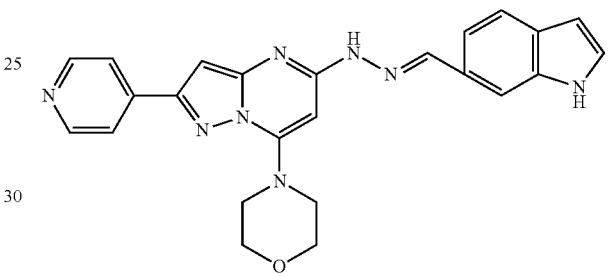

There was suspended, in ethanol (3.0 mL), 5-chloro-7-morpholin-4-yl-2-pyridin-4-yl-pyrazolo[1,5-a]pyrimidine (70 mg, 0.22 mM), then acetic acid (6.3 μL, 0.11 mM) and 1H-indole-6-carbaldehyde (35 mg, 0.24 mM) were added to the suspension and the mixture was stirred at room temperature for 16 hours. This reaction liquid was filtered and the resulting solid was washed with ethanol and then with diethyl ether to thus give the title compound (45 mg, yield: 10%).

$^1$H-NMR (300 MHz, DMSO-d6); δ 3.48 (bs, 4H), 3.91 (bs, 4H), 6.40 (s, 1H), 6.47 (s, 1H), 6.73 (s, 1H), 7.42-7.50 (m, 2H), 7.58-7.64 (m, 2H), 7.92 (d, 2H, J=6 Hz), 8.17 (s, 1H), 8.66 (d, 2H, J=6.3 Hz), 11.1 (s, 1H), 11.3 (s, 1H); MS (ESI) m/z 439 (M+H)$^+$.

Example 118

Synthesis of N-(3-ethyl-benzylidene)-N-(7-morpholin-4-yl-2-pyridin-4-yl-pyrazolo[1,5-a]pyrimidin-5-yl)-hydrazine (Compound 118)

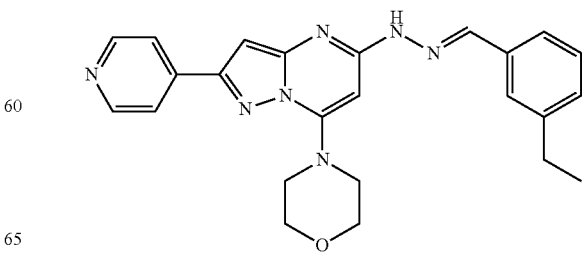

To a solution of 7-morpholin-4-yl-2-pyridin-4-yl-pyrazolo[1,5-a]pyrimidin-5-yl)-hydrazine (29 mg, 0.093 mM) in ethanol (3.0 mL), there were added 5-formyl-2,3-dimethyl-indole (24 mg, 0.14 mM) and acetic acid (5.0 μL) and the mixture was stirred at room temperature for 3 hours. The precipitated solid was filtered and washed with ethanol to thus give the title compound (29 mg, yield: 67%).

$^1$H-NMR (300 MHz, DMSO): δ 1.20 (3H, J=7.5 Hz, t), 2.64 (2H, J=7.5 Hz, q), 3.70-3.74 (4H, m), 3.86-3.89 (4H, m), 6.36 (1H, s), 6.74 (1H, s), 7.21 (1H, J=7.8 Hz, d), 7.33 (1H, J=7.8 Hz, t), 7.48 (1H, s), 7.55 (1H, J=7.8 Hz, d), 7.88 (1H, s), 7.91 (1H, s), 8.05 (1H, s), 8.63 (1H, s), 8.65 (1H, s), 11.26 (1H, s)

MS (ESI) m/z (M+H)$^+$ 467

Example 119

Synthesis of N-(3-methyl-benzylidene)-N-(7-morpholin-4-yl-2-pyrimidin-4-yl-pyrazolo[1,5-a]pyrimidin-5-yl)-hydrazine (Compound 119)

(Step 1): Synthesis of methyl 5-amino-3-pyrimidin-4-yl-pyrazole-1-carboxylate

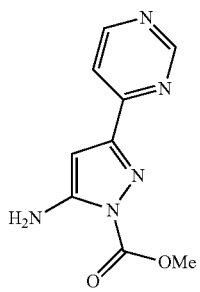

To a solution of 18-crown-6 (0.35 g, 1.3 mM) in tetrahydrofuran (5.0 mL), there were added a 1.0M potassium tert-butoxide/tetrahydrofuran solution (15 mL, 15 mM) and acetonitrile (0.76 mL, 15 mM) and the mixture was stirred at room temperature for 10 minutes. After cooling the mixture to 0° C., there was added a solution of 4-ethoxycarbonyl-pyrimidine (2.0 g, 13 mM) in tetrahydrofuran (5.0 mL), to the mixture. The temperature of the reaction liquid was raised up to 60° C., it was then stirred for one hour, then cooled down to room temperature, the precipitated solid was recovered through filtration and washed with tetrahydrofuran. The resulting solid was dried under a vacuum, suspended in ethanol (40 mL) and then methyl carbazinate (1.4 g, 16 mM) was added to the suspension. Concentrated hydrochloric acid (1.2 mL) was added to the suspension with ice-cooling and the mixture was stirred at that temperature for 14 hours. The reaction solution was concentrated under reduced pressure and the excess hydrochloric acid present therein was neutralized by the addition of a saturated aqueous sodium bicarbonate solution. The reaction solution was then extracted with ethyl acetate, the resulting organic phase was dried over anhydrous magnesium sulfate and then concentrated under reduced pressure to thus give a crude product of the title compound (1.3 g, yield: 45%).

MS (ESI) m/z (M+H)$^+$ 220

(Step 2): Synthesis of methyl 5-(ethoxycarbonyl-acetylamino)-3-pyrimidin-4-yl-pyrazole-1-carboxylate

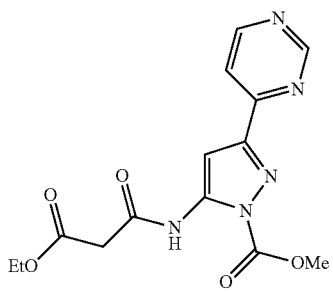

To a solution of the compound (0.75 g, 3.4 mM) prepared in the preceding step 1 in dichloromethane (40 mL), there were, in order, added ethyl malonyl chloride (0.65 mL, 5.1 mM) and triethylamine (0.71 mL, 5.1 mM) and the mixture was stirred at room temperature for 3 hours. The reaction solution was concentrated under reduced pressure and then water was added to the solution. The solution was extracted with ethyl acetate, the resulting organic phase was dried over anhydrous magnesium sulfate, concentrated under reduced pressure and the concentrate was subjected to a slurry-washing treatment (dichloromethane, diethyl ether) to thus give the title compound (1.0 g, yield: 89%).

MS (ESI) m/z (M+H)$^+$ 334

(Step 3): Synthesis of (7-morpholin-4-yl-2-pyrimidin-4-yl-pyrazolo[1,5-a]pyrimidin-5-yl)-hydrazine

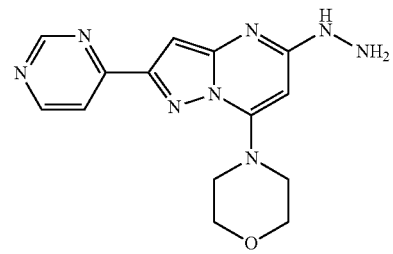

To a solution of the compound (0.19 g, 0.57 mM) prepared in the preceding step 2 in methanol (5.0 mL), there was added a 28% methanol solution of sodium methoxide (0.25 mL, 1.2 mM) and the mixture was stirred at 50° C. for one hour. After cooling the mixture to room temperature, the precipitated solid was recovered through filtration and then washed with ethanol to thus give a crude product in the form of a bis-sodium salt thereof. This was suspended in toluene (5.0 mL), then phosphorus oxychloride (5.0 mL) and pyridine (0.14 mL, 1.7 mM) were added to the suspension and the mixture was stirred at 90° C. for 5 hours. After cooling the mixture to room temperature, 1,2-dichloroethane was added thereto and then the mixture was filtered through cerite. The filtrate was concentrated under reduced pressure and the concentrate was neutralized with a saturated aqueous solution of sodium bicarbonate. The neutralized concentrate was extracted with ethyl acetate, the resulting organic phase was dried over anhydrous magnesium sulfate and then concentrated under reduced pressure. The resulting residue was dissolved in 1,4-dioxane (5.0 mL), then morpholine (0.1 mL, 1.1 mM) was added to the solution and then the mixture was stirred at room temperature for 3 hours. Water was added thereto, the mixture was extracted with ethyl acetate and the resulting organic phase was washed with a saturated aqueous common salt solution. After drying the organic phase over anhydrous magnesium sulfate, it was concentrated under reduced pressure, the resulting residue was suspended in 1,4-dioxane (7.0 mL) and then hydrazine monohydrate (0.28 mL, 5.7 mM) was added to the suspension. After stirring the mixture at 90° C. for 14 hours, it was cooled down to room temperature and then water was added thereto. The mixture was extracted with ethyl acetate, the resulting organic phase was dried over anhydrous magnesium sulfate and then concentrated under reduced pressure to thus give a crude product of the title compound (62 mg, overall yield of these four steps: 35%).

MS (ESI) m/z (M+H)+ 313

(Step 4): Synthesis of N-(3-methyl-benzylidene)-N-(7-morpholin-4-yl-2-pyrimidin-4-yl-pyrazolo[1,5-a]pyrimidin-5-yl)-hydrazine (Compound 119)

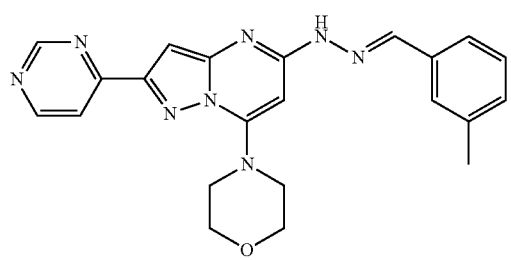

To a solution of the compound (25 mg, 0.16 mM) prepared in the preceding step 3 in ethanol (2.0 mL), there were added metatolualdehyde (14 μL, 0.12 mM) and acetic acid (5.0 μL) and the resulting mixture was stirred at room temperature for 3 hours. The precipitated solid was recovered through filtration and then washed with ethanol to thus give the title compound (25 mg, yield: 76%).

$^1$H-NMR (300 MHz, DMSO): δ 2.34 (3H, s), 3.72-3.74 (4H, m), 3.87-3.88 (4H, m), 6.40 (1H, s), 6.72 (1H, s), 7.18 (1H, J=7.8 Hz, d), 7.31 (1H, J=7.8 Hz, t), 7.48 (1H, s), 7.53 (1H, J=7.8 Hz, d), 8.04 (1H, s), 8.09 (1H, J=1.2, 5.4 Hz, dd), 8.87 (1H, J=5.4 Hz, d), 9.23 (1H, J=1.2 Hz, d), 11.32 (1H, s)

MS (ESI) m/z (M+H)+ 415

Example 120

Synthesis of N-(1H-indol-3-yl-methylidene)-N-(7-morpholin-4-yl-2-pyrimidin-4-yl-pyrazolo[1,5-a]pyrimidin-5-yl)-hydrazine (Compound 120)

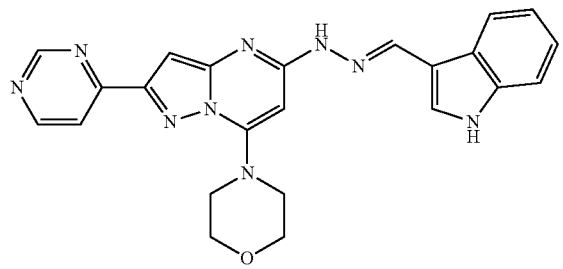

To a solution of (7-morpholin-4-yl-2-pyrimidin-4-yl-pyrazolo[1,5-a]pyrimidin-5-yl)-hydrazine (20 mg, 0.064 mM) in ethanol (2.0 mL), there were added 3-formyl-indole (14 mg, 0.096 mM) and acetic acid (5.0 μL) and the mixture was stirred at room temperature for 3 hours. The precipitated solid was filtered and washed with ethanol to thus give the title compound (24 mg, yield: 86%).

$^1$H-NMR (300 MHz, DMSO): δ 3.76-3.80 (4H, m), 3.93-3.96 (4H, m), 6.48 (1H, s), 6.68 (1H, s), 7.19-7.24 (2H, m), 7.44-7.47 (1H, m), 7.77 (1H, s), 8.11 (1H, J=5.1 Hz, d), 8.22-8.25 (1H, m), 8.30 (1H, s), 8.89 (1H, J=5.1 Hz, d), 9.25 (1H, s), 11.06 (1H, s), 11.49 (1H, s)

MS (ESI) m/z (M+H)+ 440

Example 121

Synthesis of N-(3-methyl-benzylidene)-N'-[7-(2-oxo-5-azabicyclo-[2.2.1]hept-5-yl)-2-pyridin-4-yl-pyrazolo[1,5-a]pyrimidin-5-yl]-hydrazine (Compound 121)

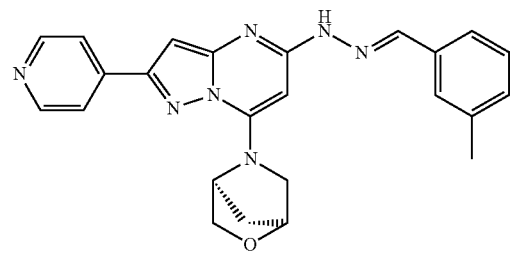

(Step 1): [7-(2-oxa-5-azabicyclo[2.2.1]hept-5-yl)-2-pyridin-4-yl-pyrazolo[1,5-a]-pyrimidin-5-yl]-hydrazine There was suspended, in ethanol (5.0 mL), 5,7-dicyclo-2-pyridin-4-yl-pyrazolo[1,5-a]pyrimidine (260 mg, 1.0 mM), then triethylamine (170 μL, 1.2 mM) and 2-oxa-5-azabicyclo[2.2.1]heptane hydrochloride (180 mg, 1.3 mM) were added to the suspension and the mixture was stirred at room temperature for 15 hours. After the stirring operation, the reaction liquid was concentrated, the concentrate was diluted with water, a saturated aqueous solution of sodium bicarbonate was then added thereto and the mixture was extracted with ethyl acetate. The resulting extracts were combined, dried over anhydrous sodium sulfate and then the solvent was distilled off.

After the resulting oil was dried under a vacuum, it was suspended in 1,4-dioxane (15 mL), then hydrazine monohydrate (560 μL, 12 mM) was added to the suspension and the mixture was stirred for 18 hours while refluxing the same with heating. After the stirring operation, the reaction liquid was concentrated, the concentrate was diluted with water, a saturated aqueous solution of sodium bicarbonate was then added to the mixture and the mixture was extracted with ethyl acetate. The resulting extracts were combined, dried over anhydrous sodium sulfate, the solvent was distilled off to thus concentrate the reaction liquid under reduced pressure and the concentrate was purified by the reversed phase HPLC (C-18 ODS Column) to thus give the 2 trifluoroacetic acid (TFA) salt of the title compound (100 mg, overall yield of these two steps: 18%).

MS (ESI) m/z 324 (M+H)+

(Step 2): N-(3-methyl-benzylidene)-N'-[7-(2-oxo-5-azabicyclo[2.2.1]hept-5-yl)-2-pyridin-4-yl-pyrazolo[1,5-a]pyrimidin-5-yl]-hydrazine There was suspended, in ethanol (2 mL), [7-(2-oxa-5-azabicyclo[2.2.1]hept-5-yl)-2-pyridin-4-yl-pyrazolo[1,5-a]pyrimidin-5-yl]-hydrazine (100 mg, 0.18 mM) prepared in the preceding step 1, then acetic acid (5.1 μL, 0.09 mM) and metatolualdehyde (25 μL, 0.22 mM) were added to the suspension and the mixture was stirred at room temperature for 3 hours. The precipitated solid was recovered through filtration, washed with diethyl ether and then purified by the reversed phase HPLC (C-18 ODS Column) to thus give the 2 trifluoroacetic acid (TFA) salt of the title compound (51 mg, yield: 43%).

$^1$H-NMR (300 MHz, DMSO-d6); δ 1.90-2.15 (m, 2H), 2.34 (s, 3H), 3.6-3.7 (d, 2H), 3.85-4.1 (m, 3H), 4.75 (s, 1H), 6.00 (bs, 2H), 6.62 (s, 1H), 7.21 (d, 1H, J=7.5 Hz), 7.29 (dd, 1H, J=7.5, 7.5 Hz), 7.59 (d, 2H, J=8.4 Hz), 7.89 (d, 2H, J=5.7 Hz), 8.00 (s, 1H), 8.63 (d, 2H, J=6 Hz), 11.0 (s, 1H); MS (ESI) m/z 426 (M+H)$^+$

Example 122

Synthesis of N-(7-morpholin-4-yl-2-pyridin-4-yl-pyrazolo[1,5-a]-pyrimidin-5-yl)-N'-quinolin-4-yl-methylidene-hydrazine (Compound 122)

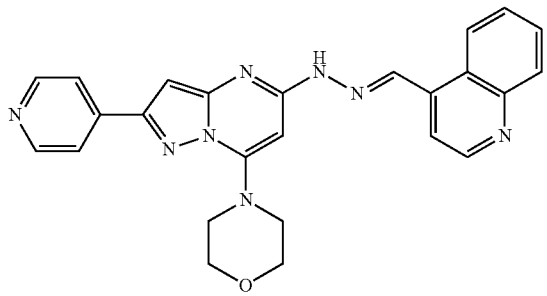

There was suspended, in ethanol (3.0 mL), 5-chloro-7-morpholin-4-yl-2-pyridin-4-yl-pyrazolo[1,5-a]pyrimidine (70 mg, 0.22 mM), then acetic acid (6.3 μL, 0.11 mM) and 4-quinoline-carboxyaldehyde (38 mg, 0.24 mM) were added to the suspension and the mixture was stirred at room temperature for 2 hours. This reaction liquid was filtered and then the resulting solid was washed with ethanol and then with diethyl ether to thus give the title compound (7.0 mg, yield: 7.1%).

$^1$H-NMR (300 MHz, DMSO-d6); δ 3.81 (bs, 4H), 3.92 (bs, 4H), 6.48 (s, 1H), 6.86 (s, 1H), 7.73-7.86 (m, 2H), 7.94-7.95 (m, 3H), 8.10 (d, 1H, J=8.4 Hz), 8.61 (d, 1H, J=8.4 Hz), 8.68 (d, 2H, J=4.2 Hz), 8.79 (s, 1H), 8.96 (d, 1H, J=4.5 Hz), 11.7 (s, 1H); MS (ESI) m/z 451 (M+H)$^+$.

Example 123

Synthesis of N-(3-methyl-benzylidene)-N'-[2-pyridin-4-yl-7-(tetra-hydro-furo[3,4-c]pyrrol-5-yl)-pyrazolo[1,5-a]pyrimidin-5-yl]-hydrazine (Compound 123)

(Step 1): 5-Chloro-2-pyridin-4-yl-7-(tetrahydro-furo[3,4-c]pyrrol-5-yl)-pyrazolo[1,5-a]pyrimidin

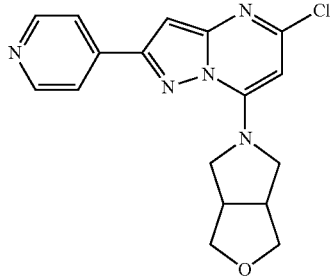

To a solution of 5,7-dichloro-4-yl-2-pyridin-4-yl-pyrazolo[1,5-a]pyrimidine (120 mg, 0.455 mM) in 1,4-dioxane (2 mL), there was added a methanol solution of hexahydro-furo[3,4-c]pyrrole (0.2M solution, 2.73 mL, 0.546 mM) and the mixture was stirred at room temperature for 2 hours. The solvent was distilled off from this reaction mixture, the resulting residue was diluted with water and then the mixture was extracted with methylene chloride. The resulting extracts were combined, dried over anhydrous sodium sulfate, the solvent was distilled off and the resulting solid was washed with diethyl ether to thus give the title compound (105 mg, yield: 67%).

$^1$H-NMR (300 MHz, DMSO): δ 3.08 (m, 2H), 368 (dd, 2H, J=3.2, 8.8 Hz), 3.84 (dd, 2H, J=6.4, 8.8 Hz), 4.04 (m, 2H), 4.17 (m, 2H), 6.08 (s, 1H), 7.06 (s, 1H), 7.95 (d, 2H, J=6.2H), 8.76 (d, 2H, J=6.2 Hz); MS (ESI) m/z 342 (M+H)$^+$.

(Step 2): N-(3-methyl-benzylidene)-N'-[2-pyridin-4-yl-7-(tetrahydro-furo[3,4-c]pyrrol-5-yl)-pyrazolo[1,5-a]pyrimidin-5-yl]-hydrazine (Compound 123)

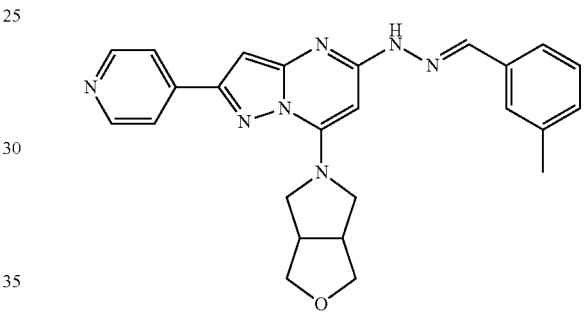

There was suspended, in 1,4-dioxane (2 mL), 5-chloro-2-pyridin-4-yl-7-(tetrahydro-furo[3,4-c]pyrrol-5-yl)-pyrazolo[1,5-a]pyrimidine (101 mg, 0.296 mM), then hydrazine monohydrate (144 μL, 2.96 mM) was added to the suspension and the mixture was stirred overnight while refluxing the same with heating. After the stirring operation, the reaction liquid was diluted with water and the mixture was then extracted with ethyl acetate. The resulting extracts were combined, dried over anhydrous sodium sulfate and the solvent was distilled off.

The resulting residue was dissolved in ethanol (2 mL), then 3-methyl-benzaldehyde (34.9 μL, 0.296 mM) was added to the solution and the mixture was stirred at room temperature for 4 hours. This reaction liquid was filtered and the resulting solid was washed with diethyl ether to thus give the title compound (85.6 mg, overall yield of these two steps: 66%).

$^1$H-NMR (300 MHz, DMSO): δ 2.34 (s, 3H), 3.08 (m, 2H), 3.69 (dd, 2H, J=2.9, 8.8 Hz), 3.88 (dd, 2H, J=6.4, 8.8 Hz), 3.97-4.97 (m, 4H), 6.07 (s, 1H), 6.64 (s, 1H), 7.17 (d, 1H, J=7.6 Hz), 7.30 (t, 1H, J=7.6 Hz), 7.46 (s, 1H), 7.51 (d, 1H, J=7.6 Hz), 7.90 (d, 2H, J=5.4 Hz), 8.01 (s, 1H), 8.63 (d, 2H, J=5.4 Hz), 11.66 (s, 1H); MS (ESI) m/z 440 (M+H)$^+$.

Example 124

Synthesis of N-(3-methyl-benzylidene)-N'-(7-morpholin-4-yl-2-pyrimidin-5-yl-pyrazolo[1,5-a]pyrimidin-5-yl)-hydrazine (Compound 124)

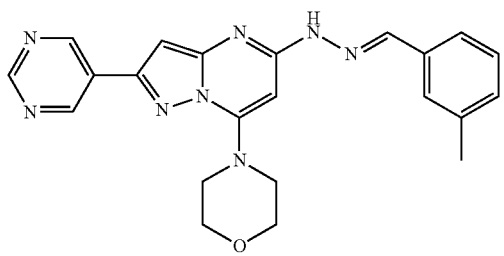

(Step 1): 5-Chloro-7-morpholin-4-yl-2-pyrimidin-5-yl-pyrazolo[1,5-a]pyrimidine

A 1.0M potassium tert-butoxide/tetrahydrofuran solution (24 mL, 24 mM) was added to 18-crown-6 (0.52 g, 2.0 mM), followed by the stirring of the mixture, the addition of acetonitrile (1.2 mL, 22 mM) and the subsequent stirring of the mixture for 5 minutes. Ethyl-5-pyrimidine carboxylate (3.0 g, 20 mM) was added to the mixture, the reaction liquid was then stirred for one hour, while raising the temperature thereof to 60° C., it was then cooled to room temperature, the precipitated solid was recovered through filtration and then washed with tetrahydrofuran and diethyl ether. The resulting solid was dried in vacuo, suspended in ethanol (40 mL) and concentrated hydrochloric acid (2.2 mL) was added to the suspension with ice-cooling. Then methyl carbazinate (2.8 g, 32 mM) was added to the suspension at room temperature and then the mixture was stirred for 18 hours. The reaction liquid was concentrated under reduced pressure followed by the addition of water to the concentrate and the extraction of the mixture with ethyl acetate. The resulting organic phase was dried over anhydrous magnesium sulfate and then concentrated under reduced pressure. The resulting solid was dried in vacuo, suspended in dichloromethane (30 mL), then ethyl malonyl chloride (0.87 mL, 6.8 mM) and triethylamine (0.94 mL, 6.8 mM) were added to the suspension with ice-cooling and then the mixture was stirred at room temperature for 3 hours. After the reaction liquid was concentrated, ethyl acetate and water were added to the resulting residue, the precipitated solid was recovered through filtration and then washed with diethyl ether.

After the resulting solid was dried in vacuo, it was suspended in ethanol (20 mL), a 5.0M sodium methoxide/methanol solution (1.9 mL, 9.6 mM) was added to the suspension, the mixture was stirred at 50° C. for 2 hours and then concentrated under reduced pressure.

The resulting solid was dried under a vacuum, suspended in toluene (20 mL), followed by the addition of phosphorus oxychloride (20 mL) and the stirring of the mixture at 90° C. To this solution, there was dropwise added pyridine (1.2 mL, 14 mM) and the mixture was further stirred at 90° C. for 5 hours. After the reaction liquid was cooled to room temperature, it was concentrated under reduced pressure, then the concentrate was suspended in 1,2-dichloroethane (20 mL), followed by the filtration of the suspension and the concentration of the residue under reduced pressure. The resulting concentrate was diluted with water and then extracted with dichloromethane. The resulting extracts were combined, dried over anhydrous sodium sulfate and the solvent was distilled off. The resulting solid was suspended in ethanol (10 mL), morpholine (0.31 mL, 3.6 mM) was added to the suspension and the mixture was stirred at room temperature for 20 hours. The reaction liquid was concentrated under reduced pressure, the resulting residue was diluted with water and then the mixture was extracted with ethyl acetate. The resulting extracts were combined, dried over anhydrous sodium sulfate and then the solvent was distilled off to thus give a crude product of the title compound (20 mg, overall yield of these six steps: %).

MS (ESI) m/z 317 (M+H)+

(Step 2): (7-Morpholin-4-yl-2-pyrimidin-5-yl-pyrazolo[1,5-a]pyrimidin-5-yl)-hydrazine There was suspended, in 1,4-dioxane (1.0 mL), 5-chloro-7-morpholin-4-yl-2-pyrimidin-5-yl-pyrazolo[1,5-a]pyrimidine (20 mg, 2.4 mM) prepared in the preceding step 1, then hydrazine monohydrate (29 μL, 0.6 mM) was added to the suspension and the mixture was stirred for 6 hours while refluxing the same with heating. After the stirring operation, the reaction liquid was concentrated, the concentrate was diluted with water and then the mixture was extracted with ethyl acetate. The resulting extracts were combined, dried over anhydrous sodium sulfate and the solvent was distilled off to thus give a crude product of the title compound (18 mg, yield: 96%).

MS (ESI) m/z 313 (M+H)+

(Step 3): N-(3-Methyl-benzylidene)-N'-(7-morpholin-4-yl-2-pyrimidin-5-yl-pyrazolo-[1,5-a]pyrimidine There was suspended, in ethanol (1.0 mL), (7-morpholin-4-yl-2-pyrimidin-5-yl-pyrazolo[1,5-a]pyrimidin-5-yl)-hydrazine (18 mg, 0.1 mM) prepared in the preceding step 2, then acetic acid (3.0 μL, 0.05 mM) and metatolualdehyde (14 μL, 0.12 mM) were added to the suspension and the mixture was stirred at room temperature for 16 hours. The precipitated solid was recovered through filtration and then washed with diethyl ether to thus give the title compound (4.0 mg, yield: 16.7%).

1H-NMR (300 MHz, DMSO-d6); δ 3.74 (bs, 4H), 3.89 (bs, 4H), 6.37 (s, 1H), 6.80 (s, 1H), 7.20 (d, 1H, J=7.5 Hz), 7.33 (dd, 1H, J=7.8, 7.5 Hz), 7.50 (s, 1H), 7.55 (d, 1H, J=7.8 Hz), 8.06 (s, 1H), 9.21 (s, 1H), 9.36 (s, 2H), 11.3 (s, 1H); MS (ESI) m/z 415 (M+H)+

Example 125

Synthesis of N-benzofuran-5-yl-methylidene-N'-(7-morpholin-4-yl-2-pyridin-4-yl-pyrazolo[1,5-a]pyrimidin-5-yl)-hydrazine (Compound 125)

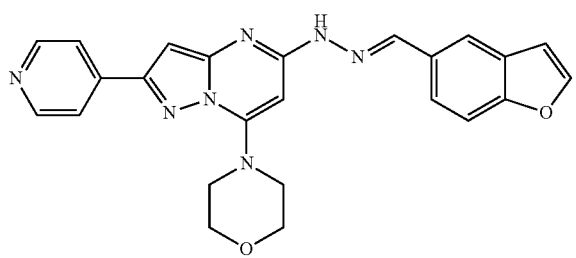

There was suspended, in ethanol (1.0 mL), 5-chloro-7-morpholin-4-yl-2-pyridin-4-yl-pyrazolo[1,5-a]pyrimidine (25 mg, 0.08 mM), then acetic acid (3.0 µL, 0.04 mM) and benzofuran-5-carboxy-aldehyde (14 mg, 0.10 mM) were added to the suspension and the mixture was stirred at room temperature for 16 hours. The reaction liquid was filtered and then the resulting solid was washed with ethanol and then with diethyl ether to thus give the title compound (22 mg, yield: 63%).

$^1$H-NMR (300 MHz, DMSO-d6); δ 3.75 (bs, 4H), 3.91 (bs, 4H), 6.41 (s, 1H), 6.76 (s, 1H), 7.03 (d, 1H, J=3 Hz), 7.65 (s, 1H), 7.68 (s, 1H), 7.77 (d, 1H, J=1.5 Hz), 7.80 (d, 1H, J=1.5 Hz), 7.91-7.96 (m, 3H), 8.05 (d, 1H, J=1.8 Hz), 8.20 (s, 1H), 8.66 (d, 2H, J=6.3 Hz), 11.3 (s, 1H); MS (ESI) m/z 440 (M+H)$^+$.

Example 126

Synthesis of N-(7-morpholin-4-yl-2-pyridin-4-yl-pyrazolo[1,5-a]-pyrimidin-5-yl)-N'-(1H-pyrrolo[2,3-b]pyridin-3-yl-methylidene)-hydrazine (Compound 126)

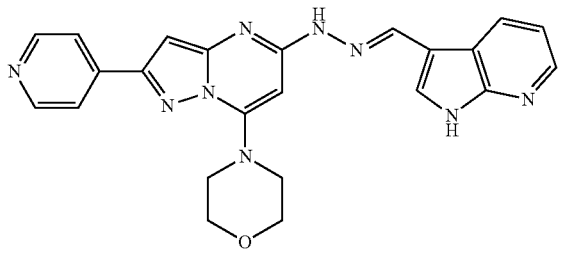

There was suspended, in ethanol (1.0 mL), 5-chloro-7-morpholin-4-yl-2-pyridin-4-yl-pyrazolo[1,5-a]pyrimidine (25 mg, 0.08 mM), then acetic acid (3.0 µL, 0.04 mM) and 1H-pyrrolo[2,3-b]pyridine-3-carbaldehyde (14 mg, 0.10 mM) were added to the suspension and the mixture was stirred at room temperature for 16 hours. The reaction liquid was filtered and then the resulting solid was washed with ethanol and then with diethyl ether to thus give the title compound (3.7 mg, yield: 11%).

$^1$H-NMR (300 MHz, DMSO-d6); δ 3.77 (bs, 4H), 3.93 (bs, 4H), 6.39 (s, 1H), 6.71 (s, 1H), 7.28 (dd, 1H, J=8.1, 4.5 Hz), 7.92 (d, 2H, J=6 Hz), 8.27 (s, 1H), 8.32 (d, 1H, J=6.3 Hz), 8.52 (d, 1H, J=9.6 Hz), 8.66 (d, 2H, J=1.5 Hz), 11.1 (s, 1H), 12.0 (s, 1H); MS (ESI) m/z 440 (M+H)$^+$.

Example 127

Synthesis of N-(3-methyl-benzylidene)-N-(2,7-di-morpholin-4-yl-pyrazolo[1,5-a]pyrimidin-5-yl)-hydrazine (Compound 127)

(Step 1): Synthesis of methyl 5-amino-3-morpholin-4-yl-pyrazole-1-carboxylate

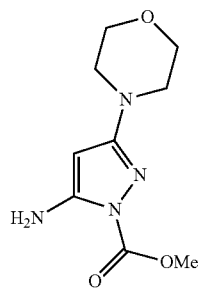

To a solution of N-cyano-acetyl-piperidine (0.60 mg, 3.9 mM) in dichloro-methane (12 mL), there was added phosphorus oxychloride (0.89 mL, 9.7 mM) and the mixture was stirred at 100° C. for 20 minutes under the irradiation with microwaves. To the reaction liquid, there was added methyl carbazinate (0.88 g, 9.7 mM) and the mixture was stirred at 100° C. for 20 minutes under the irradiation with microwaves. The reaction solution was concentrated under reduced pressure and the concentrate was neutralized by the addition of a saturated aqueous solution of sodium bicarbonate. The concentrate was then extracted with ethyl acetate, the resulting organic phase was dried over anhydrous magnesium sulfate and subsequently concentrated under reduced pressure to thus give a crude product of the title compound (0.57 g, yield: 65%).

MS (ESI) m/z (M+H)$^+$ 227

(Step 2): Synthesis of methyl 5-(ethoxy-carbonyl-acetylamino)-3-morpholin-4-yl-pyrazole-1-carboxylate

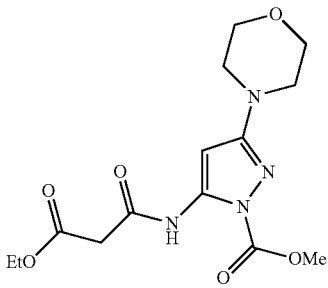

To a solution of the compound (3.3 g, 15 mM) prepared in the preceding step 1 in dichloromethane (97 mL), there were added, in order, ethyl malonyl-chloride (2.2 mL, 17 mM) and triethylamine (2.4 mL, 17 mM) and the mixture was stirred at room temperature for 3 hours. Then the reaction solution was concentrated under reduced pressure, and water was added to the resulting concentrate. The mixture was extracted with ethyl acetate, the resulting organic phase was dried over anhydrous magnesium sulfate, then concentrated under reduced pressure and the concentrate was subjected to a slurry-washing treatment (dichloromethane, diethyl ether) to thus give a crude product of the title compound (3.6 g, yield: 72%).

MS (ESI) m/z (M+H)$^+$ 341

(Step 3): Synthesis of 5,7-dichloro-2-morpholin-4-yl-pyrazolo[1,5-a]pyrimidine

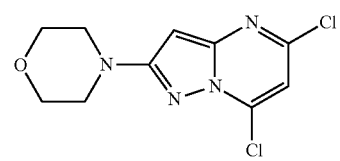

To a solution of the compound (3.6 g, 11 mM) prepared in the preceding step 2 in ethanol (40 mL), there was added a 28% methanol solution of sodium methoxide (4.2 mL, 21 mM) and the mixture was stirred at 50° C. for one hour. After cooling the mixture to room temperature, the precipitated solid was recovered through filtration and then washed with ethanol to thus give a crude product in the form of a bis-sodium salt thereof. This was suspended in toluene (15 mL), then phosphorus oxychloride (10 mL) and pyridine (0.85 mL) were added to the suspension and then the mixture was stirred at 90° C. for 5 hours. After cooling the mixture to room temperature, it was concentrated under reduced pressure and then the concentrate was neutralized with a saturated aqueous solution of sodium bicarbonate. It was then extracted with dichloromethane, the resulting organic phase was dried over anhydrous magnesium sulfate, then concentrated under reduced pressure and the resulting residue was purified by the silica gel column chromatography (SiO$_2$, ethyl acetate:hexane=3:2) to thus give the title compound (0.58 mg, overall yield of these two steps: 20%).

$^1$H-NMR (300 MHz, DMSO): δ 3.44 (4H, J=4.8 Hz, t), 3.85 (4H, J=4.8 Hz, t), 5.97 (1H, s), 6.72 (1H, s)

MS (ESI) m/z (M+H)$^+$ 273

(Step 4): Synthesis of (2,7-dimorpholin-4-yl-pyrazolo[1,5-a]pyrimidin-5-yl)-hydrazine

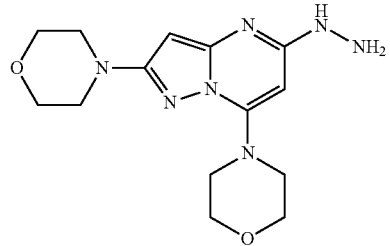

To a solution of the compound (0.17 g, 0.63 mM) prepared in the preceding step 3 in 1,4-dioxane (5.0 mL), there was added morpholine (0.11 mL, 1.3 mM) and the mixture was stirred at room temperature for 4 hours. Water was added to the mixture, the precipitated solid was recovered through filtration and then washed with methanol. The resulting solid was dissolved in 1,4-dioxane (5.0 mL), and then hydrazine monohydrate (0.26 mL, 6.3 mM) was added to the solution. After stirring the mixture at 90° C. for 14 hours, it was cooled to room temperature and then water was added thereto. The mixture was extracted with ethyl acetate, the resulting organic phase was dried over anhydrous magnesium sulfate and then concentrated under reduced pressure to thus give a crude product of the title compound (0.12 g, overall yield of these two steps: 62%).

MS (ESI) m/z (M+H)$^+$ 320

(Step 5): N-(3-methyl-benzylidene)-N-(2,7-dimorpholin-4-yl-pyrazolo[1,5-a]-pyrimidin-5-yl)-hydrazine (Compound 127)

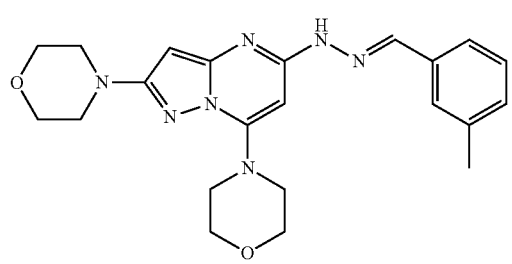

To a solution of the compound (30 mg, 0.094 mM) prepared in the foregoing step 4 in ethanol (2.0 mL), there were added metatolualdehyde (17 μL, 0.14 mM) and acetic acid (5.0 μL) and the mixture was then stirred at room temperature for 3 hours. The precipitated solid was recovered through filtration and then subjected to a slurry-washing treatment (methanol, dichloromethane) to thus give the title compound (14 mg, yield: 35%).

$^1$H-NMR (300 MHz, DMSO): δ 2.33 (3H, s), 3.18-3.23 (4H, m), 3.60-3.65 (4H, m), 3.70-3.74 (4H, m), 3.79-3.83 (4H, m), 5.56 (1H, s), 6.10 (1H, s), 7.17 (1H, J=7.5 Hz, d), 7.31 (1H, J=7.5 Hz, t), 7.45 (1H, s), 7.50 (1H, J=7.5 Hz, d), 7.99 (1H, s), 11.00 (1H, s)

MS (ESI) m/z (M+H)$^+$ 422

Example 128

Synthesis of N-(1H-indol-3-yl-methylidene)-N-(2,7-di-morpholin-4-yl-pyrazolo[1,5-a]pyrimidin-5-yl)-hydrazine (Compound 128)

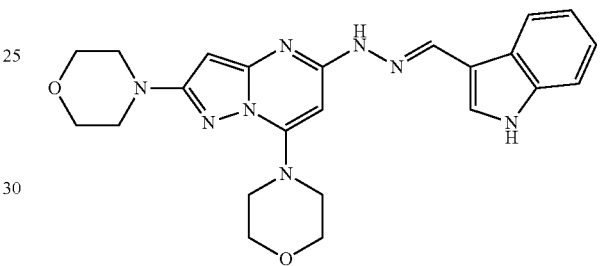

To a solution of (2,7-di-morpholin-4-yl-pyrazolo[1,5-a]pyrimidin-5-yl)-hydrazine (25 mg, 0.078 mM) in ethanol (2.0 mL), there were added 3-formyl-indole (17 mg, 0.12 mM) and acetic acid (5.0 μL) and the mixture was stirred at room temperature for 3 hours. The precipitated solid was recovered through filtration and then subjected to a slurry-washing operation (methanol, dichloromethane) to thus give the title compound (21 mg, yield: 60%).

$^1$H-NMR (300 MHz, DMSO): δ 3.16-3.23 (4H, m), 3.65-3.78 (8H, m), 3.83-3.86 (4H, m), 5.51 (1H, s), 6.17 (1H, s), 7.16-7.22 (2H, m), 7.41-7.45 (1H, m), 7.71 (1H, J=2.1 Hz, d), 8.19-8.24 (2H, m), 10.70 (1H, s), 11.43 (1H, s)

MS (ESI) m/z (M+H)$^+$ 447

Example 129

Synthesis of N-(2-hydroxy-7-morpholin-4-yl-pyrazolo[1,5-a]pyrimidin-5-yl)-N'-(3-methyl-benzylidene)-hydrazine (Compound 129)

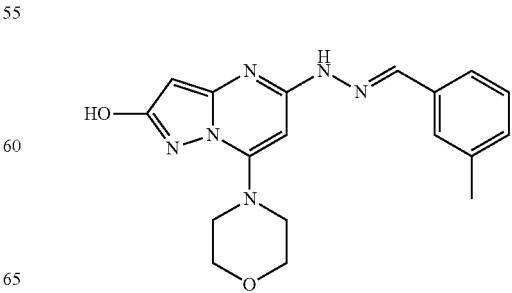

There was dissolved N-(2-benzyloxy-7-morpholin-4-yl-pyrazolo[1,5-a]-pyrimidin-5-yl)-N'-(3-methyl-benzylidene)-hydrazine (50.7 mg, 0.115 mM) in a mixed solvent of methanol/methylene chloride (1:2) (3 mL), then 10% palladium on carbon (10.1 mg) was added to the solution and the mixture was stirred for 3 hours in a hydrogen gas atmosphere. The reaction liquid was filtered, the solvent was distilled off, and the resulting residue was purified by the reversed phase HPLC and then subjected to a desalting operation to thus give the title compound (27.8 mg, yield: 69%).

¹H-NMR (300 MHz, DMSO): δ 2.33 (s, 3H), 3.57-3.60 (m, 4H), 3.77-3.80 (m, 4H), 5.27 (s, 1H), 6.11 (s, 1H), 7.15 (d, 1H, J=7.6 Hz), 7.29 (t, 1H, J=7.6 Hz), 7.44 (s, 1H), 7.48 (d, 1H, J=7.6 Hz), 7.44 (s, 1H), 7.48 (d, 1H, J=7.6 Hz), 7.98 (s, 1H), 10.98 (s, 1H); MS (ESI) m/z 353 (M+H)⁺.

Example 130

Synthesis of N-(3-fluoro-benzylidene)-N'-(7-morpholin-4-yl-2-pyridin-4-yl-pyrazolo[1,5-a]pyrimidin-5-yl)-hydrazine (Compound (130)

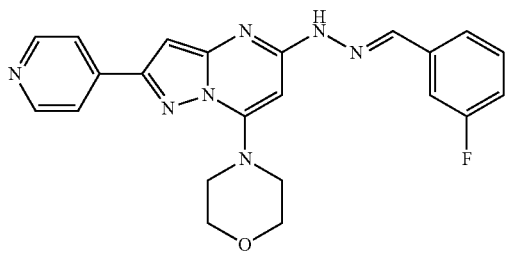

There was suspended, in ethanol (1.0 mL), 5-chloro-7-morpholin-4-yl-2-pyridin-4-yl-pyrazolo[1,5-a]pyrimidine (25 mg, 0.08 mM), then acetic acid (3.0 μL, 0.04 mM) and m-fluorobenzaldehyde (ion L, 0.10 mM) were added to the suspension and the mixture was stirred at room temperature for one hour. This reaction liquid was filtered, the resulting solid was washed with ethanol and then with diethyl ether to thus give the title compound (4.2 mg, yield: 13%).

¹H-NMR (300 MHz, DMSO-d6); δ 3.76 (bs, 4H), 3.89 (bs, 4H), 6.40 (s, 1H), 6.78 (s, 1H), 7.18-7.24 (m, 1H), 7.47-7.60 (m, 3H), 7.92 (d, 2H, J=6 Hz), 8.08 (s, 1H), 8.66 (d, 2H, J=6 Hz), 7.80 (d, 1H, J=1.5 Hz), 7.91-7.96 (m, 3H), 8.05 (d, 1H, J=1.8 Hz), 8.20 (s, 1H), 8.66 (d, 2H, J=6.3 Hz), 11.4 (s, 1H); MS (ESI) m/z 418 (M+H)⁺.

Example 131

Synthesis of N-[2-(1-benzyloxy-carbonyl-piperidin-4-yl)-7-morpholin-4-yl-pyrazolo[1,5-a]pyrimidin-5-yl]-N'-(3-methyl-benzylidene)-hydrazine (Compound 131)

(Step 1): Benzyl 4-(5-amino-1-methoxycarbonyl-1H-pyrazol-3-yl)-piperidine-1-carboxylate

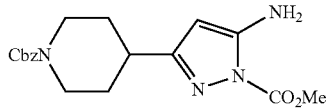

Acetonitrile (0.542 mL, 10.3 mM) was dissolved in tetrahydrofuran (30 mL) in an argon gas atmosphere, then a hexane solution of n-butyl lithium (2.64M, 3.12 mL, 8.23 mM) was added to the solution at −78° C. and the mixture was stirred for 2 hours. To this reaction liquid, there was added a solution obtained by dissolving piperidine-1,4-dicarboxylic acid-1-benzyl-4-ethyl (2.00 g, 6.86 mM) in tetrahydro-furan (10 mL). After stirring this reaction liquid at −78° C. for one hour, it was diluted with a 2M hydrochloric acid solution and then extracted with ethyl acetate. The resulting extracts were combined, dried over anhydrous sodium sulfate and the solvent was distilled off. The resulting residue was dissolved in ethanol (100 mL), followed by the addition of methyl carbazinate (742 mg, 8.23 mM) to the solution and the stirring of the mixture at room temperature overnight. The solvent was distilled off from this reaction liquid, the residue was diluted with water and the mixture was extracted with ethyl acetate. The resulting extracts were combined, dried over anhydrous sodium sulfate and the solvent was distilled off to thus give the title compound (1.89 g, yield: 77%).

(Step 2): 2-(1-Benzyloxy-carbonyl-piperidin-4-yl)-5,7-dichloro-pyrazolo[1,5-a]-pyrimidine

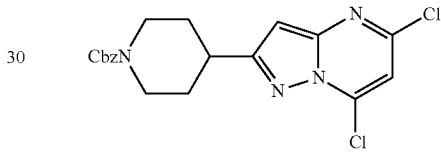

There was dissolved, in ethanol (20 mL), benzyl 4-(5-amino-1-methoxy-carbonyl-1H-pyrazol-3-yl)-piperidine-1-carboxylate (1.89 g, 5.27 mM) and there were then added, to the solution, a methanol solution of sodium methoxide (5.03M, 5.00 mL, 25.2 mM) and diethyl malonate (2.00 mL, 13.1 mM). After this reaction liquid was stirred for 2 hours while refluxing the same with heating, the solvent was distilled off, the resulting residue was diluted with a 2M hydrochloric acid solution and then the mixture was extracted with ethyl acetate. The resulting extracts were combined, dried over anhydrous sodium sulfate, the solvent was distilled off and the resulting residue was washed with diethyl ether. To the resulting residue, there were added phosphoryl chloride (18 mL) and diethyl-aniline (1.38 mL, 8.60 mM) and the mixture was stirred at 90° C. for one hour. The phosphoryl chloride was distilled off from this reaction liquid, ethanol was added to the resulting residue with ice-cooling and the mixture was stirred for 15 minutes.

After the concentration of this reaction liquid, the concentrate was purified by the silica gel column chromatography (ethyl acetate/hexane=1:3 to 1:2) to thus give the title compound (836 mg, overall yield of these two steps: 39%).

1H-NMR (300 MHz, CDCl₃): δ 1.68-1.82 (m, 2H), 2.02-2.07 (m, 2H), 2.93-3.13 (m, 3H), 4.28-4.31 (m, 2H), 5.15 (s, 2H), 6.51 (s, 1H), 6.91 (s, 1H), 7.30-7.37 (m, 5H); MS (ESI) m/z 405 (M+H)⁺.

(Step 3): 2-(1-Benzyloxy-carbonyl-piperidin-4-yl)-5-chloro-7-morpholin-4-yl-pyrazolo[1,5-a]pyrimidine

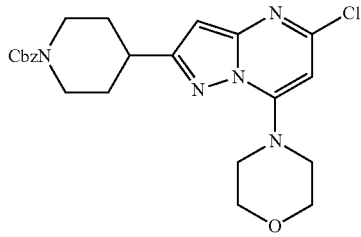

There was dissolved, in 1,4-dioxane (5 mL), 2-(1-benzyloxy-carbonyl-piperidin-4-yl)-5,7-dichloro-pyrazolo[1,5-a]-pyrimidine (192 mg, 0.474 mM), then morpholine (82.7 µL, 0.948 mM) was added to the solution and the mixture was stirred at room temperature for one hour. The solvent was distilled off from this reaction mixture, the residue thus obtained was diluted with water and then the mixture was extracted with ethyl acetate. The resulting extracts were combined, dried over anhydrous sodium sulfate, the solvent was distilled off and the resulting solid was washed with diethyl ether to thus give the title compound (191 mg, yield: 88%).
$^1$H-NMR (300 MHz, CDCl$_3$): δ 1.68-1.79 (m, 2H), 2.01-2.05 (m, 2H), 2.94-3.02 (m, 3H), 3.76-3.79 (m, 4H), 3.92-3.95 (m, 4H), 4.25-4.28 (m, 2H), 5.15 (s, 2H), 6.02 (s, 1H), 6.28 (s, 1H), 7.31-7.38 (m, 5H); MS (ESI) m/z 456 (M+H)$^+$.

(Step 4): N-[2-(1-benzyloxy-carbonyl-piperidin-4-yl)-7-morpholin-4-yl-pyrazolo[1,5-a]pyrimidin-5-yl]-N'-(3-methyl-benzylidene)-hydrazine

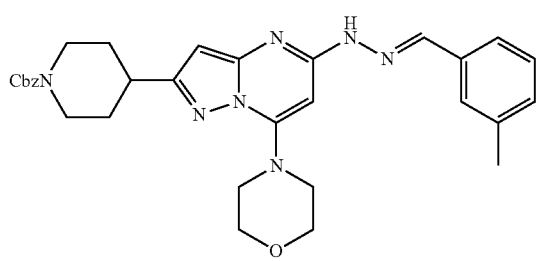

There was suspended, in 1,4-dioxane (5 mL), 2-(1-benzyloxy-carbonyl-piperidin-4-yl)-5-chloro-7-morpholin-4-yl-pyrazolo[1,5-a]pyrimidine (190 mg, 0.417 mM), there was then added, to the suspension, hydrazine monohydrate (202 µL, 4.17 mM) and the mixture was stirred overnight while refluxing the same with heating. After the stirring operation, the reaction liquid was diluted with water and then the mixture was extracted with ethyl acetate. The resulting extracts were combined, dried over anhydrous sodium sulfate and the solvent was then distilled off.
The resulting residue was dissolved in ethanol (3 mL), then 3-methyl-benzaldehyde (49.1 µL, 0.417 mM) was added to the solution and the mixture was stirred at room temperature for 2 hours. This reaction liquid was filtered and the resulting solid was washed with diethyl ether to thus give the title compound (166 mg, overall yield of these two steps: 72%).
$^1$H-NMR (300 MHz, DMSO): δ 1.51-1.62 (m, 2H), 1.91-1.94 (m, 2H), 2.33 (s, 3H), 2.84-2.97 (m, 3H), 3.63-3.66 (m, 4H), 3.80-3.83 (m, 4H), 4.03-4.08 (m, 2H), 5.08 (s, 2H), 5.93 (s, 1H), 6.22 (s, 1H), 7.16 (d, 1H, J=7.6 Hz), 7.27-7.37 (m, 6H), 7.45 (s, 1H), 7.50 (d, 1H, J=7.6 Hz), 7.99 (s, 1H), 11.10 (s, 1H); MS (ESI) m/z 554 (M+H)$^+$.

Example 132

Synthesis of N-(3-methyl-benzylidene)-N'-(7-morpholin-4-yl-2-piperidin-4-yl-pyrazolo[1,5-a]pyrimidin-5-yl)-hydrazine (Compound 132)

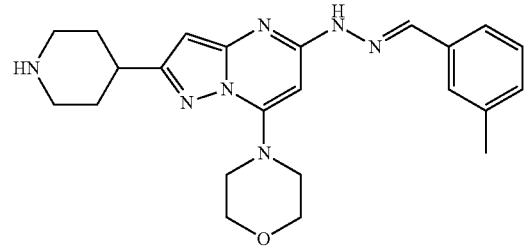

There was dissolved, in a mixed solvent of methylene chloride/methanol (1:2) (3 mL), N-[2-(1-benzyloxy-carbonyl-piperidin-4-yl)-7-morpholin-4-yl-pyrazolo[1,5-a]-pyrimidin-5-yl]-N'-(3-methyl-benzyliodene)-hydrazine (30.8 mg, 0.0556 mM), followed by the addition of 20% palladium hydroxide on carbon (6.2 mg) to the solution and the stirring of the mixture for one hour and a half in a hydrogen gas atmosphere. The reaction liquid was filtered, the solvent was then distilled off and the resulting residue was washed with ethyl acetate to thus give the title compound (18.5 mg, yield: 79%).
$^1$H-NMR (300 MHz, DMSO): δ 1.78-1.89 (m, 2H), 2.06-210 (m, 2H), 2.33 (s, 3H), 2.95-3.03 (m, 4H), 3.63-3.67 (m, 4H), 3.80-3.83 (m, 4H), 5.93 (s, 1H), 6.24 (s, 1H), 7.16 (d, 1H, J=7.6 Hz), 7.30 (t, 1H, J=7.6 Hz), 7.45 (s, 1H), 7.50 (d, 1H, J=7.6 Hz), 8.01 (s, 1H), 11.13 (s, 1H); MS (ESI) m/z 420 (M+H)$^+$.

Example 133

Synthesis of N-[2-(1-acetyl-piperidin-4-yl)-7-morpholin-4-yl-pyrazolo-[1,5-a]pyrimidin-5-yl]-N'-(3-methyl-benzylidene)-hydrazine (Compound 133)

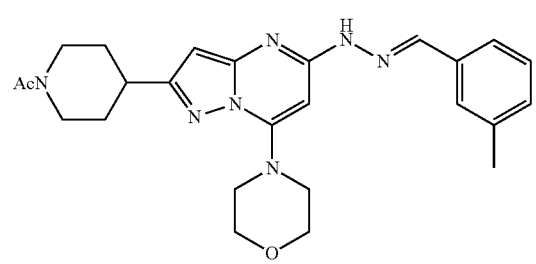

There was suspended, in methylene chloride (2 mL), N-(3-methyl-benzylidene)-N'-(7-morpholin-4-yl-2-piperidin-4-yl-pyrazolo[1,5-a]pyrimidin-5-yl)-hydrazine (31.0 mg, 0.0739 mM) and then acetic acid anhydride (1 mL) was added to the suspension. After this reaction liquid was heated to 90° C. and stirred for 15 minutes, the solvent was distilled off, the resulting residue was diluted with a saturated aqueous solution of sodium bicarbonate and then the mixture was extracted with ethyl acetate. The resulting extracts were combined, dried over anhydrous sodium sulfate, the solvent was distilled off and the resulting solid was washed with diethyl ether to thus give the title compound (25.0 mg, yield: 73%).

¹H-NMR (300 MHz, DMSO): δ 1.41-1.68 (m, 2H), 1.89-1.97 (m, 2H), 2.00 (s, 3H), 2.33 (s, 3H), 2.69 (m, 1H), 2.92 (m, 1H), 3.16 (m, 1H), 3.64-3.66 (m, 4H), 3.80-3.82 (m, 4H), 3.88 (m, 1H), 4.39 (d, 1H, J=13 Hz), 5.93 (s, 1H), 6.22 (s, 1H), 7.16 (d, 1H, J=7.6 Hz), 7.29 (t, 1H, J=7.6 Hz), 7.45 (s, 1H), 7.50 (d, 1H, J=7.6 Hz), 7.99 (s, 1H), 11.10 (s, 1H); MS (ESI) m/z 462 (M+H)⁺.

Example 134

Synthesis of N-(2-benzyloxy-7-morpholin-4-yl-pyrazolo[1,5-a]-pyrimidin-5-yl)-N'-(3-methyl-benzylidene)-hydrazine (Compound 134)

(Step 1): 2-Benzyloxy-5,7-dichloro-pyrazolo[1,5-a]-pyrimidine

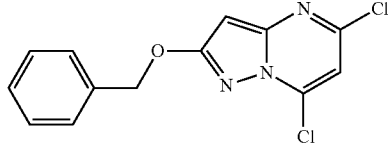

There was dissolved, in ethanol (30 mL), 5-benzyloxy-2H-pyrazol-3-yl-amine (1.52 g, 8.03 mM) and then a methanol solution of sodium methoxide (5.03M, 3.51 mL, 17.7 mM) and diethyl malonate (1.47 mL, 9.64 mM) were added to the solution. This reaction liquid was stirred for 2 hours while refluxing the same with heating. This reaction mixture was filtered and the resulting solid was washed with diethyl ether. After the addition of phosphoryl chloride (10 mL) to the resulting solid with ice-cooling, the resulting suspension was stirred for 3 hours while refluxing the same with heating. The phosphoryl chloride was distilled off from this reaction liquid, ethanol was then added to the residue thus obtained with ice-cooling and the mixture was stirred for 15 minutes. After the concentration of this reaction liquid, the concentrate was purified by the silica gel column chromatography (ethyl acetate/hexane=1:100) to thus give the title compound (167 mg, overall yield of these two steps: 7%).

¹H-NMR (300 MHz, CDCl₃): δ 5.41 (s, 2H), 6.12 (s, 1H), 6.83 (s, 1H), 7.34-7.40 (m, 3H), 7.48-7.51 (m, 2H); MS (ESI) m/z 294 (M+H)⁺.

(Step 2): 2-Benzyloxy-5-chloro-7-morpholin-4-yl-pyrazolo[1,5-a]-pyrimidine

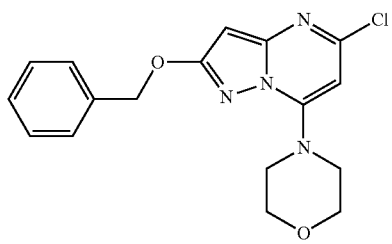

There was dissolved, in 1,4-dioxane (3 mL), 2-benzyloxy-5,7-dichloro-pyrazolo-[1,5-a]-pyrimidine (167 mg, 0.568 mM), then morpholine (99.1 µL, 1.14 mM) was added to the solution and the mixture was stirred at room temperature for one hour. The solvent was distilled off from this reaction mixture, followed by the dilution of the residue with water and the subsequent extraction of the mixture with methylene chloride. The resulting extracts were combined, dried over anhydrous sodium sulfate, the solvent was distilled off and the resulting solid was washed with methanol to thus give the title compound (188 mg, yield: 96%).

¹H-NMR (300 MHz, CDCl₃): δ 3.67-3.70 (m, 4H), 3.89-3.92 (m, 4H), 5.31 (s, 2H), 5.92 (s, 1H), 5.97 (s, 1H), 7.32-7.46 (m, 5H); MS (ESI) m/z 345 (M+H)⁺.

(Step 3): N-(2-benzyloxy-7-morpholin-4-yl-pyrazolo[1,5-a]pyrimidin-5-yl)-N'-(3-methyl-benzylidene)-hydrazine (Compound 134)

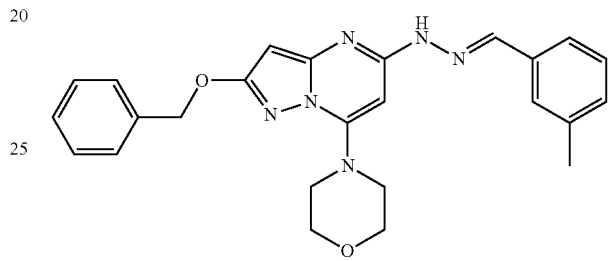

There was suspended, in 1,4-dioxane (5 mL), 2-benzyloxy-5-chloro-7-morpholin-4-yl-pyrazolo[1,5-a]-pyrimidine (187 mg, 0.542 mM), then hydrazine monohydrate (263 µL, 5.42 mM) was added to the suspension and the mixture was stirred overnight while refluxing the same with heating. After the stirring operation, the reaction liquid was diluted with water and the mixture was extracted with ethyl acetate. The resulting extracts were combined, dried over anhydrous sodium sulfate and the solvent was distilled off.

The resulting residue was dissolved in ethanol (5 mL), then 3-methyl-benzaldehyde (63.8 µL, 0.542 mM) was added to the solution and the mixture was stirred at room temperature for one hour. This reaction liquid was filtered and the resulting solid was washed with diethyl ether to thus give the title compound (129 mg, overall yield of these two steps: 54%).

¹H-NMR (300 MHz, DMSO): δ 2.33 (s, 3H), 3.55-3.58 (m, 4H), 3.78-3.81 (m, 4H), 5.24 (s, 2H), 5.54 (s, 1H), 6.15 (s, 1H), 7.16 (d, 1H, J=7.6 Hz), 7.27-7.50 (m, 8H), 7.99 (s, 1H), 11.05 (s, 1H); MS (ESI) m/z 443 (M+H)⁺.

Example 135

Synthesis of 5-[N-(3-methyl-benzylidene)-hydrazino]-7-morpholin-4-yl-pyrazolo[1,5-a]pyrimidine-2-carboxylic acid methyl-pyridin-4-yl-amide (Compound 135)

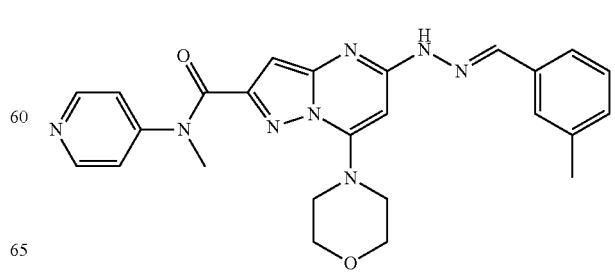

To a solution of 5-[N-(3-methyl-benzylidene)-hydrazino]-7-morpholin-4-yl-pyrazolo[1,5-a]pyrimidine-2-carboxylic acid (18 mg, 0.047 mM) in dimethyl-formamide (1.5 mL), there were, in order, added 4-methylamino-pyridine (7.7 mg, 0.071 mM), O-(benzotriazol-1-yl)-N,N,N',N'-tetramethyl-uronium hexafluoroacetic acid salt (27 mg, 0.071 mM) and 1-hydroxy-7-azabenzotriazole (a very small amount) and the mixture was then stirred at room temperature for 5 hours. Water was added to the mixture, followed by the extraction thereof with ethyl acetate, the washing of the resulting organic phase with a saturated aqueous common salt solution and the subsequent drying of the organic phase over anhydrous magnesium sulfate. The organic phase was concentrated under reduced pressure, the resulting residue was subjected to the reversed phase high performance liquid chromatography in which chemically bonded octadodecyl group-containing silica gel was used as the loading material and the elution was carried out using a water/acetonitrile mixed solvent containing trifluoroacetic acid in an amount of 0.1% (v/v), and the target compound-containing fractions were lyophilized to thus give the trifluoroacetic acid salt of the title compound (16 mg, yield: 48%).

$^1$H-NMR (300 MHz, DMSO): δ 2.35 (3H, s), 3.20-3.24 (4H, m), 3.56 (3H, s), 3.57-3.63 (4H, m), 6.33 (1H, s), 6.48 (1H, s), 7.20 (1H, J=7.5 Hz, d), 7.30-7.35 (1H, m), 7.47-7.56 (2H, m), 7.62-7.65 (2H, m), 8.05 (1H, s), 8.63-8.67 (2H, m), 11.42 (1H, s)

MS (ESI) m/z (M+H)$^+$ 471

Example 136

Synthesis of N-(3-methyl-benzylidene)-N'-(7-morpholin-4-yl-2-quinolin-6-yl-pyrazolo[1,5-a]pyrimidin-5-yl)-hydrazine (Compound 136)

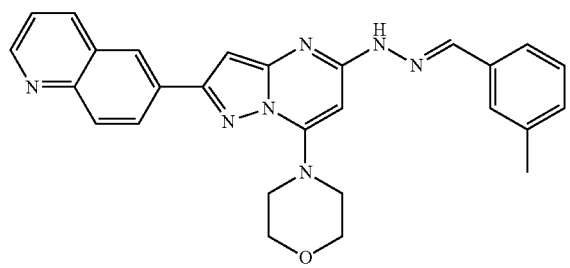

(Step 1): 6-(5-Chloro-7-morpholin-4-yl-pyrazolo[1,5-a]pyrimidin-2-yl)-quinoline

Acetonitrile (0.7 mL, 13 mM) was suspended in tetrahydrofuran (30 mL) in an argon gas atmosphere, then a 1.6M n-butyl lithium/hexane solution (8.2 mL, 13 mM) was added to the suspension at a temperature of −78° C. and the mixture was stirred for one hour. To this solution, there was added quinoline-6-carboxylic acid methyl ester (2.0 g, 11 mM), the mixture was stirred at room temperature for one hour, the precipitated solid was recovered through filtration and then it was washed with tetrahydrofuran and diethyl ether. The resulting solid was dried in vacuo and then suspended in ethanol (25 mL) and concentrated hydrochloric acid (1.1 mL) was added to the suspension with ice-cooling. Subsequently, methyl carbazinate (1.3 g, 14 mM) was added to the suspension at room temperature and then the mixture was stirred for 24 hours. It was concentrated under reduced pressure, water was then added to the resulting concentrate, the mixture was extracted with ethyl acetate, the resulting organic phase was dried over anhydrous magnesium sulfate and then it was concentrated under reduced pressure. The resulting solid was dried in vacuo, suspended in ethanol (17 mL), then there was added, to the suspension, a 5.0M sodium methoxide/methanol solution (1.4 mL, 6.8 mM), the resulting mixture was stirred at room temperature for one hour, there were further added, thereto, diethyl malonate (1.8 mL, 12 mM) and a 5.0M sodium methoxide/methanol solution (3.0 mL, 15 mM) and the mixture was stirred at 90° C. for 16 hours. After cooling the reaction liquid to room temperature, the precipitated solid was recovered through filtration and then washed with diethyl ether. After the solid was dried under reduced pressure, it was suspended in toluene (30 mL), followed by the addition of phosphorus oxychloride (30 mL) to the suspension and the stirring of the mixture at 90° C. Pyridine (2.0 mL, 25 mM) was dropwise added to this solution and the mixture was further stirred at 90° C. for 5 hours. After cooling the mixture to room temperature, it was concentrated under reduced pressure, the resulting residue was suspended in 1,2-dichloroethane (20 mL), the suspension was filtered and the resulting residue was concentrated under reduced pressure. The concentrated residue was diluted with water and then the dispersion was extracted with dichloromethane. The resulting extracts were combined, dried over anhydrous sodium sulfate and the solvent was then distilled off. Morpholine (1.4 mL, 16 mM) was added to the resulting solid with ice-cooling and the mixture was stirred at room temperature for 2 hours. It was concentrated under reduced pressure, the resulting residue was diluted with water and then the mixture was extracted with ethyl acetate. The resulting extracts were combined, dried over anhydrous sodium sulfate and the solvent was distilled off to thus give a crude product of the title compound (83 mg, overall yield of these five steps: 2.1%).

MS (ESI) m/z 366 (M+H)$^+$ (Step 2): N-(3-methyl-benzylidene)-N'-(7-morpholin-4-yl-2-quinolin-6-yl-pyrazolo-[1,5-a]pyrimidin-5-yl)-hydrazine There was suspended, in 1,4-dioxane (2.0 mL), 6-(5-chloro-7-morpholin-4-yl-pyrazolo[1,5-a]pyrimidin-2-yl)-quinoline (83 mg, 0.23 mM) prepared in the preceding step 1, then hydrazine monohydrate (110 μL, 2.3 mM) was added to the suspension and the mixture was stirred for 8 hours while refluxing the same with heating. After the stirring operation, the reaction liquid was concentrated, the concentrate thus obtained was diluted with water and then the mixture was extracted with ethyl acetate. The resulting extracts were combined, dried over anhydrous sodium sulfate and the solvent was distilled off. The resulting solid was dried in vacuo, suspended in ethanol (2.0 mL), then acetic acid (6.5 μL, 0.11 mM) and metatolualdehyde (30 μL, 0.25 mM) were added to the suspension and the mixture was stirred at room temperature for 2 hours. The precipitated solid was recovered through filtration and then washed with diethyl ether to thus give the title compound (60 mg, overall yield of these two steps: 56%).

$^1$H-NMR (300 MHz, DMSO-d6); δ 3.79 (bs, 4H), 3.93 (bs, 4H), 6.36 (s, 1H), 6.75 (s, 1H), 7.20 (d, 1H, J=7.5 Hz), 7.33 (t,

1H, J=7.8 Hz), 7.50 (s, 1H), 8.06-8.12 (m, 2H), 8.38-8.46 (m, 2H), 8.55 (d, 1H, J=1.5 Hz), 8.91 (dd, 1H, J=4.2, 1.8 Hz), MS (ESI) m/z 464 (M+H)⁺

Example 137

Synthesis of N-(3-vinyl-benzylidene)-N-(7-morpholin-4-yl-2-pyridin-4-yl-pyrazolo[1,5-a]pyrimidin-5-yl)-hydrazine (Compound 137)

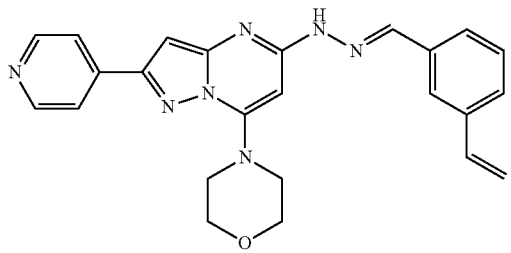

To a solution of (7-morpholin-4-yl-2-pyridin-4-yl-pyrazolo[1,5-a]pyrimidin-5-yl)-hydrazine (20 mg, 0.064 mM) in ethanol (2.0 mL), there were added 3-vinyl-benzaldehyde (17 mg, 13 mM) and acetic acid (5.0 μL) and then the mixture was stirred at room temperature for 3 hours. The precipitated solid was recovered through filtration and then washed with ethanol to thus give the title compound (20 mg, yield: 74%).

¹H-NMR (300 MHz, DMSO): δ 3.75-3.77 (4H, m), 3.88-3.90 (4H, m), 5.34 (1H, J=11.4 Hz, d), 5.93 (1H, J=17.7 Hz, d), 6.40 (1H, s), 6.77 (1H, s), 6.81 (1H, J=11.4, 17.7 Hz, dd), 7.42 (1H, J=7.8 Hz, t), 7.50 (1H, J=7.8 Hz, d), 7.68 (1H, J=7.8 Hz, d), 7.75 (1H, s), 7.91 (1H, J=1.5 Hz, d), 7.92 (1H, J=1.5 Hz, d), 8.10 (1H, s), 8.65 (1H, J=1.5 Hz, d), 8.67 (1H, J=1.5 Hz, d), 11.35 (1H, s)
MS (ESI) m/z (M+H)⁺ 426

Example 138

Synthesis of N-(1H-indol-2-yl-methylidene)-N-(7-morpholin-4-yl-2-pyridin-4-yl-pyrazolo[1,5-a]pyrimidin-5-yl)-hydrazine (Compound 138)

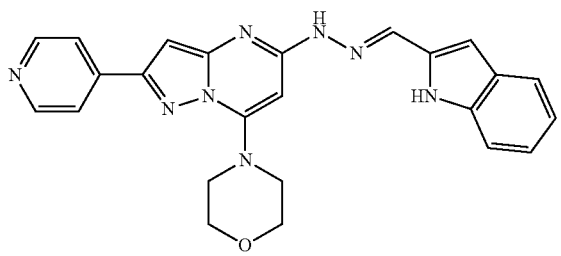

To a solution of (7-morpholin-4-yl-2-pyridin-4-yl-pyrazolo[1,5-a]pyrimidin-5-yl)-hydrazine (20 mg, 0.064 mM) in ethanol (2.0 mL), there were added 2-formyl-indole (19 mg, 0.13 mM) and acetic acid (5.0 μL) and the mixture was stirred at room temperature for 3 hours. The precipitated solid was recovered through filtration and then washed with ethanol to thus give the title compound (13 mg, yield: 46%).

¹H-NMR (300 MHz, DMSO): δ 3.78 (4H, s), 3.91-3.93 (4H, m), 6.56 (1H, s), 6.74 (1H, s), 6.75 (1H, s), 7.01 (1H, J=7.2 Hz, t), 7.14-7.19 (1H, m), 7.45 (1H, J=7.8 Hz, d), 7.55 (1H, J=7.8 Hz, d), 7.91 (1H, J=1.5 Hz, d), 7.93 (1H, J=1.5 Hz, d), 8.11 (1H, s), 8.65 (1H, J=1.5 Hz, d), 8.67 (1H, J=1.5 Hz, d), 11.32 (1H, s), 11.37 (1H, s)
MS (ESI) m/z (M+H)⁺ 439

Example 139

Synthesis of N-(3-boronyl-benzylidene)-N-(7-morpholin-4-yl-2-phenyl-pyrazolo[1,5-a]pyrimidin-5-yl)-hydrazine (Compound 139)

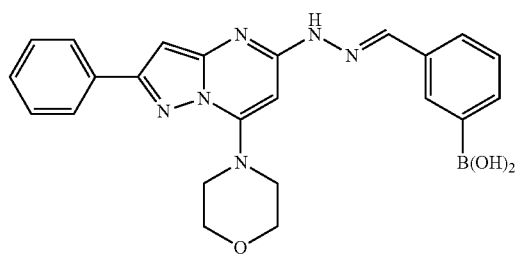

To a solution of (7-morpholin-4-yl-2-phenyl-pyrazolo[1,5-a]pyrimidin-5-yl)-hydrazine (20 mg, 0.065 mM) in ethanol (2.0 mL), there were added 2-boronyl-benzaldehyde (19 mg, 0.13 mM) and acetic acid (5.0 μL) and the mixture was stirred at room temperature for 3 hours. The precipitated solid was recovered through filtration and then washed with ethanol to thus give the title compound (10 mg, yield: 35%).

¹H-NMR (300 MHz, DMSO): δ 3.73 (4H, m), 3.86-3.88 (4H, m), 6.32 (1H, s), 6.56 (1H, s), 7.37-7.47 (4H, m), 7.75-7.82 (2H, m), 7.93 (1H, s), 7.96 (1H, s), 8.01 (1H, s), 8.08 (1H, s), 8.15 (2H, s), 11.19 (1H, s)
MS (ESI) m/z (M+H)⁺ 443

Example 140

Synthesis of N-(3-amino-benzylidene)-N-(7-morpholin-4-yl-2-phenyl-pyrazolo[1,5-a]pyrimidin-5-yl)-hydrazine (Compound 140)

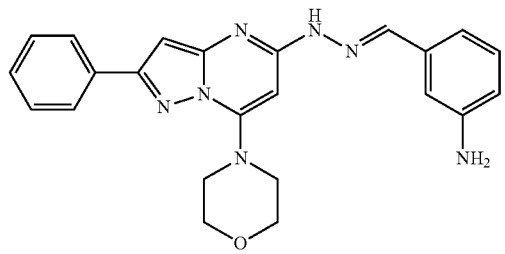

To a solution of (7-morpholin-4-yl-2-phenyl-pyrazolo[1,5-a]pyrimidin-5-yl)-hydrazine (30 mg, 0.097 mM) in ethanol (4.0 mL), there were added 3-tert-butoxy-carbonylamino-benzaldehyde (32 mg, 0.15 mM) and acetic acid (5.0 μL) and the mixture was stirred at room temperature for 3 hours. The precipitated solid was recovered through filtration and then washed with ethanol. The resulting solid was suspended in dichloromethane (1.0 mL), then a 4N hydrochloric acid/1,4-dioxane solution (3.0 mL) was added to the suspension and the mixture was stirred at room temperature for 3 hours. After basifying the mixture by the addition of an excess amount of a saturated aqueous solution of sodium bicarbonate, it was extracted with ethyl acetate, the resulting organic phase was dried over anhydrous magnesium sulfate and then concentrated under reduced pressure to thus give the title compound (15 mg, overall yield of these two steps: 38%).

$^1$H-NMR (300 MHz, DMSO): δ 3.73 (4H, m), 3.88 (4H, m), 6.26 (1H, s), 6.56 (1H, s), 6.65 (1H, J=7.2 Hz, d), 6.93 (1H, J=7.2 Hz, d), 6.99 (1H, s), 7.09-7.14 (2H, m), 7.38-7.46 (3H, m), 7.94-7.96 (3H, m), 11.15 (1H, s)

MS (ESI) m/z (M+H)$^+$ 414

Example 141

Synthesis of N-[7-(3-aza-bicyclo[3.1.0]-3-hexyl)-2-phenyl-pyrazolo-[1,5-a]pyrimidin-5-yl]-N'-(3-methyl-benzylidene)-hydrazine (Compound 141)

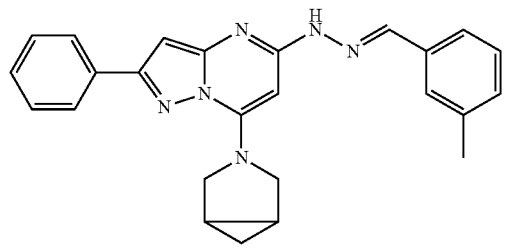

There was dissolved, in 1,4-dioxane (3 mL), 5,7-dichloro-2-phenyl-pyrazolo-[1,5-a]pyrimidine (40 mg, 0.152 mM). Then there was added, to the solution, 3-aza-bicyclo[3.1.0]hexane (20 mg, 0.241 mM) prepared according to the method disclosed in the literature (U.S. Pat. No. 4,183,857) and the mixture was stirred at room temperature for 30 minutes. The solvent was distilled off from this reaction mixture, the residue thus obtained was diluted with water and then the mixture was extracted with methylene chloride. The resulting extracts were combined, dried over anhydrous sodium sulfate, the solvent was distilled off and the resulting solid was washed with methanol. The resulting residue was suspended in ethanol (3 mL) and, to the suspension, there were added potassium carbonate (23.1 mg, 0.152 mM) and hydrazine monohydrate (36.9 μL, 0.760 mM). This suspension was stirred at 150° C. for 50 minutes under the irradiation with microwaves, followed by the addition of a saturated aqueous solution of sodium bicarbonate and the subsequent extraction of the mixture with methylene chloride. The resulting extracts were combined, dried over anhydrous sodium sulfate and the solvent was distilled off. The resulting residue was suspended in ethanol (2 mL), then acetic acid (5.0 μL, 0.087 mM) and 3-methyl-benzaldehyde (18.6 μL, 0.152 mM) were added to the suspension and then the mixture was stirred at room temperature for 2 hours. The solvent was distilled off and the resulting residue was purified by the reversed phase HPLC (C-18 ODS Column) to thus give the trifluoroacetic acid salt of the title compound (9.1 mg, overall yield of these three steps: 11.4%).

$^1$H-NMR (300 MHz, DMSO-d6): δ 0.37 (dd, 1H, J=4.2, 8.7 Hz), 0.80-0.90 (m, 1H), 1.72-1.90 (m, 2H), 2.40 (s, 3H), 3.80-4.20 (m, 2H), 4.30-4.70 (m, 2H), 5.70 (bs, 1H), 6.62 (bs, 1H), 7.25-7.35 (m, 1H), 7.36-7.80 (m, 7H), 7.99 (d, 2H, J=7.2 Hz), 8.13 (s, 1H); MS (ESI) m/z 409 (M+H)$^+$.

Example 142

Synthesis of N-(3-acetyl-benzylidene)-N'-(7-morpholin-4-yl-2-pyridin-4-yl-pyrazolo[1,5-a]pyrimidin-5-yl)-hydrazine (Compound 142)

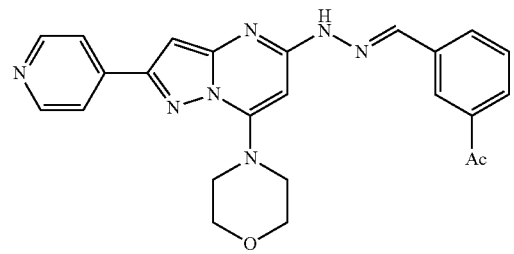

There was dissolved, in ethanol (2 mL), (7-morpholin-4-yl-2-pyridin-4-yl-pyrazolo[1,5-a]pyrimidin-5-yl)-hydrazine (30.6 mg, 0.0983 mM), then 3-acetyl-benzaldehyde (14.6 mg, 0.0983 mM) was added to the solution and the mixture was stirred at room temperature overnight. The reaction liquid was filtered and then the resulting solid was washed with diethyl ether to thus give the title compound (33.6 mg, yield: 77%).

$^1$H-NMR (300 MHz, DMSO): δ 2.63 (s, 3H), 3.72-3.76 (m, 4H), 3.87-3.90 (m, 4H), 6.40 (s, 1H), 6.77 (s, 1H), 7.58 (t, 1H, J=7.9 Hz), 7.89-7.94 (m, 3H), 8.04 (d, 1H, J=7.9 Hz), 8.15 (s, 1H), 8.17 (s, 1H), 8.64 (d, 2H, J=5.9 Hz), 11.42 (s, 1H); MS (ESI) m/z 442 (M+H)$^+$.

Example 143

Synthesis of N-(3-isopropenyl-benzylidene)-N'-(7-morpholin-4-yl-2-pyridin-4-yl-pyrazolo[1,5-a]pyrimidin-5-yl)-hydrazine (Compound 143)

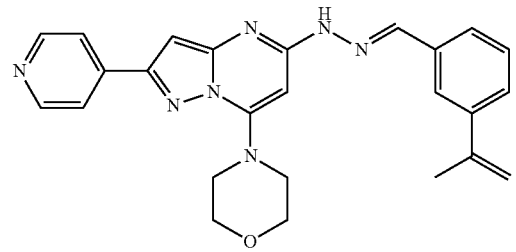

There was dissolved, in ethanol (2 mL), (7-morpholin-4-yl-2-pyridin-4-yl-pyrazolo[1,5-a]pyrimidin-5-yl)-hydrazine (30.4 mg, 0.0976 mM), then 3-isopropenyl-benzaldehyde (14.3 mg, 0.0976 mM) was added to the solution and the mixture was stirred at room temperature overnight. The reaction liquid was filtered and then the resulting solid was washed with diethyl ether to thus give the title compound (26.6 mg, yield: 62%).

$^1$H-NMR (300 MHz, DMSO): δ 2.15 (s, 3H), 3.72-3.75 (m, 4H), 3.87-3.89 (m, 4H), 5.16 (s, 1H), 5.50 (s, 1H), 6.39 (s, 1H), 6.75 (s, 1H), 7.41 (t, 1H, J=7.6 Hz), 7.50 (d, 1H, J=7.6

Hz), 7.70 (d, 1H, J=7.6 Hz), 7.74 (s, 1H), 7.90 (d, 2H, J=6.2 Hz), 8.09 (s, 1H), 8.64 (d, 2H, J=6.2 Hz), 11.34 (s, 1H); MS (ESI) m/z 440 (M+H)⁺.

Example 144

Synthesis of N-benzo[b]thiophen-5-yl-methylidene-N'-(7-morpholin-4-yl-2-pyridin-4-yl-pyrazolo[1,5-a]pyrimidin-5-yl)-hydrazine (Compound 144)

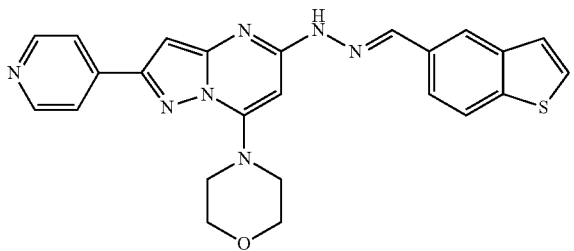

There was suspended, in ethanol (1.0 mL), 5-chloro-7-morpholin-4-yl-2-pyridin-4-yl-pyrazolo[1,5-a]pyrimidine (20 mg, 0.06 mM), then acetic acid (3.0 µL, 0.04 mM) and benzo[b]thiophene-5-carbaldehyde (11 mg, 0.07 mM) were added to the suspension and the mixture was stirred at room temperature for 3 hours. The reaction liquid was filtered and then the resulting solid was washed with ethanol and then with diethyl ether to thus give the title compound (19 mg, yield: 65%).

¹H-NMR (300 MHz, DMSO-d6); δ 3.77 (bs, 4H), 3.90 (bs, 4H), 6.42 (s, 1H), 6.76 (s, 1H), 7.53 (d, 1H, J=5.4 Hz), 7.82-7.87 (m, 2H), 7.92 (d, 2H, J=5.7 Hz), 8.05-8.11 (m, 2H), 8.21 (s, 1H), 8.66 (d, 1H, J=6.3 Hz), 11.3 (s, 1H); MS (ESI) m/z 456 (M+H)⁺.

Example 145

Synthesis of N-(3-isopropyl-benzylidene)-N'-(7-morpholin-4-yl-2-Pyridin-4-yl-pyrazolo[1,5-a]pyrimidin-5-yl)-hydrazine (Compound 145)

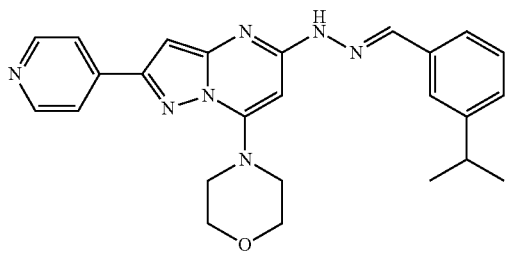

There was dissolved, in ethanol (2 mL), (7-morpholin-4-yl-2-pyridin-4-yl-pyrazolo[1,5-a]pyrimidin-5-yl)-hydrazine (30.1 mg, 0.0967 mM), then 3-isopropyl-benzaldehyde (14.3 mg, 0.0967 mM) was added to the solution and the mixture was stirred at room temperature overnight. The solvent was distilled off from this reaction liquid, the resulting residue was purified by the reversed phase HPLC and then subjected to a desalting treatment to thus give the title compound (11.3 mg, yield: 26%).

¹H-NMR (300 MHz, DMSO): δ 1.23 (d, 6H, J=6.7 Hz), 2.94 (1H, J=6.7 Hz), 3.71-3.74 (m, 4H), 3.87-3.89 (m, 4H), 6.37 (s, 1H), 6.74 (s, 1H), 7.25 (d, 1H, J=7.6 Hz), 7.35 (t, 1H, J=7.6 Hz), 7.51 (s, 1H), 7.57 (d, 1H, J=7.6 Hz), 7.90 (d, 2H, J=6.2 Hz), 8.06 (s, 1H), 8.64 (d, 2H, J=6.2 Hz), 11.27 (s, 1H); MS (ESI) m/z 442 (M+H)⁺.

Example 146

Synthesis of N-(1-methyl-1H-indol-6-yl-methylidene)-N'-(7-morpholin-4-yl-2-pyridin-4-yl-pyrazolo[1,5-a]pyrimidin-5-yl)-hydrazine (Compound 146)

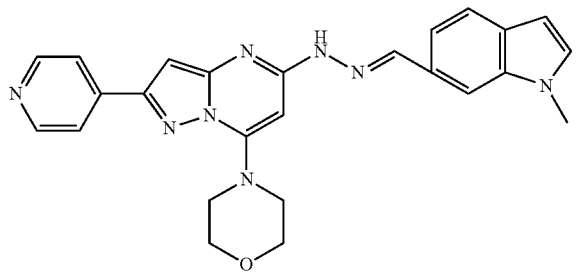

There was suspended, in ethanol (1.0 mL), 5-chloro-7-morpholin-4-yl-2-pyridin-4-yl-pyrazolo[1,5-a]pyrimidine (20 mg, 0.06 mM), then acetic acid (3.0 µL, 0.04 mM) and 1-methyl-1H-indole-6-carbaldehyde (15 mg, 0.1 mM) were added to the suspension and the mixture was stirred at room temperature for 5 hours. The reaction liquid was filtered and then the resulting solid was washed with ethanol and then with diethyl ether to thus give the title compound (5.0 mg, yield: 17%).

¹H-NMR (300 MHz, DMSO-d6); δ 3.76 (bs, 4H), 3.85 (s, 3H), 3.90 (bs, 4H), 6.42 (s, 1H), 6.46 (d, 1H, J=2.4 Hz), 6.74 (s, 1H), 7.41 (d, 1H, J=3.3 Hz), 7.58-7.59 (m, 2H), 7.66 (s, 1H), 7.92 (d, 2H, J=6 Hz), 8.20 (s, 1H), 8.66 (d, 1H, J=6 Hz), 11.2 (s, 1H); MS (ESI) m/z 453 (M+H)⁺.

The following Tables I to VI show the structural formulas of the compounds (Compound 25 to Compound 93) synthesized in Examples 25 to 93:

TABLE I
| Compound No. | Structure |
|---|---|
| 25 | 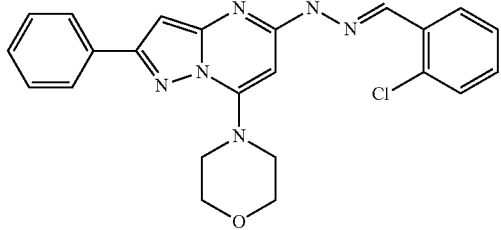 |
| 26 | 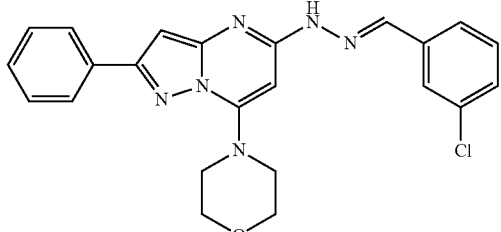 |
| 27 | 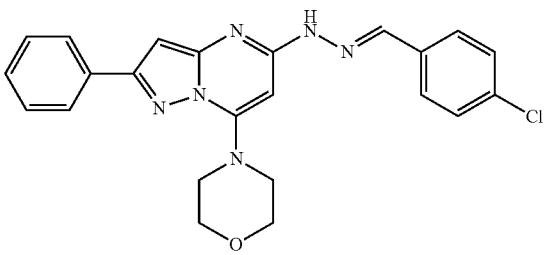 |
| 28 | 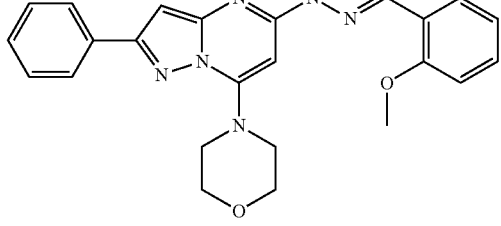 |
| 29 | 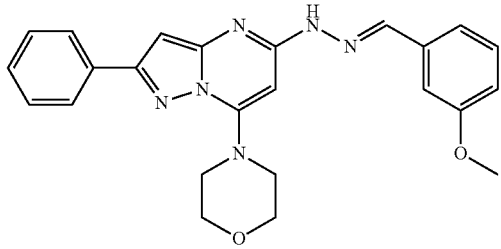 |
| 30 | 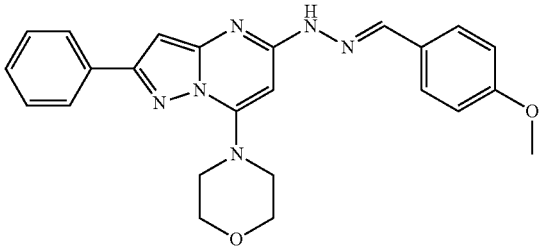 |

TABLE I-continued
| Compound No. | Structure |
|---|---|
| 31 | 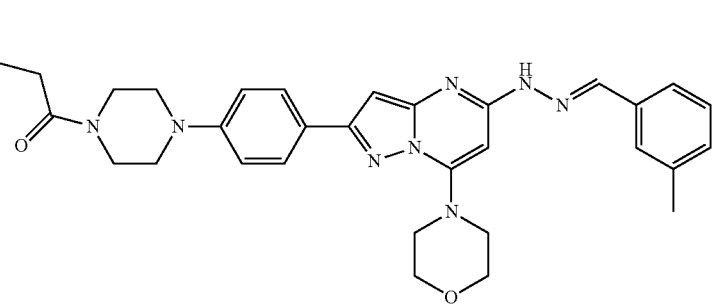 |
| 32 | 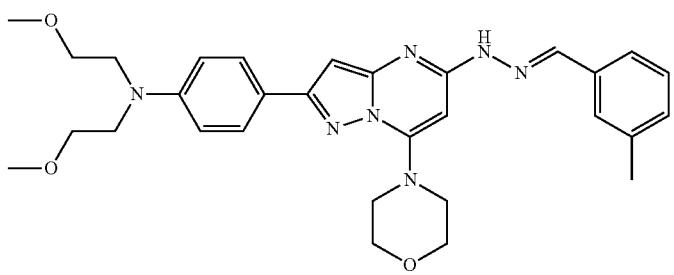 |
| 33 | 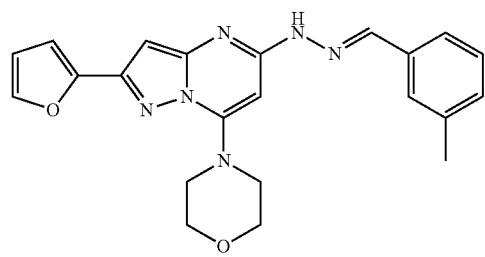 |
| 34 | 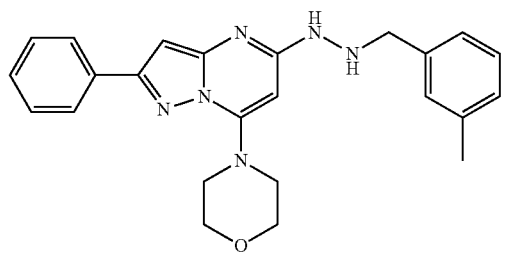 |

TABLE I-continued
| Compound No. | Structure |
|---|---|
| 35 | 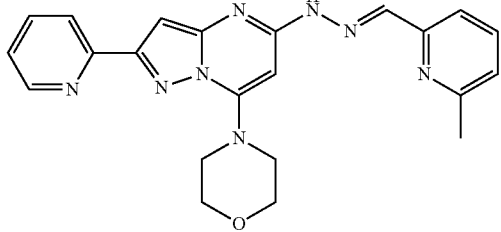 |
| 36 | 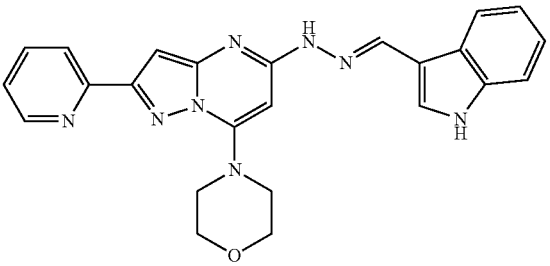 |
TABLE II
| Compound No. | Structure |
|---|---|
| 37 | 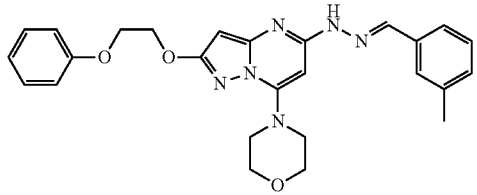 |
| 38 | 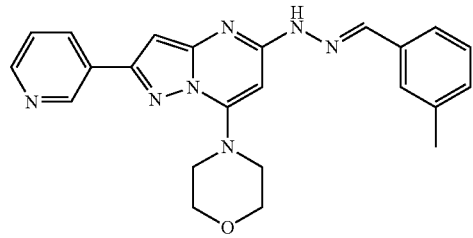 |
| 39 | 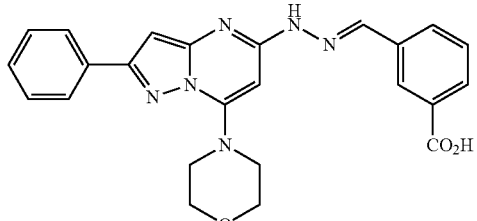 |
| 40 | 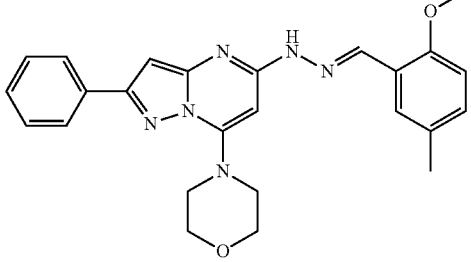 |
| 41 | 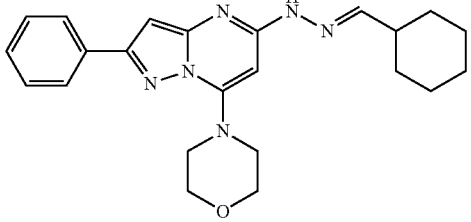 |
| 42 | 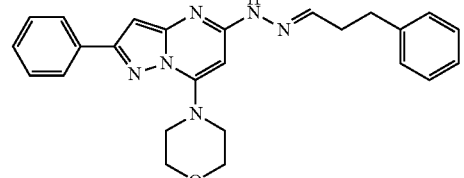 |

TABLE II-continued

| Compound No. | Structure |
|---|---|
| 43 | 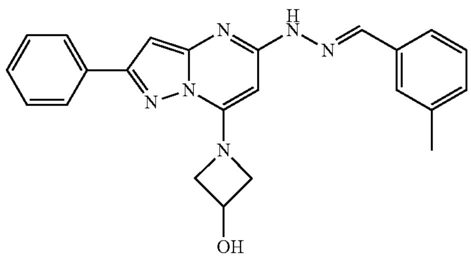 |
| 44 | 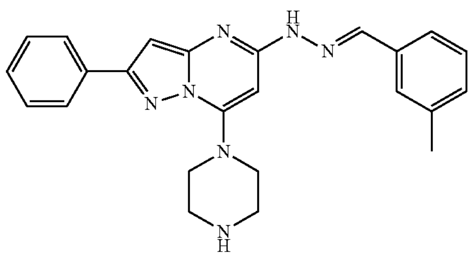 |
| 45 | 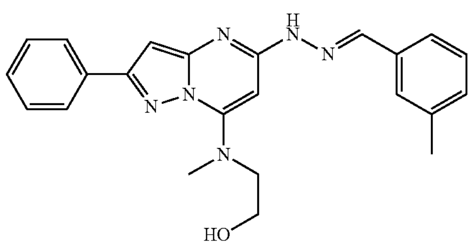 |
| 46 | 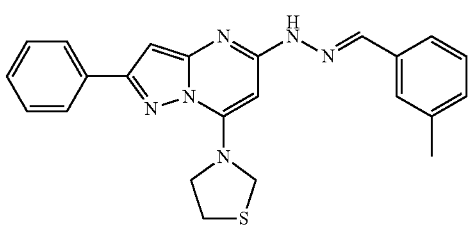 |
| 47 | 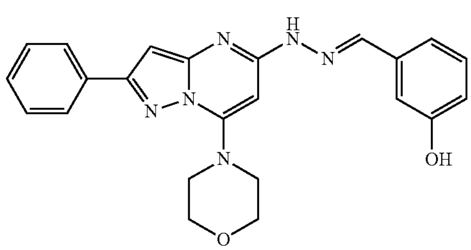 |
| 48 | 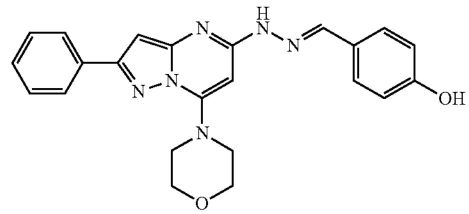 |
| 49 | 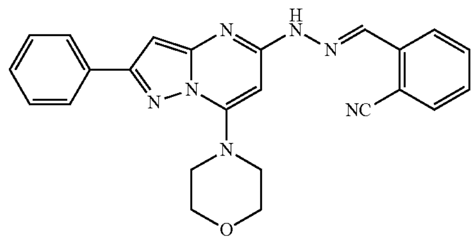 |
| 50 | 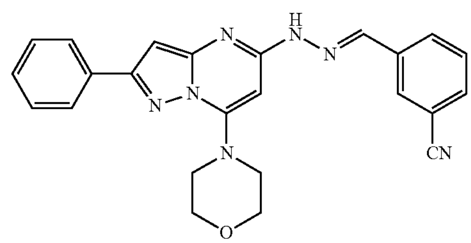 |
| 51 | 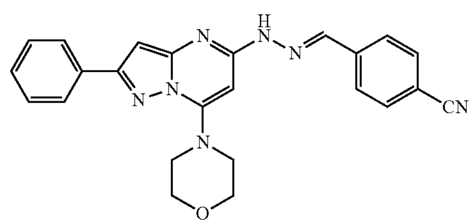 |
| 52 | 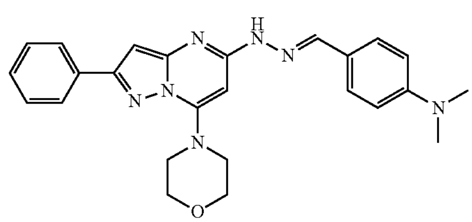 |
| 53 | 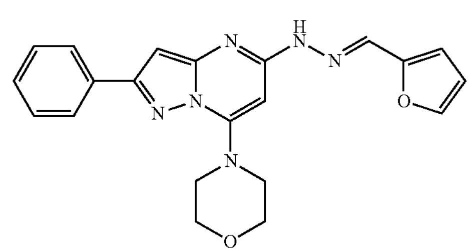 |

-continued

| Compound No. | Structure |
|---|---|
| 54 | 2-phenyl-pyrazolo[1,5-a]pyrimidine with morpholine at 7-position and hydrazone linked to 5-methylfuran-2-yl |
| 55 | 2-phenyl-pyrazolo[1,5-a]pyrimidine with morpholine at 7-position and hydrazone linked to 4,5-dimethylfuran-2-yl |
| 56 | 2-phenyl-pyrazolo[1,5-a]pyrimidine with 4-(2-hydroxyethyl)piperazin-1-yl at 7-position and hydrazone linked to 3-methylphenyl |

-continued

| Compound No. | Structure |
|---|---|
| 57 | 2-phenyl-pyrazolo[1,5-a]pyrimidine with morpholine at 7-position and hydrazone linked to 2-methylphenyl |
| 58 | 2-phenyl-pyrazolo[1,5-a]pyrimidine with morpholine at 7-position and hydrazone linked to 4-methylphenyl |
| 59 | 2-phenyl-pyrazolo[1,5-a]pyrimidine with morpholine at 7-position and hydrazone linked to 3-(trifluoromethyl)phenyl |

TABLE IV

| Compound No. | Structure |
|---|---|
| 60 | 2-phenyl-pyrazolo[1,5-a]pyrimidine with morpholine at 7-position and hydrazone linked to 1H-imidazol-5-yl |
| 61 | 2-phenyl-pyrazolo[1,5-a]pyrimidine with morpholine at 7-position and hydrazone linked to thiophen-2-yl |

TABLE IV-continued
| Compound No. | Structure |
|---|---|
| 62 | 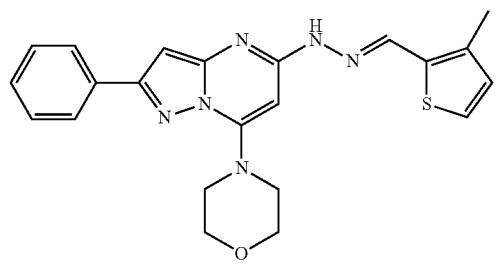 |
| 63 | 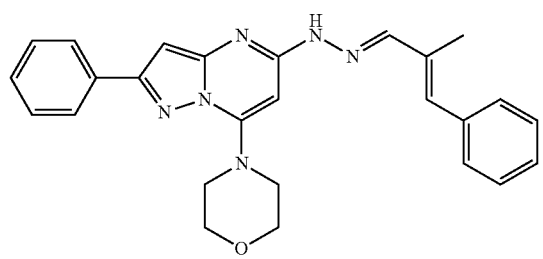 |
| 64 | 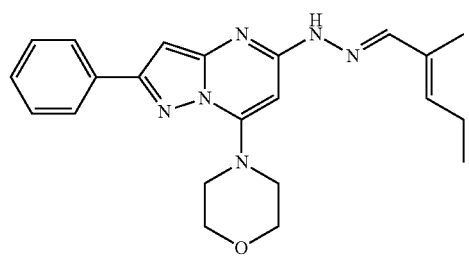 |
| 65 | 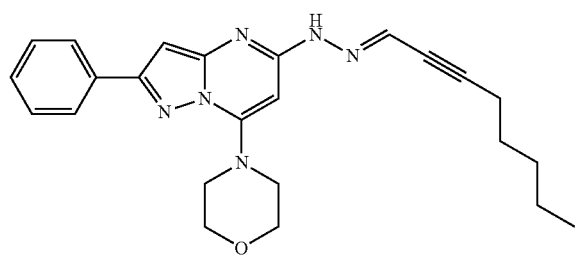 |
| 66 | 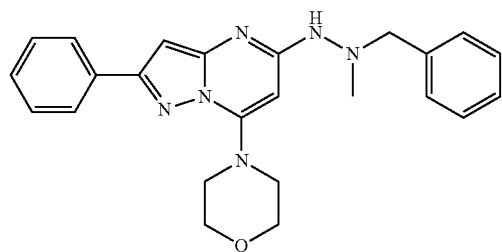 |
| 67 | 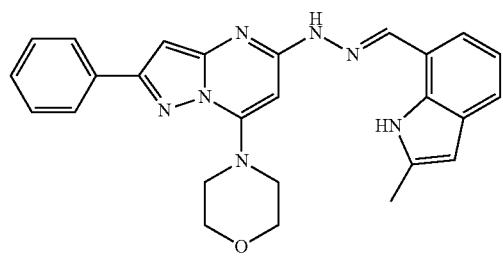 |

TABLE IV-continued
| Compound No. | Structure |
|---|---|
| 68 | 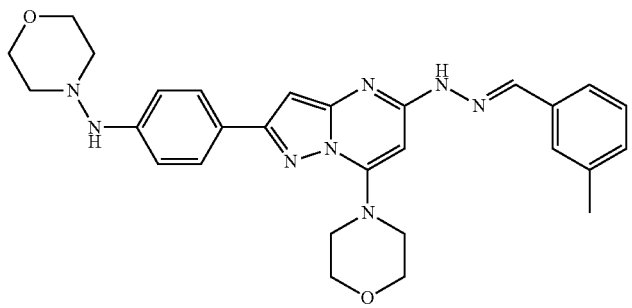 |
| 69 | 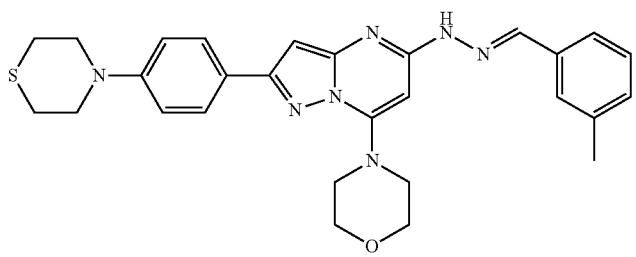 |
TABLE V
| Compound No. | Structure |
|---|---|
| 70 | 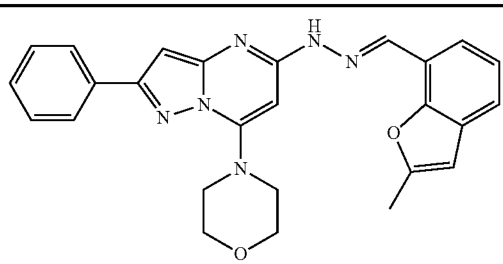 |
| 71 | 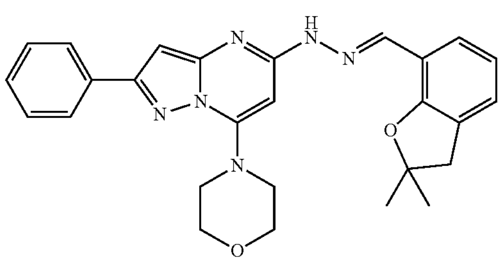 |
| 72 | 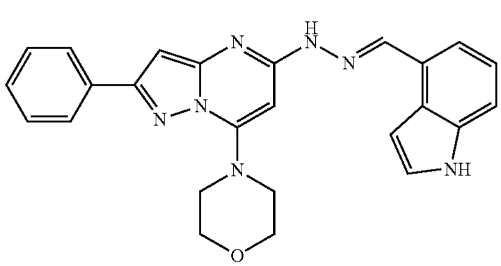 |
| 73 | |
| 74 | |
| 75 | |

TABLE V-continued

| Compound No. | Structure |
|---|---|
| 76 | (structure) |
| 77 | (structure) |
| 78 | (structure) |
| 79 | (structure) |
| 80 | (structure) |
| 81 | (structure) |

TABLE VI

| Compound No. | Structure |
|---|---|
| 82 | (structure) |
| 83 | (structure) |

TABLE VI-continued
| Compound No. | Structure |
|---|---|
| 84 | 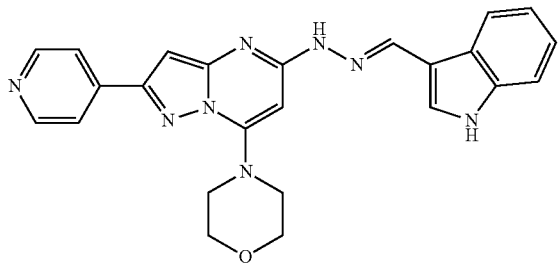 |
| 85 | 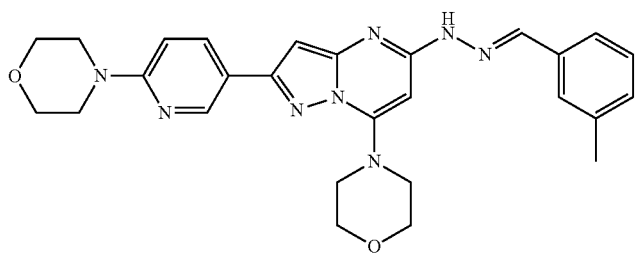 |
| 86 | 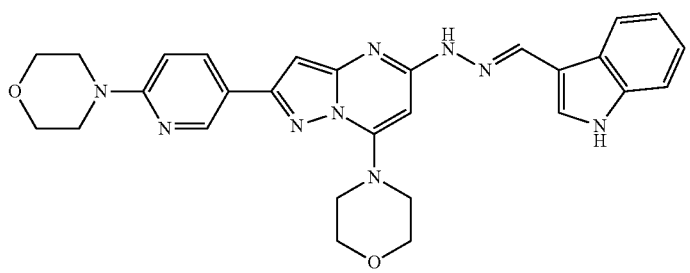 |
| 87 | 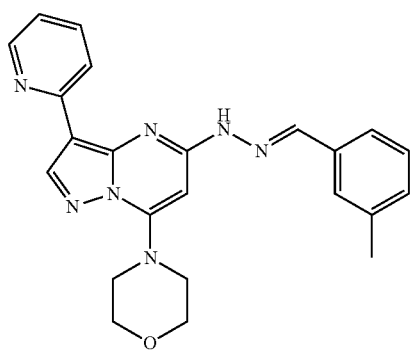 |
| 88 | 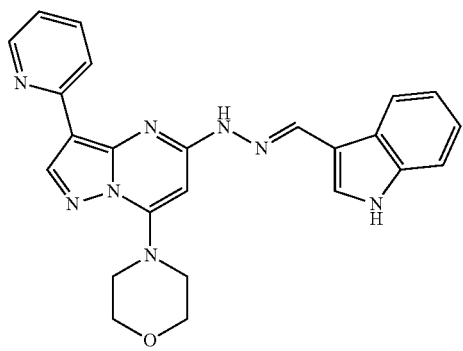 |

TABLE VI-continued
| Compound No. | Structure |
|---|---|
| 89 | 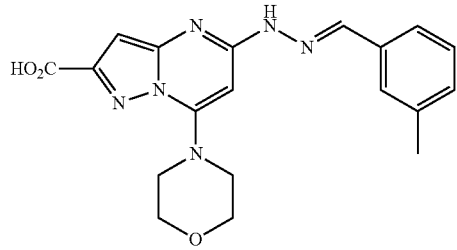 |
| 90 | 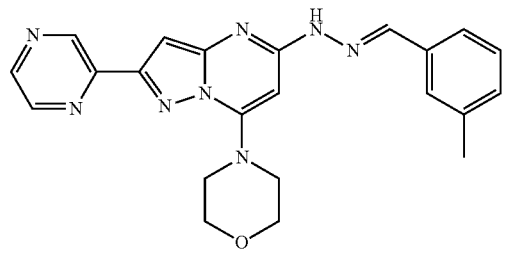 |
| 91 | 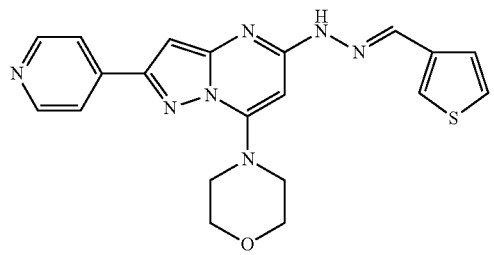 |
| 92 | 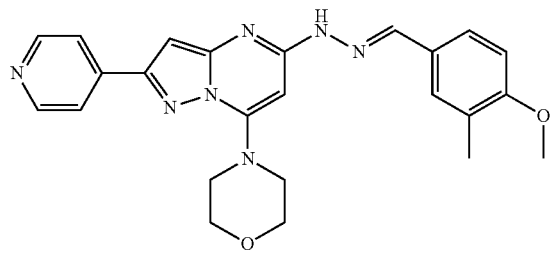 |
| 93 | 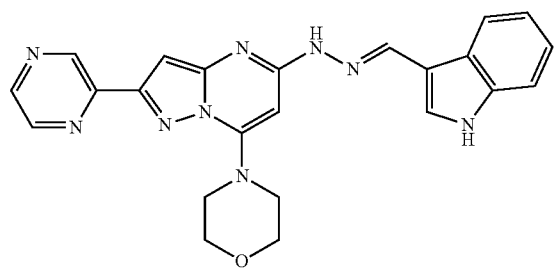 |

The following Tables VII to XVII show the structural formulas of the compounds (Compound 94 to Compound 146) synthesized in Examples 94 to 146:
TABLE VII
| Compound No. | Structure |
|---|---|
| Compound 94 | 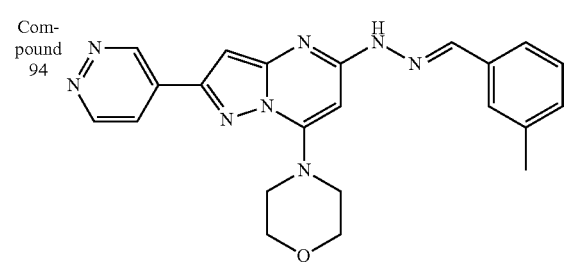 |
| Compound 95 | 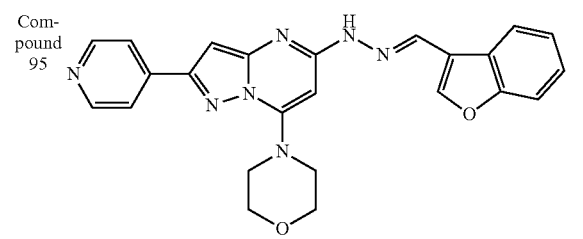 |
| Compound 96 | 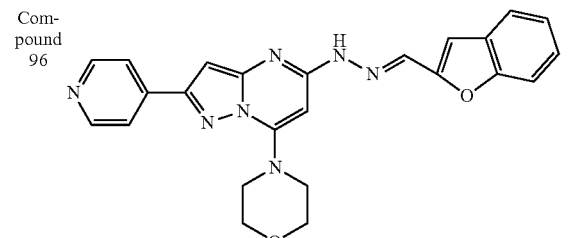 |
| Compound 97 | 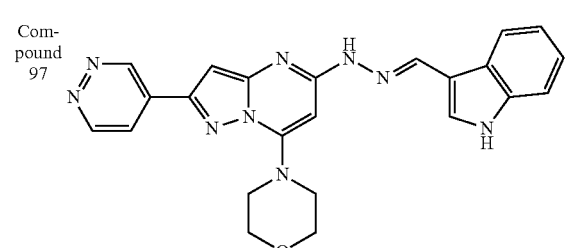 |
| Compound 98 | 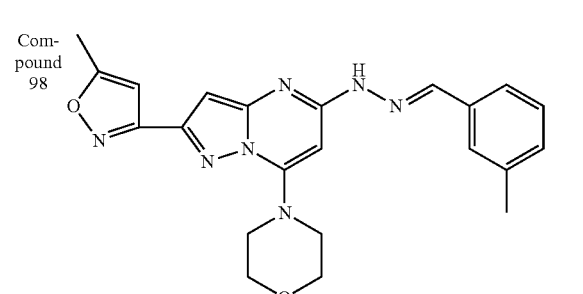 |
TABLE VIII
| Compound No. | Structure |
|---|---|
| Compound 99 | 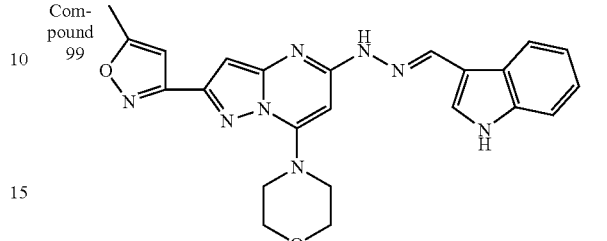 |
| Compound 100 | 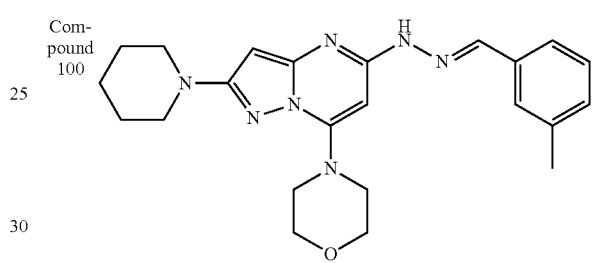 |
| Compound 101 | 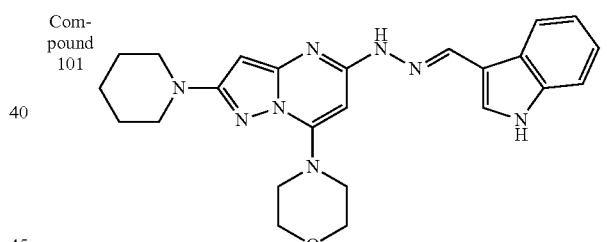 |
| Compound 102 | 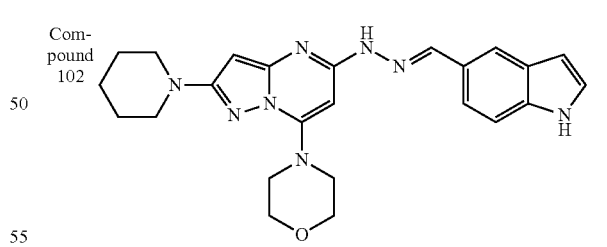 |
| Compound 103 | 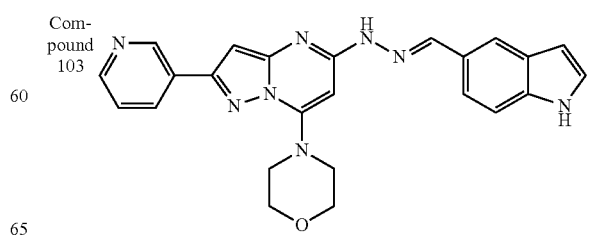 |

TABLE IX

| Compound No. | Structure |
|---|---|
| Compound 104 | 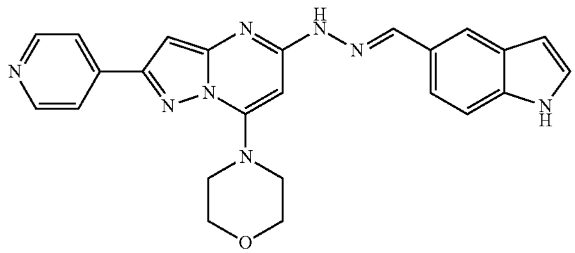 |
| Compound 105 | 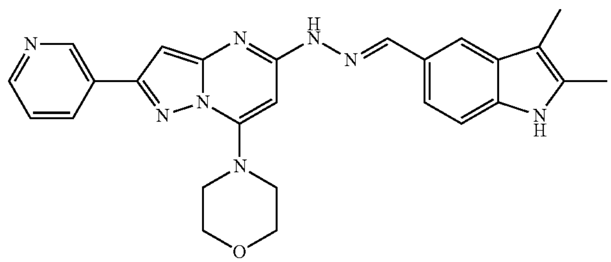 |
| Compound 106 | 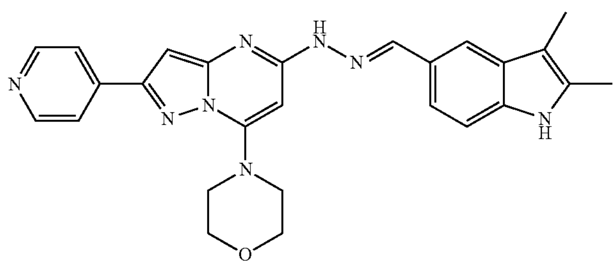 |
| Compound 107 | 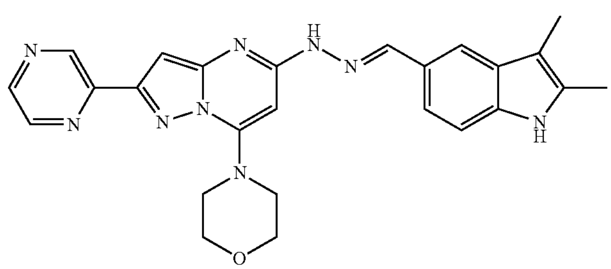 |
| Compound 108 | 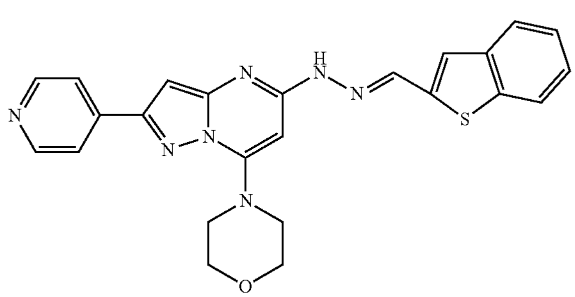 |

TABLE IX-continued
| Compound No. | Structure |
|---|---|
| Compound 109 | 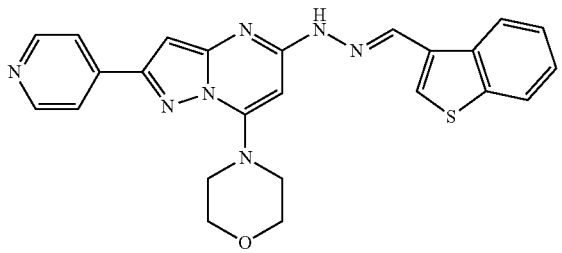 |
TABLE X
| Compound No. | Structure |
|---|---|
| Compound 110 | 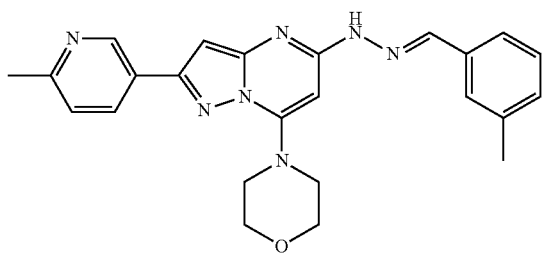 |
| Compound 111 | 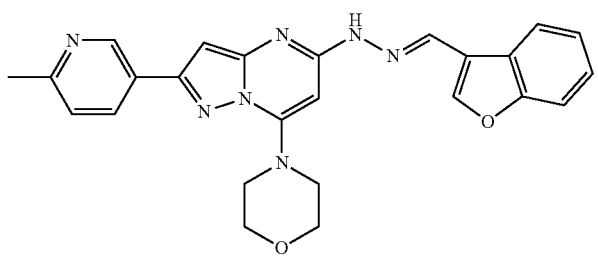 |
| Compound 112 | 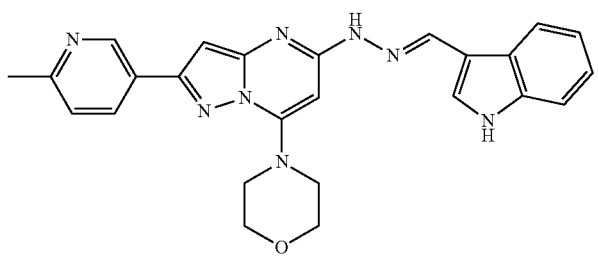 |
| Compound 113 | 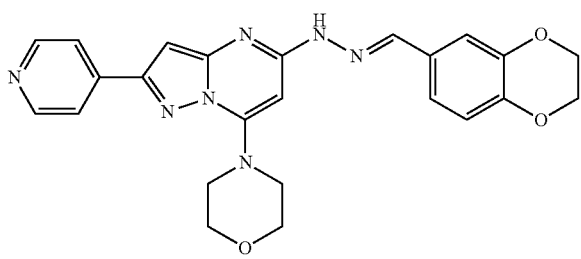 |

TABLE X-continued

| Compound No. | Structure |
|---|---|
| Compound 114 | (structure) |

TABLE XI

| Compound No. | Structure |
|---|---|
| Compound 115 | (structure) |
| Compound 116 | (structure) |
| Compound 117 | (structure) |
| Compound 118 | (structure) |
| Compound 119 | (structure) |

TABLE XII

| Compound No. | Structure |
|---|---|
| Compound 120 | (structure) |
| Compound 121 | (structure) |

TABLE XII-continued
| Compound No. | Structure |
|---|---|
| Compound 122 | 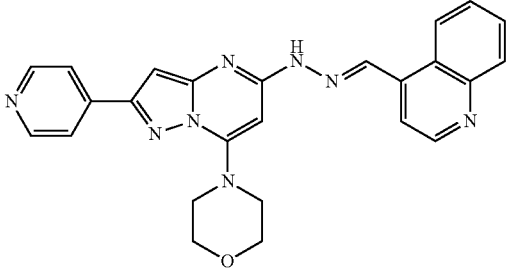 |
| Compound 123 | 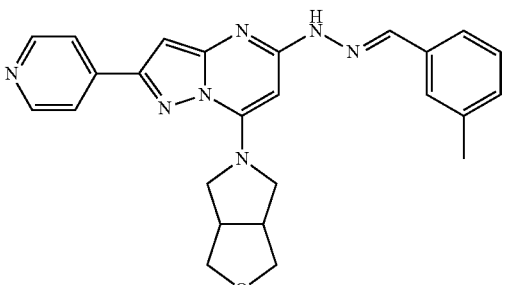 |
| Compound 124 | 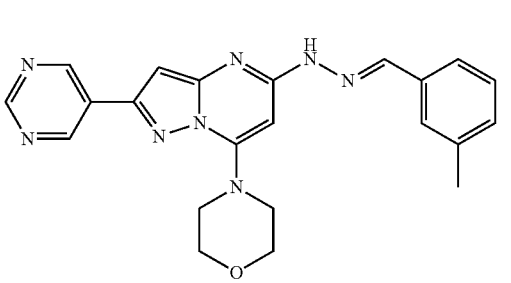 |
TABLE XIII
| Compound No. | Structure |
|---|---|
| Compound 125 | 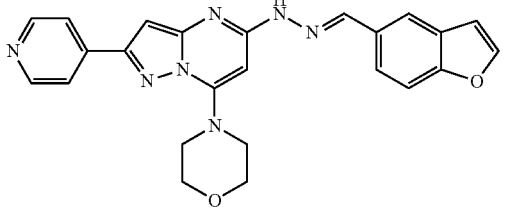 |
| Compound 126 | 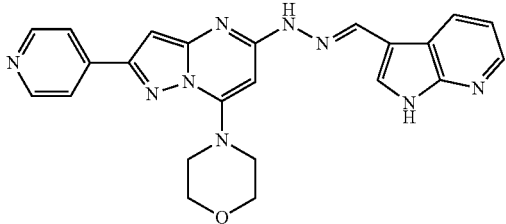 |
TABLE XIII-continued
| Compound No. | Structure |
|---|---|
| Compound 127 | 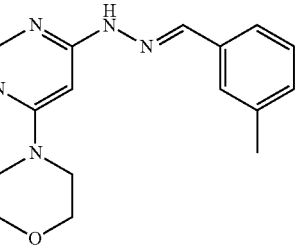 |
| Compound 128 | 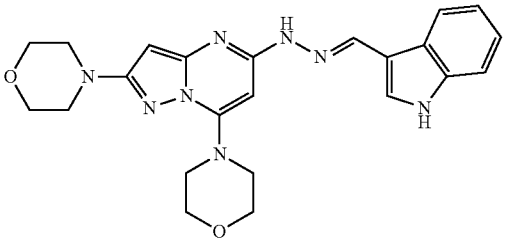 |
| Compound 129 | 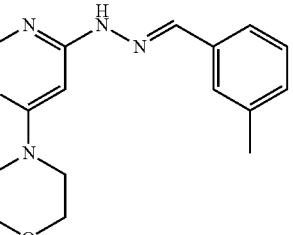 |
TABLE XIV
| Compound No. | Structure |
|---|---|
| Compound 130 | 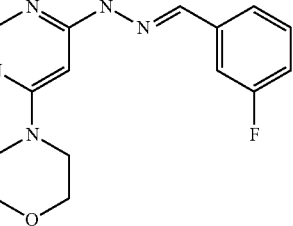 |
| Compound 131 | 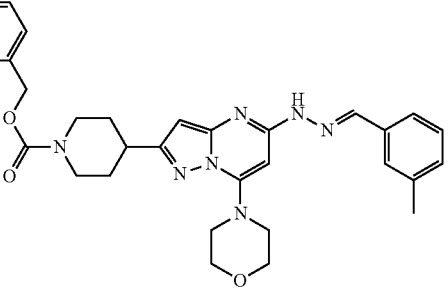 |

TABLE XIV-continued

| Compound No. | Structure |
|---|---|
| Compound 132 | (structure) |
| Compound 133 | (structure) |
| Compound 134 | (structure) |

TABLE XV

| Compound No. | Structure |
|---|---|
| Compound 135 | (structure) |
| Compound 136 | (structure) |

TABLE XV-continued

| Compound No. | Structure |
|---|---|
| Compound 137 | (structure) |
| Compound 138 | (structure) |
| Compound 139 | (structure) |

TABLE XVI

| Compound No. | Structure |
|---|---|
| Compound 140 | (structure) |
| Compound 141 | (structure) |

TABLE XVI-continued

| Compound No. | Structure |
|---|---|
| Compound 142 | (pyrazolo-pyrimidine with pyridyl, morpholino, and 3-acetylphenyl hydrazone) |
| Compound 143 | (pyrazolo-pyrimidine with pyridyl, morpholino, and 3-isopropenylphenyl hydrazone) |
| Compound 144 | (pyrazolo-pyrimidine with pyridyl, morpholino, and N-methylindol-6-yl hydrazone) |

TABLE XVII

| Compound No. | Structure |
|---|---|
| Compound 145 | (pyrazolo-pyrimidine with pyridyl, morpholino, and 3-isopropylphenyl hydrazone) |
| Compound 146 | (pyrazolo-pyrimidine with pyridyl, morpholino, and N-methylindol-6-yl hydrazone) |

Test Example 1

Evaluation of Cytokine-Inhibitory Action Using Macrophages Derived from Mouse Abdomen One milliliter each of a 3% (w/v) thioglycolate solution was intraperitoneally administered to mice (female Balb/c mice), the abdominal cells of each mouse were recovered after 5 or 6 days from the administration of the thioglycolate solution and the adhesive cells were collected and used in the exaluation procedures. To a culture medium containing such adhesive cells, there were added 100 ng/mL of mouse interferon-γ and a 0.05% (v/v) liquid containing killed cells derived from *Staphylococcus aureus* Cowan I strain (SAC) and a candidate compound and then the mixture was cultivated overnight. After the completion of the cultivation, the survival ratios were determined, there were quantitatively determined the quantities of IL-12p70 (the complex of IL-12p35 and p40) and IL-12p40 or TNF-α according to the ELISA assays while making use of the recovered supernatant of the culture medium and the 50% production-inhibitory concentration ($IC_{50}$) was calculated for each case (see Table 1 and Tables 1-9 for IL-12p70 and TNF-α and Tables 1 to 10 for IL-12p40).

These results clearly show that the pyrazolo-pyrimidine compounds according to the present invention possess excellent IL-12 production-inhibitory activities.

Moreover, regarding IL-23, the evaluation can likewise be carried out using the ELISA assay to thus confirm the fact that the pyrazolo-pyrimidine compounds according to the present invention clearly show excellent IL-23 production-inhibitory activities.

TABLE 1
| Compound | Structure | IL-12p70-Inhibitory Activity IC50 nM | TNF-α-Inhibitory Activity IC50 μM |
|---|---|---|---|
| Compound 1 | 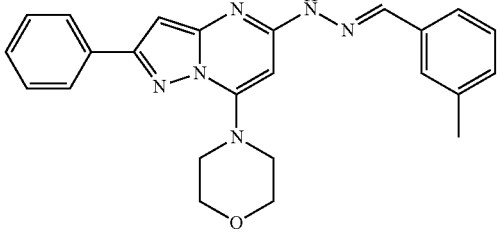 | 19 | 10< |
| Compound 2 | 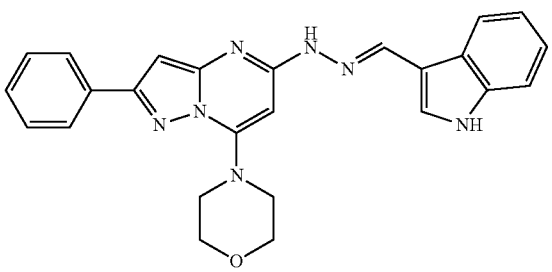 | 33 | 10< |
| Compound 3 | 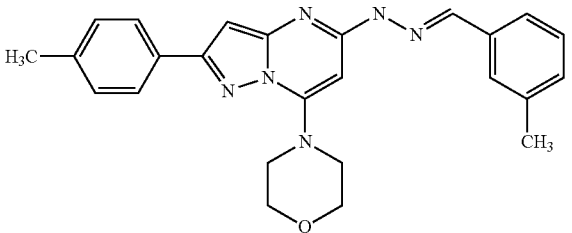 | 35 | 10< |
| Compound 4 | 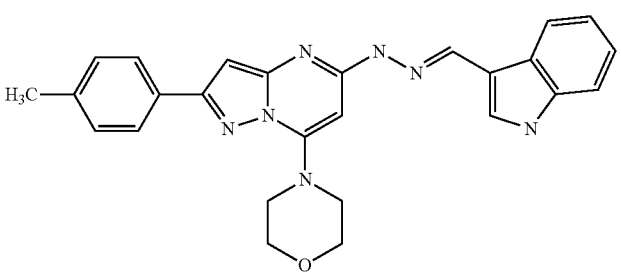 | 23 | 10< |
| Compound 5 | 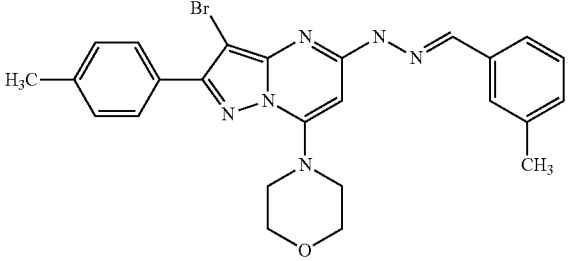 | 124 | 10< |

TABLE 1-continued

| Compound | Structure | IL-12p70-Inhibitory Activity IC50 nM | TNF-α-Inhibitory Activity IC50 μM |
|---|---|---|---|
| Compound 6 | 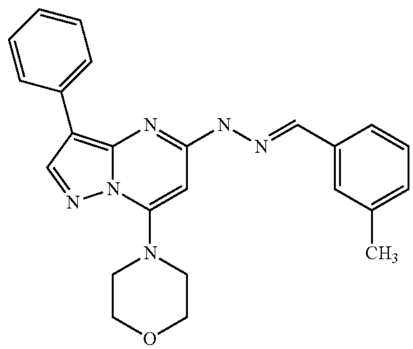 | 642 | 10< |
| Compound 7 | 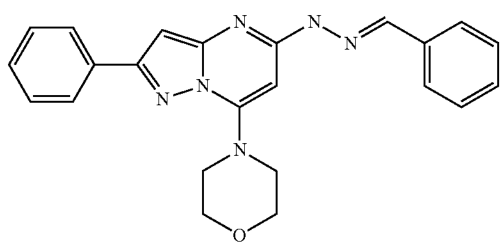 | 113 | 10< |
| Compound 8 | 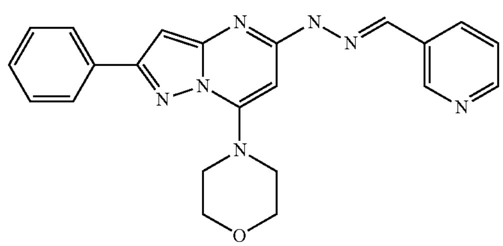 | 407 | 10< |
| Compound 9 | 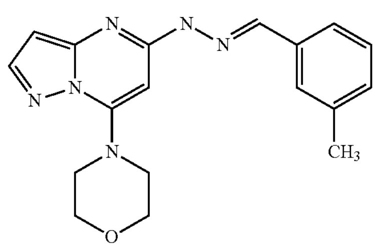 | 141 | 10< |
| Compound 10 | 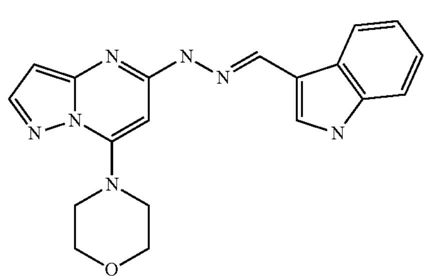 | 165 | 10< |

TABLE 1-continued
| Compound | Structure | IL-12p70-Inhibitory Activity IC50 nM | TNF-α-Inhibitory Activity IC50 μM |
|---|---|---|---|
| Compound 11 | 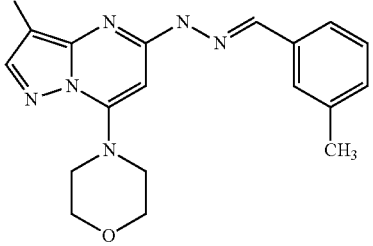 | 340 | 10< |
| Compound 12 | 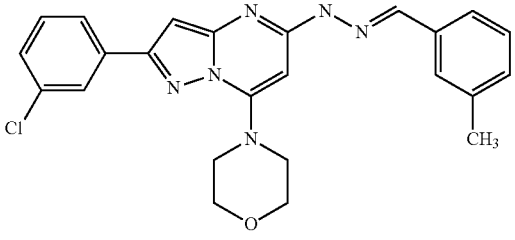 | 17 | 10< |
| Compound 13 | 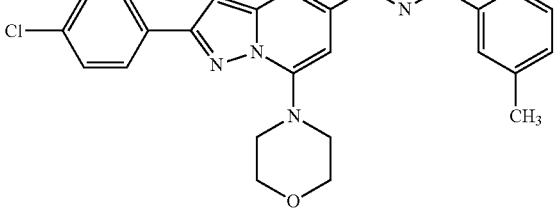 | 34 | 10< |
| Compound 14 | 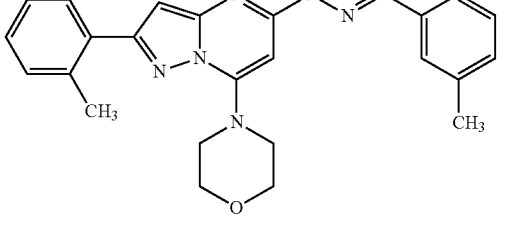 | 38 | 10< |
| Compound 15 | 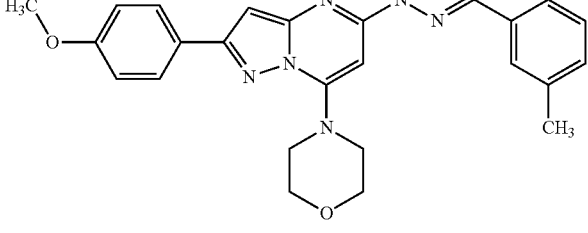 | 11 | 10< |
| Compound 16 | 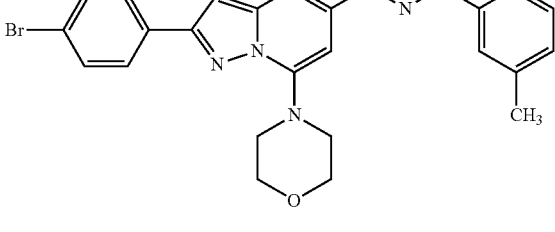 | 18 | 10< |

TABLE 1-continued

| Compound | Structure | IL-12p70-Inhibitory Activity IC50 nM | TNF-α-Inhibitory Activity IC50 μM |
| --- | --- | --- | --- |
| Compound 17 | 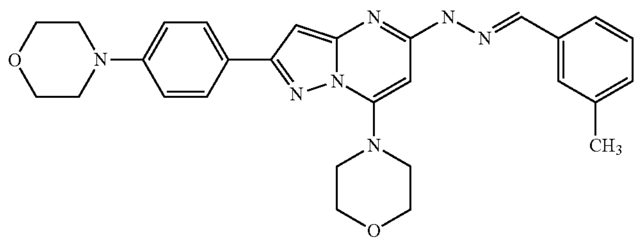 | 4 | 10< |
| Compound 18 | 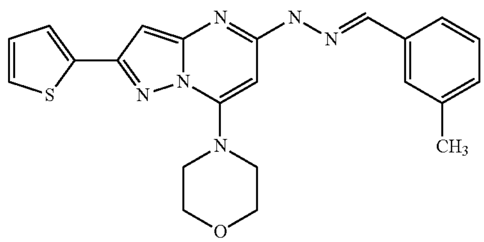 | 11 | 10< |
| Compound 19 | 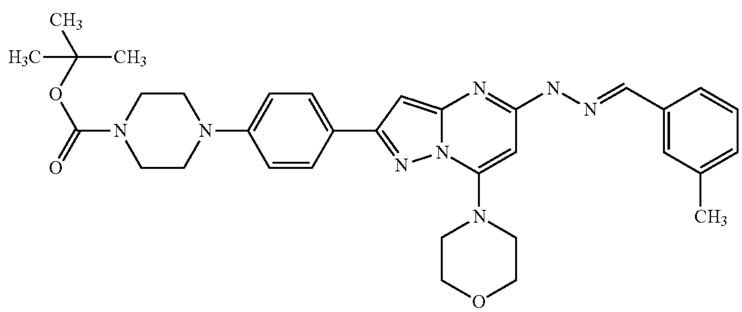 | 60 | 10< |
| Compound 20 | 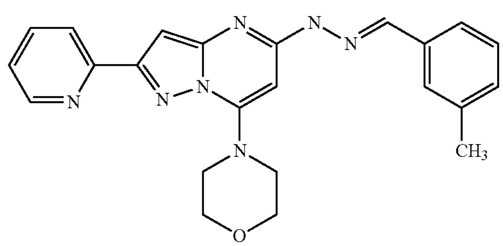 | 8 | 10< |
| Compound 21 | 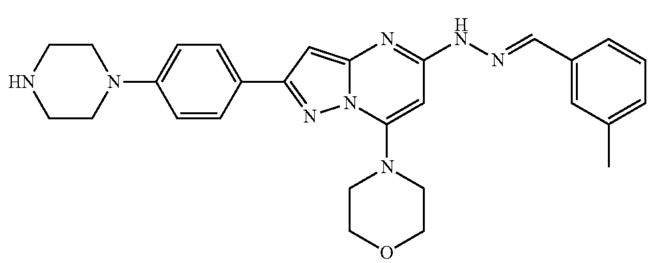 | 22 | 10< |
| Compound 22 | 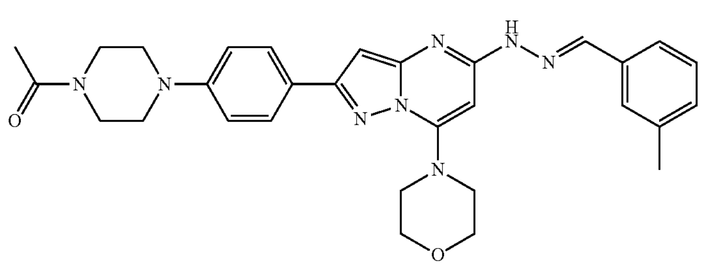 | 5 | 10< |

TABLE 1-continued

| Compound | Structure | IL-12p70-Inhibitory Activity IC50 nM | TNF-α-Inhibitory Activity IC50 μM |
|---|---|---|---|
| Compound 23 | 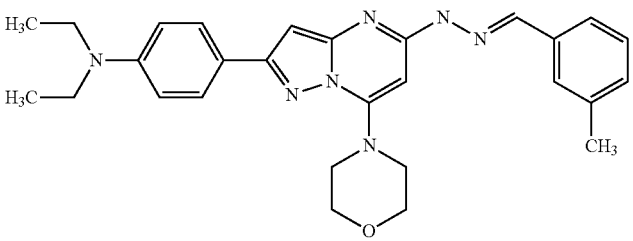 | 14 | 10< |
| Compound 24 | 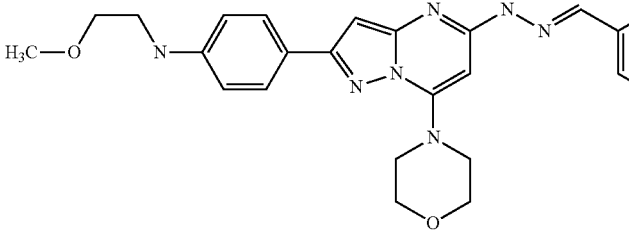 | 6 | 10< |

The following Table 1-2 and Table 1-3 show the 50% production-inhibitory concentrations ($IC_{50}$) of Compound 25 and preferred Compounds subsequent thereto for IL-12p70 (the complex of IL-12p35 and p40) and IL-12p40 or TNF-α. In this connection, the blank columns in these Tables 1-2 and 1-3 mean that the corresponding data were not determined.

TABLE 1-2

| Compound No. | IL-12p70-Inhibitory Activity $IC_{50}$ nM | TNF-α-Inhibitory Activity $IC_{50}$ μM |
|---|---|---|
| 25 | 150 | |
| 26 | 120 | |
| 28 | 160 | |
| 29 | 40 | >10 μM |
| 30 | 180 | |
| 31 | 18 | >10 μM |
| 32 | 9.6 | |
| 33 | 17 | |
| 34 | 24 | >10 μM |
| 36 | 7.0 | >10 μM |
| 37 | 110 | |
| 38 | 11 | >10 μM |
| 40 | 64 | >10 μM |
| 54 | 300 | |
| 57 | 420 | |
| 61 | 370 | |
| 62 | 320 | |
| 63 | 320 | |
| 66 | 330 | |

TABLE 1-3

| Compound No. | IL-12p70-Inhibitory Activity $IC_{50}$ nM | TNF-α-Inhibitory Activity $IC_{50}$ μM |
|---|---|---|
| 68 | 8.7 | >10 μM |
| 69 | 8.2 | >10 μM |
| 72 | 190 | |
| 75 | 290 | |
| 78 | 440 | |
| 79 | 220 | >10 μM |
| 80 | 160 | >10 μM |
| 81 | 55 | >10 μM |
| 82 | 4.1 | >10 μM |
| 83 | 8.4 | >10 μM |
| 84 | 3.2 | >10 μM |
| 85 | 3.2 | >10 μM |
| 86 | 1.8 | |
| 88 | 420 | >10 μM |
| 90 | 8.3 | |
| 91 | 48 | |
| 92 | 44 | |
| 93 | 6.5 | |

The following Table 1-4 to Table 1-8 show the 50% production-inhibitory concentrations ($IC_{50}$) of Compound 94 and preferred Compounds subsequent thereto observed for IL-12p70 (the complex of IL-12p35 and p40). Moreover, Table 1-9 shows the 50% production-inhibitory concentrations ($IC_{50}$) of Compound 140 observed for TNF-α.

TABLE 1-4

| Compound No. | IL-12p70-Inhibitory Activity $IC_{50}$ nM |
|---|---|
| Compound 94 | 18 |
| Compound 95 | 28 |
| Compound 96 | 50 |
| Compound 97 | 8.3 |
| Compound 98 | 26 |
| Compound 99 | 16 |

TABLE 1-5

| Compound No. | IL-12p70-Inhibitory Activity $IC_{50}$ nM |
|---|---|
| Compound 100 | 360 |
| Compound 101 | 380 |
| Compound 103 | 160 |
| Compound 104 | 100 |
| Compound 105 | 89 |
| Compound 107 | 170 |
| Compound 108 | 110 |
| Compound 109 | 490 |
| Compound 110 | 7.3 |

TABLE 1-6

| Compound No. | IL-12p70-Inhibitory Activity $IC_{50}$ nM |
|---|---|
| Compound 111 | 37 |
| Compound 112 | 7.5 |
| Compound 113 | 98 |
| Compound 115 | 55 |
| Compound 116 | 49 |
| Compound 117 | 56 |
| Compound 118 | 29 |
| Compound 119 | 47 |

TABLE 1-7

| Compound No. | IL-12p70-Inhibitory Activity $IC_{50}$ nM |
|---|---|
| Compound 120 | 40 |
| Compound 121 | 79 |
| Compound 122 | 5.6 |
| Compound 123 | 300 |
| Compound 124 | 20 |
| Compound 125 | 36 |
| Compound 126 | 110 |
| Compound 127 | 160 |
| Compound 128 | 140 |

TABLE 1-8

| Compound No. | IL-12p70-Inhibitory Activity $IC_{50}$ nM |
|---|---|
| Compound 130 | 140 |
| Compound 131 | 100 |
| Compound 132 | 470 |
| Compound 133 | 96 |
| Compound 134 | 130 |
| Compound 135 | 130 |
| Compound 139 | 250 |

TABLE 1-9

| Compound No. | IL-12p70-Inhibitory Activity, $IC_{50}$ nM | TNF-α Inhibitory Activity, $IC_{50}$ nM |
|---|---|---|
| Compound 140 | 170 | >10 μM |

TABLE 1-10

| Compound No. | IL-12p40, $IC_{50}$ nM |
|---|---|
| 9 | 136.5 |
| 83 | 11.3 |
| 117 | 97.8 |
| 119 | 70.0 |
| 121 | 150.5 |

In this connection, the trifluoroacetic acid salts were used in the evaluation tests, in cases in which the compounds in the foregoing Examples were prepared in the form of trifluoroacetic acid salts.

Test Example 2

Evaluation of the Effect of the Addition of Proteins Present in Human Plasma on the Cytokine-Inhibitory Action of Candidate Compounds, while Using Macrophages Derived from Mouse Abdomen To mouse's abdominal macrophages, there were added 100 ng/mL of mouse interferon-γ, a 0.05% (v/v) SAC-killed cell-containing liquid and a candidate compound and human a 1-acidic sugar protein (α1-AGP) or human setum albumin (HSA), while variously changing the concentration thereof, and then the mixture was cultivated overnight. After the completion of the cultivation, the survival ratios were determined, there were quantitatively determined the quantity of IL-12p70 according to the ELISA assays while making use of the recovered supernatant of the culture medium and the inhibitory effect was evaluated in terms of the 50% production-inhibitory concentration ($IC_{50}$) (see Table 2). Incidentally, all of the values included in the Tables are expressed in terms of the reciprocal number of the specific activity while the activity observed when any protein was not added to the culture medium was defined to be 1. The compound of Comparative Example 1 was one prepared in Example 12 of WO 2003/047516 and synthesized according to the method disclosed therein.

These data clearly indicate that the preferred pyrazolopyrimidine compounds according to the present invention can hold their excellent activities even in the coexistence of HSA and/or α1-AGP as the proteins present in the human plasma and currently used when investigating the ability of a drug to form a linkage with the same.

TABLE 2

Table 2

| Compound No. | HSA (140 mg/mL) | α 1-AGP (4 mg/mL) |
|---|---|---|
| Comparative Compound 1 | 18.9 | 12.2 |
| Compound 1 | 6.5 | 2.9 |
| Compound 2 | 4.3 | 2.9 |
| Compound 3 | 10.0 | 5.9 |
| Compound 4 | 3.3 | 3.1 |

Test Example 3

Evaluation of Cytokine-Inhibitory Action Using Whole Blood of Mouse

The blood was recovered from the mice (female Balb/c mice) (containing added EDTA) and it was used for the evaluation. To a cell culture medium, there were added 100 ng/mL of mouse interferon-γ, 1.25% (v/v) of a liquid containing killed cells derived from Staphylococcus aureus Cowan I strain (SAC) and a candidate compound, the resulting mixture was diluted to a volume equivalent to the blood and then the diluted medium was cultivated overnight. After the completion of the cultivation, the amount of IL-12p70 (the complex of IL-12p35 and p40) was quantitatively determined according to the ELISA assays while making use of the recovered supernatant of the culture medium and the 50% production-inhibitory concentrations ($IC_{50}$) were calculated for Compounds 38, 80, 82, 83, 84, 85, 87, 90 and 91. (see Table 3). These results clearly indicate that the pyrazolo-pyrimidine compounds according to the present invention never show any significant reduction of the IL-12/IL-23 production-inhibitory activities even in the whole blood and can maintain their excellent activities.

TABLE 3

| Compound No. | nM |
|---|---|
| 38 | 2700 |
| 80 | 4900 |
| 82 | 3200 |
| 83 | 880 |
| 84 | 2300 |
| 85 | 4200 |
| 87 | 2400 |
| 90 | 2500 |
| 91 | 4600 |

The 50% production-inhibitory concentrations ($IC_{50}$) were likewise calculated for Compounds 94, 95, 96, 97, 104, 108, 116, 117, 118, 119, 121, 122, 123, 126 and 128, by repeating the same procedures used above (see Table 3-2 and Table 3-3).

TABLE 3-2

| Compound No. (Patent) | Whole Blood Activity $IC_{50}$ nM |
|---|---|
| Compound 94 | 1000 |
| Compound 95 | 810 |
| Compound 96 | 1100 |
| Compound 97 | 3200 |
| Compound 104 | 2500 |
| Compound 108 | 3700 |

TABLE 3-3

| Compound No. (Patent) | Whole Blood Activity $IC_{50}$ nM |
|---|---|
| Compound 116 | 3800 |
| Compound 117 | 280 |
| Compound 118 | 640 |
| Compound 119 | 1000 |
| Compound 121 | 840 |
| Compound 122 | 2400 |
| Compound 123 | 440 |
| Compound 126 | 760 |
| Compound 128 | 4600 |

Incidentally, the trifluoroacetic acid salts were used in the evaluation tests, in cases in which the compounds in the foregoing Examples were prepared in the form of trifluoroacetic acid salts.

Test Example 4

Evaluation of Inflammation-Inhibitory Action of Compounds in Mouse's Enteritis Model The method for establishing the mouse enteritis model by the immigration of IL-10−/−cells is, for instance, disclosed in Gastroenterology. 2009 February; 136(2): 564-74.e2. Epub 2008 Oct. 7.

TABLE 4

| Group No. | Animal Used | Drug | Dose (mg/kg) | No. of Animals Used |
|---|---|---|---|---|
| 1 | Normal | — | — | 8 |
| 2 | Enteritis Model | Vehicle | — | 8 |
| 3 | Enteritis Model | Compound 83 | 3 | 8 |
| 4 | Enteritis Model | Compound 83 | 10 | 8 |
| 5 | Enteritis Model | Compound 83 | 30 | 8 |

The following method was used for the determination of the weight of intestinal tract as an indication of the drug efficacy: On the final day of the autopsy, the large intestine extending from the anus to immediately before the blind gut was surgically excised, the contents of the intestinal tract were washed away with physiological saline, the moisture adhered thereto was roughly removed and then the weight thereof was determined.

The inflammation-inhibitory effect of Compound 1 on the mouse enteritis model was evaluated using this evaluation system and the results obtained were plotted on FIG. 1. The data plotted on FIG. 1 shows that the weight of the large intestine increased due to the immigration of IL-10−/−cells was controlled in a dose of Compound 83-dependent manner. A significant control effect was observed for the animal group to which 30 mg/kg of the compound was administered once a day.

What is claimed is:

1. A pyrazolo-pyrimidine compound represented by the following general formula (I), or a pharmaceutically acceptable salt thereof:

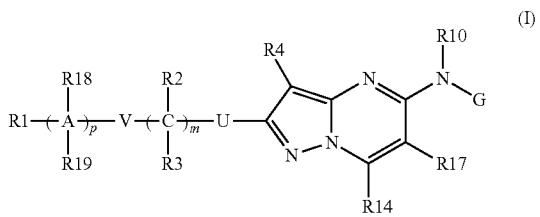

wherein m=0, 1, 2, 3, 4 or 5;
p=0 or 1;
U and V independently represent a single bond, O, S, S(O), S(O$_2$), NR$^a$, C(O), C(O)O, C(O)NR$^a$, OC(O), NR$^a$C(O), NR$^a$C(O)NR$^b$, OC(O)NR$^a$, NR$^a$C(O)O, S(O)NR$^a$, S(O$_2$)NR$^a$, NR$^a$S(O), NR$^a$S(O$_2$), CR$^{20}$=CR$^{21}$, C≡C, or C=NR$^b$;
A is an aryl group, a heterocyclic group or an aliphatic ring group;
R$^1$, R$^{18}$ and R$^{19}$ may be the same or different, and independently represent a hydrogen atom, a halogeno group, a hydroxyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, a sulfonamido group which may have a substituent(s), a sulfinamido group which may have a substituent(s), an aliphatic ring group which may have a substituent(s), an alkenyl group which may have a substituent(s), an alkynyl group which may have a substituent(s), a benzyloxy group which may have a substituent(s), an aryloxy group which may have a substituent(s), an aryl-vinyl group which may have a substituent(s), a hetero-aryloxy group which may have a substituent(s), an arylamino group which may have a substituent(s), a hetero-arylamino group which may have a substituent(s), an aryl-ethynyl group which may have a substituent(s), an aryl group which may have a substituent(s) or a heterocyclic group which may have a substituent(s);
R$^2$ and R$^3$ may be the same or different, and independently represent a hydrogen atom, a halogeno group, a hydroxyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, a sulfonamido group which may have a substituent(s), a sulfinamido group which may have a substituent(s), an aliphatic ring group which may have a substituent(s), an alkenyl group which may have a substituent(s), an alkynyl group which may have a substituent(s), a benzyloxy group which may have a substituent(s), an aryloxy group which may have a substituent(s), an aryl-vinyl group which may have a substituent(s), a hetero-aryloxy group which may have a substituent(s), an arylamino group which may have a substituent(s), a hetero-arylamino group which may have a substituent(s), an aryl-ethynyl group which may have a substituent(s), an aryl group which may have a substituent(s) or a heterocyclic group which may have a substituent(s);

R$^{20}$ and R$^{21}$ may be the same or different and independently represent a hydrogen atom, a halogeno group, an alkyl group which may have a substituent(s), an alkoxy group which may have a substituent(s), an alkylthio group which may have a substituent(s), an alkylsulfonyl group which may have a substituent(s), an acyl group which may have a substituent(s), an acyloxy group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, a sulfonamido group which may have a substituent(s), a sulfinamido group which may have a substituent(s), an aliphatic ring group which may have a substituent(s), an alkenyl group which may have a substituent(s), an alkynyl group which may have a substituent(s), a benzyloxy group which may have a substituent(s), an aryloxy group which may have a substituent(s), an aryl-vinyl group which may have a substituent(s), a hetero-aryloxy group which may have a substituent(s), an arylamino group which may have a substituent(s), a hetero-arylamino group which may have a substituent(s), an aryl-ethynyl group which may have a substituent(s), an aryl group which may have a substituent(s) or a heterocyclic group which may have a substituent(s);

R$^4$ represents a hydrogen atom, a halogeno group, a hydroxyl group, a nitro group, a cyano group, an acyloxy group, a carboxyl group, a sulfonic acid group, a sulfonamido group which may have a substituent(s), a sulfinamido group which may have a substituent(s), an amino group which may have a substituent(s), an alkyl group which may have a substituent(s), an alkoxy group which may have a substituent(s), a mono- or di-alkylamino group which may have a substituent(s), an aryl group which may have a substituent(s), or a heterocyclic group which may have a substituent(s);

R$^{10}$ represents a hydrogen atom, an alkyl group which may have a substituent(s), an acyl group which may have a substituent(s), an alkylsulfonyl group which may have a substituent(s), an alkoxycarbonyl group which may have a substituent(s), a carbamoyl group which may have a substituent(s), an aryl group which may have a substituent(s), an aliphatic ring group which may have a substituent(s), or a heterocyclic group which may have a substituent(s);

R$^{14}$ represents NR$^c$R$^d$, an aliphatic ring group which may have a substituent(s), or a heterocyclic group which may have a substituent(s);

R$^{17}$ is a hydrogen atom;

G is a member selected from the group consisting of those represented by the following general formulas:

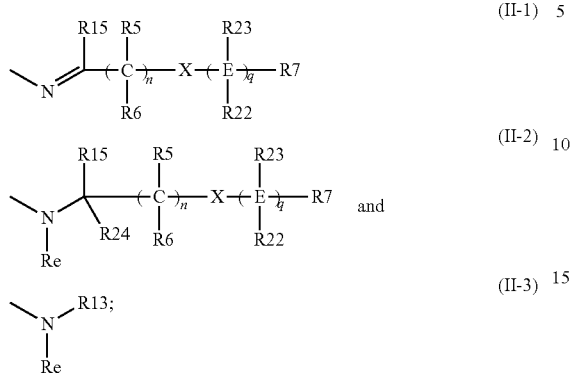

n=0, 1, 2, 3, 4 or 5;
q=0 or 1;
$R^{15}$ and $R^{24}$ may be the same or different and independently represent a hydrogen atom, an alkyl group which may have a substituent(s), an aliphatic ring group which may have a substituent(s), an aryl group which may have a substituent(s), or a heterocyclic group which may have a substituent(s);
$R^5$ and $R^6$ may be the same or different and independently represent a hydrogen atom, a halogeno group, a hydroxyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, a sulfonamido group which may have a substituent(s), a sulfinamido group which may have a substituent(s), an aliphatic ring group which may have a substituent(s), an alkenyl group which may have a substituent(s), an alkynyl group which may have a substituent(s), a benzyloxy group which may have a substituent(s), an aryloxy group which may have a substituent(s), an aryl-vinyl group which may have a substituent(s), a hetero-aryloxy group which may have a substituent(s), an arylamino group which may have a substituent(s), a hetero-arylamino group which may have a substituent(s), an aryl-ethynyl group which may have a substituent(s), an aryl group which may have a substituent(s), or a heterocyclic group which may have a substituent(s);
X represents a single bond, O, S, S(O), S(O$_2$), NR$^a$, C(O), C(O)O, C(O)NR$^a$, OC(O), NR$^a$C(O), NR$^a$C(O)NR$^b$, OC(O)NR$^a$, NR$^a$C(O)O, S(O)NR$^a$, S(O$_2$)NR$^a$, NR$^a$S(O), NR$^a$S(O$_2$), CR$^{20}$=CR$^{21}$, C≡C, or C=NR$^b$;
E represents an aryl group, a heterocyclic group or an aliphatic ring group;
$R^7$, $R^{22}$ and $R^{23}$ may be the same or different and independently represent a hydrogen atom, a halogeno group, a hydroxyl group, a boronyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, a sulfonamido group which may have a substituent(s), a sulfinamido group which may have a substituent(s), an aliphatic ring group which may have a substituent(s), an alkenyl group which may have a substituent(s), an alkynyl group which may have a substituent(s), a benzyloxy group which may have a substituent(s), an aryloxy group which may have a substituent(s), an aryl-vinyl group which may have a substituent(s), a hetero-aryloxy group which may have a substituent(s), an arylamino group which may have a substituent(s), a hetero-arylamino group which may have a substituent(s), an aryl-ethynyl group which may have a substituent(s), an aryl group which may have a substituent(s), or a heterocyclic group which may have a substituent(s);
$R^a$ and $R^b$ may be the same or different and independently represent a hydrogen atom, an alkyl group which may have a substituent(s), an alkoxy group which may have a substituent(s), an acyl group which may have a substituent(s), an alkylsulfonyl group which may have a substituent(s), an alkoxycarbonyl group which may have a substituent(s), carbamoyl group which may have a substituent(s), an aliphatic ring group which may have a substituent(s), an aryl group which may have a substituent(s), or a heterocyclic group which may have a substituent(s);
$R^{13}$ represents a hydrogen atom, an aryl group which may have a substituent(s), a heterocyclic group which may have a substituent(s) or an aliphatic ring group which may have a substituent(s);
$R^c$ and $R^d$ may be the same or different and independently represent an alkyl group which may have a substituent(s), an alkoxy group which may have a substituent(s), an acyl group which may have a substituent(s), an alkylsulfonyl group which may have a substituent(s), an alkoxycarbonyl group which may have a substituent(s), a carbamoyl group which may have a substituent(s), an aliphatic ring group which may have a substituent(s), an aryl group which may have a substituent(s) or a heterocyclic group which may have a substituent(s);
$R^e$ represents a hydrogen atom, an alkyl group which may have a substituent(s), an alkoxy group which may have a substituent(s), an acyl group which may have a substituent(s), an alkylsulfonyl group which may have a substituent(s), an alkoxycarbonyl group which may have a substituent(s), a carbamoyl group which may have a substituent(s), an aliphatic ring group which may have a substituent(s), an aryl group which may have a substituent(s) or a heterocyclic group which may have a substituent(s);
provided that each of the foregoing substituents may be one selected from the group consisting of halogeno groups, hydroxyl group, lower alkyl groups, mercapto groups, alkoxy groups, alkylthio groups, alkylsulfonyl groups, acyl groups, acyloxy groups, amino groups, alkylamino groups, carboxyl groups, alkoxycarbonyl groups, carbamoyl groups, nitro groups, cyano groups, trifluoromethyl group, aryl groups, and heterocyclic groups.

2. The compound or the pharmaceutically acceptable salt thereof as set forth in claim 1, wherein, in the general formula (I), G is a group represented by the foregoing general formula (II-1) or (II-2), wherein $R^7$, $R^{22}$ and $R^{23}$ may be the same or different and independently represent a hydrogen atom, a halogeno group, a hydroxyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, a sulfonamido group which may have a substituent(s), a sulfinamido group which may have a substituent(s), an aliphatic ring group which may have a substituent(s), an alkenyl group which may have a substituent(s), an alkynyl group which may have a substituent(s), a benzyloxy group which may have a substituent(s), an aryloxy group which may have a substituent(s), an aryl-vinyl group which may have a substituent(s), a hetero-aryloxy group which may have a substituent(s), an arylamino group which may have a substituent(s), a hetero-arylamino group which may have a substituent(s), an aryl-ethynyl group which may have a substituent(s), an aryl group which may have a substituent(s), or a heterocyclic group which may have a substituent(s).

3. The compound or the pharmaceutically acceptable salt thereof as set forth in claim 1, wherein, in the general formula (I), $R^{14}$ represents the following general formula:

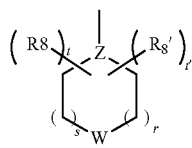

(III)

wherein
r=0, 1 or 2;
s=0, 1 or 2;
t=0, 1, 2, 3 or 4;
t'=0, 1, 2, 3 or 4;
Z is N or CH;
W is O, S, S(O), S(O$_2$), NR$^g$, C(O)NR$^g$, CR$^{20}$=CR$^{21}$, C≡C or NR$^g$C(O);
$R^g$ is a hydrogen atom, a hydroxyl group, an alkyl group which may have a substituent(s), an alkoxy group which may have a substituent(s), an acyl group which may have a substituent(s), an alkoxycarbonyl group which may have a substituent(s), a carbamoyl group which may have a substituent(s), an aliphatic ring group which may have a substituent(s), an aryl group which may have a substituent(s), or a heterocyclic group which may have a substituent(s);

$R^8$ and $R^{8'}$ may be the same or different and each independently represent a hydrogen atom, a halogeno group, a hydroxyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, an aliphatic ring group which may have a substituent(s), an alkenyl group which may have a substituent(s), an alkynyl group which may have a substituent(s), a benzyloxy group which may have a substituent(s), an aryloxy group which may have a substituent(s), an arylvinyl group which may have a substituent(s), a hetero-aryloxy group which may have a substituent(s), an arylamino group which may have a substituent(s), a hetero-arylamino group which may have a substituent(s), an aryl-ethynyl group which may have a substituent(s), an aryl group which may have a substituent(s), or a heterocyclic group which may have a substituent(s); or alternatively $R^8$ and $R^{8'}$ may be bonded together to form an aryl group which may have a substituent(s), a 3- to 7-membered aliphatic ring ring which may have a substituent(s) or a 5- to 7-membered heterocyclic ring which may have a substituent(s); and G is a group represented by the general formula (II-1).

4. The compound or the pharmaceutically acceptable salt thereof as set forth in claim 1, wherein, in the general formula (I), m is 0, 1 or 2;
n is 0, 1 or 2;
$R^{10}$ is a hydrogen atom;
U and V each independently represent a single bond, O, S, NR$^a$, CR$^{20}$=CR$^{21}$, C≡C, C(O)NR$^a$, or NR$^a$C(O);
X represents a single bond, O, S, NR$^a$, C(O)O, C(O)NR$^a$, OC(O), NR$^a$C(O), CR$^{20}$=CR$^{21}$, or C≡C;
Z is N;
r is 1;
s is 1; and
W is O, S, S(O), S(O$_2$) or NR$^g$.

5. The compound or the pharmaceutically acceptable salt thereof as set forth in claim 1, wherein, in the general formula (I), G is a group represented by the general formula (II-1), wherein
n=0,
q=1, and
X represents a single bond.

6. The compound or the pharmaceutically acceptable salt thereof as set forth in claim 1, wherein, in the general formula (I), $R^{14}$ is a group represented by the general formula (III), wherein
Z is N,
W is O,
t=0, and
t'=0.

7. The compound or the pharmaceutically acceptable salt thereof as set forth in claim 1, wherein, in the general formula (I),
p=1;
$R^4$ is a hydrogen atom;
G is a group represented by the general formula (II-1), wherein
n=0,
q=1, and
X represents a single bond; and
$R^{14}$ is a group represented by the general formula (III), wherein
Z is N,
W is O,
t=0, and
t'=0.

8. The compound or the pharmaceutically acceptable salt thereof as set forth in claim 1, wherein the group represented by $-(E(R^{22})(R^{23}))_q-R^7$ in the general formula (II-1) is a 6-indolyl group, an m-tolyl group or a 3-indolyl group.

9. The compound or the pharmaceutically acceptable salt thereof as set forth in claim 1, wherein the group represented by $-(E(R^{22})(R^{23}))_q-R^7$ in the general formula (II-1) is an m-tolyl group or a 3-indolyl group.

10. The compound or the pharmaceutically acceptable salt thereof as set forth in claim 7, wherein, in the general formula (I),
p=1;
$R^4$ is a hydrogen atom;
m=0;
U is a single bond;
V is a single bond;
G is a group represented by the general formula (II-1), wherein
n=0,
q=1, and
X is a single bond; and
$R^{14}$ is a group represented by the general formula (III), wherein
Z is N;
W is O;
t=0; and
t'=0.

11. The compound or the pharmaceutically acceptable salt thereof as set forth in claim 10, wherein the group represented by $-(E(R^{22})(R^{23}))_q-R^7$ in the general formula (II-1) is a 6-indolyl group, an m-tolyl group or a 3-indolyl group.

12. The compound or the pharmaceutically acceptable salt thereof as set forth in claim 10, wherein the group represented by $-(E(R^{22})(R^{23}))_q-R^7$ in the general formula (II-1) is an m-tolyl group or a 3-indolyl group.

13. The compound or the pharmaceutically acceptable salt thereof as set forth in claim 1, wherein
m=0, 1 or 2;
n=0, 1 or 2;
$R^{10}$ is a hydrogen atom; and
U and V each independently represent a single bond, O, S, S(O), S(O_2), C(O), C(O)O or OC(O).

14. The compound or the pharmaceutically acceptable salt thereof as set forth in claim 1, wherein
G is a group represented by the general formula (II-1) or (II-2); and
X is a single bond, $CR^{20}=CR^{21}$, or $C≡C$.

15. The compound or the pharmaceutically acceptable salt thereof as set forth in claim 1, wherein, in the general formula (I),
$R^{14}$ is $NR^cR^d$ or a group represented by the following general formula (III);

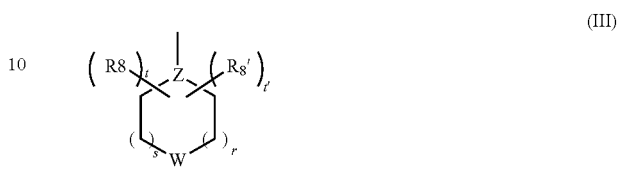

wherein r=0, 1 or 2;
s=0, 1 or 2;
t=0, 1, 2, 3 or 4;
t'=0, 1, 2, 3 or 4;
Z is N or CH;
W is O, S, S(O), S(O_2), $NR^g$, $CR^g$, $C(O)NR^g$, $CR^{20}=CR^{21}$, $C≡C$ or $NR^gC(O)$;
$R^g$ is a hydrogen atom, a hydroxyl group, an alkyl group which may have a substituent(s), an alkoxy group which may have a substituent(s), an acyl group which may have a substituent(s), an alkoxycarbonyl group which may have a substituent(s), a carbamoyl group which may have a substituent(s), an aliphatic ring group which may have a substituent(s), an aryl group which may have a substituent(s), or a heterocyclic group which may have a substituent(s); and
$R^8$ and $R^{8'}$ may be the same or different and each independently represent a hydrogen atom, a halogeno group, a hydroxyl group, an alkyl group which may have a substituent(s), a mercapto group, an alkoxy group which may have a substituent(s), an alkylthio group which may have a substituent(s), an alkylsulfonyl group which may have a substituent(s), an acyl group which may have a substituent(s), an acyloxy group which may have a substituent(s), an amino group which may have a substituent(s), a carboxyl group, an alkoxycarbonyl group which may have a substituent(s), a carbamoyl group which may have a substituent(s), a nitro group, a cyano group, a trifluoromethyl group, a sulfonic acid group, an aliphatic ring group which may have a substituent(s), an alkenyl group which may have a substituent(s), an alkynyl group which may have a substituent(s), a benzyloxy group which may have a substituent(s), an aryloxy group which may have a substituent(s), an arylvinyl group which may have a substituent(s), a hetero-aryloxy group which may have a substituent(s), an arylamino group which may have a substituent(s), a hetero-arylamino group which may have a substituent(s), an aryl-ethynyl group which may have a substituent(s), an aryl group which may have a substituent(s), or a heterocyclic group which may have a substituent(s); or alternatively $R^8$ and $R^{8'}$ may be bonded together to form an aryl group which may have a substituent(s), a 3- to 7-membered aliphatic ring ring which may have a substituent(s) or a 5- to 7-membered heterocyclic ring which may have a substituent(s).

16. The compound or the pharmaceutically acceptable salt thereof as set forth in claim 1, wherein, in the general formula (I),
$R^{14}$ is $NR^cR^d$ or a group represented by the general formula (III);
Z is N;
t=0; and
t'=0.

17. A compound represented by the following general formula (IA), or a pharmaceutically acceptable salt thereof:

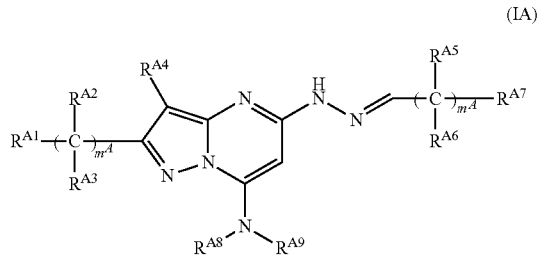

(IA)

wherein $m^A$=0, 1, or 2;
$n^A$=0, 1, or 2;
$R^{A1}$ and $R^{A4}$ each independently represent a hydrogen atom, a halogeno group, a hydroxyl group, a nitro group, a sulfonic acid group, an amino group, an alkyl group which may have a substituent(s), an alkoxy group which may have a substituent(s), a mono- or di-alkylamino group which may have a substituent(s), a carbamoyl group which may have a substituent(s), or an aryl group which may have a substituent(s), a heteroaryl group which may have a substituent(s), or a heterocyclic group which may have a substituent(s);
$R^{A2}$, $R^{A3}$, $R^{A5}$ and $R^{A6}$ each independently represent a hydrogen atom, halogeno groups, a hydroxyl group, a nitro group, a sulfonic acid group, an amino group, an alkyl group which may have a substituent(s), an alkoxy group which may have a substituent(s), or mono- or di-alkylamino groups each of which may have a substituent(s);
$R^{A7}$ represents an aryl group which may have a substituent(s), or a heteroaryl group which may have a substituent(s); and
$R^{A8}$ and $R^{A9}$ each independently represent an alkyl group which may have a substituent(s), or the group: $NR^{A8}R^{A9}$ represents a cyclic amino group which may have a substituent(s).

18. The compound or the pharmaceutically acceptable salt thereof as set forth in claim 17, wherein, in the general formula (IA),
$R^{A1}$ and $R^{A4}$ each independently represent a hydrogen atom, a halogeno group, a hydroxyl group, a nitro group, a sulfonic acid group, an amino group, an alkyl group which may have a substituent(s), an alkoxy group which may have a substituent(s), a mono- or di-alkylamino group which may have a substituent(s), or an aryl group which may have a substituent(s) or a heteroaryl group which may have a substituent(s).

19. The compound or the pharmaceutically acceptable salt thereof as set forth in claim 17, wherein, in the general formula (IA),
$m^A$ is 0;
$n^A$ is 0;

$R^{A1}$ and $R^{A4}$ each independently represent a hydrogen atom, a halogeno group, or a member selected from the group consisting of phenyl groups and 5- or 6-membered monocyclic heteroaryl groups, which may be substituted with a substituent(s) selected from the group consisting of halogeno groups, alkyl groups having 1 to 3 carbon atoms, alkoxy groups having 1 to 3 carbon atoms, mono- or di-alkylamino groups each having 1 to 6 carbon atoms or a group represented by the following formula:

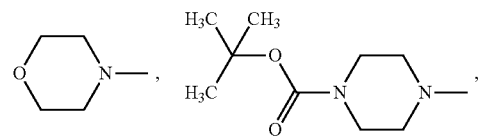

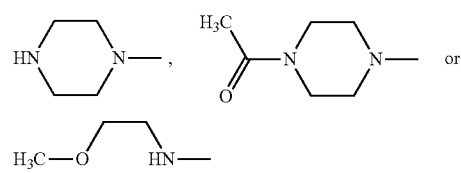

$R^{A7}$ represents a group selected from the group consisting of phenyl groups, 5- or 6-membered monocyclic heteroaryl groups and fused bicyclic heteroaryl groups, each of which may be substituted with a substituent(s) selected from the group consisting of halogeno groups, alkyl groups each having 1 to 3 carbon atoms and alkoxy groups each having 1 to 3 carbon atoms; and $NR^{A8}R^{A9}$ is a 5- or 6-membered cyclic amino group.

20. The compound or the pharmaceutically acceptable salt thereof as set forth in claim 19, wherein
$R^{A1}$ represents a halogeno group, an alkyl group having 1 to 3 carbon atoms, an alkoxy group having 1 to 3 carbon atoms, a mono- or di-alkylamino group having 1 to 6 carbon atoms, or a member selected from the group consisting of phenyl groups and 5- or 6-membered heteroaryl groups, each of which may be substituted with a substituent(s) selected from the group consisting of those represented by the following formulas:

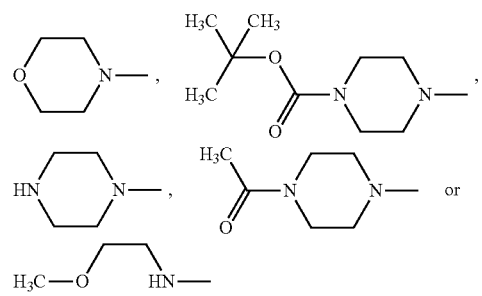

$R^{A4}$ represents a hydrogen atom; and
$NR^{A8}R^{A9}$ is a 4-morpholinyl group.

21. The compound or the pharmaceutically acceptable salt thereof as set forth in claim 17, which is a compound represented by one of the following structural formulas:
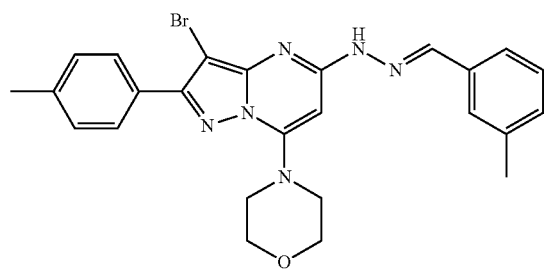
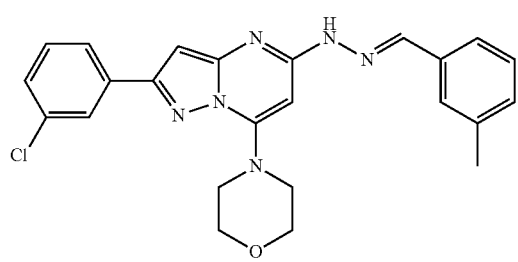
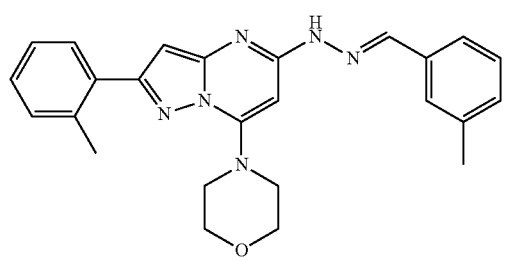
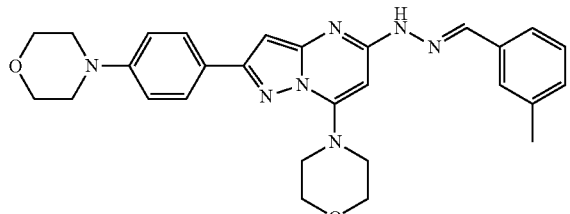
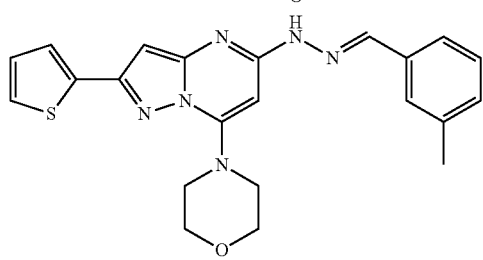
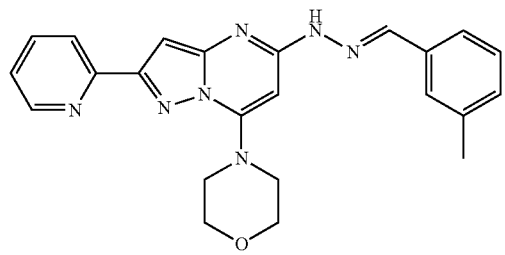
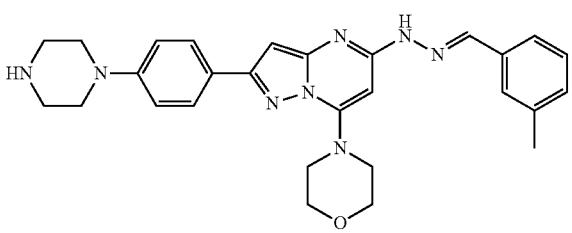
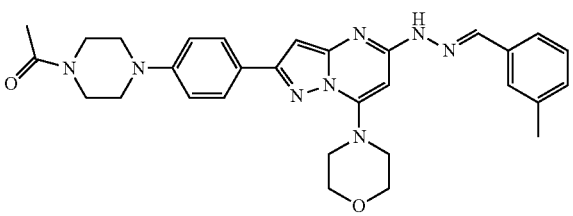
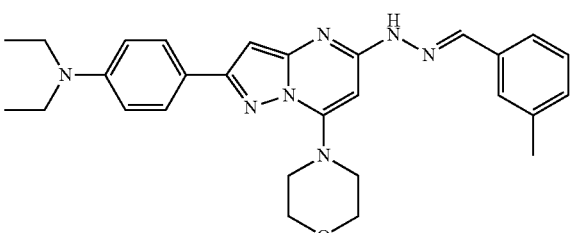
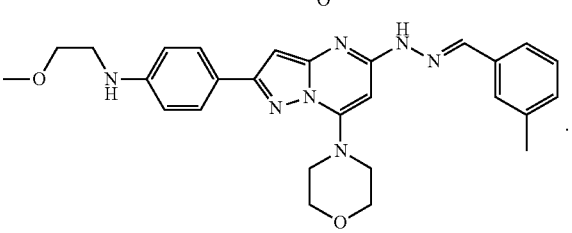
22. The compound or the pharmaceutically acceptable salt thereof as set forth in claim 17, which is a compound represented by one of the following structural formulas:
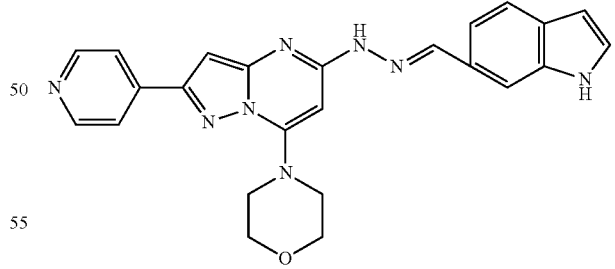
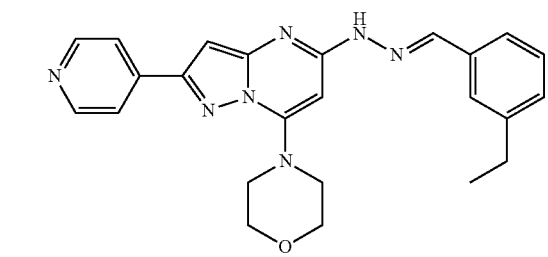

201
-continued
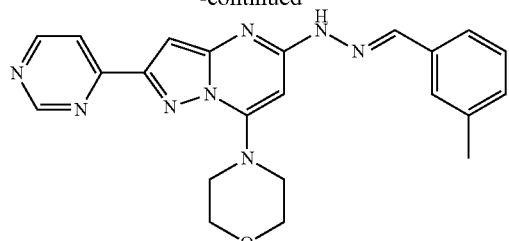
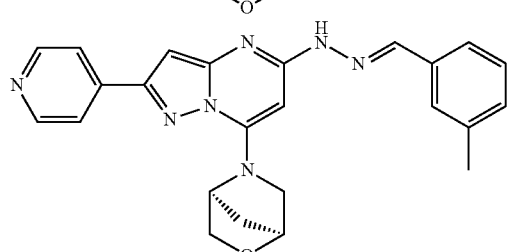
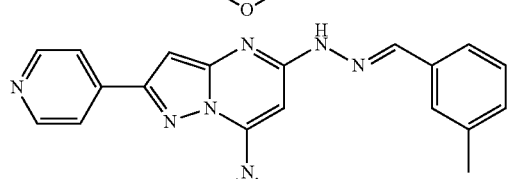
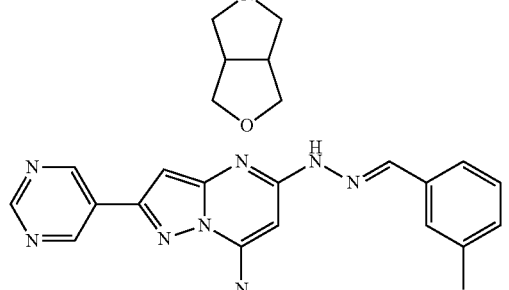
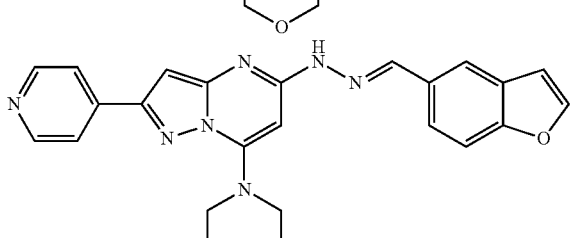
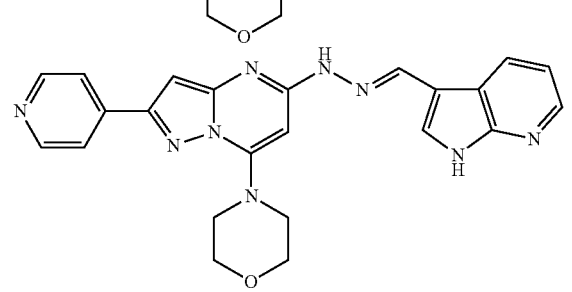
202
-continued
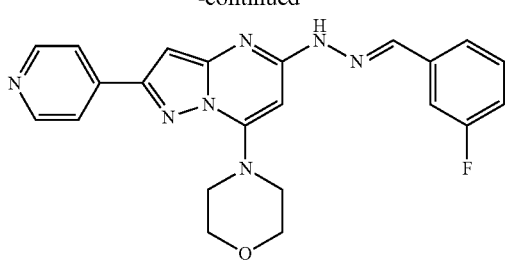
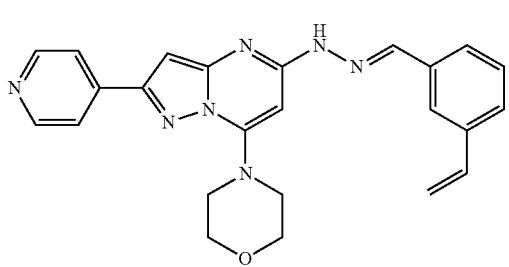
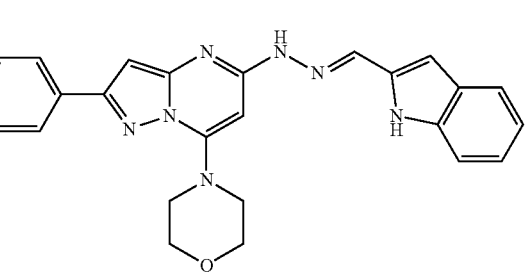
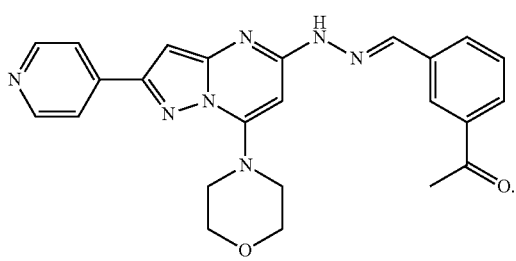
23. A pharmaceutical composition comprising a compound or a pharmaceutically acceptable salt thereof as set forth in any one of claims 1 to 22.
* * * * *